US008150626B2

(12) United States Patent
Fan et al.

(10) Patent No.: US 8,150,626 B2
(45) Date of Patent: Apr. 3, 2012

(54) METHODS AND COMPOSITIONS FOR DIAGNOSING LUNG CANCER WITH SPECIFIC DNA METHYLATION PATTERNS

(75) Inventors: Jian-Bing Fan, San Diego, CA (US); Marina Bibikova, San Diego, CA (US)

(73) Assignee: Illumina, Inc., San Diego, CA (US)

(*) Notice: Subject to any disclaimer, the term of this patent is extended or adjusted under 35 U.S.C. 154(b) by 953 days.

(21) Appl. No.: 10/973,783

(22) Filed: Oct. 25, 2004

(65) Prior Publication Data

US 2005/0164246 A1 Jul. 28, 2005

Related U.S. Application Data

(63) Continuation-in-part of application No. 10/845,667, filed on May 14, 2004, now abandoned.

(60) Provisional application No. 60/471,488, filed on May 15, 2003.

(51) Int. Cl.
*G01N 33/48* (2006.01)
*C12Q 1/00* (2006.01)

(52) U.S. Cl. .............................................. 702/19; 435/4

(58) Field of Classification Search ........................ None
See application file for complete search history.

(56) References Cited

U.S. PATENT DOCUMENTS

| | | | | |
|---|---|---|---|---|
| 5,786,146 | A | 7/1998 | Herman et al. | |
| 5,856,101 | A | 1/1999 | Hubbell et al. | |
| 5,981,733 | A | 11/1999 | Gamble et al. | |
| 6,001,309 | A | 12/1999 | Gamble et al. | |
| 6,017,704 | A | 1/2000 | Herman | |
| 6,023,540 | A | 2/2000 | Walt et al. | |
| 6,110,426 | A | 8/2000 | Shalon et al. | |
| 6,200,737 | B1 | 3/2001 | Walt et al. | |
| 6,232,072 | B1 | 5/2001 | Fisher | |
| 6,251,594 | B1 | 6/2001 | Gonzalgo et al. | |
| 6,265,171 | B1 | 7/2001 | Herman et al. | |
| 6,280,949 | B1 | 8/2001 | Lizardi | |
| 6,327,410 | B1 | 12/2001 | Walt et al. | |
| 6,329,150 | B1 | 12/2001 | Lizardi et al. | |
| 6,331,393 | B1 | 12/2001 | Laird et al. | |
| 6,379,895 | B1 | 4/2002 | Fodor et al. | |
| 6,429,027 | B1 | 8/2002 | Chee et al. | |
| 6,667,394 | B2 | 12/2003 | Pease et al. | |
| 2002/0102578 | A1 | 8/2002 | Dickinson | |
| 2003/0170684 | A1 | 9/2003 | Fan | |
| 2004/0137473 | A1 | 7/2004 | Wigler et al. | |
| 2004/0259100 | A1 | 12/2004 | Gunderson et al. | |
| 2005/0026183 | A1 | 2/2005 | Fan | |
| 2005/0164246 | A1 | 7/2005 | Fan | |
| 2007/0128592 | A1* | 6/2007 | Burger et al. | 435/6 |

FOREIGN PATENT DOCUMENTS

| | | |
|---|---|---|
| WO | WO 98/40726 | 9/1998 |
| WO | WO 98/50782 | 11/1998 |
| WO | WO 99/18434 | 4/1999 |
| WO | WO 02/086163 | 10/2002 |
| WO | WO 03/052135 | 12/2002 |
| WO | WO 03/048732 | 6/2003 |
| WO | WO 2004/051224 | 6/2004 |

OTHER PUBLICATIONS

Dai et al., Global Methylation Profiling of Lung Cancer Identities Novel Methylated Genes, Neoplasia, 2001, 3(4),314-323.*

Ferguson et al., High Frequency of Hypermethylation at the 14-3-3 sigma Locus Leads of Gene Silencing in Breaast Cancer, PNAS, 2000, 97(11), 6049-6054.*

Umbricht et al., Hypermethylation of 14-3-3 sigma (Stratifin) is an Early Event in Breast Cancer, Oncogene, 2001, 20, 3348-3353.*

Tsujiuchi et al., Hypomethylation of CpG Sites and c-myc Gene Overexpression in Hepatocellular Carcinomas, but Not Hyperplastic Nodules, Induced by a choline-deficient L-Amino Acid-defined Diet in Rats, Jpn. J. Cancer Res., 1999, 90, 909-913.*

Akama et al., "Restriction landmark genomic scanning (RLGS-M)-based genome-wide scanning of mouse liver tumors for alterations in DNA methylation status," *Cancer Res*. 57(15):3294-3299 (1997).

Aldred et al., "Caveolin-1 and caveolin-2,together with three bone morphogenetic protein-related genes, may encode novel tumor suppressors down-regulated in sporadic follicular thyroid carcinogenesis," *Cancer Res* 63, 2864-71 (2003).

Bhattacharjee, et al., "Classification of human lung carcinomas by mRNA expression profiling reveals distinct adenocarcinoma subclasses," *Proc Natl Acad Sci U S A* 98(24): 13790-5 (2001).

Bird, "CpG-rich islands and the function of DNA methylation," *Nature* 321:209-213 (1986).

Bird, "The essentials of DNA methylation," *Cell* 70:5-8(1992).

Cedar, "DNA methylation and gene activity," *Cell* 53:3-4, (1988).

Chen et al., "Methylation target array for rapid analysis of CpG island hypermethylation in multiple tissue genomes," *Am J Pathol* 163, 37-45 (2003).

Chen, et al., "Gene expression patterns in human liver cancers," *Mol Biol Cell* 13(6):1929-39 (2002).

Chen, et al., "Heterozygous disruption of Hic1 predisposes mice to a gender-dependent spectrum of malignant tumors," *Nat Genet*. 33(2): 197-202 (2003).

Costello et al., "Aberrant CpG-island methylation has non-random and tumour-type-specific patterns," *Nat Genet*. 24(2):132-138 (2000).

Cui, et al., "Loss of IGF2 imprinting: a potential marker of colorectal cancer risk," *Science* 299(5613): 1753-5 (2003).

Dahl et al., "DNA methylation analysis techniques," *Biogerontology*. 4(4):233-250.

Dennis, "Epigenetics and disease: Altered states," *Nature* 421:686-688 (2003).

Dhanasekaran, et al., "Delineation of prognostic biomarkers in prostate cancer," *Nature* 412(6849): 822-6 (2001).

Eads et al., "CpG island hypermethylation in human colorectal tumors is not associated with DNA methyltransferase overexpression," *Cancer Res*. 59(10):2302-2306 (1999).

(Continued)

*Primary Examiner* — Marjorie Moran
*Assistant Examiner* — Larry D Riggs, II
(74) *Attorney, Agent, or Firm* — Lisa de Berg

(57) ABSTRACT

The present invention provides a method for identification of differentially methylated genomic CpG dinucleotide sequences within genomic target sequences that are associated with cancer in an individual by comparing the level of methylated genomic CpG dinucleotide sequences in the sample to a reference level of methylated genomic CpG dinucleotide sequences.

9 Claims, 27 Drawing Sheets
(23 of 27 Drawing Sheet(s) Filed in Color)

OTHER PUBLICATIONS

Esteller, "CpG island hypermethylation and tumor suppressor genes: a booming present, a brighter future," *Oncogene* 21(35): 5427-40 (2002).
Fackler et al., "DNA methylation of RASSF1A, HIN-1, RAR-beta, Cyclin D2 and Twist in in situ and invasive lobular breast carcinoma," *Int J Cancer* 107, 970-5 (2003).
Fan, et al., "A versatile assay for high-throughput gene expression profiling on universal array matrices," *Genome Res.* 14:878-885 (2004).
Feil et al., "Methylation analysis on individual chromosomes: improved protocol for bisulphite genomic sequencing," *Nucleic Acids Res.* 22(4):695-696 (1994).
Feinberg et al., "Hypomethylation distinguishes genes of some human cancers from their normal counterparts," *Nature.* 301(5895):89-92 (1983).
Frommer et al., "A genomic sequencing protocol that yields a positive display of 5-methylcytosine residues in individual DNA strands," *Proc Natl Acad Sci U S A.* 89(5):1827-1831 (1992).
Fujii, et al., "Methylation of the HIC-1 candidate tumor suppressor gene in human breast cancer," *Oncogene* 16(16): 2159-64 (1998).
Gardiner-Garden et al., "CpG islands in vertebrate genomes," *J Mol. Biol.* 196:261-282 (1987).
Golub, et al., "Molecular classification of cancer: class discovery and class prediction by gene expression monitoring," *Science* 286(5439): 531-7 (1999).
Gonzalgo et al., "Identification and characterization of differentially methylated regions of genomic DNA by methylation-sensitive arbitrarily primed PCR," *Cancer Res.* 57(4):594-599 (1997).
Gonzalgo et al., "Rapid quantitation of methylation differences at specific sites using methylation-sensitive single nucleotide primer extension (Ms-SNuPE)," *Nucleic Acids Res.* 25(12):2529-2531 (1997).
Hanada et al., "bcl-2 gene hypomethylation and high-level expression in B-cell chronic lymphocytic leukemia," *Blood.* 82(6):1820-1828 (1993).
Heid et al., "Real time quantitative PCR," *Genome Res.* 6(10):986-994 (1996).
Herman et al., "Methylation-specific PCR: a novel PCR assay for methylation status of CpG islands," *Proc Natl Acad Sci U S A.* 93(18):9821-9826 (1996).
Herman, et al., "Inactivation of the CDKN2/p16/MTS1 gene is frequently associated with aberrant DNA methylation in all common human cancers," *Cancer Res.* 55(20): 4525-30 (1995).
Hibi et al., "CDH13 promoter region is specifically methylated in poorly differentiated colorectal cancer," *Br J Cancer* 90, 1030-3 (2004).
Hibi et al., "Methylation pattern of CDH13 gene in digestive tract cancers," *Br J Cancer.* 91:1139-1142 (2004).
Huang et al., "Methylation profiling of CpG islands in human breast cancer cells," *Hum Mol Genet.* 8(3):459-470 (1999).
Issa et al., "Methylation of the oestrogen receptor CpG island links ageing and neoplasia in human colon," *Nat Genet.* 7(4):536-540 (1994).
Kanai, et al., "DNA hypermethylation at the D17S5 locus and reduced HIC-1 mRNA expression are associated with hepatocarcinogenesis," *Hepatology* 29(3): 703-9 (1999).
Kawai et al., "Comparison of DNA methylation patterns among mouse cell lines by restriction landmark genomic scanning" *Mol Cell Biol.* 14(11):7421-7427 (1994).
Klimasauskas et al., "HhaI methyltransferase flips its target base out of the DNA helix," *Cell* 76:357-369(1994).
Kuppuswamy et al., "Single nucleotide primer extension to detect genetic diseases: experimental application to hemophilia B (factor IX) and cystic fibrosis," *Proc. Natl. Acad. Sci USA* 88:1143-1147 (1991).
Laird et al., "DNA methylation and cancer," *Human Mol. Genet.* 3:1487-1495(1994).
Li et al, "Targeted mutation of the DNA methyltransferase gene results in embryonic lethality," *Cell* 69:915-926 (1992).
Li, et al., "Causal relationship between the loss of RUNX3 expression and gastric cancer," *Cell* 109(1): 113-24 (2002).
Liu et al., "Epigenetic regulation of human telomerase reverse transcriptase promoter activity during cellular differentiation," *Genes Chromosomes Cancer* 41, 26-37 (2004).
Ogama et al., "Prevalent hyper-methylation of the CDH13 gene promoter in malignant B cell lymphomas," *Int J Oncol* 25, 685-91 (2004).
Otterson, et al., "CDKN2 gene silencing in lung cancer by DNA hypermethylation and kinetics of p16INK4 protein induction by 5-aza 2'deoxycytidine," *Oncogene* 11(6): 1211-6 (1995).
Perou, et al., "Molecular portraits of human breast tumours," *Nature* 406(6797): 747-52 (2000).
Ramaswamy, et al., "A molecular signature of metastasis in primary solid tumors," *Nat Genet.* 33(1): 49-54 (2003).
Ramaswamy, et al., "Multiclass cancer diagnosis using tumor gene expression signatures," *Proc Natl Acad Sci U S A.* 98(26): 15149-54 (2001).
Rein et al., "Identifying 5-methylcytosine and related modifications in DNA genomes," *Nucleic Acids Res.* 26(10):2255-2264 (1998).
Schorderet et al., "Analysis of CpG suppression in methylated and nonmethylated species," *Proc. Natl. Acad. Sci. USA* 89:957-961(1992).
Shipp, et al., "Diffuse large B-cell lymphoma outcome prediction by gene-expression profiling and supervised machine learning," *Nat Med.* 8(1): 68-74 (2002).
Singer-Sam et al., "A quantitative HpaII-PCR assay to measure methylation of DNA from a small number of cells," *Nucleic Acids Res.* 18(3):687 (1990).
Smiraglia et al., "A new tool for the rapid cloning of amplified and hypermethylated human DNA sequences from restriction landmark genome scanning gels," *Genomics.* 58(3):254-262 (1999).
Taylor et al., "The diagnositc significance of Myf-3 hypermethylation in malignant lymphoproliferative disorders," *Leukemia.* 15(4):583-589 (2001).
Toyota et al., "Identification of differentially methylated sequences in colorectal cancer by methylated CpG island amplification," *Cancer Res.* 59(10):2307-2312 (1999).
Welsh, et al., "Analysis of gene expression profiles in normal and neoplastic ovarian tissue samples identifies candidate molecular markers of epithelial ovarian cancer," *Proc Natl Acad Sci U S A.* 98(3): 1176-81 (2001).
Wong, et al., "New markers for cancer detection," *Curr Oncol Rep.* 4(6): 471-7 (2002).
Yeakley, et al., "Profiling alternative splicing on fiber-optic arrays," *Nat Biotechnol.* 20(4): 353-8 (2002).
Anderson and Brown, "Variability of X chromosome inactivation: effects on levels of TIMP1 RNA and role of DNA methylation," *Hum. Genet.* 110(3):271-278 (2002).
Baylin, "DNA hypermethylation in tumorigenesis: epigenetics joins genetics," Trends Genet. 16(4):168-174.
Beck, Olek and Walter, "From genomics to epigenomics: a loftier view of life." *Nat. Biotechnol.* 17(12):1144 (1999).
Bestor, "Gene silencing. Methylation meets acetylation." *Nature* 393(6683):311-312 (1998).
Bird, "CpG-rich islands and the function of DNA methylation," *Nature* 321:209-213(1986).
Chen, et al., "Gene expression patterns in human liver cancers," *Mol Biol Cell* 13(6): 1929-39 (2002).
Costello et al., "Aberrant CpG-island methylation has non-random and tumour-typespecific patterns," *Nat Genet.* 24(2):132-138 (2000).
Dahl et al., "DNA methylation analysis techniques," *Biogerontology.* 4(4):233-250 (2003).
Dai et al., "Global Methylation Profiling of Lung Cancer identifies Novel Methylated Genes," *Neoplasia* 3(4):314-323 (2001).
Ferguson et al., "High frequency of hypermethylation at the 14-3-3 σ locus leads to gene silencing in breast cancer," *PNAS* 97(11):6049-6054 (2000).
Gonzalgo et al., "Rapid quantitation of methylation differences at specific sites using methylation-sensitive single nucleotide primer extension (Ms-SNuPE)," *Nucleic Acids. Res.* 25(12):2529-2531 (1997).
Grunau, et al., "DNA Methylation Database "MethDB": a user guide." *J. Nutr.* 132 (8): 2435S-2439S (2002).
Grunau, et al., "MethDB—a public database for DNA methylation data.," *Nucleic Acids Res.* 29(1):270-274 (2001).

Hibi et al., "Methylation pattern of CDH13 gene in digestive tract cancers," *Br J Cancer* 91:1139-1142 (2004).
Jones and Laird, "Cancer epigenetics comes of age," *Nat. Genet.* 21(2):163-167.
Jones and Takai, "The role of DNA methylation in mammalian epigenetics," 293(5532):1068-1070 (2001).
Kawai et al., "Comparison of DNA methylation patterns among mouse cell lines by restriction landmark genomic scanning," *Mol Cell Biol.* 14(11):7421-7427 (1994).
Kumar, "Rett and ICF syndromes, methylation moves into medicine." *J. Biosci.* 2000, 25(3):213-214 (2000).
Lander, et al., "Initial sequencing and analysis of the human genome," *Science*, 291(5507):1304-1351.
Razin, "CPG methylation, chromatin structure and gene silencing—a three-way connection." *EMBO J*, 17(17):4905-4908 (1998).
Sano, et al., "Random Monoallelic Expression of Three Genes Clustered within 60 kb of Mouse Complex Genomic DNA." *Genome Res.* 11(11):1833-1841.
Sasaki, et al., "DNA methylation and genomic imprinting in mammals." 64:469-486 (1993).
Strichman-Almashanu, et al., "A genome-wide screen for normally methylated human CpG islands that can identify novel imprinted genes." *Genome Res.* 12(4):543-554 (2002).
Umbricht et al., "Hypermethylation of 14-3-3 σ (statifin) is an early event in breast cancer," *Oncogene* 20:3348-3353 (2001).
Venter, et al., "The sequence of the human genome," *Science* 291(5507):1304-1351 (2001).
Yan et al., "Role of DNA methylation and histone acetylation in steroid receptor expression in breast cancer," *J. Mammary Gland Biol. Neoplasia*, 6(2):183-192 (2001).
Zhong, et al., "A survey of FRAXE allele sizes in three populations." *Am. J. Med. Genet.* 64(2):415-419 (1996).
U.S. Appl. No. 60/471,488, Fan.
Adorjan, et al., "Tumor class prediction and discovery by microarray-based DNA methylation analysis", *Nucleic Acids Res.*, 30(5):e21 (2002).
Antequera, et al., "No. Of CpG islands and genes in human and mouse", *Proc Natl Acad Sci USA* 90(24):11995-11999 (1993).
Balmain, et al., "The genetics and genomics of cancer", *Nature Genetics*, 33 Suppl:238-244 (2003).
Chen, "A Microsphere-Based Assy for Multiplexed Single Nucleotide Polymorphism Analysis Using Single Base Chain Extension", *Genome Research*, vol. 10(4):549-557 (2000).
Cross, et al., "Purification of CpG islands using a methylated DNA binding column", *Nature Genetics*, 6(3):236-244 (1994).
Davuluri, et al., "Computational identification of promoters and first exons in the human genome", *Nature Genetics*, 29(4):412-417 (2001).
Eisen, et al., "Cluster analysis and display of genome-wide expression patterns", *Proc Natl Acad Sci USA*, 95(25):14863-14868 (1998).
Ewing, et al., "Analysis of expressed sequence tags indicates 35,000 human genes", *Nature Genetics*, 25(2):232-234 (2000).
Fan, "Parallel Genotyping of Human SNPs Using Generic High-density Oligonucleotide Tag Arrays", *Genome Research*, vol. 10:853-860 (2000).
Gerry, et al., "Universal DNA Microarray Method for Multiplex Detection of Low Abundance Point Mutations", *J. Mol. Biol.*, vol. 292:251-262 (1999).
Grunau et al., "DNA Methylation Database "MethDB": a User Guide," *J. Nutr.* 132:2435S-2439S (2002).
Iannone, "Multiplexed Single Nucleotide Polymorphism Genotyping by Oligonucleotide Ligation and Flow Cytometry", *Cytometry*, 39(2)131-140 (2000).
Ivanova, et al., "Methylation and silencing of the retinoic acid receptor 2 gene in cervical cancer", *BMC Cancer*, 2:4 (2002).
Khan, et al., "Classification and diagnostic prediction of cancers using gene expression profiling and artificial neural networks", *Nat. Med*, 7(6):673-679 (2001).
Kerr, et al., "Bootstrapping cluster analysis: assessing the reliability of conclusions from microarray experiments", *Proc Natl Acad Sci USA* 98(16):8961-8965 (2001).
Laird, "The power and the promise of DNA methylation markers", *Nat. Rev. Cancer*, 3(4):253-266 (2003).
Lander, "Initial sequencing and analysis of the human genome," *Nature*, 409(6822):860-921.
Lockhart, et al., "Genomics, gene expression and DNA arrays", *Nature*, 405(6788):827-836 (2000).
Michael, "Randomly Ordered Addressable High-Density Optical Sensor Arrays", *Analytical Chemistry*, 70(7):1242-1248 (1998).
Oliphant, et al., "BeadArray Technology: Enabling an Accurate, Cost Effective Approach to High-Throughput Genotyping", *Biotechniques*, Jun. 2002 Suppl.:56-61 (2002).
Pollack, et al., "Microarray analysis reveals a major direct role of DNA copy number alteration in the transcriptional program of human breast tumors", *Proc Natl Acad Sci USA*, 99(20):12963-12968 (2002).
Praz, et al., "The Eukaryotic Promoter Database, EPD: new entry types and links to gene expression data", *Nucleic Acids Research*, 30(1):322-324 (2002).
Roth, et al., "Bringing out the best features of expression data", *Genome Research*, 11(11):1801-1802 (2001).
Russo, "Comparative study of the influence of pregnancy and hormonal treatment on mammary carcinogenesis", *Br. J. Cancer*, 64(3):481-484 (1991).
Sivaraman, et al., "Hormone-induced refractoriness to mammary carcinogenesis in Wistar-Furth rats", *Carcinogenesis*, 19(9):1573-1581 (1998).
Tsou, et al., "DNA methylation analysis: a powerful new tool for lung cancer diagnosis", *Oncogene*, 21(35):5450-5461 (2002).
Tsujiuch et al., "Hypomethylation of CpG Sites and *c-myc* Gene Overexpression in Hepatocellular Carcinomas, but Not Hyperplastic Nodules, Induced by a Choline-deficient L-Amino Acid-defined Diet in Rats," *Jpn. J. Cancer Res.* 90:909-913 (1999).
Walt, "Bead Based Fiber-Optic Arrays", *Science*, 287:451-452 (1999).
Widschewendter, et al., "DNA methylation and breast carcinogenesis", *Oncogene* 21(35):5462-5482 (2002).

* cited by examiner

FIG. 2
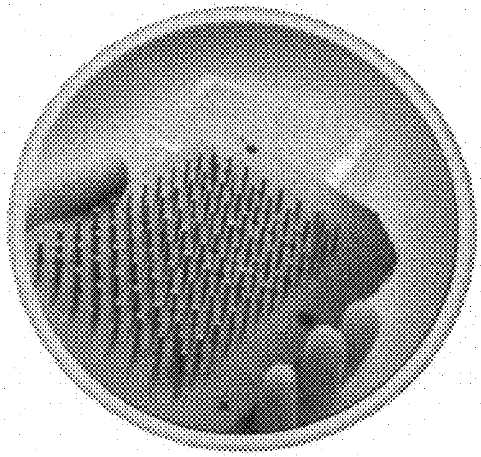
Fig. 2 A
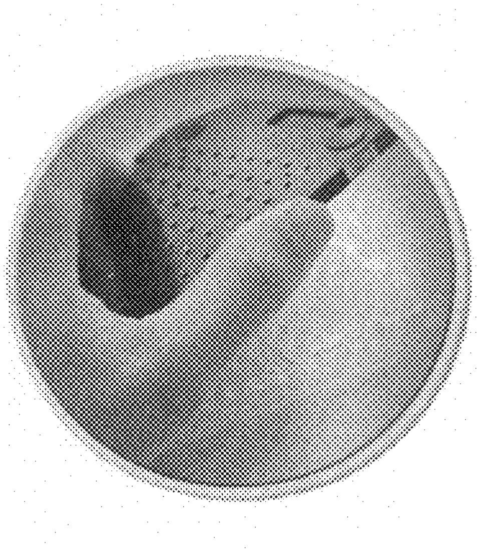
Fig. 2 B

FIG. 10
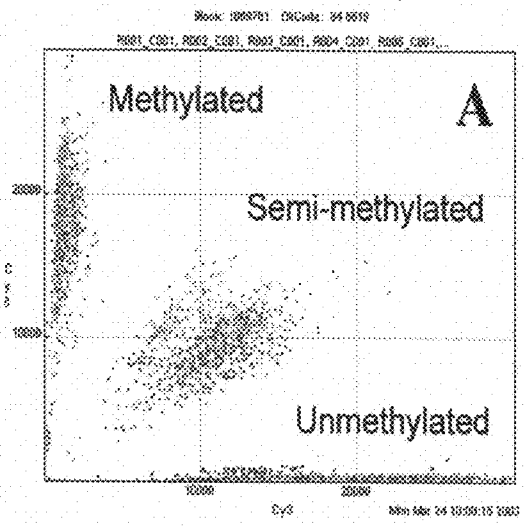
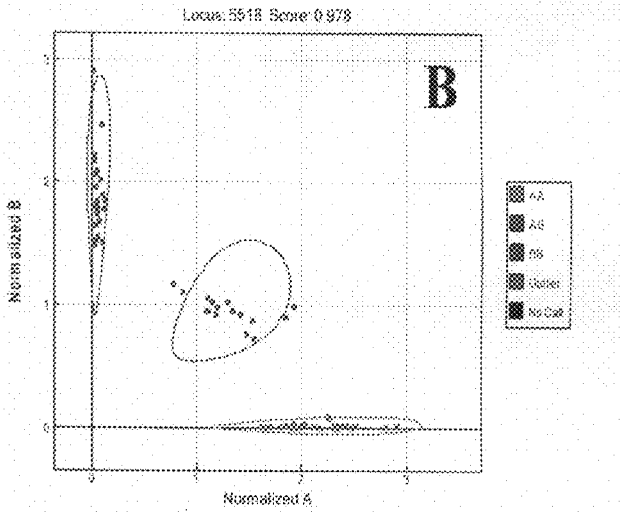
Fig. 10 A
Fig. 10 B

Methylation of G6PD and GLA

- Unmethylated (Green), semi-methylated (Yellow) and fully-methylated (Red)

Cluster analysis of methylation profiles in 46 lung cancer samples

- Based on methylation profile, cancer samples separate well from their normal matching pairs.

Validation of Adenocarcinoma markers

METHODS AND COMPOSITIONS FOR DIAGNOSING LUNG CANCER WITH SPECIFIC DNA METHYLATION PATTERNS

This application is a continuation-in-part of U.S. Ser. No. 10/845,667, filed May 14, 2004, now abandoned which is based on, and claims the benefit of, U.S. Provisional Application No. 60/471,488, filed May 15, 2003, entitled METHODS AND COMPOSITIONS FOR DIAGNOSING CANCER, each of which is incorporated herein by reference.

This invention was made with government support under grant numbers 1 R43 CA097851-01 and 2 R44 CA097851-02 awarded by the National Institutes of Health. The United States Government has certain rights in this invention.

FIELD OF THE INVENTION

The present invention relates to conditions characterized by differentially methylated genomic CpG dinucleotide sequences and, in particular, to diagnostic and prognostic methods that exploit the presence of such genomic DNA sequences that exhibit altered CpG methylation patterns.

BACKGROUND OF THE INVENTION

Methylation of DNA is widespread and plays a critical role in the regulation of gene expression in development, differentiation and diseases such as multiple sclerosis, diabetes, schizophrenia, aging, and cancers. Methylation in particular gene regions, for example in their promoters, can inhibit the expression of these genes. Recent work has shown that the gene silencing effect of methylated regions is accomplished through the interaction of methylcytosine binding proteins with other structural components of chromatin. which, in turn, makes the DNA inaccessible to transcription factors through histone deacetylation and chromatin structure changes. Differentially methylated CpG islands have long been thought to function as genomic imprinting control regions (ICRs).

Deregulation of imprinting has been implicated in several developmental disorders. Identification of the ICRs in a large number of human genes and their regulation patterns during development can shed light on genomic imprinting as well as other fundamental epigenetic control mechanisms. Moreover, rapid advances in genomics, both in terms of technology, for example, high-throughput low-cost capillary sequencers and microarray technologies, as well as in terms of availability of information, for example, information gained by virtue of whole genome sequencing, bioinformatics tools and databases, have paved the way for new opportunities in epigenetic studies. For example, it is known that random autosomal inactivation is one of the mechanisms that mammals use to achieve gene dosage control, in addition to random X-chromosome inactivation in females and genomic imprinting. However, genes belonging to this category are just now emerging, with only a few identified so far. Technologies are needed that can provide a systematic survey for identification of genes regulated by this kind of random monoallelic expression control, and determination of when and how such genes are regulated through a wide screening of samples from different tissues or different disease stages.

Changes in DNA methylation have been recognized as one of the most common molecular alternations in human neoplasia. Hypermethylation of CpG islands located in the promoter regions of tumor suppressor genes are now firmly established as the most frequent mechanisms for gene inactivation in cancers. In contrast, a global hypomethylation of genomic DNA and loss of IGF imprinting are observed in tumor cells; and a correlation between hypomethylation and increased gene expression has been reported for many oncogenes. In addition, monitoring global changes in methylation pattern has been applied to molecular classification of cancers. Most recently, gene hypermethylation has been associated with clinical risk groups in neuroblastoma and hormone receptor status and response to tamoxifen in breast cancer.

Lung cancer is the second most common cancer among both men and women and is the leading cause of cancer death in both sexes. There is no established early detection test for the disease, and only 15% of lung cancer cases are diagnosed when the disease is localized. The ability to accurately detect malignant cells in a wide range of clinical specimens including sputum, blood, or tissue would provide significant implications for screening high-risk individuals for this cancer.

A Human Epigenome Consortium was formed in 1999 with a mission to systematically map and catalogue the genomic positions of distinct methylation variants. It is likely that large-scale discovery of methylation patterns through de novo DNA sequencing of bisulfite-treated DNA is be carried out in the near future. This would provide a resource for methylation studies analogous to SNP databases for genetic studies, and would be expected to greatly increase the demand for high-throughput, cost-effective methods of carrying out site-specific methylation assays. A publicly accessible database, which carries information about methylation patterns in various biologically significant samples would be the first outcome of these efforts. There is a need for methods for analysis of large sample sets useful for discovering such associations.

Presently, the analysis of DNA methylation patterns in genomic DNA has been significantly hampered by the fact that methylation information is not retained during standard DNA amplification steps such as PCR or biological amplification by cloning in bacteria. Therefore, DNA methylation analysis methods generally rely on a methylation-dependent modification of the original genomic DNA before any amplification step. A battery of DNA methylation detection methods has been developed, including methylation-specific enzyme digestion (Singer-Sam, et al., Nucleic Acids Res. 18(3): 687 (1990), Taylor, et al., Leukemia 15(4): 583-9 (2001)), bisulfite DNA sequencing (Frommer, et al., Proc Natl Acad Sci USA. 89(5): 1827-31 (1992), Feil, et al., Nucleic Acids Res. 22(4): 695-6 (1994)), methylation-specific PCR (MSP) (Herman, et al., Proc Natl Acad Sci USA. 93(18): 9821-6 (1996)), methylation-sensitive single nucleotide primer extension (MS-SnuPE) (Gonzalgo, et al., Nucleic Acids Res. 25(12): 2529-31 (1997)), restriction landmark genomic scanning (RLGS) (Kawai, Mol Cell Biol. 14(11): 7421-7 (1994), Akama, et al., Cancer Res. 57(15): 3294-9 (1997)), and differential methylation hybridization (DMH) (Huang, et al., Hum Mol Genet. 8(3): 459-70 (1999)). However, a need exists to use the methylation pattern to classify and predict different types and stages of cancer, cancer therapeutic outcomes and patient survival through analysis of large sample sets required to discover such associations. This invention satisfies this need and provides related advantages as well.

SUMMARY OF THE INVENTION

The present invention provides a method for identification of differentially methylated genomic CpG dinucleotide sequences associated with cancer in an individual by obtaining a biological sample comprising genomic DNA from the individual measuring the level or pattern of one or more methylated genomic CpG dinucleotide sequences in two or more of the genomic targets in the sample, and comparing the level of said one or more methylated genomic CpG dinucleotide sequences in the sample to a reference level of methylated genomic CpG dinucleotide sequences, wherein a difference in the level or pattern of methylation of the genomic CpG dinucleotide sequences in the sample compared to the reference level identifies differentially methylated genomic CpG dinucleotide sequences associated with cancer.

The methods of the invention enable detection of differentially methylated genomic CpG dinucleotide sequences associated with lung cancer, for example, adenocarcenomas and sqamous cell carcinomas of the lung. In a particular embodiment, the present invention provides genomic targets that are differentially methylated in adenocarcinoma of the lung. In a further embodiment, the present invention provides genomic targets that are differentially methylated in sqamous cell carcinoma of the lung. Notably, the invention also discloses a novel cancer marker. As disclosed herein, the methods of the invention have numerous diagnostic and prognostic applications. The methods of the invention can be combined with a miniaturized array platform that allows for a high level of assay multiplexing and scalable automation for sample handling and data processing.

BRIEF DESCRIPTION OF THE DRAWINGS

FIG. 2 shows a photograph of a 96-array matrix. Each array is located on the end of an optical fiber bundle containing ~50,000 individual fibers. The spacing of the arrays matches that of a 96-well plate, allowing 96 separate samples to be processed simultaneously.

FIG. 10 shows methylation status of any particular locus determined using a clustering algorithm. Panel A shows raw intensity data (of each bead) for one locus across all 96 replicates. Panel B shows analyzed clusters. Unmethylated, methylated and semi-methylated loci can be distinguished and called correctly by this algorithm.

DETAILED DESCRIPTION OF THE INVENTION

This application file contains drawings executed in color. Copies of this patent or application publication with color drawings will be provided by the Office upon request and payment of the necessary fee.

The invention disclosed herein provides diagnostic and prognostic methods for a condition that is characterized by differential methylation of genomic CpG dinucleotide sequences. Also provided are populations of genomic targets and corresponding nucleic acid probes that useful for the detection of differentially methylated genomic CpG dinucleotide sequences that can be correlated to the presence of or susceptibility to cancer in an individual.

In particular, the present invention provides genomic targets that are differentially methylated in adenocarcinoma of the lung. The following 14 genomic targets are disclosed herein as differentially methylated in adenocarcinoma: ADCYAP1_2, CDH13_3, GDF10_2, GDF10_3, HOXA5_2, MAGEA1_3, RUNX3_1, SCGB3A1_3, SERPINB5_1, SFN_2, SFTPA1_2, TERT_1, TERT_2, and TNF_2. The 14 genomic targets correspond to eleven gene targets.

Figure 23A:
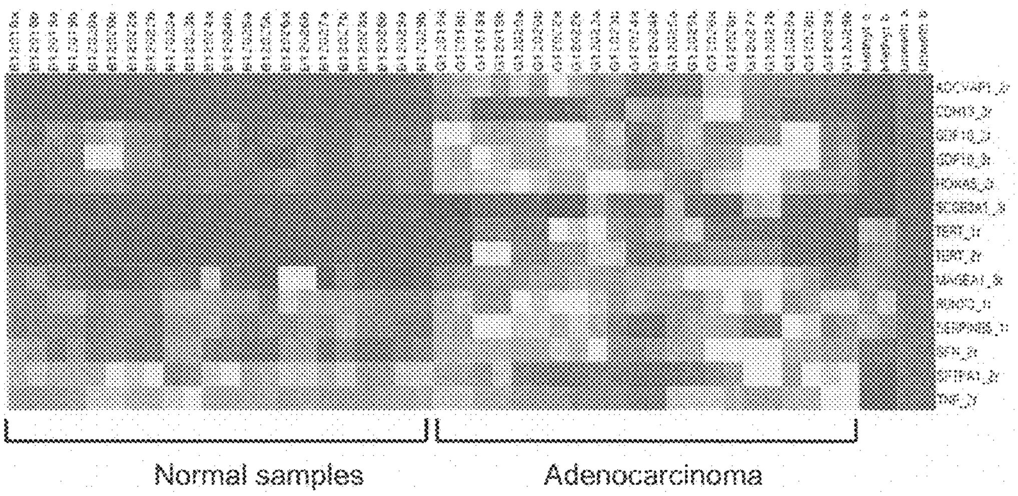
FIG. 23 shows methylation profiles of the lung adenocarcinoma markers and the squamous cell carcinoma markers in the training set of samples. Panel 23A shows 11 adenocarcinomas and 11 matching normal tissues. Panel 23B shows 14 squamous cell carcinomas and 10 matching normal tissues. Replicate measurements are shown in adjacent for each sample.
Figure 23B:
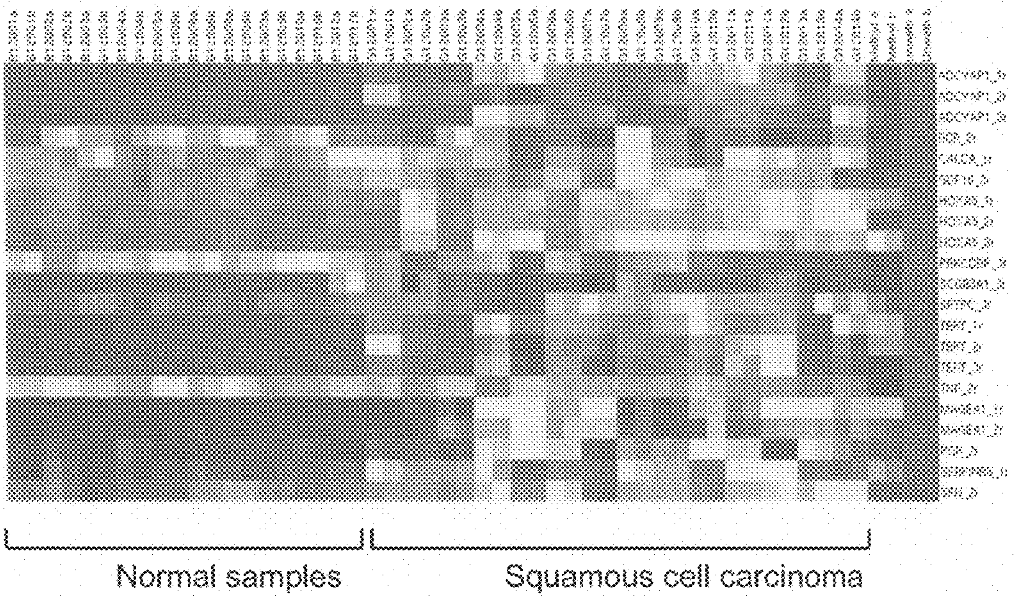

In a further embodiment, the present invention provides genomic targets that are differentially methylated in sqamous cell carcinoma of the lung. The following 21 genomic targets are disclosed herein as differentially methylated in squamous cell carcinoma: ADCYAP1_1, ADCYAP1_2, ADCYAP1_3, BCR_2, CALCA_1, GDF10_3, HOXA5_1, HOXA5_2, HOXA5_3, MAGEA1_1, MAGEA1_2, PGR_2, PRKCDBP_3, SCGB3A1_3, SERPINB5_1, SFN_2, SFTPC_3, TERT_1, TERT_2, TERT_3, TNF_2 (FIG. 23B). The 21 genomic targets correspond to 14 gene targets.

Notably, the invention also discloses a novel cancer marker. As described herein, the gene target adenylate cyclase activating polypeptide 1 (ADCYAP1) provided by the present invention and shown to be methylated in adenocarcinoma and squamous cell carcinoma represents a novel cancer marker based on methylation status. Genomic targets designated SEQ ID NOS: 264, 265 and 266 correspond to gene target adenylate cyclase activating polypeptide 1 (ADCYAP1) and are shown herein to be methylated in squamous cell carcinoma, while SEQ ID NO: 265 is shown to be methylated in adenocarcinoma (FIGS. 23A and B).

The methods of the invention are directed to methods for diagnosing an individual with a condition that is characterized by a level and/or pattern of methylated genomic CpG dinucleotide sequences distinct from the level and/or pattern of methylated genomic CpG dinucleotide sequences exhibited in the absence of the particular condition. This invention also is directed to methods for predicting the susceptibility of an individual to a condition that is characterized by a level and/or pattern of methylated genomic CpG dinucleotide sequences that is distinct from the level and/or pattern of methylated genomic CpG dinucleotide sequences exhibited in the absence of the condition.

In various distinct embodiments, the present invention is based, in part, on the identification of reliable CpG methylation markers for the improved prediction of susceptibility, diagnosis and staging of lung cancer. The invention provides a population of reliable genomic target sequences or genomic targets for use in the diagnostic and prognostic methods provided by the present invention, which have been designated herein as SEQ ID NOS: 57, 58, 59, 72, 76, 139, 140, 141, 174, 264, 265, 266, 293, 294, 305, 309, 313, 314, 315, 345, 350, 353, 360, 364, 371 and 373. The genomic targets provided by the invention are associated with the following gene targets: ADCYAP1, BCR, CALCA, CDH13, GDF 10, HOXA5, MAGEA1, PGR, PRKCDBP, RUNX3, SCGB3A1, SERPINB5, SFNT, SFTPA1, SFTPC, TERT and TNF (Table 1). The genomic targets provided by the invention thus represent gene targets for methylation of genomic CpG dinucleotide sequences associated with lung cancer. Also provided are nucleic acid probes that correspond to the genomic target sites of the invention and that can be used to detect differential methylation of selected genomic CpG dinucleotide sequences that serve as markers associated with lung cancer.

It is understood that the genomic target sequences provides the context for the one or more selected genomic CpG dinucleotide sequences being measured within a particular genomic target sequence. Furthermore, according to the invention, any fraction of the total genomic CpG dinucleotide sequences within a genomic target sequence can be measured, including one or more, two or more three or more, four or more, five or more or all of the genomic CpG dinucleotide sequences within a genomic target sequence. In addition, since it is understood that the genomic target sequence provides the context for the one or more selected genomic CpG dinucleotide sequences being measured, the invention encompasses measurement of the particular genomic CpG dinucleotide sequences encompassed within any of the genomic target sequences designated as SEQ ID NOS: 1-366, regardless of the particular nucleic probes that may be used for detecting the methylation of the particular genomic CpG dinucleotide sequence. Althought Table 1 sets forth particular nucleic acid probes provided by the invention that correspond to the genomic targets of SEQ ID NOS: 1-366, the skilled person can practice the invention using any desired nucleic acid probe capable of detecting the methylation status of one or more genomic CpG dinucleotide sequences within a particular genomic target sequence.

The genomic targets and nucleic acid probes provided by the present invention are set forth in Table 1, below, and provide diagnostic and prognostic tools based on their ability to detect differential methylation of selected genomic CpG dinucleotide sequences associated with cancer. In the methods provided by the invention, the genomic targets and nucleic acid probes capable of detecting markers located within the genomic targets can be employed to detect altered levels of methylation of genomic CpG dinucleotide sequences in a biological sample compared to a reference level. Furthermore, the methods of the invention allow for use of the genomic markersand nucleic acid probes for the determination of methylation patterns, which are represented by differential methylation of selected genomic CpG dinucleotide sequences that serve as markers in particular sets or subsets of genomic targets. In embodiments directed to the detection of methylation patterns, it is possible to diagnose or predict the susceptibility of an individual to a specific tumor-type based on the correlation between the pattern and the tumor type.

DNA methylation is a mechanism for changing the base sequence of DNA without altering its coding function. DNA methylation is a heritable, reversible and epigenetic change. Yet, DNA methylation has the potential to alter gene expression, which has profound developmental and genetic consequences. The methylation reaction involves flipping a target cytosine out of an intact double helix to allow the transfer of a methyl group from S adenosylmethionine in a cleft of the enzyme DNA (cytosine-5)-methyltransferase (Klimasauskas et al., *Cell* 76: 357-369, 1994) to form 5-methylcytosine (5-mCyt). This enzymatic conversion is the most common epigenetic modification of DNA known to exist in vertebrates and is essential for normal embryonic development (Bird, Cell 70: 5-8, 1992; Laird and Jaenisch, Human Mol. Genet. 3: 1487-1495, 1994; and Bestor and Jaenisch, Cell 69: 915-926, 1992). The presence of 5-mCyt at CpG dinucleotides has resulted in a 5-fold depletion of this sequence in the genome during vertebrate evolution, presumably due to spontaneous deamination of 5-mCyt to T (Schoreret et al., Proc. Natl. Acad. Sci. USA 89: 957-961, 1992). Those areas of the genome that do not show such suppression are referred to as “CpG islands” (Bird, Nature 321: 209-213, 1986; and Gardiner-Garden et al., J. Mol. Biol. 196: 261-282, 1987). These CpG island regions comprise about 1% of vertebrate genomes and also account for about 15% of the total number of CpG dinucleotides. CpG islands are typically between 0.2 to about 1 kb in length and are located upstream of many housekeeping and tissue-specific genes, but may also extend into gene coding regions. Therefore, the methylation of cytosine residues within CpG islands in somatic tissues can modulate gene expression throughout the genome (Cedar, *Cell* 53: 3-4, 1988; *Nature* 421: 686-688, 2003).

Methylation of cytosine residues contained within CpG islands of certain genes has been inversely correlated with gene activity. Thus, methylation of cytosine residues within CpG islands in somatic tissue is generally associated with decreased gene expression and can be the effect a variety of mechanisms including, for example, disruption of local chromatin structure, inhibition of transcription factor-DNA binding, or by recruitment of proteins which interact specifically with methylated sequences indirectly preventing transcription factor binding. Despite a generally inverse correlation between methylation of CpG islands and gene expression, however, most CpG islands on autosomal genes remain unmethylated in the germline and methylation of these islands is usually independent of gene expression. Tissue-specific genes are usually unmethylated at the receptive target organs but are methylated in the germline and in non-expressing adult tissues. CpG islands of constitutively-expressed housekeeping genes are normally unmethylated in the germline and in somatic tissues.

Abnormal methylation of CpG islands associated with tumor suppressor genes can cause decreased gene expression. Increased methylation of such regions can lead to progressive reduction of normal gene expression resulting in the selection of a population of cells having a selective growth advantage. Conversely, decreased methylation (hypomethylation) of oncogenes can lead to modulation of normal gene expression resulting in the selection of a population of cells having a selective growth advantage.

The present invention harnesses the potential of genomic methylation of CpG islands as indicators of the presence of a condition in an individual and provides a reliable diagnostic and/or prognostic method applicable to any condition associated with altered levels or patterns of genomic methylation of CpG islands. CpG islands are contiguous regions of genomic DNA that have an elevated frequency of CpG dinucleotides compared to the rest of the genome. CpG islands are typically, but not always, between about 0.2 to about 1 kb in length, and may be as large as about 3 Kb in length. Generally, for the methods provided by the invention at least two or more, at least three or more, at least four or more CpG dinucleotide sequences are selected that are located within a genomic marker so as to allow for determination of co-methylation status in the genomic DNA of a given tissue sample. Preferably the primary and secondary CpG dinucleotide sequences are co-methylated as part of a larger co-methylated pattern of differentially methylated CpG dinucleotide sequences in the genomic marker. The size of such context regions varies, but generally reflects the size of CpG islands as described above, or the size of a gene promoter region, including the first one or two exons.

With particular regard to cancer, changes in DNA methylation have been recognized as one of the most common molecular alternations in human neoplasia. Hypermethylation of CpG islands located in the promoter regions of tumor suppressor genes is a well-established and common mechanism for gene inactivation in cancer (Esteller, *Oncogene* 21(35): 5427-40 (2002)). In contrast, a global hypomethylation of genomic DNA is observed in tumor cells; and a correlation between hypomethylation and increased gene expression has been reported for many oncogenes (Feinberg, *Nature* 301(5895): 89-92 (1983), Hanada, et al., *Blood* 82(6): 1820-8 (1993)). Thus, a detailed study of methylation pattern in selected, staged tumor samples compared to matched normal tissues from the same patient offers a novel approach to identify unique molecular markers for cancer classification.

Monitoring global changes in methylation pattern has been applied to molecular classification in breast cancer (Huang, et al., *Hum Mol Genet.* 8(3): 459-70 (1999)). In addition, many studies have identified a few specific methylation patterns in tumor suppressor genes, for example, p16, a cyclin-dependent kinase inhibitor, in certain human cancer types (Otterson, et al., *Oncogene* 11(6): 1211-6 (1995), Herman, et al., *Cancer Res.* 55(20): 4525-30 (1995)). Some of the most recent examples include the discoveries of causal relationship between the loss of RUNX3 expression, due to hypermethylation, and gastric cancer (Li, et al., *Cell* 109(1): 113-24 (2002)); loss of IGF2 imprinting in colorectal cancer (Cui, et al., Science 299(5613): 1753-5 (2003); and reduced Hic gene expression in several types of human cancer (Chen, et al., Nat Genet. 33(2): 197-202 2003), Fujii, et al., Oncogene 16(16): 2159-64 (1998), Kanai, et al., Hepatology 29(3): 703-9 (1999)).

In one embodiment, the invention provides a method for identification of differentially methylated genomic CpG dinucleotide sequences associated with cancer in an individual by obtaining a biological sample comprising genomic DNA from the individual; measuring the level of one or more methylated genomic CpG dinucleotide sequences in two or more of the genomic target sequences set forth herein and designated as SEQ ID NOS: 1-366 in the sample, and comparing the level of the one or more methylated genomic CpG dinucleotide sequences in the sample to a reference level of methylated genomic CpG dinucleotide sequences, wherein a difference in the level of methylation of said one or more genomic CpG dinucleotide sequences in the sample compared to the reference level identifies differentially methylated genomic CpG dinucleotide sequences associated with cancer. In additional embodiments, the level of methylated genomic CpG dinucleotide sequences is measured for one or more, three or more, four or more, five or more, six ore more, seven or more, eight or more, nine or more, ten or more, eleven or more, twelwe or more, thirteen or more, fourteen or more, fifteen or more, twenty or more, twenty-five or more, thirty or more, fifty or more, of the genomic target sequences set forth herein and designated as SEQ ID NOS: 1-377 in the sample. A subset of the genomic target sequences or nucleic acid probes of the invention can be one ore more nucleic acid sequences.

In a further embodiment, the invention provides a method for identification of differentially methylated genomic CpG dinucleotide sequences associated with lung cancer in an individual by obtaining a biological sample comprising genomic DNA from the individual; measuring the level of one or more methylated genomic CpG dinucleotide sequences in two or more of the genomic target sequences set forth herein and designated as SEQ ID NOS: 57, 58, 59, 72, 76, 139, 140, 141, 174, 264, 265, 266, 293, 294, 305, 309, 313, 314, 315, 345, 350, 353, 360, 364, 371 and 373, in the sample, and comparing the level of the one or more methylated genomic CpG dinucleotide sequences in the sample to a reference level of methylated genomic CpG dinucleotide sequences, wherein a difference in the level of methylation of said genomic CpG dinucleotide sequences in the sample compared to the reference level identifies differentially methylated genomic CpG dinucleotide sequences associated with cancer. In additional embodiments, the level of one or more methylated genomic CpG dinucleotide sequences is measured for one or more, three or more, four or more, five or more, six ore more, seven or more, eight or more, nine or more, ten or more, eleven or more, twelwe or more, thirteen or more, fourteen or more, fifteen or more, twenty or more, twenty-two or more, twenty-four or more, of the markers set forth herein and designated as SEQ ID NOS: 57, 58, 59, 72, 76, 139, 140, 141, 174, 264, 265, 266, 293, 294, 305, 309, 313, 314, 315, 345, 350, 353, 360, 364, 371 and 373 in the sample. A subset of the genomic markers or nucleic acid probes of the invention can be one ore more nucleic acid sequences.

In one embodiment, the invention provides a method for identification of differentially methylated genomic CpG dinucleotide sequences associated with adenocarcinoma of the lung in an individual by obtaining a biological sample comprising genomic DNA from the individual; measuring the level of one or more methylated genomic CpG dinucleotide sequences for two or more of the markers set forth herein and designated as SEQ ID NOS: 59, 140, 266, 293, 294, 140, 174, 371, 313, 314, 353, 360, 364 and 373 in the sample, and comparing the level of one or more methylated genomic CpG dinucleotide sequences in the sample to a reference level of methylated genomic CpG dinucleotide sequences, wherein a difference in the level of methylation of said genomic CpG dinucleotide sequences in the sample compared to the reference level identifies differentially methylated genomic CpG dinucleotide sequences associated with cancer. In additional embodiments, the level of one or more methylated genomic CpG dinucleotide sequences is measured for one or more, three or more, four or more, five or more, six ore more, seven or more, eight or more, nine or more, ten or more, eleven or more, twelwe or more, thirteen or more, of the markers set forth herein and present in SEQ ID NOS: 59, 140, 266, 293, 294, 140, 174, 371, 313, 314, 353, 360, 364 and 373 in the sample. A subset of the genomic markers or nucleic acid probes of the invention can be one ore more nucleic acid sequences.

In one embodiment, the invention provides a method for identification of differentially methylated genomic CpG dinucleotide sequences associated with squamous cell carcinoma of the lung in an individual by obtaining a biological sample comprising genomic DNA from the individual; measuring the level of one or more methylated genomic CpG dinucleotide sequences for two or more of the markers set forth herein and designated as SEQ ID NOS: 57, 58, 72, 76, 139, 140, 141, 174, 264, 265, 266, 294, 305, 309, 313, 314, 315, 345, 350, 360 and 371, in the sample, and comparing the level of one or more methylated genomic CpG dinucleotide sequences in the sample to a reference level of methylated genomic CpG dinucleotide sequences, wherein a difference in the level of methylation of said genomic CpG dinucleotide sequences in the sample compared to the reference level identifies differentially methylated genomic CpG dinucleotide sequences associated with cancer. In additional embodiments, the level of one or more methylated genomic CpG dinucleotide sequences is measured for one or more, three or more, four or more, five or more, six ore more, seven or more, eight or more, nine or more, ten or more, eleven or more, twelwe or more, thirteen or more, fourteen or more, fifteen or more, twenty or more, of the markers set forth herein and designated as SEQ ID NOS: 57, 58, 72, 76, 139, 140, 141, 174, 264, 265, 266, 294, 305, 309, 313, 314, 315, 345, 350, 360 and 371, in the sample. A subset of the genomic markers or nucleic acid probes of the invention can be one ore more nucleic acid sequences.

The level of methylation of the differentially methylated genomic CpG dinucleotide sequences can provide a variety of information about the cancer and can be used, for example, to diagnose cancer in the individual; to predict the course of the cancer in the individual; to predict the susceptibility to cancer in the individual, to stage the progression of the cancer in the individual; to predict the likelihood of overall survival for the individual; to predict the likelihood of recurrence of cancer for the individual; to determine the effectiveness of a treatment course undergone by the individual.

As described herein, the level of methylation that is detected in a biological sample can be decreased or increased in comparison to the reference level and alterations that increase or decrease methylation can be detected and provide useful prognostic or diagnostic information. For example, hypermethylation of CpG islands located in the promoter regions of tumor suppressor genes have been established as common mechanisms for gene inactivation in cancers (Esteller, *Oncogene* 21(35): 5427-40 (2002)). Thus, a detailed study of methylation pattern in selected, staged tumor samples compared to matched normal tissues from the same patient can identify unique molecular markers for cancer classification.

In addition to detecting levels of methylation, the present invention also allows for the detection of patterns of methylation. It has been confirmed previously that neoplastic cells can exhibit unusual patterns of gene methylation (Feinberg and Vogelstein, *Nature* 301: 89-92 (1983)). Previous genetic studies of various conditions, for example, schizophrenia and bipolar disorder, seemed to implicate regions of particular chromosomes 22, but studies failed to identify a susceptibility gene. Analysis of methylation patterns across these chromosome in biological samples from afflicted individuals can reveal epigenetic changes in the form of altered levels of methylation of subsets of genomic CpG dinucleotide sequences that make up a pattern of affected genomic targets that can be correlated with a condition.

In one embodiment of the invention, an altered level of methylation of genomic CpG dinucleotide sequences is observed only in a subset of the genomic targets set forth in Table 1 and designated SEQ ID NOS: 1-377. In this embodiment, the subset can represent a methylation pattern characteristic of a particular type of cancer. A particular subset provided by the invention encompasses genomic targets that are differentially methylated in lung cancer and set forth herein and designated as SEQ ID NOS: 57, 58, 59, 72, 76, 139, 140, 141, 174, 264, 265, 266, 293, 294, 305, 309, 313, 314, 315, 345, 350, 353, 360, 364, 371 and 373. A further subset provided by the invention encompasses genomic targets that are differentially methylated in adenocarcinoma of the lung and set forth herein and designated as SEQ ID NOS: 59, 140, 266, 293, 294, 140, 174, 371, 313, 314, 353, 360, 364 and 373. An additional subset provided by the invention encompasses genomic targets that are differentially methylated in squamous cell carcinoma of the lung and set forth herein and designated as SEQ ID NOS: 57, 58, 72, 76, 139, 140, 141, 174, 264, 265, 266, 294, 305, 309, 313, 314, 315, 345, 350, 360 and 371. Therefore, as described herein with reference to cancer, methylation patterns can be correlated with a particular type, class or origin of a condition and detection and comparison of methylation patterns across samples that share a phenotypic characteristic can be useful to identify further methylation patterns.

In a further embodiment the present invention provides a population of genomic targets comprising nucleic acid sequences designated SEQ ID NOS: 1-377, and set forth in Table 1. Also provided in a distinct, but related embodiment is a population of genomic targets selected from the group consisting of nucleic acid sequences designated SEQ ID NOS: 1-377. In a further embodiment the invention provides a population of genomic targets comprising a subset of the nucleic acid sequences designated SEQ ID NOS: 1-366, and set forth in Table 1. Differential methylation of genomic CpG dinucleotide sequences in a subset of SEQ ID NOS: 1-366 can be characteristic of a particular type, class or origin of cancer. Detection of differential methylation in a subset of genomic targets can be useful to diagnose or predict susceptibility for a particular type, class or origin of cancer.

In one embodiment, a population of genomic targets selected from the group consisting of nucleic acid sequences designated SEQ ID NOS: 1-366 can encompass SEQ ID NOS: 57, 58, 59, 72, 76, 139, 140, 141, 174, 264, 265, 266, 293, 294, 305, 309, 313, 314, 315, 345, 350, 353, 360, 364, 371 and 373. In yet another embodiment, a population of genomic targets selected from the group consisting of nucleic acid sequences designated SEQ ID NOS: 1-377 can encompass SEQ ID NOS: 59, 140, 266, 293, 294, 140, 174, 371, 313, 314, 353, 360, 364 and 373. In a further embodiment, a population of genomic targets selected from the group consisting of nucleic acid sequences designated SEQ ID NOS: 1-377 can encompass SEQ ID NOS: 57, 58, 72, 76, 139, 140, 141, 174, 264, 265, 266, 294, 305, 309, 313, 314, 315, 345, 350, 360 and 371. In a further embodiment, a population of genomic targets selected from the group consisting of nucleic acid sequences designated SEQ ID NOS: 1-377 can encompass SEQ ID NOS: 57, 58, 59, 72, 76, 139, 141, 264, 265, 293, 309, 315, 345, 350, 353, 364 and 373. In a further embodiment, a population of genomic targets selected from the group consisting of nucleic acid sequences designated SEQ ID NOS: 1-377 can encompass SEQ ID NOS: 59, 293, 353, 364 and 373. The genomic targets are capable of exhibiting altered levels of methylation of genomic CpG dinucleotide sequences that are predictive of the presence or susceptibility of an individual for cancer.

Also provided by the present invention is a population of nucleic acid probes capable of detecting methylation of genomic CpG dinucleotide sequences of two or more genomic targets selected from the group consisting of the nucleic acid sequences designated SEQ ID NOS: 1-377, and set forth in Table 1. The population of nucleic acid probes provided by the invention consists of two or more nucleic acid sequences selected from the group consisting of SEQ ID NOS: 378-1889, and set forth in Table 1, which sets forth four probes for each genomic target of SEQ ID NOS: 1-377. The nucleic acid probes of the invention are capable of detecting altered levels of methylation of genomic CpG dinucleotide sequences of two or more genomic targets, wherein altered levels are predictive of the presence or susceptibility of an individual for cancer. Based on the observation that adjacent CpG sites tend to be co-methylated or co-de-methylated, a design scheme can be applied in which a “CG” sequence was used for all the CpG sites within the vicinity of the design, in particular for the landing sites for both ASO and LSO, to target any methylated CpG site; while a “TG” sequence was used for all the CpG sites within the vicinity of the design, to target any un-methylated CpG site. This approach requires two separate LSO oligos, but adds better discrimination between the methylated and unmethylated alleles.

In a further embodiment aimed at determination of patterns of DNA methylation, a population of nucleic acid probes is utilized that is capable of detecting altered levels of methylation of genomic CpG dinucleotide sequences of a subset of a population of two or more genomic targets. Thus, the detection of differential methylation of genomic CpG dinucleotide sequences in only a subset of genomic targets can be used to identify a pattern that correlates with a particular type, class or origin of cancer.

As disclosed herein, the present invention provides a subset of genomic targets consisting of nucleic acid sequences set forth in Table 1 and designated SEQ ID NOS: 57, 58, 72, 76, 139, 140, 141, 174, 264, 265, 266, 294, 305, 309, 313, 314, 315, 345, 350, 360 and 371 which exhibits differential methylation of genomic CpG dinucleotide sequences associated with lung squamous cell carcinoma. FIG. 23B shows the differential methylation pattern observed for genomic targets designated SEQ ID NOS: 57, 58, 72, 76, 139, 140, 141, 174, 264, 265, 266, 294, 305, 309, 313, 314, 315, 345, 350, 360 and 371, which correspond to gene targets MAGEA1 (SEQ ID NOS: 57 and 58), BCR (SEQ ID NO: 72), CALCA (SEQ ID NO: 76), HOXA5 (SEQ ID NO:S:139, 140, and 141), TNF (SEQ ID NO: 174), ADCYAP1 (SEQ ID NOS: 264, 265 and 266), GDF10 (SEQ ID NO: 294), SFN (SEQ ID NO: 305), SFTPC (SEQ ID NO: 309), TERT (SEQ ID NOS: 313, 314 and 315), PRKCDBP (SEQ ID NO: 345), PGR (SEQ ID NO: 350), SERPINB (SEQ ID NO: 360) and SCGB3A1 (SEQ ID NO: 371).

In a further embodiment, the present invention provides a subset of genomic targets consisting of nucleic acid sequences set forth in Table 1 and designated SEQ ID NOS: 59, 140, 265, 293, 294, 140, 174, 371, 313, 314, 353, 360, 364 and 373 which exhibits differential methylation of genomic CpG dinucleotide sequences associated with lung adenocarcinoma. FIG. 23A shows the differential methylation pattern observed for genomic targets designated SEQ ID NOS: 59, 140, 174, 265, 293, 294, 305, 313, 314, 353, 360, 364, 371, and 373, which correspond to gene targets MAGEA1 (SEQ ID NO: 59), HOXA5 (SEQ ID NO: 140), ADCYAP1 (SEQ ID NO: 265), GDF10 (SEQ ID NOS: 293 and 294), TNF (SEQ ID NO: 174), ADCYAP1 (SEQ ID NO: 265), GDF10 (SEQ ID NO: 293, 294), SFN (SEQ ID NO: 305), TERT (SEQ ID NO: 313, and 314), CDH13 (SEQ ID NO: 353), SERPINB (SEQ ID NO: 360) RUNX3 (SEQ ID NO: 364) and SFTPA1 (SEQ ID NO: 373).

As demonstrated in Example IV, the differentially methylated markers identified from squamous cell carcinomas largely overlap with those identified from adenocarcinomas. Methylation of the gene target adenylate cyclase activating polypeptide 1 (ADCYAP1) as shown in the present disclosure for adenocarcinoma and squamous cell carcinoma has not previously been reported. Genomic targets designated SEQ ID NOS: 264, 265 and 266 correspond to gene target adenylate cyclase activating polypeptide 1 (ADCYAP1) and are shown herein to be methylated in squamous cell carcinoma, while SEQ ID NO: 265 is shown to be hypermethylated in adenocarcinoma and squamous cell carcinoma (FIGS. 23A and B). Gene targets ADCYAP1, CDH13, GDF10, HOXA5, SCGB3A1 and TERT had increased methylation levels in adenocarcinoma samples compared to normal (FIGS. 23A & 26), while MAGEA1, RUNX3, SERPINB5, SFN, SFTPA1 and TNF were less methylated in cancer (FIG. 23A). Methylation of CDH13, HoxA5, SCGB3A1 and GDF10 is associated with tumor progression in various types of cancer as described by Hibi et al., *Br J Cancer* 91: 1139-1142 (2004); Hibi et al., *Br J Cancer* 90, 1030-3 (2004); Ogama et al. *Int J Oncol* 25, 685-91 (2004); Chen et al., *Am J Pathol* 163, 37-45 (2003); Fackler et al., *Int J Cancer* 107, 970-5 (2003); Aldred et al., *Cancer Res* 63, 2864-71 (2003). The human telomerase reverse transcriptase gene (TERT) is shown to be inactivated in most differentiated cells, but is reactivated in the majority of cancer cells (Liuet al., *Genes Chromosomes Cancer* 41, 26-37 (2004)).

Also provided are target nucleic acid probes for detection of a subset of genomic targets consisting of nucleic acid sequences designated SEQ ID NOS: 57, 58, 72, 76, 139, 140, 141, 174, 264, 265, 266, 294, 305, 309, 313, 314, 315, 345, 350, 360, and 371, which exhibits differential methylation of genomic CpG dinucleotide sequences associated with squamous cell carcinoma (FIG. 23 B). In the presence of differentially methylated genomic CpG dinucleotide sequences, the subsets of genomic targets signify a pattern distinctive of a particular type of cancer, for example, adenocarcinoma or sqamous cell carcinoma of the lung tissue. The p value can be calculated for each individual marker. More than one CpG dinucleotide sequence that serves as genomic marker can be selected from the same gene if desired. Thus a gene can provide the context for more than one genomic CpG dinucleotide sequence such that methylation is determined for more than one CpG dinucleotide sequence within a single gene.

The p-value can be calculated based on a t-test of the level of methylation [i.e. methylation allele intensity/(methylation allele intensity+un-methylation allele intensity)] as is shown among 9 lung squamous cell carcinoma and 5 matching normal samples or 14 other normal samples in Table 2 and among 16 lung adenocarcinoma and 11 normal samples in Table 3.

As demonstrated in Example IV, a data matrix of β values can be used to identify CpG loci which show differential methylation in cancer. A p-value cutoff can be chosen by the skilled person to minimize the number of false positives and additional filters can be incorporated to select markers which have the largest difference between cancer and normal tissues. As shown in FIG. 23A for adenocarcinoma, a list of 14 differentially methylated markers was obtained: ADCYAP1_2, CDH13_3, GDF10_2, GDF10_3, HOXA5_2, MAGEA1_3, RUNX3_1, SCGB3A1_3, SERPINB5_1, SFN_2, SFTPA1_2, TERT_1, TERT_2, and TNF_2. Utilizing the same methylation analysis with the normal and squamous cell carcinoma samples, a list 21 differentially methylated markers was obtained: ADCYAP1_1, ADCYAP1_2, ADCYAP1_3, BCR_2, CALCA_1, GDF10_3, HOXA5_1, HOXA5_2, HOXA5_3, MAGEA1_1, MAGEA1_2, PGR_2, PRKCDBP_3, SCGB3A1_3, SERPINB5_1, SFN_2, SFTPC_3, TERT_1, TERT_2, TERT_3, TNF_2 (FIG. 23B).

The invention also provides subsets of target nucleic acid probes capable of detecting a pattern of methylation of genomic CpG dinucleotide sequences that is associated with a particular type of cancer. Thus, the invention provides a subset of genomic targets consisting of nucleic acid sequences designated SEQ ID NOS: 59, 140, 266, 293, 294, 140, 174, 371, 313, 314, 353, 360, 364 and 373, which exhibits differential methylation of genomic CpG dinucleotide sequences associated with adenocarcinoma (FIG. 23A). The population of nucleic acid probes capable of detecting altered levels of methylation of genomic CpG dinucleotide sequences of a subset of said two or more genomic targets associated with adenocarcinoma are set forth in Table 1 and designated as SEQ ID NOS: 59, 140, 266, 293, 294, 140, 174, 371, 313, 314, 353, 360, 364 and 373.

In a further embodiment, the invention provides a subset of genomic targets consisting of nucleic acid sequences set forth in FIG. 23B and designated SEQ ID NOS: 57, 58, 72, 76, 139, 140, 141, 174, 264, 265, 266, 294, 305, 309, 313, 314, 315, 345, 350, 360 and 371, which exhibits differential methylation of genomic CpG dinucleotide sequences associated with sqamous cell carcinoma. The population of nucleic acid probes capable of detecting altered levels of methylation of genomic CpG dinucleotide sequences of a subset of said two or more genomic targets associated with sqamous cell carcinoma are set forth in Table 1 and designated as SEQ ID NOS: 57, 58, 72, 76, 139, 140, 141, 174, 264, 265, 266, 294, 305, 309, 313, 314, 315, 345, 350, 360 and 371.

In one embodiment, this invention provides diagnostic markers for cancer. The markers of the invention are genomic sequences having methylation states that are diagnostic or prognostic of the presence or severity of cancer. A list of exemplary genes for which methylation state can be used to determine the presence or severity of cancer is provided in Table 1. Cancer diagnosis or prognosis in a method of the invention can be made in a method of the invention based on the methylation state of particular sequence regions of the gene including, but not limited to, the coding sequence, the 5'-regulatory regions, or other regulatory regions that influence transcription efficiency.

The prognostic methods of the invention are useful for determining if a patient is at risk for recurrence. Cancer recurrence is a concern relating to a variety of types of cancer. For example, of patients undergoing complete surgical removal of colon cancer, 25-40% of patients with stage II colon carcinoma and about 50% of patients with stage III colon carcinoma experience cancer recurrence. One explanation for cancer recurrence is that patients with relatively early stage disease, for example, stage II or stage III, already have small amounts of cancer spread outside the affected organ that were not removed by surgery. These cancer cells, referred to as micrometastases, cannot typically be detected with currently available tests.

The prognostic methods of the invention can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The prognostic methods of the invention also are useful for determining a proper course of treatment for a patient having cancer. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated. As described herein, the diagnosis or prognosis of cancer state is typically correlated with the degree to which one or more of the genes in Table I is methylated. Thus, the invention can include a determination made based on the methylation state for the entire set of genes in Table I or a subset of the genes.

Furthermore, as the list in Table I is exemplary, the methylation state of other genes or genomic sequences can also be used in a method of the invention to determine the presence or severity of cancer. Exemplary cancers that can be evaluated using a method of the invention include, but are not limited to hematoporetic neoplasms, Adult T-cell leukemia/lymphoma, Lymphoid Neoplasms, Anaplastic large cell lymphoma, Myeloid Neoplasms, Histiocytoses, Hodgkin Diseases (HD), Precursor B lymphoblastic leukemia/lymphoma (ALL), Acute myclogenous leukemia (AML), Precursor T lymphoblastic leukemia/lymphoma (ALL), Myclodysplastic syndromes, Chronic Mycloproliferative disorders, Chronic lymphocytic leukemia/small lymphocytic lymphoma (SLL), Chronic Myclogenous Leukemia (CML), Lymphoplasmacytic lymphoma, Polycythemia Vera, Mantle cell lymphoma, Essential Thrombocytosis, Follicular lymphoma, Myelofibrosis with Myeloid Metaplasia, Marginal zone lymphoma, Hairy cell leukemia, Hemangioma, Plasmacytoma/plasma cell myeloma, Lymphangioma, Glomangioma, Diffuse large B-cell lymphoma, Kaposi Sarcoma, Hemanioendothelioma, Burkitt lymphoma, Angiosarcoma, T-cell chronic lymphocytic leukemia, Hemangiopericytoma, Large granular lymphocytic leukemia, head & neck cancers, Basal Cell Carcinoma, Mycosis fungoids and sezary syndrome, Squamous Cell Carcinoma, Ceruminoma, Peripheral T-cell lymphoma, Osteoma, Nonchromaffin Paraganglioma, Angioimmunoblastic T-cell lymphoma, Acoustic Neurinoma, Adenoid Cystic Carcinoma, Angiocentric lymphoma, Mucoepidermoid Carcinoma, NK/T-cell lymphoma, Malignant Mixed Tumors, Intestinal T-cell lymphoma, Adenocarcinoma, Malignant Mesothelioma, Fibrosarcoma, Sarcomotoid Type lung cacer, Osteosarcoma, Epithelial Type lung cancer, Chondrosarcoma, Melanoma, cancer of the gastrointestinal tract, olfactory Neuroblastoma, Squamous Cell Carcinoma, Isolated Plasmocytoma, Adenocarcinoma, Inverted Papillomas, Carcinoid, Undifferentiated Carcinoma, Malignant Melanoma, Mucoepidermoid Carcinoma, Adenocarcinoma, Acinic Cell Carcinoma, Gastric Carcinoma, Malignant Mixed Tumor, Gastric Lymphoma, Gastric Stromal Cell Tumors, Amenoblastoma, Lymphoma, Odontoma, Intestinal Stromal Cell tumors, thymus cancers, Malignant Thymoma, Carcinids, Type I (Invasive thymoma), Malignant Mesethelioma, Type II (Thymic carcinoma), Non-mucin producing adenocarcinoma, Squamous cell carcinoma, Lymph epithelioma, cancers of the liver and biliary tract, Squamous Cell Carcinoma, Hepatocellular Carcinoma, Adenocarcinoma, Cholangiocarcinoma, Hepatoblastoma, papillary cancer, Angiosarcoma, solid Bronchioalveolar cancer, Fibrolameller Carcinoma, Small Cell Carcinoma, Carcinoma of the Gallbladder, Intermediate Cell carcinaoma, Large Cell Carcinoma, Squamous Cell Carcinoma, Undifferentiated cancer, cancer of the pancreas, cancer of the female genital tract, Squamous Cell Carcinoma, Cystadenocarcinoma, Basal Cell Carcinoma, Insulinoma, Melanoma, Gastrinoma, Fibrosarcoma, Glucagonamoa, Intaepithelial Carcinoma, Adenocarcinoma Embryonal, cancer of the kidney, Rhabdomysarcoma, Renal Cell Carcinoma, Large Cell Carcinoma, Nephroblastoma (Wilm's tumor), Neuroendocrine or Oat Cell carcinoma, cancer of the lower urinary tract, Adenosquamous Carcinoma, Urothelial Tumors, Undifferentiated Carcinoma, Squamous Cell Carcinoma, Carcinoma of the female genital tract, Mixed Carcinoma, Adenoacanthoma, Sarcoma, Small Cell Carcinoma, Carcinosarcoma, Leiomyosarcoma, Endometrial Stromal Sarcoma, cancer of the male genital tract, Serous Cystadenocarcinoma, Mucinous Cystadenocarcinoma, Sarcinoma, Endometrioid Tumors, Speretocytic Sarcinoma, Embyonal Carcinoma, Celioblastoma, Choriocarcinoma, Teratoma, Clear Cell Carcinoma, Leydig Cell Tumor, Unclassified Carcinoma, Sertoli Cell Tumor, Granulosa-Theca Cell Tumor, Sertoli-Leydig Cell Tumor, Disgerminoma, Undifferentiated Prostatic Carcinoma, Teratoma, Ductal Transitional carcinoma, breast cancer, Phyllodes Tumor, cancer of the bones joints and soft tissue, Paget's Disease, Multiple Myeloma, Insitu Carcinoma, Malignant Lymphoma, Invasive Carcinoma, Chondrosacrcoma, Mesenchymal Chondrosarcoma, cancer of the endocrine system, Osteosarcoma, Adenoma, Ewing Tumor, endocrine Carcinoma, Malignant Giant Cell Tumor, Meningnoma, Adamantinoma, Cramiopharlingioma, Malignant Fibrous Histiocytoma, Papillary Carcinoma, Histiocytoma, Follicular Carcinoma, Desmoplastic Fibroma, Medullary Carcinoma, Fibrosarcoma, Anoplastic Carcinoma, Chordoma, Adenoma, Hemangioendothelioma, Memangispericytoma, Pheochromocytoma, Liposarcoma, Neuroblastoma, Paraganglioma, Histiocytoma, Pineal cancer, Rhabdomysarcoms, Pineoblastoma, Leiomyosarcoma, Pineocytoma, Angiosarcoma, skin cancer, cancer of the nervous system, Melanoma, Schwannoma, Squamous cell carcinoma, Neurofibroma, Basal cell carcinoma, Malignant Periferal Nerve Sheath Tumor, Merkel cell carcinoma, Sheath Tumor, Extramamary Paget's Disease, Astrocytoma, Paget's Disease of the nipple, Fibrillary Astrocytoma, Glioblastoma Multiforme, Brain Stem Glioma, Cutaneous T-cell lymphoma, Pilocytic Astrocytoma, Xanthorstrocytoma, Histiocytosis, Oligodendroglioma, Ependymoma, Gangliocytoma, Cerebral Neuroblastoma, Central Neurocytoma, Dysembryoplastic Neuroepithelial Tumor, Medulloblastoma, Malignant Meningioma, Primary Brain Lymphoma, Primary Brain Germ Cell Tumor, cancers of the eye, Squamous Cell Carcinoma, Mucoepidermoid Carcinoma, Melanoma, Retinoblastoma, Glioma, Meningioma, cancer of the heart, Myxoma, Fibroma, Lipoma, Papillary Fibroelastoma, Rhasdoyoma, or Angiosarcoma among others.

This invention provides methods for determining a prognosis for survival for a cancer patient. One method involves (a) measuring a level of methylation for one or more of the genes listed in Table 1 in a neoplastic cell-containing sample from the cancer patient, and (b) comparing the level of methylation in the sample to a reference level of methylation for the gene, wherein a low level of methylation for the gene in the sample correlates with increased survival of the patient.

In a particular embodiment, the invention provides methods for determining a prognosis for survival for a lung cancer patient. In this embodiment, the method involves (a) measuring a level of methylation for one or more of the genes listed in Table 1 and described herein to be associated with genomic targets differentially methylated in lung cancer in a neoplastic cell-containing sample from the lung cancer patient, and (b) comparing the level of methylation in the sample to a reference level of methylation for the one or more genes, wherein a low level of methylation for the one or more genes in the sample correlates with increased survival of the patient. In this embodiment, the level of methylation can be measured for one or more gene targets, including, for example, ADCYAP1, BCR, CALCA, CDH13, GDF10, HOXA5, MAGEA1, PGR, PRKCDBP, RUNX3, SCGB3A1, SERPINB5, SFN, SFTPA1, SFTPC, TERT, and TNF. Genomic markers associated with each of these genes are described throughout this application and are set forth in Table 1 along with their corresponding proble sequences.

Another method involves (a) measuring a level of methylation for one or more of the genes listed in Table 1 in a neoplastic cell-containing sample from the cancer patient, and (b) classifying the patient as belonging to either a first or second group of patients, wherein the first group of patients having low levels of methylation for a gene is classified as having an increased likelihood of survival compared to the second group of patients having high level of methylation for a gene.

In a particular embodiment, the invention provides methods for determining a prognosis for survival for a lung cancer patient. In this embodiment, the method involves (a) measuring a level of methylation for one or more of the genes listed in Table 1 and described herein to be associated with genomic targets differentially methylated in lung cancer in a neoplastic cell-containing sample from the cancer patient, and (b) classifying the patient as belonging to either a first or second group of patients, wherein the first group of patients having low levels of methylation for a gene is classified as having an increased likelihood of survival compared to the second group of patients having high level of methylation for a gene. In this embodiment, the level of methylation can be measured for one or more gene targets, including, for example, ADCYAP1, BCR, CDH13, CALCA, GDF10, HOXA5, PRKCDBP, SCGB3A1 SFTPC, TERT. Genomic markers associated with each of these genes are described throughout this application and are set forth in Table 1 along with corresponding probe sequences.

Another method involves (a) measuring a level of methylation for one or more of the genes listed in Table 1 in a neoplastic cell-containing sample from the cancer patient, and (b) classifying the patient as belonging to either a first or second group of patients, wherein the first group of patients having high levels of methylation for a gene is classified as having an increased likelihood of survival compared to the second group of patients having low level of methylation for a gene.

In a particular embodiment, the invention provides methods for determining a prognosis for survival for a lung cancer patient. In this embodiment, the method involves (a) measuring a level of methylation for one or more of the genes listed in Table 1 and described herein to be associated with genomic targets differentially methylated in lung cancer in a neoplastic cell-containing sample from the cancer patient, and (b) classifying the patient as belonging to either a first or second group of patients, wherein the first group of patients having high levels of methylation for a gene is classified as having an increased likelihood of survival compared to the second group of patients having low level of methylation for a gene. In this embodiment, the level of methylation can be measured for one or more gene targets, including, for example, MAGEA1, PGR, RUNX3, SERPINB5, SFN, SFTPA1, and TNF. Genomic markers associated with each of these genes are described throughout this application and are set forth in Table 1 along with their corresponding proble sequences.

The invention also provides a method for monitoring the effectiveness of a course of treatment for a patient with cancer. The method involves (a) determining a level of one or more of the genes listed in Table 1 in a neoplastic cell containing sample from the cancer patient prior to treatment, and (b) determining the level of methylation for the gene in a neoplastic cell-containing sample from the patient after treatment, whereby comparison of the level of methylation for the gene prior to treatment with the level of methylation for the gene after treatment indicates the effectiveness of the treatment.

In a particular embodiment, the invention also provides a method for monitoring the effectiveness of a course of treatment for a patient with lung cancer. The method involves (a) determining a level of one or more of the genes listed in Table 1 and described herein to be associated with genomic targets differentially methylated in lung cancer in a neoplastic cell containing sample from the lung cancer patient prior to treatment, and (b) determining the level of methylation for the gene in a neoplastic cell-containing sample from the patient after treatment, whereby comparison of the level of methylation for the gene prior to treatment with the level of methylation for the gene after treatment indicates the effectiveness of the treatment. In this embodiment, the level of methylation can be measured for one or more gene targets, including, for example, ADCYAP1, BCR, CALCA, CDH13, GDF10, HOXA5, MAGEA1, PGR, PRKCDBP, RUNX3, SCGB3A1, SERPINB5, SFN, SFTPA1, SFTPC, TERT, and TNF. Genomic markers associated with each of these genes are described throughout this application and are set forth in Table 1 along with their corresponding proble sequences.

For adenocarcinoma, the level of methylation is elevated compared to normal tissue samples for genomic targets corresponding to gene targets, including, for example, ADCYAP1, CDH13, GDF10, HOXA5, SCGB3A1, SERPINB5, SFN, SFTPA1, TERT; and decreased compared to normal tissue samples for genomic targets corresponding to gene targets, including, for example, MAGEA1, RUNX3, SERPINB5, SFN, SFTPA1, and TNF (Table 23 A). For squamous cell carcima, the level of methylation is elevated compared to normal tissue samples for genomic targets corresponding to gene targets, including, for example, ADCYAP1, BCR, CALCA, GDF10, HOXA5, PRKCDBP, SCGB3A1, SFTPC, and TERT; and decreased compared to normal tissue samples for genomic targets corresponding to gene targets, including, for example, TNF, MAGEA1, PGR, SERPINB5 and SFN (Table 23 B). Based on discovery of these differential methylation states associated with lung cancer, the skilled person can design various application of the present invention by selecting whether to measure for elevated or decreased methylation within one or more gene targets.

As used herein, the term "reference level" refers to a control level of expression of a marker used to evaluate a test level of expression of a biomarker in a neoplastic cell-containing sample of a patient. For example, when the level of methylation of one or more genes, referred to herein as "genomic targets," in the neoplastic cells of a patient are higher than the reference level of methylation for the genes, the cells are considered to have a low level of expression of the gene. Conversely, when the level of methylation of one or more genes in the neoplastic cells of a patient are lower than the reference level, the cells are considered to have a low level of expression, of the gene. It is also possible that the level of methylation of one or more genes in the neoplastic cells of a patient can be higher than the reference level and the cells are considered to have a high level of expression, of the gene. Furthermore, the level of methylation of one or more genes in the neoplastic cells of a patient can be lower than the reference level and the cells are considered to have a low level of expression, of the gene.

A reference level can be determined based on reference samples collected from age-matched normal classes of adjacent tissues, and with normal peripheral blood lymphocytes. The reference level can be determined by any of a variety of methods, provided that the resulting reference level accurately provides a level of a marker above which exists a first group of patients having a different probability of survival than that of a second group of patients having levels of the biomarker below the reference level. The reference level can be determined by, for example, measuring the level of expression of a biomarker in non-tumorous cells from the same tissue as the tissue of the neoplastic cells to be tested. The reference level can also be a level of a biomarker of in vitro cultured cells which can be manipulated to simulate tumor cells, or can be manipulated in any other manner which yields expression levels which accurately determine the reference level. The reference level can also be determined by comparison of the level of a biomarker, such as methylation of one or more genes, in populations of patients having the same cancer. This can be accomplished, for example, by histogram analysis, in which an entire cohort of patients are graphically presented, wherein a first axis represents the level of the biomarker, and a second axis represents the number of patients in the cohort whose neoplastic cells express the biomarker at a given level.

Two or more separate groups of patients can be determined by identification of subset populations of the cohort which have the same or similar levels of the biomarker. Determination of the reference level can then be made based on a level which best distinguishes these separate groups. A reference level also can represent the levels of two or more markers. Two or more markers can be represented, for example, by a ratio of values for levels of each biomarker. The reference level can be a single number, equally applicable to every patient, or the reference level can vary, according to specific subpopulations of patients. For example, older individuals might have a different reference level than younger individuals for the same cancer. In another example, the reference level might be a certain ratio of a biomarker in the neoplastic cells of a patient relative to the biomarker levels in non-tumor cells within the same patient. Thus the reference level for each patient can be proscribed by a reference ratio of one or more-genomic markers, such as methylation of one or more genes, wherein the reference ratio can be determined by any of the methods for determining the reference levels described herein.

It is understood that the reference level has to correspond to the level of one or more methylated genomic CpG dinucleotide sequences present in a corresponding sample that allows comparison to the desired phenotype. For example, in a diagnostic application a reference level can be based on a sample that is derived from a cancer-free origin so as to allow comparison to the biological test sample for purposes of diagnosis. In a method of staging a cancer it can be useful to apply in parallel a series of reference levels, each based on a sample that is derived from a cancer that has been classified based on parameters established in the art, for example, phenotypic or cytological characteristics, as representing a particular cancer stage so as to allow comparison to the biological test sample for purposes of staging. In addition, progression of the course of a condition can be determined by determining the rate of change in the level or pattern of methylation of genomic CpG dinucleotide sequences by comparison to reference levels derived from reference samples that represent time points within an established progression rate. It is understood, that the user will be able to select the reference sample and establish the reference level based on the particular purpose of the comparison.

As used herein, the term "neoplastic cell" refers to any cell that is transformed such that it proliferates without normal homeostatic growth control. Such cells can result in a benign or malignant lesion of proliferating cells. Such a lesion can be located in a variety of tissues and organs of the body. Exemplary types of cancers from which a neoplastic cell can be derived are set forth above.

As used herein, the term "cancer" is intended to mean a class of diseases characterized by the uncontrolled growth of aberrant cells, including all known cancers, and neoplastic conditions, whether characterized as malignant, benign, soft tissue or solid tumor. Specific cancers include digestive and gastrointestinal cancers, such as anal cancer, bile duct cancer, gastrointestinal carcinoid tumor, colon cancer, esophageal cancer, gallbladder cancer, liver cancer, pancreatic cancer, rectal cancer, appendix cancer, small intestine cancer and stomach (gastric) cancer; breast cancer; ovarian cancer; lung cancer; renal cancer; CNS 30 cancer; leukemia and melanoma. By exemplification, a list of known cancers is set forth above.

As used herein, the term "sample" is intended to mean any biological fluid, cell, tissue, organ or portion thereof, that contains genomic DNA suitable for methylation detection via the invention methods. A test sample can include or be suspected to include a neoplastic cell, such as a cell from the colon, rectum, breast, ovary, prostate, kidney, lung, blood, brain or other organ or tissue that contains or is suspected to contain a neoplastic cell. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. A reference sample can be used to establish a reference level and, accordingly, can be derived from the source tissue that meets having the particular phenotypic characteristics to which the test sample is to be compared.

A sample may be obtained in a variety of ways known in the art. Samples may be obtained according to standard techniques from all types of biological sources that are usual sources of genomic DNA including, but not limited to cells or cellular components which contain DNA, cell lines, biopsies, bodily fluids such as blood, sputum, stool, urine, cerebrospinal fluid, ejaculate, tissue embedded in paraffin such as tissue from eyes, intestine, kidney, brain, heart, prostate, lung, breast or liver, histological object slides, and all possible combinations thereof. A suitable biological sample can be sourced and acquired subsequent to the formulation of the diagnostic aim of the marker. A sample can be derived from a population of cells or from a tissue that is predicted to be afflicted with or phenotypic of the condition. The genomic DNA can be derived from a high-quality source such that the sample contains only the tissue type of interest, minimum contamination and minimum DNA fragmentation. In particular, samples should be representative of the tissue or cell type of interest that is to be handled by the diagnostic assay. It is understood that samples can be analyzed individually or pooled depending on the purpose of the user. In addition, a population or set of samples from an individual source can be analyzed to maximize confidence in the results and can be a sample set size of 10, 15, 20, 25, 50, 75, 100, 150 or sample set sizes in the hundreds.

In subsequent steps of the method, the methylation levels of CpG positions are compared to a reference sample, to identify differentially methylated CpG positions. Each class may be further segregated into sets according to predefined parameters to minimize the variables between the at least two classes. In the following stages of the method, all comparisons of the methylation status of the classes of tissue, are carried out between the phenotypically matched sets of each class. Examples of such variables include, age, ethnic origin, sex, life style, patient history, drug response etc.

As used herein, the term “disease-free survival” refers to the lack of tumor recurrence and/or spread and the fate of a patient after diagnosis, for example, a patient who is alive without tumor recurrence.

The phrase “overall survival” refers to the fate of the patient after diagnosis, regardless of whether the patient has a recurrence of the tumor. As used herein, the term “risk of recurrence” refers to the probability of tumor recurrence or spread in a patient subsequent to diagnosis of cancer, wherein the probability is determined according to the process of the invention. Tumor recurrence refers to further growth of neoplastic or cancerous cells after diagnosis of cancer. Particularly, recurrence can occur when further cancerous cell growth occurs in the cancerous tissue. Tumor spread refers to dissemination of cancer cells into local or distant tissues and organs, for example during tumor metastasis. Tumor recurrence, in particular, metastasis, is a significant cause of mortality among patients who have undergone surgical treatment for cancer. Therefore, tumor recurrence or spread is correlated with disease free and overall patient survival.

The methods of the invention can be applied to the characterization, classification, differentiation, grading, staging, diagnosis, or prognosis of a condition characterized by a pattern of one or more methylated genomic CpG dinucleotide sequences that is distinct from the pattern of one or more methylated genomic CpG dinucleotide sequences exhibited in the absence of the condition. A condition that is suitable for practicing the methods of the invention can be, for example, cell proliferative disorder or predisposition to cell proliferative disorder; metabolic malfunction or disorder; immune malfunction, damage or disorder; CNS malfunction, damage or disease; symptoms of aggression or behavioural disturbance; clinical, psychological and social consequences of brain damage; psychotic disturbance and personality disorder; dementia or associated syndrome; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headache or sexual malfunction, and combinations thereof.

Methylation of CpG dinucleotide sequences can be measured using any of a variety of techniques used in the art for the analysis of specific CpG dinucleotide methylation status. For example, methylation can be measured by employing a restriction enzyme based technology, which utilizes methylation sensitive restriction endonucleases for the differentiation between methylated and unmethylated cytosines. Restriction enzyme based technologies include, for example, restriction digest with methylation-sensitive restriction enzymes followed by Southern blot analysis, use of methylation-specific enzymes and PCR, restriction landmark genomic scanning (RLGS) and differential methylation hybridization (DMH).

Restriction enzymes characteristically hydrolyze DNA at and/or upon recognition of specific sequences or recognition motifs that are typically between 4- to 8-bases in length. Among such enzymes, methylation sensitive restriction enzymes are distinguished by the fact that they either cleave, or fail to cleave DNA according to the cytosine methylation state present in the recognition motif, in particular, of the CpG sequences. In methods employing such methylation sensitive restriction enzymes, the digested DNA fragments can be separated, for example, by gel electrophoresis, on the basis of size, and the methylation status of the sequence is thereby deduced, based on the presence or absence of particular fragments. Preferably, a post-digest PCR amplification step is added wherein a set of two oligonucleotide primers, one on each side of the methylation sensitive restriction site, is used to amplify the digested genomic DNA. PCR products are not detectable where digestion of the subtended methylation sensitive restriction enzyme site occurs. Techniques for restriction enzyme based analysis of genomic methylation are well known in the art and include the following: differential methylation hybridization (DMH) (Huang et al., Human Mol. Genet. 8, 459-70, 1999); Not I-based differential methylation hybridization (see e.g., WO 02/086163 A1); restriction landmark genomic scanning (RLGS) (Plass et al., *Genomics* 58: 254-62, 1999); methylation sensitive arbitrarily primed PCR (AP-PCR) (Gonzalgo et al., *Cancer Res.* 57: 594-599, 1997); methylated CpG island amplification (MCA) (Toyota et. al., *Cancer Res.* 59: 2307-2312, 1999). Other useful methods for detecting genomic methylation are described, for example, in U.S. Pat. App. pub. No. 2003/0170684 or WO 04/05122.

Methylation of CpG dinucleotide sequences also can be measured by employing cytosine conversion based technologies, which rely on methylation status-dependent chemical modification of CpG sequences within isolated genomic DNA, or fragments thereof, followed by DNA sequence analysis. Chemical reagents that are able to distinguish between methylated and non methylated CpG dinucleotide sequences include hydrazine, which cleaves the nucleic acid, and bisulfite treatment. Bisulfite treatment followed by alkaline hydrolysis specifically converts non-methylated cytosine to uracil, leaving 5-methylcytosine unmodified as described by Olek A., *Nucleic Acids Res.* 24: 5064-6, 1996 or Frommer et al., *Proc. Natl. Acad. Sci. USA* 89: 1827-1831 (1992). The bisulfite-treated DNA can subsequently be analyzed by conventional molecular techniques, such as PCR amplification, sequencing, and detection comprising oligonucleotide hybridization.

Techniques for the analysis of bisulfite treated DNA can employ methylation-sensitive primers for the analysis of CpG methylation status with isolated genomic DNA as described by Herman et al., *Proc. Natl. Acad. Sci. USA* 93: 9821-9826, 1996, and in U.S. Pat. Nos. 5,786,146 and 6,265,171. Methylation sensitive PCR (MSP) allows for the detection of a specific methylated CpG position within, for example, the regulatory region of a gene. The DNA of interest is treated such that methylated and non-methylated cytosines are differentially modified, for example, by bisulfite treatment, in a manner discernable by their hybridization behavior. PCR primers specific to each of the methylated and non-methylated states of the DNA are used in a PCR amplification. Products of the amplification reaction are then detected, allowing for the deduction of the methylation status of the CpG position within the genomic DNA. Other methods for the analysis of bisulfite treated DNA include methylation-sensitive single nucleotide primer extension (Ms-SNuPE) (Gonzalgo & Jones, Nucleic Acids Res. 25: 2529-2531, 1997; and see U.S. Pat. No. 6,251,594), and the use of real time PCR based methods, such as the art-recognized fluorescence-based real-time PCR technique MethyLight.™ (Eads et al., Cancer Res. 59: 2302-2306, 1999; U.S. Pat. No. 6,331,393 to Laird et al.; and see Heid et al., Genome Res. 6: 986-994, 1996). It is understood that a variety of methylation assay methods can be used for the determination of the methylation status of particular genomic CpG positions. Methods which require bisulfite conversion include, for example, bisulfite sequencing, methylation-specific PCR, methylation-sensitive single nucleotide primer extension (Ms-SnuPE), MALDI mass spectrometry and methylation-specific oligonucleotide arrays and are described, for example, in U.S. patent application Ser. No. 10/309,803 and international application International Patent Application No.: PCT/US03/38582.

In one embodiment, methylation of genomic CpG positions in a sample can be detected using an array of probes. In particular embodiments, a plurality of different probe molecules can be attached to a substrate or otherwise spatially distinguished in an array. Exemplary arrays that can be used in the invention include, without limitation, slide arrays, silicon wafer arrays, liquid arrays, bead-based arrays and others known in the art or set forth in further detail below. In preferred embodiments, the methods of the invention can be practiced with array technology that combines a miniaturized array platform, a high level of assay multiplexing, and scalable automation for sample handling and data processing.

An array of arrays, also referred to as a composite array, having a plurality of individual arrays that is configured to allow processing of multiple samples can be used. Exemplary composite arrays that can be used in the invention are described in U.S. Pat. No. 6,429,027 and U.S. 2002/0102578 and include, for example, one component systems in which each array is located in a well of a multi-well plate or two component systems in which a first component has several separate arrays configured to be dipped simultaneously into the wells of a second component. A substrate of a composite array can include a plurality of individual array locations, each having a plurality of probes and each physically separated from other assay locations on the same substrate such that a fluid contacting one array location is prevented from contacting another array location. Each array location can have a plurality of different probe molecules that are directly attached to the substrate or that are attached to the substrate via rigid particles in wells (also referred to herein as beads in wells).

In a particular embodiment, an array substrate can be fiber optical bundle or array of bundles, such as those generally described in U.S. Pat. Nos. 6,023,540, 6,200,737 and 6,327,410; and PCT publications WO9840726, WO9918434 and WO9850782. An optical fiber bundle or array of bundles can have probes attached directly to the fibers or via beads. Other substrates having probes attached to a substrate via beads are described, for example, in U.S. 2002/0102578. A substrate, such as a fiber or silicon chip, can be modified to form discrete sites or wells such that only a single bead is associated with the site or well. For example, when the substrate is a fiber optic bundle, wells can be made in a terminal or distal end of individual fibers by etching, with respect to the cladding, such that small wells or depressions are formed at one end of the fibers. Beads can be non-covalently associated in wells of a substrate or, if desired, wells can be chemically functionalized for covalent binding of beads. Other discrete sites can also be used for attachment of particles including, for example, patterns of adhesive or covalent linkers. Thus, an array substrate can have an array of particles each attached to a patterned surface.

In a particular embodiment, a surface of a substrate can include physical alterations to attach probes or produce array locations. For example, the surface of a substrate can be modified to contain chemically modified sites that are useful for attaching, either-covalently or non-covalently, probe molecules or particles having attached probe molecules. Chemically modified sites can include, but are not limited to the linkers and reactive groups set forth above. Alternatively, polymeric probes can be attached by sequential addition of monomeric units to synthesize the polymeric probes in situ. Probes can be attached using any of a variety of methods known in the art including, but not limited to, an ink-jet printing method as described, for example, in U.S. Pat. Nos. 5,981,733; 6,001,309; 6,221,653; 6,232,072 or 6,458,583; a spotting technique such as one described in U.S. Pat. No. 6,110,426; a photolithographic synthesis method such as one described in U.S. Pat. Nos. 6,379,895 or 5,856,101; or printing method utilizing a mask as described in U.S. Pat. No. 6,667,394. Accordingly, arrays described in the aforementioned references can be used in a method of the invention.

The size of an array used in the invention can vary depending on the probe composition and desired use of the array. Arrays containing from about 2 different probes to many millions can be made. Generally, an array can have from two to as many as a billion or more probes per square centimeter. Very high density arrays are useful in the invention including, for example, those having from about 10,000,000 probes/$cm^2$ to about 2,000,000,000 probes/$cm^2$ or from about 100,000,000 probes/$cm^2$ to about 1,000,000,000 probes/$cm^2$. High density arrays can also be used including, for example, those in the range from about 100,000 probes/$cm^2$ to about 10,000,000 probes/$cm^2$ or about 1,000,000 probes/$cm^2$ to about 5,000,000 probes/$cm^2$. Moderate density arrays useful in the invention can range from about 10,000 probes/$cm^2$ to about 100,000 probes/$cm^2$, or from about 20,000 probes/$cm^2$ to about 50,000 probes/$cm^2$. Low density arrays are generally less than 10,000 probes/$cm^2$ with from about 1,000 probes/$cm^2$ to about 5,000 probes/$cm^2$ being useful in particular embodiments. Very low density arrays having less than 1,000 probes/$cm^2$, from about 10 probes/$cm^2$ to about 1000 probes/$cm^2$, or from about 100 probes/$cm^2$ to about 500 probes/$cm^2$ are also useful in some applications.

Thus, the invention provides a robust and ultra high-throughput technology for simultaneously measuring methylation at many specific sites in a genome. The invention further provides cost-effective methylation profiling of thousands of samples in a reproducible, well-controlled system. In particular the invention allows implementation of a process, including sample preparation, bisulfite treatment, genotyping-based assay and PCR amplification that can be carried out on a robotic platform.

The methods of the invention can be carried out at a level of multiplexing that is 96-plex or even higher including, for example, as high as 1,500-plex. An advantage of the invention is that the amount of genomic DNA used for detection of methylated sequences is low including, for example, less that 1 ng of genomic DNA per locus. In one embodiment, the throughput of the methods can be 96 samples per run, with 1,000 to 1,500 methylation assays per sample (144,000 data points or more per run). In the embodiment exemplified herein, the system is capable of carrying out as many as 10 runs per day or more. A further object of the invention is to provide assays to survey methylation status the 5'-regulatory regions of at least 1,000 human genes per sample. Particular genes of interest are tumor suppressor genes or other cancer-related genes, as well as genes identified through RNA profiling.

Therefore, the invention makes available diagnostic and/or prognostic assays for the analysis of the methylation status of CpG dinucleotide sequence positions as markers for disease or disease-related conditions. As exemplified herein for lung cancer, the invention provides a systematic method for the identification, assessment and validation of genomic targets as well as a systematic means for the identification and verification of multiple condition relevant CpG positions to be used alone, or in combination with other CpG positions, for example, as a panel or array of markers, that form the basis of a clinically relevant diagnostic or prognostic assay. The inventive method enables differentiation between two or more phenotypically distinct classes of biological matter and allows for the comparative analysis of the methylation patterns of CpG dinucleotides within each of the classes.

A further object of the invention is to provide assays for specific identifying methylation patterns in different cancer types and cancer stages. The invention provides assays for specific methylation patterns characteristic of different cancer types and cancer stages. For example, the invention provides genomic targets that give rise to differential methylation patterns characteristic of lung cancer in general, adenocarcinoma of the lung, squamous cell carcinoma of the lung as well as methylation patterns that can distinguish between adenocarcinoma and squamous cell carcinoma of the lung. As described herein, the genomic targets designated SEQ ID NOS: 57, 58, 59, 72, 76, 139, 140, 141, 174, 264, 265, 266, 293, 294, 305, 309, 313, 314, 315, 345, 350, 353, 360, 364, 371 and 373 show differential methylation patterns characteristic of lung cancer. The subset of genomic targets designated SEQ ID NOS: 59, 140, 266, 293, 294, 140, 174, 371, 313, 314, 353, 360, 364 and 373 shows differential methylation patterns characteristic of adenocarcinoma of the lung, while the genomic targets designated SEQ ID NOS: 57, 58, 72, 76, 139, 140, 141, 174, 264, 265, 266, 294, 305, 309, 313, 314, 315, 345, 350, 360 and 371 show differential methylation patterns characteristic of squamous cell carcinoma of the lung. The genomic targets designated SEQ ID NOS: 59, 293, 353, 364 and 373 show differential methylation patterns in adenocarcinoma of the lung, but not in sqamous cell carcinoma of the lung and can thus be used to distinguish between the two types of lung cancer. The genomic targets designated SEQ ID NOS: 57, 58, 59, 72, 76, 139, 141, 264, 265, 293, 309, 315, 345, 350, 353, 364 and 373 show differential methylation patterns in sqamous cell carcinoma of the lung, but not in adenocarcinoma of the lung and can also be used to distinguish between the two types of lung cancer.

A further object of the invention is to provide software to retrieve and annotate CpG island sequence information, design and analyze primers, track sample information, and analyze and report results obtained from methylation profiling methods of the invention. An advantage of the invention is that it provides a high throughput methylation analysis system that can be commercialized, both through a service business—in which customers can provide samples and a gene list (CpG site list) for analysis in the methods—and through products that can used in standard laboratory conditions.

RLGS profiling of the methylation pattern of 1184 CpG islands in 98 primary human tumors revealed that the total number of methylated sites is variable between and in some cases within different tumor types, suggesting there may be methylation subtypes within tumors having similar histology (Costello, et al., Nat Genet. 24(2): 132-8 (2000)). Aberrant methylation of some of these genes correlates with loss of gene expression. Based on these observations, it should be feasible to use the methylation pattern of a sizable group of tumor suppressor genes or other cancer-related genes to classify and predict different kinds of cancer, or the same type of cancer in different stages. It promises to provide a useful tool for cancer diagnosis, or preferably, for detection of premalignant changes. When combined with the development of sensitive, non-invasive methods (e.g. a blood test; indeed, circulating tumor nucleic acids in blood have been demonstrated to reflect the biologic characteristics of tumors (Cui, et al., *Science* 299 (5613): 1753-5 (2003)), to detect such methylation signatures) this may provide a viable method to screen subjects at risk for cancer as well as to monitor cancer progression and response to treatment.

Because methylation detection interrogates genomic DNA, but not RNA or protein, it offers several technological advantages in a clinical diagnostic setting: (1) readily available source materials. This is particularly important for prognostic research, when only DNA can be reliably extracted from archived paraffin-embedded samples for study; (2) capability for multiplexing, allowing simultaneous measurement of multiple targets to improve assay specificity; (3) easy amplification of assay products to achieve high sensitivity; (4) robust measurement in tumors that arise from methylation inactivation of one allele of tumor suppressor genes—a process called "functional haploinsufficiency" (Balmain, et al., Nat Genet. 33 Suppl: 238-44 (2003)). It is much easier to detect a methylation change (from negative to positive) than to detect a two-fold gene expression change in these tumors. In summary, when combined with RNA-based gene expression profiling and/or protein-based immunoassays, DNA methylation profiling should provide a sensitive, accurate and robust tool for cancer diagnosis and prognosis (Wong, et al., Curr Oncol Rep. 4(6): 471-7 (2002)).

The present invention is directed to a method for the identification of differentially methylated CpG dinucleotides within genomic DNA that are particularly informative with respect to disease states. These may be used either alone or as components of a gene panel in diagnostic and/or prognostic assays.

In particular embodiments, the invention is directed to methods of prediction and diagnosis of conditions characterized by a pattern of one or more methylated genomic CpG dinucleotide sequences that is distinct from the pattern of methylated genomic CpG dinucleotide sequences exhibited in the absence of the particular condition, for example, cell proliferative disorders, such as cancer; dysfunctions, damages or diseases of the central nervous system (CNS), including aggressive symptoms or behavioral disorders; clinical, psychological and social consequences of brain injuries; psychotic disorders and disorders of the personality, dementia and/or associates syndromes; cardiovascular diseases, malfunctions or damages; diseases, malfunctions or damages of the gastrointestine diseases; malfunctions or damages of the respiratory system; injury, inflammation, infection, immunity and/or reconvalescence, diseases; malfunctions or damages as consequences of modifications in the developmental process; diseases, malfunctions or damages of the skin, muscles, connective tissue or bones; endocrine or metabolic diseases malfunctions or damages; headache; and sexual malfunctions; or combinations thereof.

It is understood that modifications which do not substantially affect the activity of the various embodiments of this invention are also included within the definition of the invention provided herein. Accordingly, the following examples are intended to illustrate but not limit the present invention.

EXAMPLE I

Design of Target Nucleic Acid Probes

This Example shows design of target nucleic acid probes for detection of genomic loci.

Figure 4:
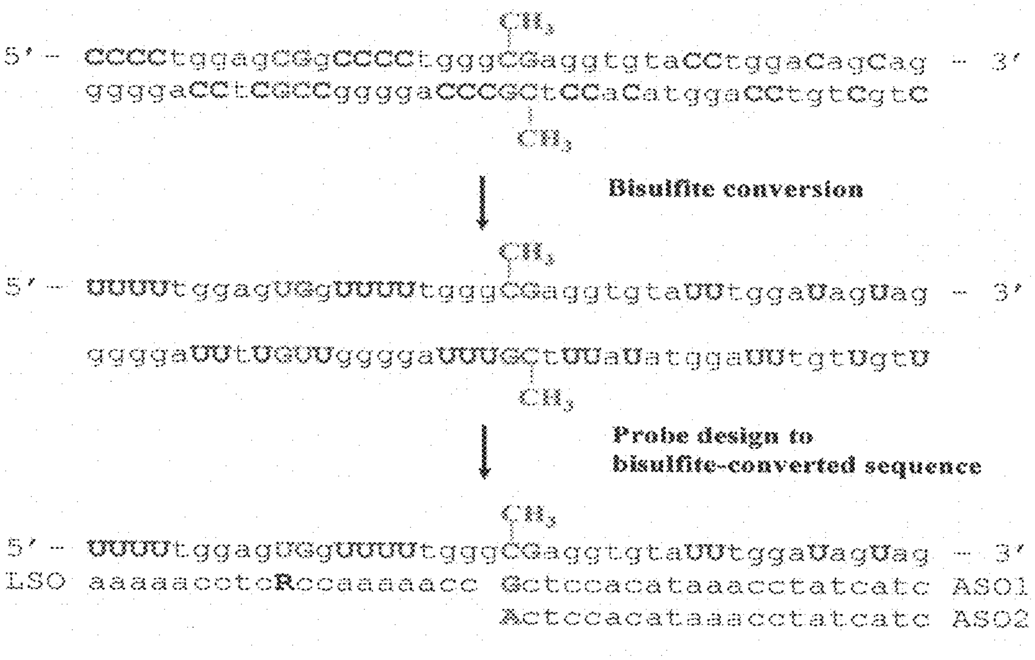
FIG. 4 shows an oligonucleotide design scheme.

First, a human gene promoter database was prepared that includes all CpG regions of potential interest for methylation profiling. A fully automated SNP genotyping assay design program was adapted for methylation application and CpG islands of interest are selected and "converted by bisulfite" computationally. For each CpG locus, three probes are designed: two allele-specific oligonucleotides, one corresponding to the methylated, and the other to the unmethylated state of the CpG site and one locus-specific oligo (FIG. 4). If other CpG loci are present in the close vicinity of the chosen CpG site, a wobble base [A or G] is used for the corresponding probe position. Assays for more than 60 CpG sites from 20 different genes were designed, mostly selected from the methylation database on the world-wide-web at methdb.de. Approximately half of the sites were used in the assay development.

EXAMPLE II

Development of Internal Controls and Confirmation of Completeness of Bisulfite Conversion This example shows the development of internal controls that allow optimization of protocols, determination of assay specificity, troubleshooting, and evaluation of overall assay performance.

Plasmids pUC19, pACYC184 and phage phiX174 were selected to serve as control DNAs. These DNAs can be spiked into the genomic DNA assays to provide internal controls, and would not interfere with human genomic DNA reactions. It is easy to prepare completely unmethylated plasmid DNAs and then methylate them in vitro using Sss I (CpG) methylase to produce substrates with known methylation status. Plasmids can be methylated virtually to completion. The quality of in vitro methylation was tested by restriction enzyme digestion of unmethylated and methylated DNAs using the methylation sensitive enzyme Hpa II and its isoschisomer Msp I, which is not sensitive to methylation. It was not possible to detect any bands resulting from restriction digest on the agarose gel after incubation of methylated pUC19, pACYC184 and phiX174 with Hpa II for two hours at 37° C., while the unmethylated DNAs were completely digested. Both methylated and unmethylated DNAs were completely digested by Msp I.

Figure 5:
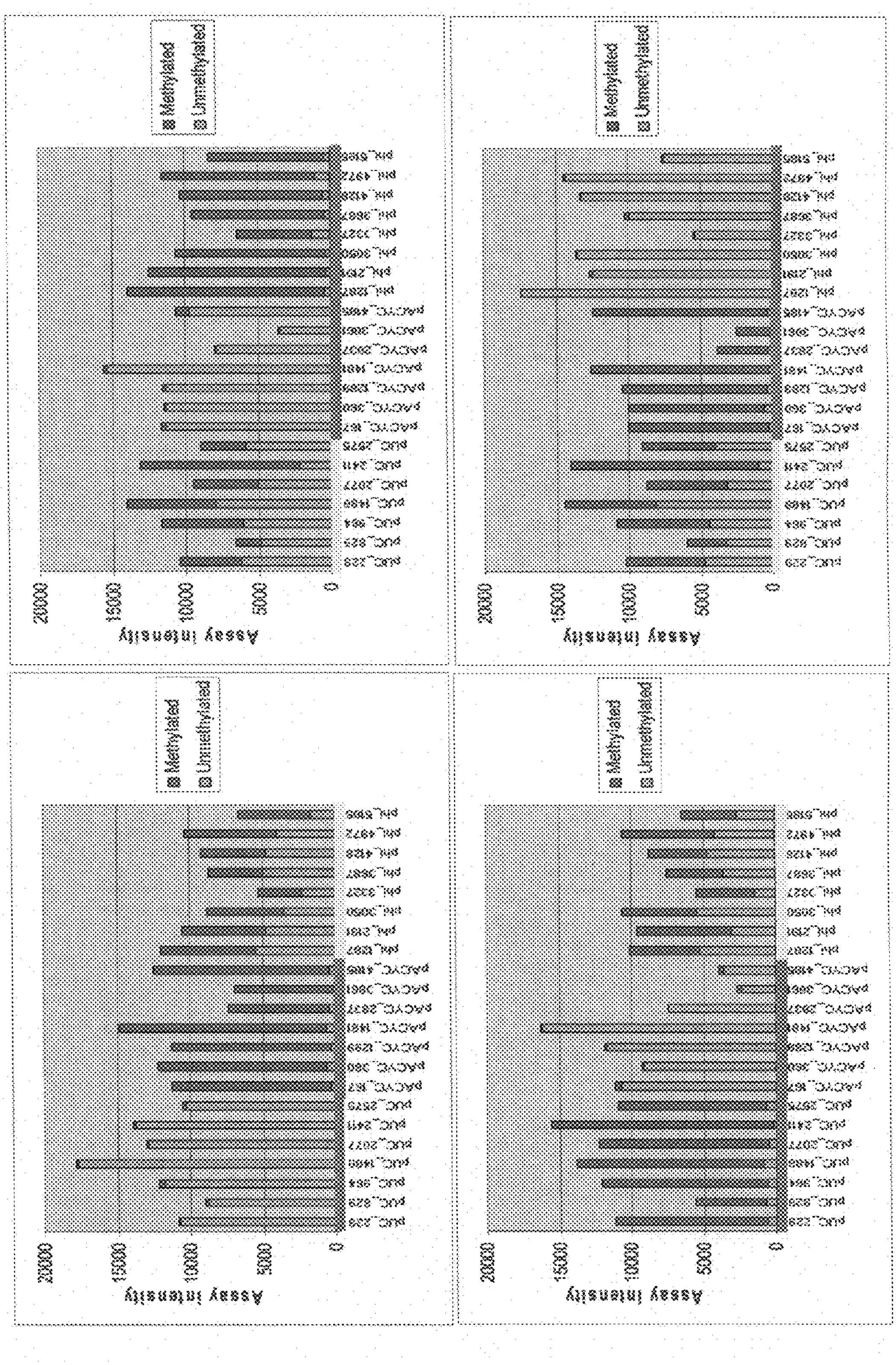
FIG. 5 shows plasmid controls used in the assay development. Unmethylated (green), semi-methylated (yellow) and fully-methylated (red) plasmid loci can be correctly scored in the human genomic DNA background.

Plasmid controls (unmethylated, methylated or mixed at a 1:1 ratio) were spiked into human genomic DNA at a 1:1 molar ratio (at approximately 2-4 pg plasmid DNA/1 μg gDNA, depending on the plasmid size), and were used in every methylation experiment to monitor both bisulfite conversion efficiency and accuracy of methylation detection. As shown in FIG. 5, unmethylated, semi-methylated and fully-methylated loci can be easily distinguished by the assay.

Figure 6:
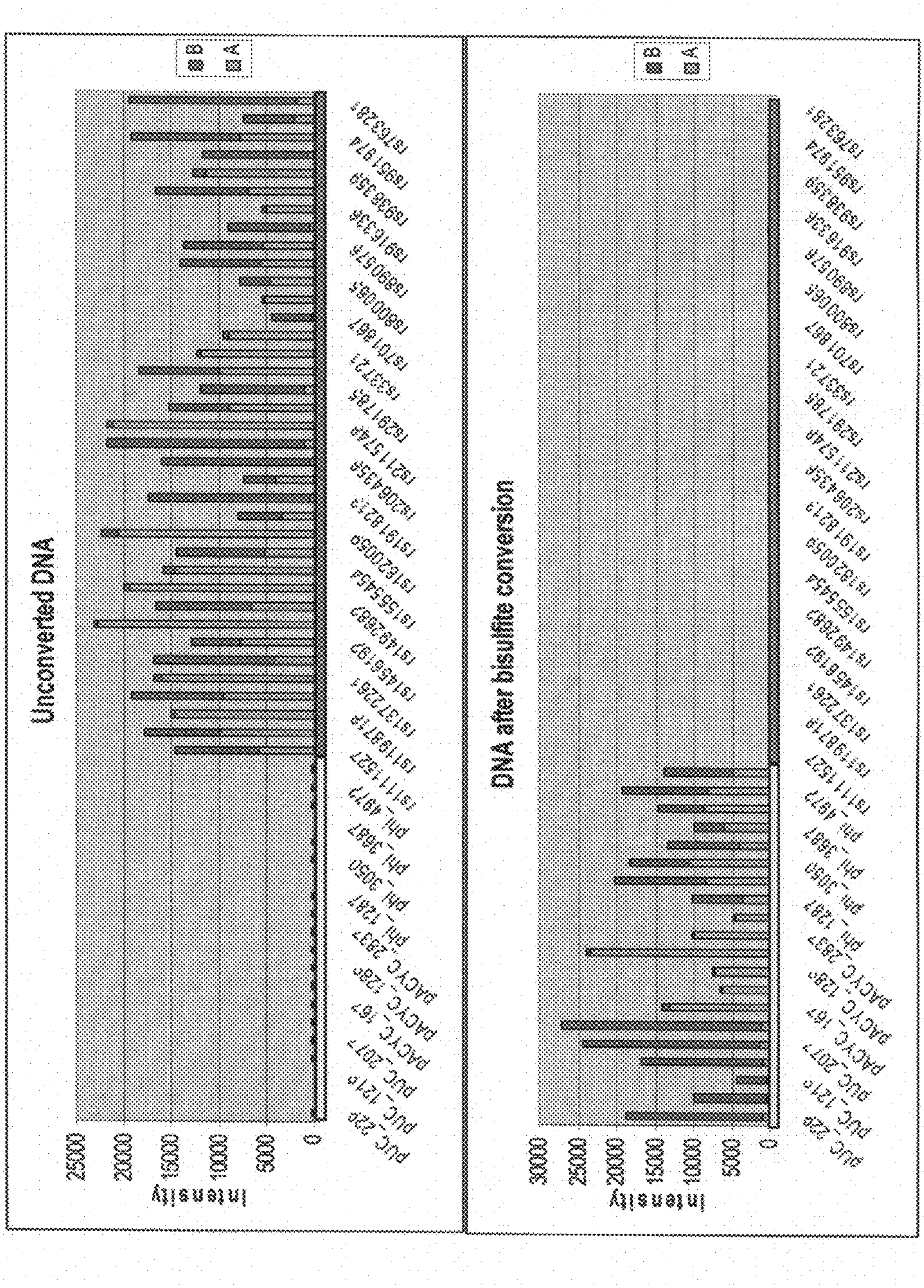
FIG. 6 shows bisulfite conversion of DNA monitored with internal controls. Top panel: unconverted DNA; bottom panel: DNA after bisulfite conversion. Query oligonucleotides for converted plasmid loci (yellow) and unconverted genomic loci (green) are present in both assays. After bisulfite conversion, signal corresponding to unconverted loci disappears, and signal from converted loci becomes detectable.

The utility of bisulfite conversion of DNA for methylation detection is based on the different sensitivity of cytosine and 5-methylcytosine to deamination by bisulfite. Under acidic conditions, cytosine undergoes conversion to uracil, while methylated cytosine remains unreactive. An efficient bisulfite conversion protocol is a necessary prerequisite for a high-throughput methylation profiling assay. Incomplete conversion of cytosine to uracil by bisulfite can result in appearance of false-positive signals for 5-methylcytosine, and reduce the overall quality of the assay data. In order to monitor the effectiveness of bisulfite treatment, a set of oligonucleotides (a standard set of SNP genotyping probes) designed for unconverted genomic DNA sequences was included with the plasmid control oligos in the assay. As shown in FIG. 6, if bisulfite conversion is successful, the signal from oligonucleotides targeted to the unconverted DNA (the SNP set) will disappear, and signals from oligonucleotides targeted to the converted DNA will be present. Incomplete conversion will result in low and inconsistent signals across all targeted loci.

Data Processing

Figure 7:
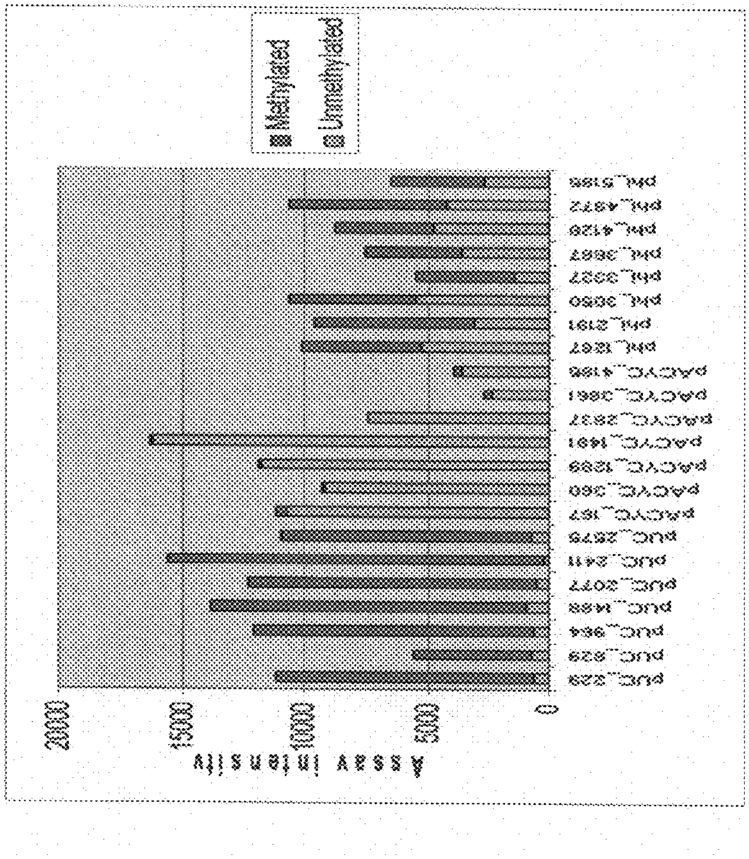
FIG. 7 shows methylation assay development and data processing. Left panel: unmethylated, semi-methylated, and fully-methylated loci on the plasmids can be distinguished in the human genomic DNA background. These plasmid DNAs were spiked into human genomic DNA at a 1:1 molar ratio. Right panel: each data point is represented in a red/green/yellow plot, where red indicates a methylated state, green—unmethylated, and yellow—semi-methylated. The whole left panel (bar graph) is represented by one column on a red/green/yellow plot.
Figure 7:
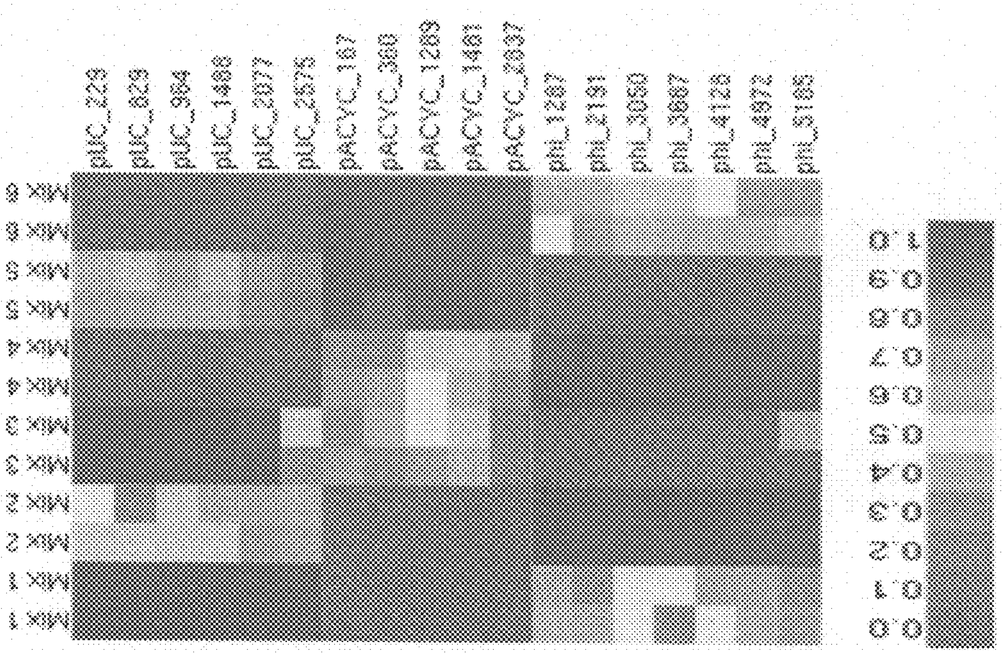

Development of a robust and high-throughput method for simultaneous measurement of methylation at many specific sites in many samples requires a highly efficient analysis and data export process. Each data point in the methylation assay can be represented as a ratio of the fluorescent signals from M (methylated) and U (unmethylated) specific PCR products after array hybridization. This value indicates the methylation status of the CpG locus and may range from 0 in the case of completely unmethylated sites to 1 in completely methylated sites. The value also can be visually presented as a red/green/yellow plot (FIG. 7). In addition, each locus is characterized by a locus intensity value, which allows filtering of failed loci. This combination of numerical and color outputs allows for quick comparison of genes and samples of interest, and processing of thousands of loci across hundreds of samples.

Reference Samples for Genome-wide Methylation Profiling

Figure 8:
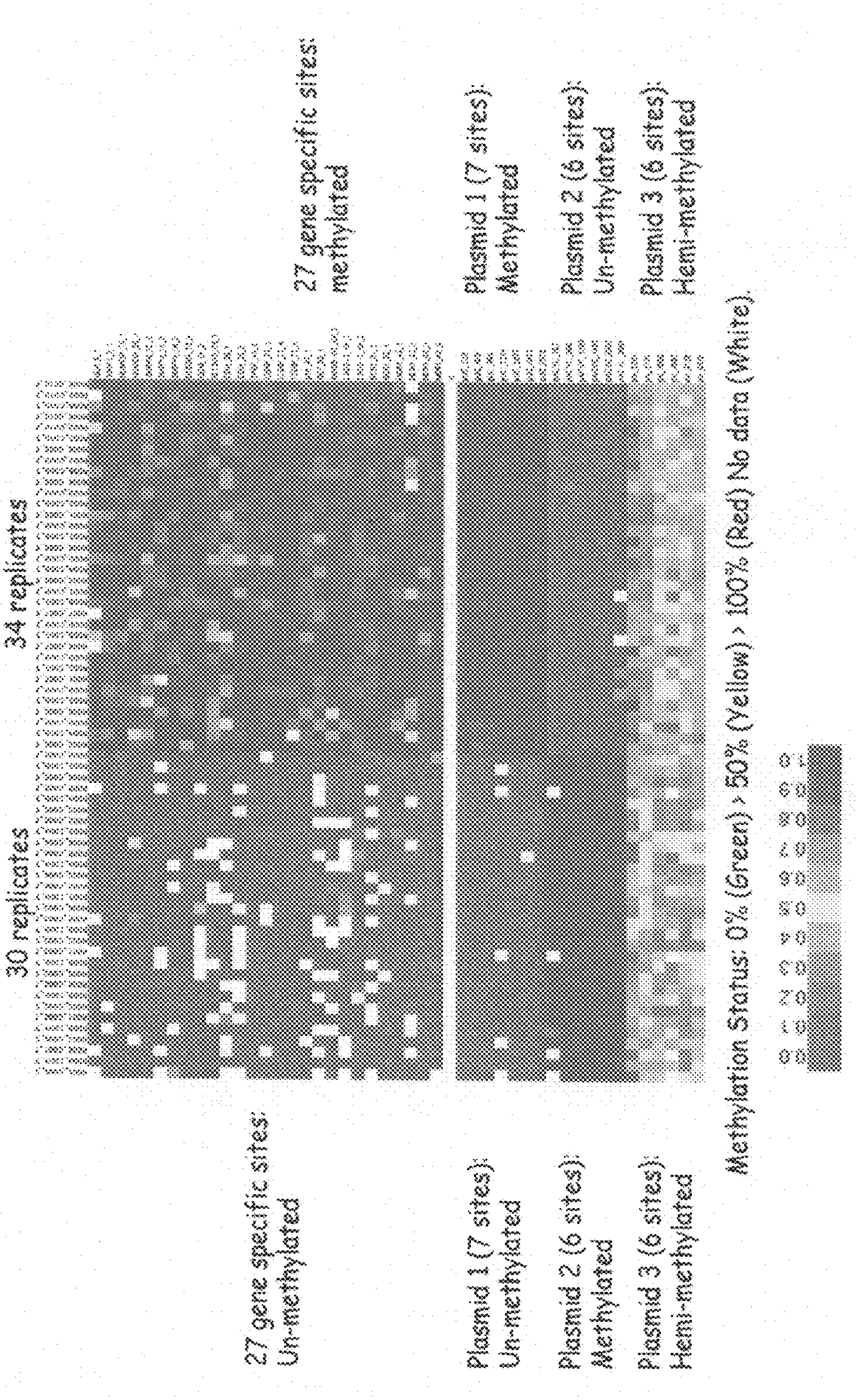
FIG. 8 shows reproducible methylation detection in two human reference DNAs: unmethylated (left panel) and methylated (right panel). The red color indicates a methylated state, green—unmethylated, and yellow—semi-methylated. White squares represent the loci with low intensity values, for which the methylation status call could not be made. In the case of amplified gDNA (left panel), some genomic loci may become underrepresented after amplification procedure.

To calibrate quantitative measurements of methylation, "fully methylated" and "unmethylated" genomic templates were developed (FIG. 8). The fully unmethylated templates were generated by genome-wide amplification of human genomic DNA. With more than 1000-fold amplification, any endogenous methylation is effectively "diluted/erased", and the sample can be used as an "unmethylated" reference DNA. Methylated templates were generated by in vitro methylation of amplified gDNA using Sss I (CpG-methylase) enzyme. The reproducibility of the methylation detection method was confirmed by typing 27 human gene-specific CpG sites in these reference DNAs over 30 times. A high degree of reproducibility was obtained (FIG. 8).

Methylation Profiles of Randomly Selected Human Genomic DNAs

Figure 9:
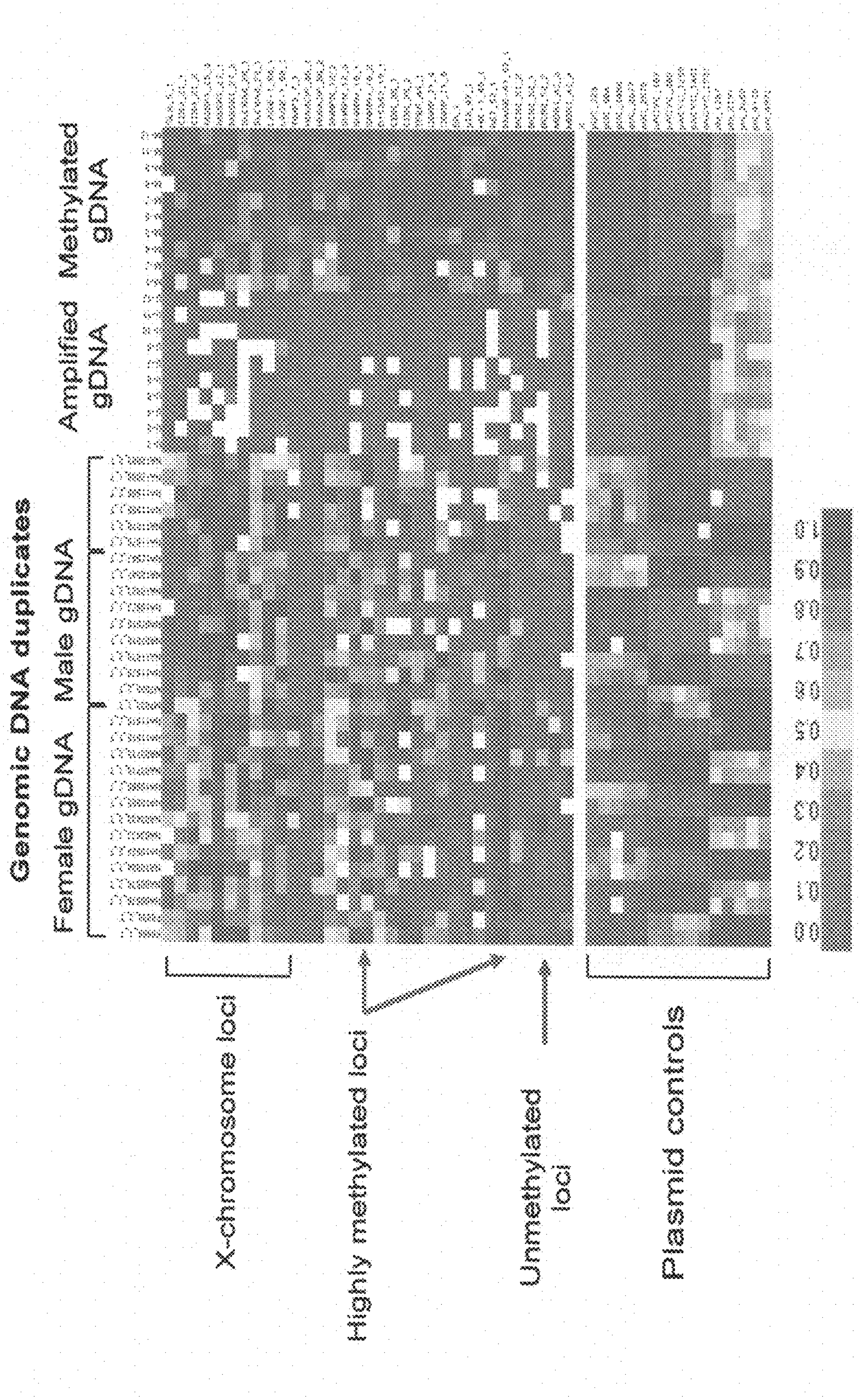
FIG. 9 shows methylation measurement in 15 Coriell genomic DNAs and the reference DNAs.
Figure 11:
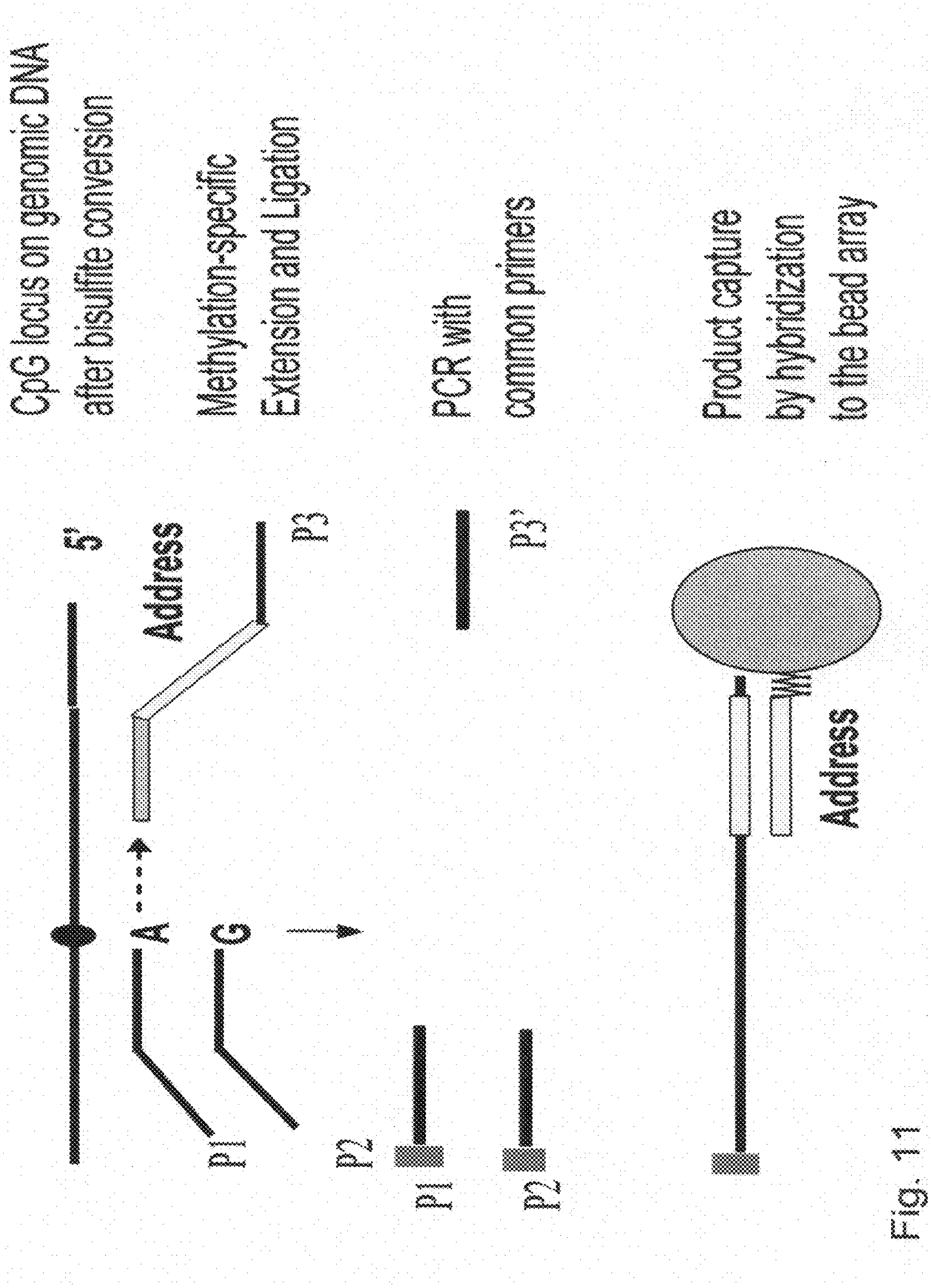
FIG. 11 shows a schematic overview of a methylation assay that incorporates bisulfite conversion and a bead array format.
Figure 12:
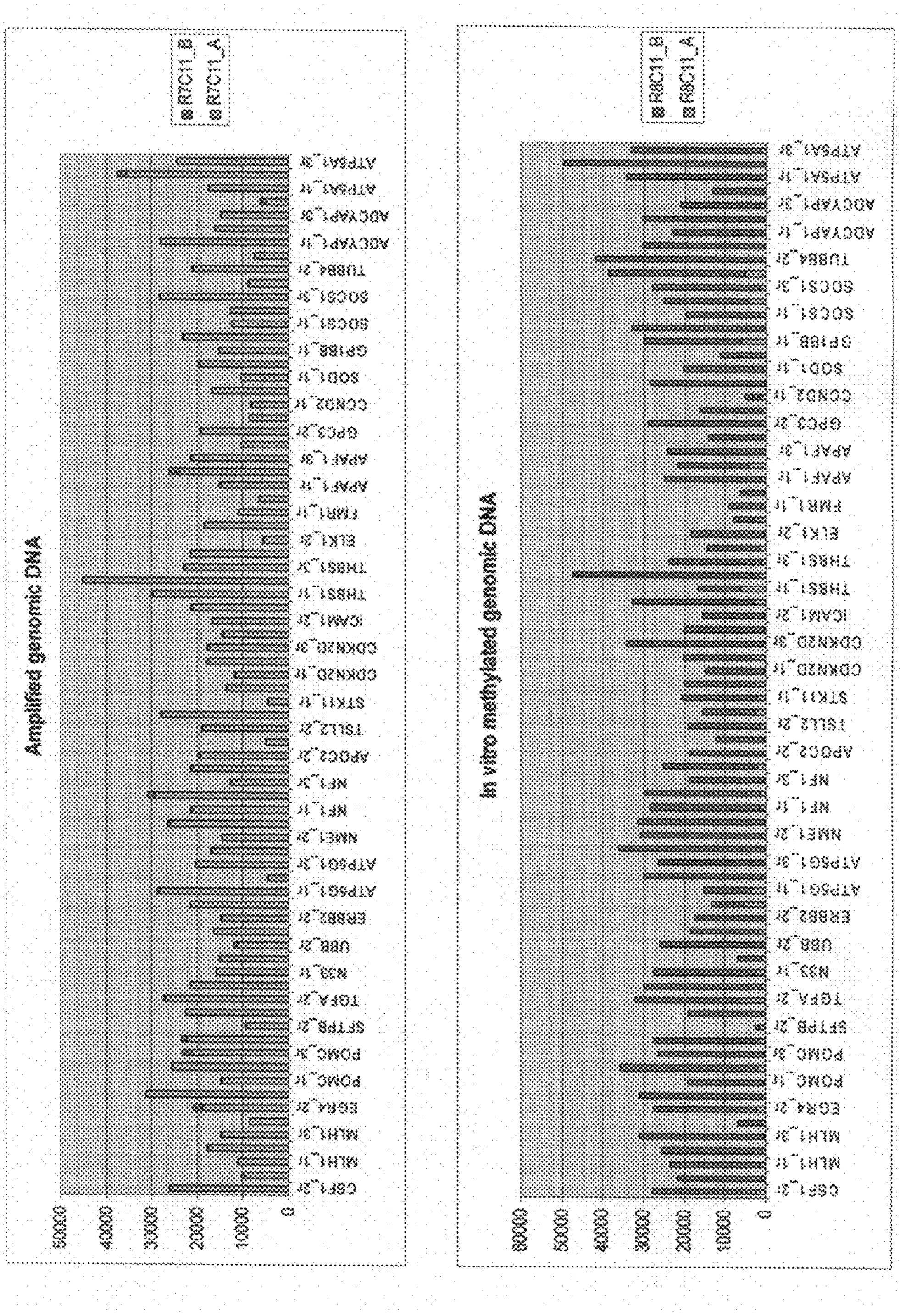
FIG. 12 shows reference samples for a methylation assay encompassing amplified genomic DNA in Panel A and corresponding in vitro methylated genomic DNA in Panel B.
Figure 13:
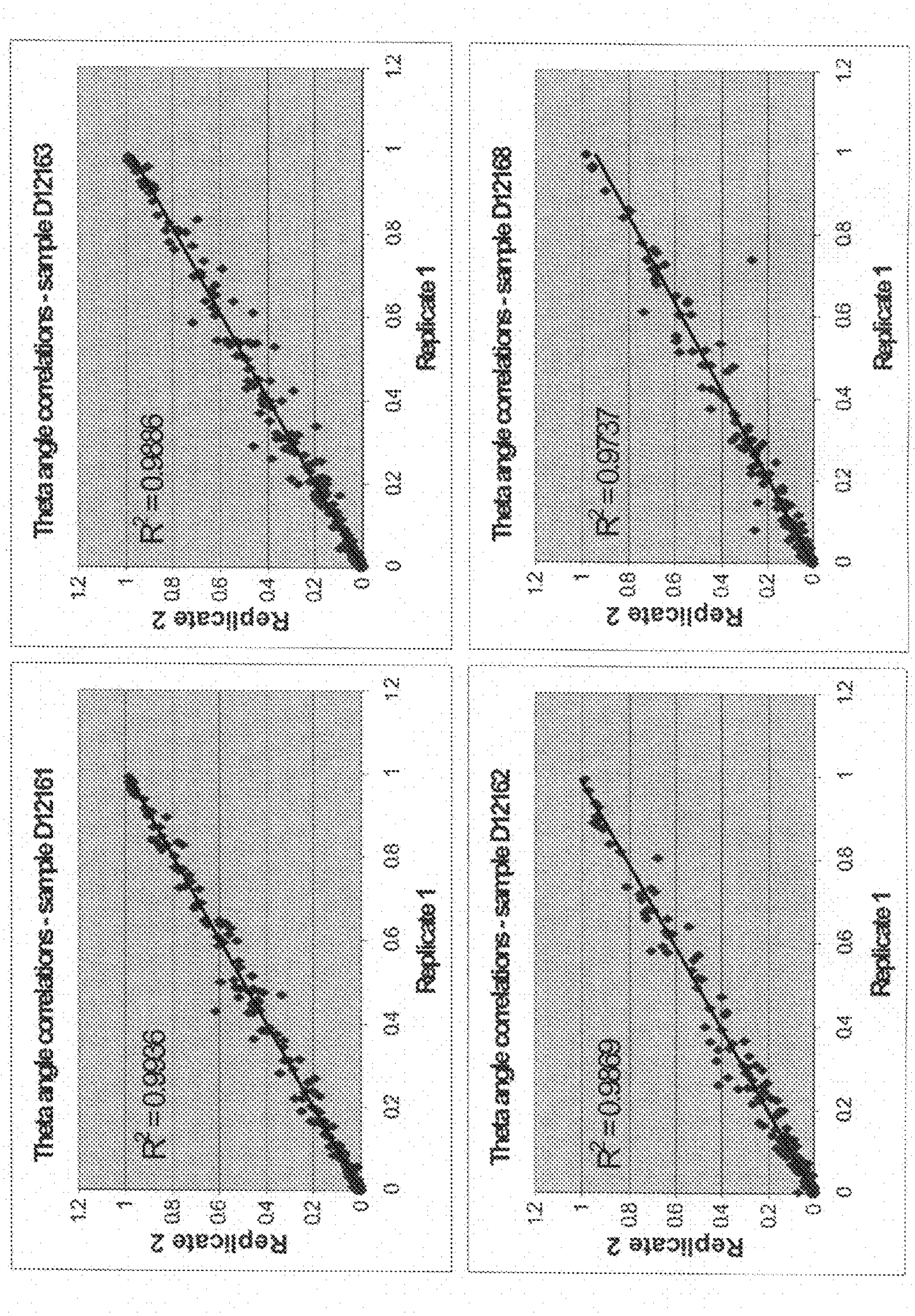
FIG. 13 shows correlation in methylation status between replicates of lung cancer clinical samples containing 389 loci across four independent arrays.
Figure 14:
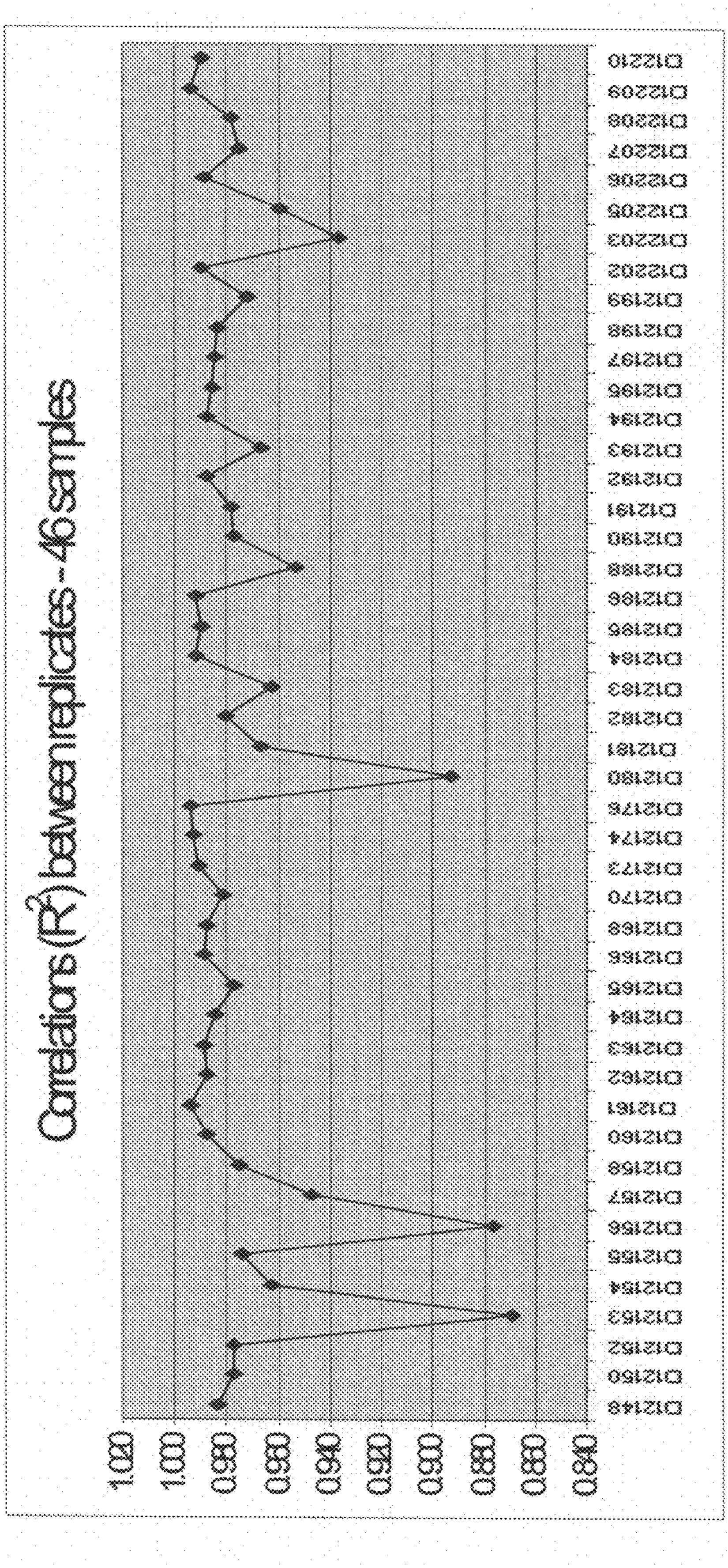
FIG. 14 shows reproducibility of the methylation assay between technical replicates as observed in 46 lung cancer clinical samples containing 389 loci across four independent arrays.
Figure 15:
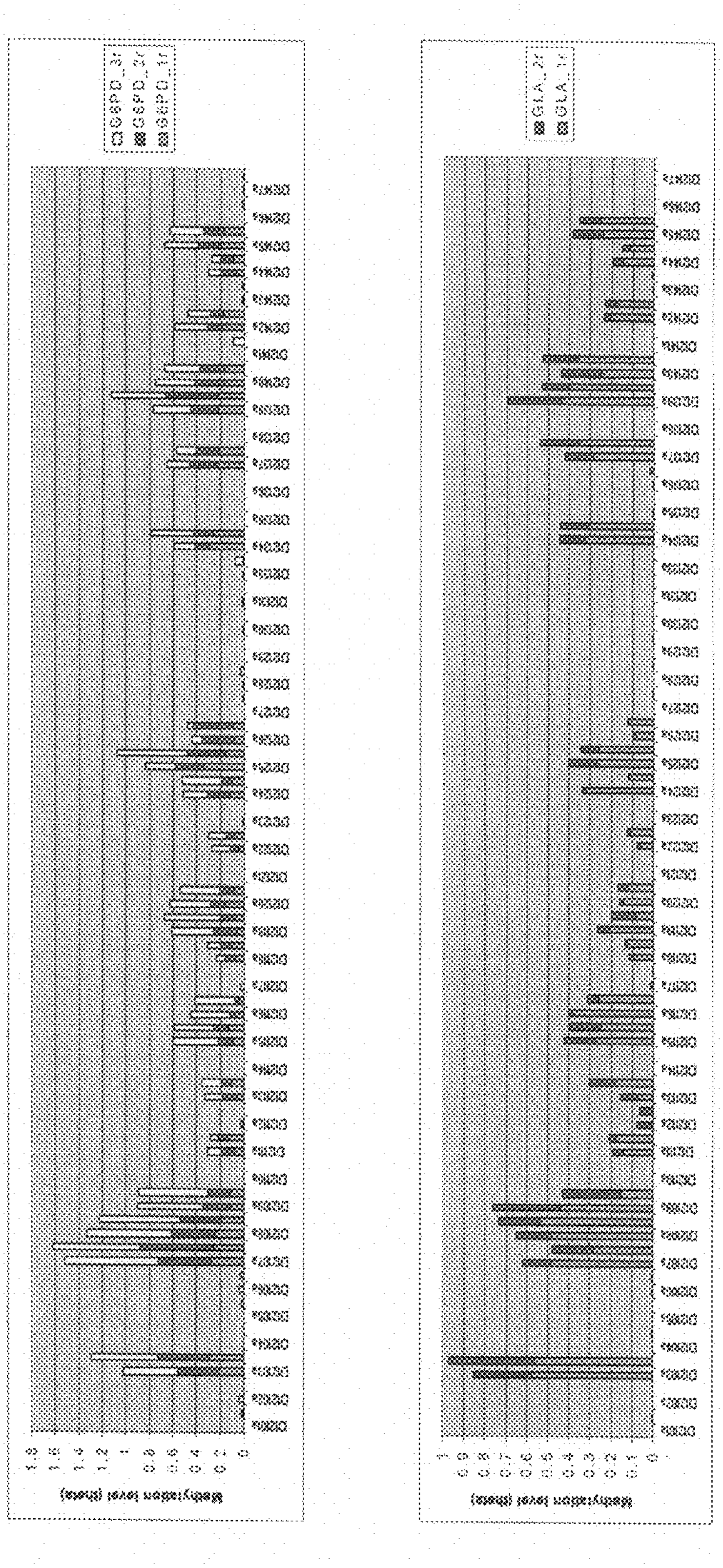
FIG. 15 shows methylation status of two housekeeping genes located on the X chromosome. In females X inactivation correlates with promoter methylation, and methylation pattern determined for both genes in 46 samples (in duplicates) allows to match the methylation status of the promoter with the gender of the sample source.

We have also monitored a set of CpG sites in randomly selected human genomic DNAs. The DNA samples were obtained from the Human Genetic Cell Repository, Coriell Institute for Medical Research, NJ. In this experiment, we measured 7 females, 5 males and 3 of unknown gender specificity; each was done in duplicate and the results are shown in columns next to each other in FIG. 9. Distinguishable methylation patterns were obtained with DNAs isolated from male and female cell lines, especially in genes that are located on the X-chromosome (FIG. 9). The overall methylation profiles are quite reproducible among the duplicates.

Assay Reproducibility

One of the most important assay characteristics is its reproducibility. This was addressed by monitoring several plasmid loci with known methylation status across multiple replicates in several independent experiments. The experimental setup also allowed for estimation of the assay accuracy. A mixture of unmethylated, methylated and 1:1 mixed plasmid DNAs was prepared, and spiked into 1 μg of human genomic DNA in a 1:1 molar ratio. Each experiment included three plasmid mixtures:

| | | | |
|---|---|---|---|
| 1 | pUC19 U | pACYC 184 M | phiX174 U:M |
| 2 | pUC19 U:M | pACYC 184 U | phiX174 M |
| 3 | pUC19 M | pACYC 184 U:M | phiX174 U |

A typical experiment included 32 replicates of each set of the three plasmid mixtures assayed on a 96 fiber bundle assay matrix. Results of the reproducibility study are summarized in Table 2, which involves (79+96+95+95) replicates×14 CpG sites=5,110 measurements. It is noticeable that some loci (e.g. phi_4972) tend to perform better than others (e.g. pACYC_360). There are also some performance variations from experiment to experiment. The overall call accuracy is averaged at ~97% with a high call rate of 99.6%. The accuracy was calculated using our existing SNP genotyping software, which uses a clustering algorithm to determine if a locus methylated, unmethylated or semi-methylated (FIG. 10).

Note: Experiment 1 included 80 replicates of bisulfite converted DNA and 16 replicates of unconverted samples for background control. The other 3 experiments included only bisulfite converted DNA.

As demonstrated above, assay sensitivity and specificity were shown to be sufficient to detect changes in methylation status at more than 50 loci simultaneously in 1 microgram of human genomic DNA. A minimum of three levels of methylation was clearly distinguished: fully methylated, hemi-methylated, and unmethylated. The ability to distinguish three levels of methylation was confirmed by using plasmid control DNAs with known methylation status, spiked into human genomic DNA in a 1:1 molar ratio. Furthermore, reproducibility of methylation determination was shown to be 96.6% (which is a more stringent measurement than reproducibility), at a call rate exceeding 90% (Table 2). A set of three reference samples for 14 CpG sites was analyzed in four independent experiments. The number of measurements in each experiment was 1106, 1344, 1330 and 1330 respectively.

Overall, this example demonstrates the development of a microtiter plate based, high throughput bisulfite conversion, which as described in the following Example, can be fully integrated into the SNP genotyping system for high-throughput methylation profiling. The methylation assays can be enlarged in both the scope and capacity of methylation detection with as many as 1500 methylation sites in each assay, while using reduced amounts of genomic DNA. Since the data collection and processing are largely automated, it is possible to do at least one, two, five or ten array matrix runs per day per system, with each run providing data from 96

TABLE 5

Methylation measurement with 14 plasmid CpG loci.

| | Experiment 1, 79 replicates | | | Experiment 2, 96 replicates | | | Experiment 3, 95 replicates | | | Experiment 4, 95 replicates | | | Summary | | | |
|---|---|---|---|---|---|---|---|---|---|---|---|---|---|---|---|---|
| Locus | No call, % | Correct, % | Wrong call, % | No call, % | Correct, % | Wrong call, % | No call, % | Correct, % | Wrong call, % | No call, % | Correct, % | Wrong call, % | No call, % | Wrong call, % | Correct, % | Correct, CV (%) |
| pUC_229 | 0 | 100 | 0 | 0 | 93.75 | 6.25 | 0 | 93.68 | 6.32 | 0 | 100 | 0 | 0 | 3.14 | 96.86 | 3.75 |
| pUC_964 | 0 | 100 | 0 | 0 | 89.58 | 10.42 | 0 | 94.74 | 5.26 | 0 | 100 | 0 | 0 | 3.92 | 96.08 | 5.20 |
| pUC_1488 | 1.27 | 100 | 0 | 0 | 96.88 | 3.13 | 0 | 91.58 | 8.42 | 0 | 100 | 0 | 0.32 | 2.89 | 97.11 | 4.09 |
| pUC_2077 | 0 | 100 | 0 | 8.33 | 88.64 | 11.36 | 6.32 | 91.01 | 8.99 | 0 | 96.84 | 3.16 | 3.66 | 5.88 | 94.12 | 5.55 |
| pUC_2575 | 0 | 100 | 0 | 0 | 88.54 | 11.46 | 0 | 90.53 | 9.47 | 0 | 100 | 0 | 0 | 5.23 | 94.77 | 6.43 |
| pACYC_167 | 0 | 100 | 0 | 0 | 88.54 | 11.46 | 0 | 97.89 | 2.11 | 0 | 100 | 0 | 0 | 3.39 | 96.61 | 5.66 |
| pACYC_360 | 0 | 98.73 | 1.27 | 1.04 | 74.74 | 25.26 | 0 | 91.58 | 8.42 | 0 | 97.89 | 2.11 | 0.26 | 9.26 | 90.73 | 12.27 |
| pACYC_1289 | 0 | 100 | 0 | 1.04 | 89.47 | 10.53 | 0 | 95.79 | 4.21 | 0 | 97.89 | 2.11 | 0.26 | 4.21 | 95.79 | 4.75 |
| pACYC_1481 | 0 | 100 | 0 | 1.04 | 92.63 | 7.37 | 0 | 95.79 | 4.21 | 0 | 100 | 0 | 0.26 | 2.89 | 97.11 | 3.69 |
| phi_2191 | 0 | 100 | 0 | 0 | 98.96 | 1.04 | 0 | 95.79 | 4.21 | 0 | 100 | 0 | 0 | 1.31 | 98.69 | 2.02 |
| phi_3050 | 0 | 100 | 0 | 0 | 100 | 0 | 0 | 98.95 | 1.05 | 0 | 98.95 | 1.05 | 0 | 0.53 | 99.47 | 0.61 |
| phi_3687 | 0 | 97.47 | 2.53 | 2.08 | 94.68 | 5.32 | 3.16 | 92.39 | 7.61 | 0 | 97.89 | 2.11 | 1.31 | 4.39 | 95.61 | 2.69 |
| phi_4128 | 0 | 100 | 0 | 0 | 100 | 0 | 0 | 98.95 | 1.05 | 0 | 98.95 | 1.05 | 0 | 0.53 | 99.47 | 0.61 |
| phi_4972 | 0 | 100 | 0 | 0 | 100 | 0 | 0 | 100 | 0 | 0 | 100 | 0 | 0 | 0 | 100 | 0 |
| Total: | 0.09 | 99.73 | 0.27 | 0.97 | 92.60 | 7.40 | 0.68 | 94.90 | 5.10 | 0 | 99.17 | 0.83 | 0.43 | 3.40 | 96.60 | 4.09 |

samples at a time, creating a highly scalable system where multiple instruments can be run in parallel if needed.

EXAMPLE III

Integration of Microtiter Plate Based, High-throughput Bisulfite Conversion into Genotyping System for High Troughput Methylation Profiling This example demonstrates the integration of a microtiter plate based, high throughput bisulfite conversion as described in Example II, into the SNP genotyping system for high-throughput methylation profiling.

The assay optimization process includes measuring the array-to-array experimental variability, both within a matrix and between matrices, and dissect out contributions to variability from samples, sample processing (bisulfite conversion, allele-specific extension, ligation, and PCR amplification), and array hybridization, using carefully designed controls. The resulting data also is useful in determining thresholds of significance for analyzing and interpreting results.

Improve Assay Performance with Fully “Methylated” and “Un-methylated” Genomic Templates Currently, all the methods used to validate methylation status of any methylation site in any given sample, such as bisulfite sequencing and methylation-specific PCR, are either laborious and time consuming, or inaccurate and expensive. Indeed, a high performance methylation quantitation (or calibration) system is needed for large-scale genome-wide methylation assay development and validation. As described in Example II, a system has been developed that uses fully “methylated” and “un-methylated” genomic templates.

The un-methylated templates can be generated by genome-wide amplification of any genomic DNA, using random primed DNA amplification with enzymes such as Phi-29, Taq DNA polymerase or Klenow Fragment (3'->5'-exo-). After this amplification, the endogenous DNA methylation is diluted at least 100 to 1000-fold, effectively rendering the amplified genome DNA “un-methylated”.

The methylated templates can be generated by in vitro methylation using the SssI CpG-methylase. However, not all the CpG sites can be fully methylated in vitro. Some of these can result from base substitution at the CpG sites in the DNA tested, in particular, these sites become “methylation-resistant”. It is well known that CpG sites are mutation hot spots. In order to achieve higher levels of genomic DNA methylation, different experimental conditions are tested, for example, varying the concentration of magnesium in the methylation reaction and using multiple methylases.

The above-described templates are used for assay development and calibration. The fully methylated and unmethylated genomic DNA templates can be mixed at different ratio, for example, 0%, 25%, 50%, 75%, and 100% of methylated template. Methylation assays on these mixed templates generate a calibration curve for quantitative methylation measurement in unknown samples for any CpG site in the genome. The mixed templates can also be used to determine the sensitivity of methylation detection, for example, what percentage of the methylated template can be detected in the presence of un-methylated template.

Since this approach can be used to evaluate the methylation assay designed for any specific CpG site across the entire genome, it greatly aids methylation assay development such as assay specificity. For example, if an assay gives the same methylation “report” for both the unmethylated and the methylated DNA templates, it confirms that the assay is not working properly.

Finally, protocols for measuring DNA methylation in formalin-fixed, paraffin-embedded samples are created. Robust large-scale DNA methylation detection on these samples opens up a huge sample resource, for which clinical history is already available.

Improvement of Assay Sensitivity by Genomic DNA Amplification After Bisulfite Conversion In order to improve assay sensitivity, DNA is amplified after bisulfite conversion, using a random priming approach. But, instead of using all possible random primers, advantage is taken of the unique sequence feature of genomic DNAs after bisulfite treatment, i.e. that un-methylated cytosines are converted to uracil. Therefore, these DNA templates contain mostly three bases, A, G and T (and U). The genomic amplification is carried out using (i) through (iii) as set forth in the following paragraphs.

(i) A mixture of two sets of primers that contain all possible combinations of three nucleotides: (i.e. A, T and C for one set, and A, T and G for the other set). Primers from the first set have higher affinity to the original bisulfite converted DNA strand, while primers from the second set preferentially anneal to the newly synthesized complementary strand. Using this scheme, having G and C in the same primer is avoided, thus preventing the primers from crossing over any CpG sites to be interrogated. Bias that may be introduced by the un-balanced annealing efficiency of primers corresponding to the two alleles (C or T) also is avoided. Lastly, since each primer set contains all possible combinations of three, but not four nucleotides, effective primer concentration is increased.

(ii) Simple primer sequences that contain only Adenines (A). The homopoly-A primers (for example, 6-mer, 9-mer, or longer) is used for the first strand synthesis. After that, a homopoly-T tail is added to the 3'-ends of the first strand products, using terminal deoxyribonucleotide transferase (TdT). A standard PCR is then be carried out to amplify the DNAs using a poly-A primer. Human chromosome 1 sequence was used to calculate the poly-T frequencies in the genome after bisulfite conversion: on average, the physical distance between any two poly-$(T)_n$ sequences ($n>=9$) is 330 bp, a perfect amplicon size range for robust amplifications.

(iii) Similar to approach (i), except that oligo-A primer is used for the first strand synthesis and primers containing combinations of A, T and G for the complementary strand synthesis.

Probe design is one of the critical components for a successful methylation assay. The fully automated SNP genotyping assay design program described herein can be used for methylation assay development. As shown above, for each CpG locus, three probes are designed: two allele-specific oligonucleotides, one corresponding to the methylated and the other to the unmethylated state of the CpG site, and one locus-specific oligo. If other CpG loci are present close to the chosen CpG site, a wobble base [A or G] is used in the corresponding position of the probes. Based on the observation that adjacent CpG sites tend to be co-methylated or co-de-methylated, a simpler design scheme is applied in which a “CG” sequence is used for all the CpG sites within the vicinity of the design, in particular for the landing sites for both ASO and LSO, to target any methylated CpG site; while a “TG” sequence is used for all the CpG sites within the vicinity of the design, to target any un-methylated CpG site.

This approach requires two LSO oligos for some loci, but adds better discrimination between the methylated and unmethylated alleles.

A human gene promoter database, which includes all CpG regions of potential interest for methylation profiling was constructed by combining NCBI's RefSeq annotation, existing knowledge of some well-studied promoters, gene and promoter prediction algorithms, as well as observations of certain cancer-related genes. This database is continuously expanded by integrating more public information from literature and databases, and experimental observations. For the methylation study, a new database searching strategy is integrated into the primer design software. A modified genome database is generated in which all "C"s (except those located within a CpG dinucleotide sequence) are converted to "T"s in silico. The probe design program searches against this converted database to find unique sequences and compute melting temperature (Tm), self-complementarity and length for an optimal probe. An optimization program is applied to match address sequences with locus-specific oligos to minimize self-complementarities of combined address and probe sequences. A locus filtering program is used to filter out sequences predicted to be unsuitable on the basis of data from SNP genotyping experiments already carried out. Some sequence features have been shown to be troublesome, e.g. runs of six or more consecutive bases of a single type, extreme GC or AT content, inverted repeats (mostly due to secondary structure), and high numbers of hits in the human genome sequence based on similarity searches by BLAST. All of these parameters can be computed in advance. These parameters are stored in a relational database for further data analysis. In addition, the program computes the sequence complementarity between the probes designed for a given set of methylation sites, especially the sequence complementary at their 3' ends. This calculation allows assessment of the compatibility of the assays, which in turn provides guidance regarding grouping of the assays properly for multiplexing.

The main problem for the methylation assay primer design lies in the reduced complexity of the genome after bisulfite conversion of the genomic DNA. Analysis of 5'-regulatory sequences from 1200 human genes was performed and preliminary computer simulation analysis indicates that the length of the primers designed for the bisulfite-converted DNAs will have to be increased by several bases as compared to the un-converted ones to achieve the same primer specificity and melting temperature. If necessary, longer primers along with increased assay stringency is used.

In another in-silico experiment, three BLAST searchable human genomic sequence databases were created. The first database mimics methylated condition (after bisulfite treatment), where all the C residues in CpG dinucleotide sequence remains as C; the second mimics un-methylated conditions, where all the C residues in CpG dinucleotide sequence are converted into T; both of these databases have C residues from non-CpG sites converted into T. The third database has normal genomic sequences. BLAST searching against these databases using designed probes as queries was performed and, as predicted, the probes had much larger number of hits to the database that have "C" converted into "T" (the first two databases), and less number of hits to the normal database (the third database). Subsequent empirical experiments with probes that have either large or small number of BLAST hits suggested that the probes with small number of hits usually generate good assay results, while the probes with large number of hits do not. In the future, this BLAST search process is automated and integrated into the probe design software. Furthermore, probes is designed for all the CpG sites in the promoter regions. After a subsequent BLAST filtering process, only three probes are synthesized for each gene. For a small number of genes that can't have three qualified probes designed due to limited number of CpG sites in the promoter region or CpG sites too close to each other, or/and severe sequence similarity to other genomic regions.

In order to search for specific methylation patterns in different cancer types or cancer stages, we first develop methylation assays for at least 1000 human genes. These genes are selected based on the following criteria:

(i) Biological relevance. Methylation patterns in previously characterized tumor suppressor genes and oncogenes are an initial focus (Esteller, Oncogene 21(35): 5427-40 (2002), Adorjan, et al., Nucleic Acids Res. 30(5): p. e21 (2002)). Then, the target group is enlarged to include genes that are indirectly involved in cancer development, for example, DNA repair genes; metastasis-inhibitor genes, genes regulated by various signaling pathways, and/or responsible for altered cell growth and differentiation; or genes considered to be targets for oncogenic transformation.

(ii) Previous knowledge, e.g. genes located within published recurrent loss of hetrozygosity (LOH) regions or amplified genomic regions (Pollack, et al., Proc Natl Acad Sci USA. 99(20): 12963-8 (2002)).

(iii) Gene expression profiling information, for example, genes differentially expressed in cancer and normal tissues. In the past few years, due to the rapid development of microarray technology, many specific gene-expression signatures have been identified for different cancer types (Golub, et al., Science 286(5439): 531-7 (1999), Ramaswamy, et al., Proc Natl Acad Sci USA. 98(26): 15149-54 (2001), Perou, et al., Nature 406(6797): 747-52 (2000), Bhattacharjee, et al., Proc Natl Acad Sci USA 98(24): 13790-5 (2001), Chen, et al., Mol Biol Cell 13(6): 1929-39 (2002), Welsh, et al., Proc Natl Acad Sci USA. 98(3): 1176-81 (2001)), cancer stages (Dhanasekaran, et al., Nature 412(6849): 822-6 (2001), Ramaswamy, et al., Nat Genet. 33(1): 49-54 (2003)), and cancer therapeutic outcomes (Shipp, et al., Nat Med. 8(1): 68-74 (2002)). Some of these differential expressions are regulated by imprinted or somatic methylation.

The methylation targets are grouped into functionally relevant sets that are useful for focused research (e.g. based on association with a particular pathway or disease; or expressed in particular tissues of interest; or representing a particular genomic region), as well as for more global studies. For example, genes can be grouped according to their biochemical properties, such as, oncogenes/tumor suppressor genes, kinases, phosphatases, and cell surface receptors. Genes can be also grouped based on their involvement in different biological pathways/functions, for example, tumor antigen, signal transduction, apoptosis, angiogenesis, cell cycle control, cell differentiation, DNA repair, cancer metastasis/invasion, drug resistance and detoxification, and transcriptional regulation, etc. The assays are then optimized to achieve a high degree of reliability and specificity within each set.

Selection of CpG Sites to be Interrogated

Several CpG sites within each 5'-regulatory region, including CpGs over the transcriptional start site is targeted, since redundant information from multiple CpG sites can provide a better measurement of the overall methylation status in the interrogated gene. While there are many CpG sites within each CpG island, only those for which robust assays can be designed is used. Each potential CpG site is BLAST searched against human dbSNP databases to avoid any potential "polymorphic" CpG site (i.e. the "methylation-resistant" site), to ensure clean data interpretation. If desired, the consequence of the polymorphic CpG sites, for example, their effect on methylation of adjacent CpG sites, and subsequently on gene expression level can be determined.

It has been estimated that the human genome has 26,000 to 45,000 CpG islands (Antequera, et al., *Proc Natl Acad Sci USA*. 90(24): 11995-9 (1993), Ewing, et al., Nat Genet. 25(2): 232-4 (2000)). Among them, those found in gene 5'-regulatory regions are the most biologically significant ones. The work does not only utilize CpG rich promoters, but also investigates less CpG rich promoters since they might also be subjected to aberrant methylation and silencing.

In order to correctly identify genes and their upstream regulatory regions, public databases such as NCBI RefSeq, UCSC Human Genome Project (HGP) Working Draft, ENSEMBL and Unigene are utilized. These databases annotate known or verified genes according to sequence similarity to mRNA, EST and protein sequences, and novel genes predicted using gene prediction programs. They also contain reference links to genetic and physical mapping data, as well as other features such as CpG islands. The accuracy of these annotated features is confirmed by re-running gene prediction programs and searching for sequence similarity to mRNA, EST, and known protein sequences. Existing promoter databases such as Eukaryotic Promoter Database (EPD) (Praz, V., et al., Nucleic Acids Res. 30(1): 322-4 (2002)), are used to identify the 5'-regulatory sequences. Meantime, promoter and first exon prediction algorithms such as FirstEF (Davuluri, et al., Nat Genet. 29(4): 412-7 (2001)) are used to identify potential regulatory sequences. This approach provides a well-annotated collection of regulatory sequences of human genes and allow for identification of the CpG sites within these regulatory regions and design assay probes as described above.

A CpG site within a CpG island doesn't automatically qualify it as a biologically significant methylation target and art knowledge is applied in order to design most valuable methylation assays. In the past few years, tremendous progress has been made in the epigenetics field, which uncovered many epigenetic regulation mechanisms in various biological pathways (Strichman-Almashanu, et al., Genome Res. 12(4): 543-54 (2002)), and cancers (Widschwendter, et al., Oncogene 21(35): 5462-82 (2002), Tsou, et al., 21(35): p. 5450-61 (2002)). Moreover, large methylation projects such as bisulfite sequencing of CpG island-enriched libraries (Cross, et al., Nat Genet. 6(3): 236-44 (1994)), or entire human chromosomes or even the entire genome are likely to be developed. These efforts should produce tremendous amounts of methylation data and reveal hundreds of thousands of new methylation sites in many different tissue types.

Assay Development, and Array Data Extraction and Analysis

Once the assays are designed, they are tested with publicly available genomic DNAs isolated from various cancerous or normal human tissues or cell lines of different tissue origins, and obtain tissue-specific methylation profiles for individual genes (CpG sites). These methylation profiles serve as references for analyzing unknown samples. Building on SNP genotyping technology, a quantitative metric to guide the methylation assay development is formulated and provide a quality assurance to data generated in a production setting. The metric takes into consideration all aspects of assay performance and data quality (e.g. assay specificity and quantitation), including efficiency of bisulfite conversion, overall signal intensity of all targeted CpG sites, concordance among the measurements of the three CpG sites within each gene, specificity of detection in control samples (e.g. plasmids, reference samples as well mixtures of the reference samples), and measurement variations in replicated samples, etc.

In addition the quantitative performance of methylation detection is tested at various multiplexing levels, for example, high (>1000-plex), medium (~300-plex), and low (<100-plex), and validate the specificity and sensitivity of the assays at high multiplexing levels. Meanwhile, as a measurement of the assay specificity, concordance of methylation profiles generated from a given sample at different multiplexing levels are compared. Finally, methylation-specific PCR is used to validate some of the array results (Herman, et al., Proc Natl Acad Sci USA. 93(18): 9821-6 (1996)). All qualified assays are re-pooled and used for large-scale DNA methylation profiling.

Figure 3:
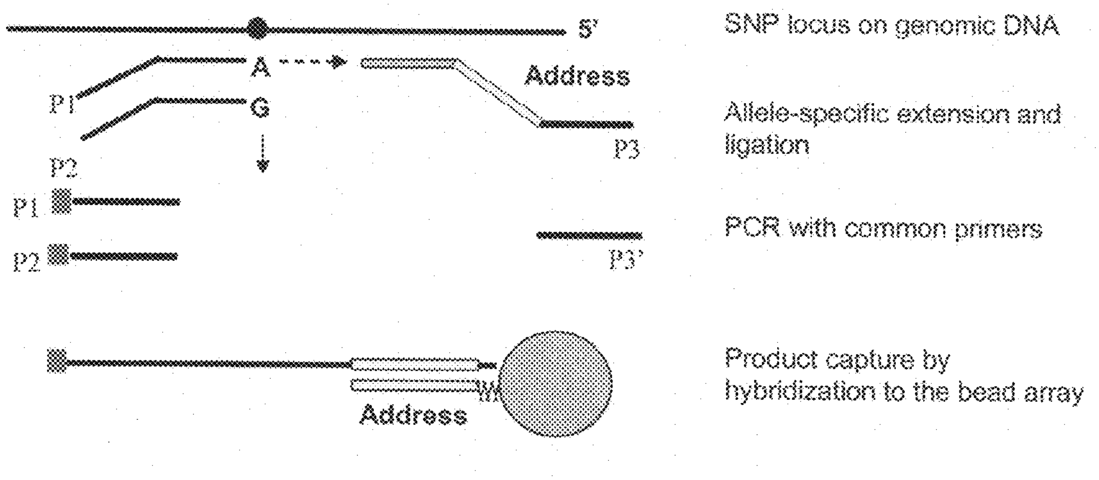
FIG. 3 shows Illumina's SNP genotyping format.

Since the sequence complexity is significantly reduced following bisulfite conversion of the genomic DNA, the assay oligo/genomic DNA annealing protocol is optimized to minimize cross-hybridization. Tetramethylammonium (TMACl) (De Murcia, et al., Biophys Chem. 8(4): 377-83 (1978), Sorg, et al., Nucleic Acids Res. 19(17): 4782 (1991)), and/or Betaine (Rees, et al., Biochemistry, 32(1): 137-44 (1993)) is used to normalize the base composition dependence of DNA/oligo hybridization. Nevertheless, high locus specificity should be achieved by the requirement that both ASO and LSO oligos need to hybridize to the same genomic target site and then get extended and ligated (FIG. 3).

The existing SNP genotyping software is modified and adapted for the methylation data analysis. The current software takes the raw intensity data and transforms them into a genotype call using a clustering algorithm (FIG. 10). However, for most of the methylation data analysis cluster analysis cannot be utilized due to the need not only to distinguish three methylation states of each locus (unmethylated, methylated and semi-methylated), but do it in a more quantitative manner, for example, estimate percentage of methylation of certain loci in a given sample. The methylated and unmethylated reference samples and assay controls are used in every experiment for software calibration. Assay intensity data of unknown sample is compared to those obtained with the reference samples, and used to calculate the methylation level of the locus of interest. Software is developed for comparison of various samples and detection of differential methylation profiles to allow for identification of differences between normal tissues and tumors, and/or create tissue-specific methylation profiles for genes and loci of interest.

Search for Specific Methylation Patterns in Different Cancer Types or Cancer Stages Once the gene-specific methylation assays are developed as described above, a large-scale DNA methylation survey is carried out in a large number of samples. The experiment is designed to compare methylation patterns in (1) normal and cancerous tissues; (2) different cancer types or cancer stages; (3) or responsive to (or associated with) treatment with certain growth factors or drugs, activation of oncogenes or inactivation of tumor suppressor genes, changes in a developmental program, etc. The main objective is to find unique methylation patterns for specific cancer types/stages and develop molecular markers for classification and diagnosis of cancers, which can be used to complement existing morphological and clinical parameters. This can be particularly useful for cancer types which appear similar by histological assessments, but follow different clinical courses (e.g. different therapeutic responses). The results also provide important clues to the mechanisms of specific cellular responses; and this information can prove critical for devising strategies for cancer prevention and treatment.

Malignant tissues obtained by laser capture microdissection (LCM) are used to identify specific cell and tissue types for methylation profiling. In these cases, a more sensitive strategy is employed, which involves DNA amplification after bisulfite conversion. If an assay can be established to detect tumor-specific methylation patterns in a very small amount of diseased tissue in the presence of a large amount of normal tissue, it may find wide application in clinical cancer diagnosis.

As a pilot study, DNA samples isolated from 50 or more lung tissues, for example, 98 lung tissues and 50 or more breast tissues, for example, 101 breast tissues, including both normal and cancerous tissues, are used. Among these tissues, a portion, for example, 169 (98 lung and 71 breast) are frozen and the remainder, for example, 30 (breast) are paraffin-fixed. These tumor tissues are classified upon resection, and basic (anonymous) data about each tumor is kept in the tumor bank database. The tissues were resected, sent to the Pathology Department for pathological examination, and then sent to the tumor bank with the initial pathology report. The tissue was quickly frozen and stored at −80° C. The tissue procurement, storage, and documentation of clinical specimens are very well documented, in accordance with guidelines for human subject research. Thirty of the 101 breast tumor tissues are formalin-fixed, paraffin-embedded tissues. Slides were made from the fixed tissue block and stored at room temperature. Each tumor sample was examined by a pathologist to confirm the clinical diagnosis. Basic (anonymous) data about each tumor, such as the information on the gender, age, and ethnic background of the patient as well as diagnosis are available to us for data analysis.

Initially, DNA methylation profiles are generated for these samples for a list of 141 genes, selected fully based on their biological functions (see Appendix I). If both DNA and RNA samples are available for a subject in the study, both DNA methylation and gene expression is measured, including allele-specific expression, using a sensitive RNA profiling method (Fan, et al., Genome Res. 14: 878-885 (2003), Yeakley, et al., Nat Biotechnol. 20(4): 353-8 (2002)). Gene-specific as well as allele-specific probes are designed to measure expression levels of specific transcripts and their isoforms. Cross-referencing gene expression results to DNA methylation data confirms not only the gene silencing caused by DNA methylation, but also helps interpret the association study results. Once specific methylation patterns are derived from this preliminary study, they are validated in (larger) independent sample sets.

Finally, comparing results obtained from human and animal studies sheds light on the underlying molecular mechanisms of tumorigenesis. For example, there is a well-characterized rat mammary tumor model involving mammary glands from virgin and parlous animals exposed to MNU (Sivaraman, et al., Carcinogenesis 19(9): 1573-81 (1998)). It provides an excellent biological model for studying molecular events in human breast cancer, especially those occurred in early cancer developments leading to mammary tumorigenesis (Russo, et al., Br J Cancer 64(3): 481-4 (1991)).

Bioinformatics, Array Information Management, and Statistical Data Analysis

Software development focuses on algorithms and software tools to process and analyze the large amount of methylation assay data as efficiently as possible. A database developer/administrator organizes, track and maintain all the methylation site information, primer design, sample information, the day-to-day experimental data, as well as design and implement web browser interfaces to provide search, query and report functions.

To develop a robust and high-throughput technology for simultaneous measurement of methylation at many specific sites in many samples, a highly efficient analysis and data export process is needed. Algorithms for analyzing data to determine methylation status automatically are developed. Again, this is based on experience with analysis of SNP genotyping data. There are some important differences in how the data is analyzed, such as the requirement for more quantitative analysis and output as described above. Experiments is designed and analysis procedures developed to determine the quantitative limits of our system, such as the limit of detection of methylated DNA in a mixed sample, and linearity of signal as a function of amount of methylated DNA.

Once tools are developed to extract information about methylation status from raw data, and to determine the significance of the measurements and assign confidence indices, the focus is on analyses of patterns of methylation and their correlations with different phenotypes. For example, analyses are carried out to detect and verify any correlations between specific methylation patterns and particular cancer types. Techniques (methods) to perform this type of analysis are the subject of intensive research in the microarray field. Many powerful algorithms/tools have been developed, such as supervised or unsupervised hierarchical clustering analysis (Dhanasekaran, et al., Nature 412(6849): 822-6 (2001), Eisen, et al., Proc Natl Acad Sci USA. 1998. 95(25): 14863-8 (1991), Khan, et al., Nat Med. 7(6): 673-9 (2001)), K-means clustering, bootstrapping or jackknife (Kerr, M. K. et al. Proc Natl Acad Sci USA. 98(16): 8961-5 (2001)), principal component analysis, etc. However, each of these methods has its own advantages and limitations; no clear advantage exists for any given algorithm in application to our study. Therefore, multiple algorithms are tested and the most suitable ones are selected to carry out the analyses.

The technology is upscaled to meet commercial requirements by implementing the entire process, including sample preparation, bisulfite treatment, genotyping-based assay and PCR amplification on a robotic platform; increasing the level of multiplexing to at least 96-plex, and as high as 1,500-plex; and reducing the amount of genomic DNA required such that, on average, <1 ng of genomic DNA is required per methylation site analyzed.

The assay described herein allows measurement of the methylation status in at least 10, 100, or 1,000 human genes' 5'-regulatory regions, and validate the sensitivity and specificity of the assays at low or high multiplexing levels. The assay further allows for a systematic search for specific methylation patterns in different cancer types and cancer stages.

Overall, this Example describes a system for methylation detection by leveraging various technologies for high-throughput array-based assays and SNP genotyping, and to validate the technology in real-world applications. The technology is highly scalable, both in terms of the number of assays carried out on a single sample, and the number of samples that can be processed in parallel. Furthermore, it can be used has the potential for broad application in many areas of cancer and fundamental biomedical research. The assays and assay protocols, and the specific methylation patterns (in various cancers) to be developed in this study can generally be useful to the research community.

EXAMPLE IV

DNA Methylation Profiling in Lung Cancer

This Example demonstrates the identification of adenocarcinoma markers by virtue of differential methylation patterns and use of the identified markers to distinguish adenocarcinoma from normal tissue with high specificity and sensitivity.

As described in detail above, the SNP genotyping system was adapted for DNA methylation detection based on "SNP" genotyping of bisulfite-converted genomic DNA. In this assay, non-methylated cytosines (C) are converted to uracil (U) when treated with bisulfite, while methylated cytosines remain unchanged. Hybridization behavior of uracil is similar to that of thymine (T). The detection of the methylation status of a particular cytosine can thus be carried out using a genotyping assay for a C/T polymorphism.

Assay Probe Design

Figure 20:
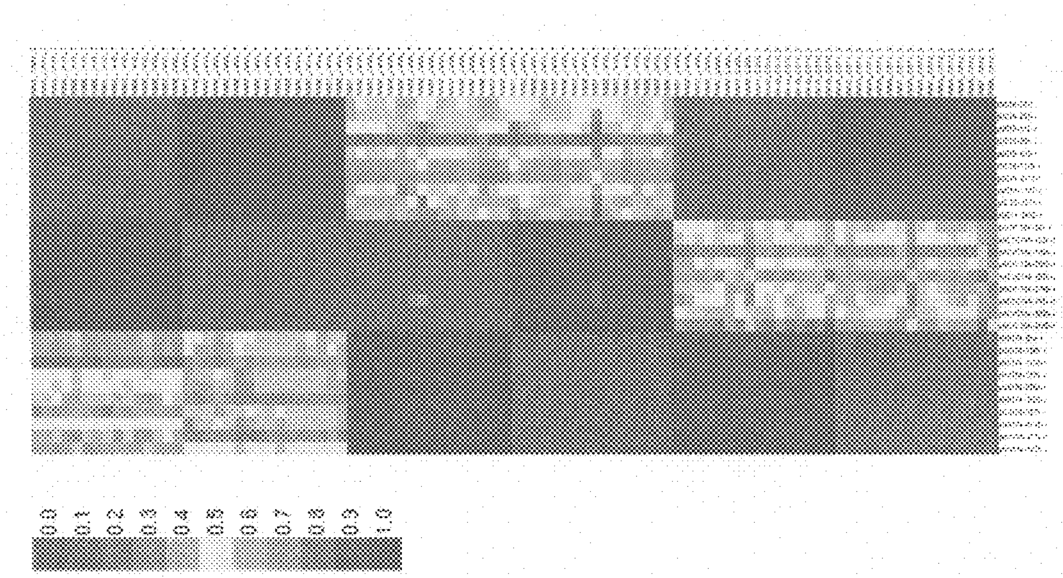
FIG. 20 shows internal methylation assay controls. Methylated, unmethylated or semi-methylated (generated by mixing the methylated and unmethylated at 1:1 ratio) plasmid DNAs were spiked into human genomic DNA at 1:1 molar ratio. Methylation states were determined in 46 such samples at 29 CpG sites from 3 plasmids: Unmethylated (Green), semi-methylated (Yellow) and fully-methylated (Red).

A 1.5 kb sequence from the 5'-regulatory region (in some cases, including the first exon) is extracted for each target gene based on human genome public databases NCBI RefSeq build 33 released on Jun. 6, 2003. CpG islands of interest from this 1.5 kb region were selected and "converted by bisulfite" computationally. As described in Example 1, an automated SNP genotyping assay design program was adapted for methylation application. For each CpG locus, four probes were designed: two allele-specific oligos and two locus-specific oligos, each corresponding to the methylated or unmethylated state of the CpG site respectively (FIG. 20). If other CpG loci were present in the close vicinity of the chosen CpG site, an assumption is made that it has the same methylation status as the site of interest. While there are many CpG sites within each CpG island, only those for which robust assays could be designed were used. Assays were designed for 389 CpG sites from 141 genes: 114 genes with three CpG assays, 20 genes with two and 7 genes with only one assay. The designed site sequence information is included in Table 1.

DNA Samples for Methylation Analysis

Lung tissue specimens were collected from subjects with lung cancer. Under an Institutional Review Board approved protocol, the samples of lung tissue classified as cancerous and samples adjacent to the cancerous tissue but classified as normal were utilized in this study. After pathological classification upon resection, the tissues were frozen and stored at −80° C. Forty-six samples were obtained from Philipps-University of Marburg, Germany, and 25 samples were from The Pennsylvania State University College of Medicine Tumor Bank. Specifically, a total of 38 lung cancer and 33 normal tissues were used, including 22 matched pairs (Table 4). The cancer samples included 14 squamous cell carcinoma and 24 adenocarcinoma cancer tissues. The samples were pulverized under liquid nitrogen. DNA was extracted from the tissue powder by QIAamp® DNA Mini Kit (Qiagen Inc. Valencia, Calif.) according to manufacturer's instruction. The DNA was eluted from the column with dH2O, and stored at −80° C. until use.

Plasmid DNA Controls.

Plasmids pUC19, pACYC184 and phage phiX174 served as control DNAs as described above in Example II.

Bisulfite Conversion of DNA and Methylation Assay

The EZ DNA Methylation Kit™ (Zymo Research, Orange Calif.) was used for bisulfite conversion of DNA samples, according to manufacturer's recommendations. One and a half microgram of genomic DNA was used for each conversion. Bisulfite-converted genomic DNA from one conversion was then used for up to 8 array experiments. After bisulfite conversion of genomic DNA, the remaining assay steps were identical to the GoldenGate™ assay (Fan et al., *Cold Spring Harbor Symposia on Quantitative Biology* 68: 69-78 (2003)), using manufacturer's reagents and conditions (BeadLab User Manual, Illumina).

Briefly, bisulfite-converted, biotinylated genomic DNA was immobilized on paramagnetic beads and washed. Pooled query oligos were annealed to the gDNA under a controlled hybridization program, and then washed to remove excess or mishybridized oligos. Hybridized oligos were then extended and ligated to generate amplifiable templates. A PCR reaction was performed with fluorescently labeled universal PCR primers. Single stranded PCR products were prepared by denaturation, then hybridized to a Sentrix® Array Matrix (Fan et al., *Cold Spring Harbor Symposia on Quantitative Biology* 68: 69-78 (2003)). The array hybridization was conducted under a temperature gradient program, and arrays were imaged using a BeadArray Reader 1000 scanner (Barker et al. *Proc. SPIE* 4966: 1-11 (2003)). Image processing and intensity data extraction software were as describe previously (Galinsky, *Bioinformatics* 19, 1832-6 (2003)).

Microarrays were assembled by loading pools of glass beads (3 μm in diameter) derivatized with oligos onto the etched ends of fiber-optic bundles (Barker et al., supra, 2003). About 50,000 optical fibers are hexagonally packed to form an approximately 1.4 mm diameter bundle. The fiber optic bundles are assembled into a 96-array matrix, Sentrix® Array Matrix, which matches the dimensions of standard microtiter plates. This arrangement allows simultaneous processing of 96 samples using standard robotics (Fan et al. supra, 2003). Because the beads are positioned randomly, a decoding process is carried out to determine the location and identity of each bead in every array location (Gunderson, *Genome Res* 14, 870-7 (2004)). Decoding is an automated part of array manufacture.

Methylation Data Analysis

Each methylation data point is represented by fluorescent signals from the M (methylated) and U (unmethylated) alleles. M and U signals were initially computed and normalized by requiring each sample to have the same average signal in each of the two fluorescent channels. Background intensity computed from a set of negative controls was subtracted from each of the analytical data point prior to normalization. The ratio of fluorescent signals from the two alleles $$\beta = \frac{\max(M, 0)}{|U| + |M| + 100}.$$

The β value reflects the methylation status of each CpG locus, ranging from 0 in the cases of completely unmethylated sites to 1 in completely methylated sites. A constant offset of 100 was added to the denominator of the formula, as a compensation for any "negative signals" which may arise from global background subtraction (i.e. over-subtraction). Hierarchical clustering was performed using average linkage method and Pierson's correlation coefficient (r) as a similarity measure. K-nearest neighbor class prediction was done using 1−r for distance calculation and k=1 (nearest neighbor).

To choose optimal number of neighbor k, classification of the training set was performed first with different values of k. Leave-one-out cross validation gave misclassification rate of 0.03 (one out of 32 samples) using k=1. This result did not improve with a larger k.

Figures 1, 1B:
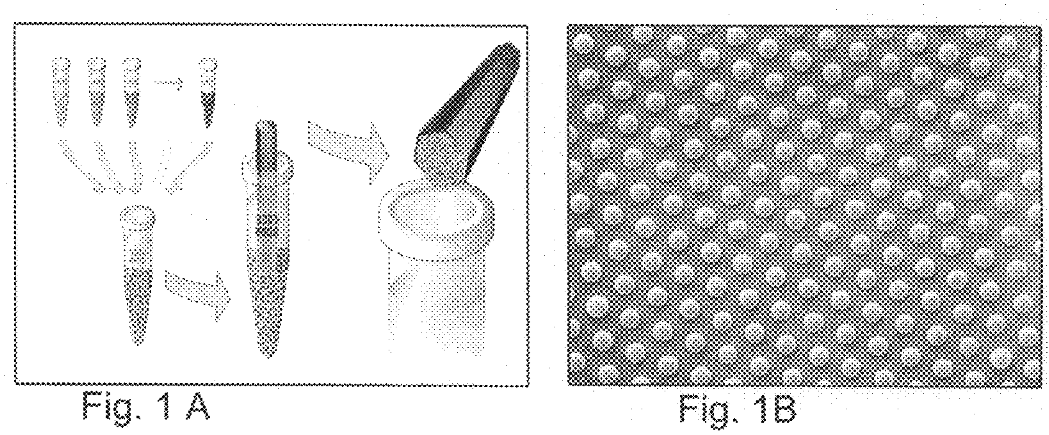
FIG. 1 shows an assembly of a randomly ordered fiber optic array. Panel A shows a collection of bead types, each with a distinct oligonucleotide capture probe, is pooled. An etched fiber optic bundle is dipped into the bead pool, allowing individual beads to assemble into the microwells at the bundle's end. Panel B shows a scanning electron micrograph of an assembled array containing 3 micron diameter silica beads with 5 micron core-to-core spacing between features. The beads are stably associated with the wells under standard hybridization conditions.

According to the above-described protocols, for each CpG locus, four probes were designed: two allele-specific oligos (ASOs) and two locus-specific oligos (LSOs), each corresponding to the methylated or unmethylated state of the CpG site respectively (FIG. 1). Each ASO consists of a 3' portion that hybridizes to the bisulfite-converted genomic DNA, with the 3' base complementary to either the "C" or "T" allele of the targeted CpG locus, and a 5' portion that incorporates a universal PCR primer sequence (P1 or P2, each associated with an allele respectively). The LSOs consists of three parts: At the 5' end is a CpG locus-specific sequence; in the middle is an address sequence, complementary to a corresponding capture sequence on the array; and at the 3' end is a universal PCR priming site (P3). The flexibility in primer design (the gap size between the ASO and LSO oligos varies from 1 base to 20 bases) is particularly important for methylation studies, since it can be implemented in a way that will avoid difficult sequences or ambiguous bases in the CpG islands of interest. In this study, assay oligos were designed for 389 CpG sites from the 5'-regulatory region of 141 genes.

Typically, 144-160 CpG sites were assayed together. Pooled assay oligos were first annealed to bisulfite-converted genomic DNA. An allele-specific primer extension step was then carried out; ASOs got extended if their 3' base is complementary to their cognate CpG site in the gDNA template. Allele-specific extension was followed by ligation of the extended ASOs to their corresponding LSOs, to create PCR templates. Requiring the joining of two fragments to create a PCR template provides an additional level of genomic specificity. Any incorrectly hybridized ASOs and LSOs are unlikely to be adjacent, and therefore should not be able to ligate.

The ligated products were then amplified by PCR using common primers P1, P2, and P3, and hybridized to a microarray bearing the complementary address sequences. P1 and P2 are fluorescently labeled, each with a different dye, and associated with the “T” (unmethylated) allele or the “C” (methylated) allele respectively. As described in this example, methylation status of an interrogated locus is determined by quantifying β, which is defined as the ratio of the fluorescent signal from the methylated allele to the sum of the fluorescent signals of both methylated and unmethylated alleles.

Development of reliable internal controls is a prerequisite for development of a robust methylation detection method. Plasmids pUC19, pACYC184 and phagephiX174 as internal control DNAs. These DNAs (unmethylated, methylated or mixed at a 1:1 ratio) were spiked into 200 ng human genomic DNA at a 1:1 molar ratio (at approximately 2-4 pg plasmid DNA/1 μg gDNA, depending on the plasmid size), and were used in every methylation experiment to monitor both bisulfite conversion efficiency and accuracy of methylation detection. As shown in FIG. 2, unmethylated, semi-methylated and fully-methylated plasmid loci can be easily distinguished by the assay.

“Methylated” and “fully unmethylated” genomic templates were developed to calibrate quantitative measurements of methylation. The fully unmethylated templates were generated by genome-wide amplification of human genomic DNA using REPLI-g® DNA amplification kit (Molecular Staging). After this amplification, the endogenous DNA methylation is diluted at least 100 to 1000-fold, effectively rendering the amplified genomic DNA “unmethylated”. Methylated templates were generated by in vitro methylation using Sss I (CpG-methylase) enzyme (New England BioLabs). Among the 389 CpG sites targeted, 70 of them can only be methylated to less than 50% completion. Some of these sites may be less accessible to methylase because of the DNA secondary structure; some may result from base substitution at the CpG sites in the DNA tested, i.e. these sites become “methylation-resistant” (it is well known that CpG sites are mutation hot spots).

The above two reference templates were used for assay development and 20 CpG assays were disqualified due to similar β values for both unmethylated and methylated templates (a threshold of $\Delta\beta>0.1$ was applied). Therefore, the data analyses is based on the remaining 369 functional CpG assays.

As described above, the use of bisulfite conversion of DNA for methylation detection is based on the different sensitivity of cytosine and 5-methylcytosine to deamination by bisulfite. Under acidic conditions, cytosine undergoes conversion to uracil, while methylated cytosine remains unreactive. Thus, an effective bisulfite conversion protocol is a necessary prerequisite for a robust methylation profiling assay. Incomplete conversion of cytosine to uracil by bisulfite can result in appearance of false-positive signals for 5-methylcytosine, and reduce the overall quality of the assay data. In order to monitor the effectiveness of bisulfite treatment, a set of oligos (a standard set of SNP genotyping probes) designed for unconverted genomic DNA sequences was used in the assay. If bisulfite conversion is successful, the signal from assays designed against the unconverted DNA (i.e. the SNP set) will disappear, and only signals from assays designed against the converted DNA are present. Incomplete conversion results in low and inconsistent signals across all loci targeted to both unconverted and converted DNA.

Figure 21:
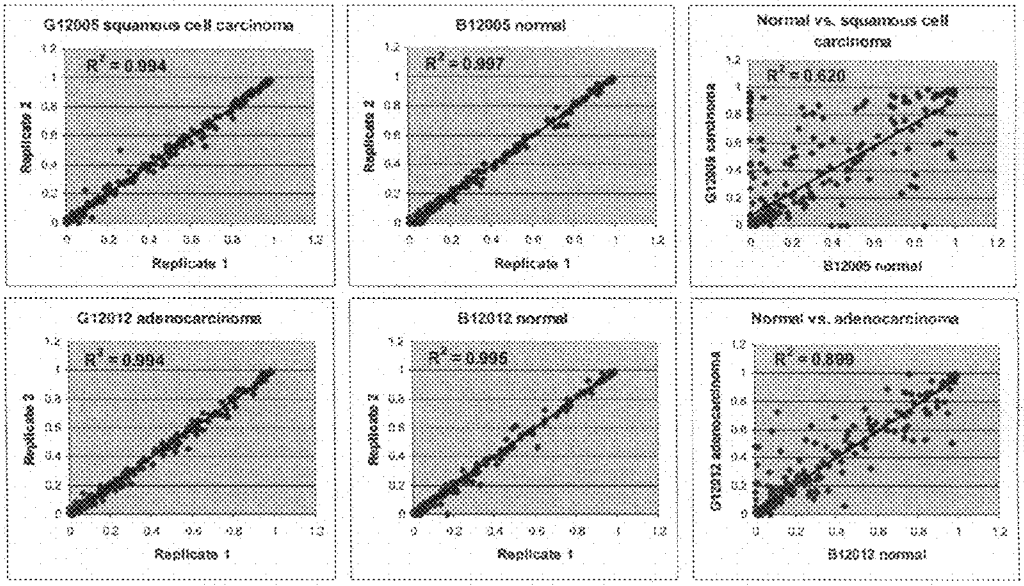
FIG. 21 shows a comparison of methylation profiles among lung cancer and matching normal tissues. The β-value (i.e. the methylation ratio measured for all the functional CpG sites) obtained from one replicate experiment is plotted against that obtained from another replicate experiment. The upper panels show the reproducibility of replicate assays on DNA derived from squamous cell carcinoma G12005 (left) and its matching normal tissue (center), and a comparison between the normal and the squamous cell carcinoma (right). The lower panels show the reproducibility of replicate assays on DNA derived from lung adenocarcinoma G12012 (left) and its matching normal tissue (center), and a comparison between the normal and the adenocarcinoma (right).

Each gDNA sample was assayed in duplicate (Table 4). According to the methods described herein, highly reproducible DNA methylation profiles within replicates were obtained with 200 ng genomic DNA (average $r^2$ was 0.97) (FIG. 21, left and center panels). As a result, differential methylation between different samples was readily detected (FIG. 3, right panel).

Figure 16:
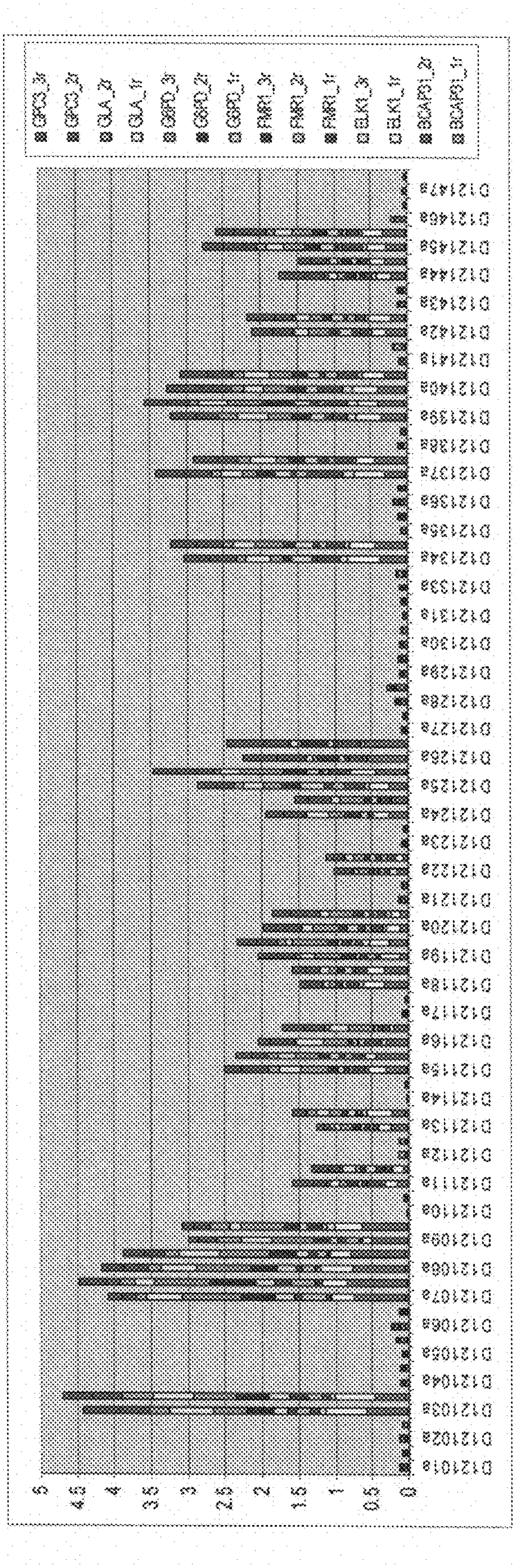
FIG. 16 shows correlation between methylation levels and gender based on methylation status of 6 genes located on the X-chromosome as monitored in 46 samples.
Figure 17:
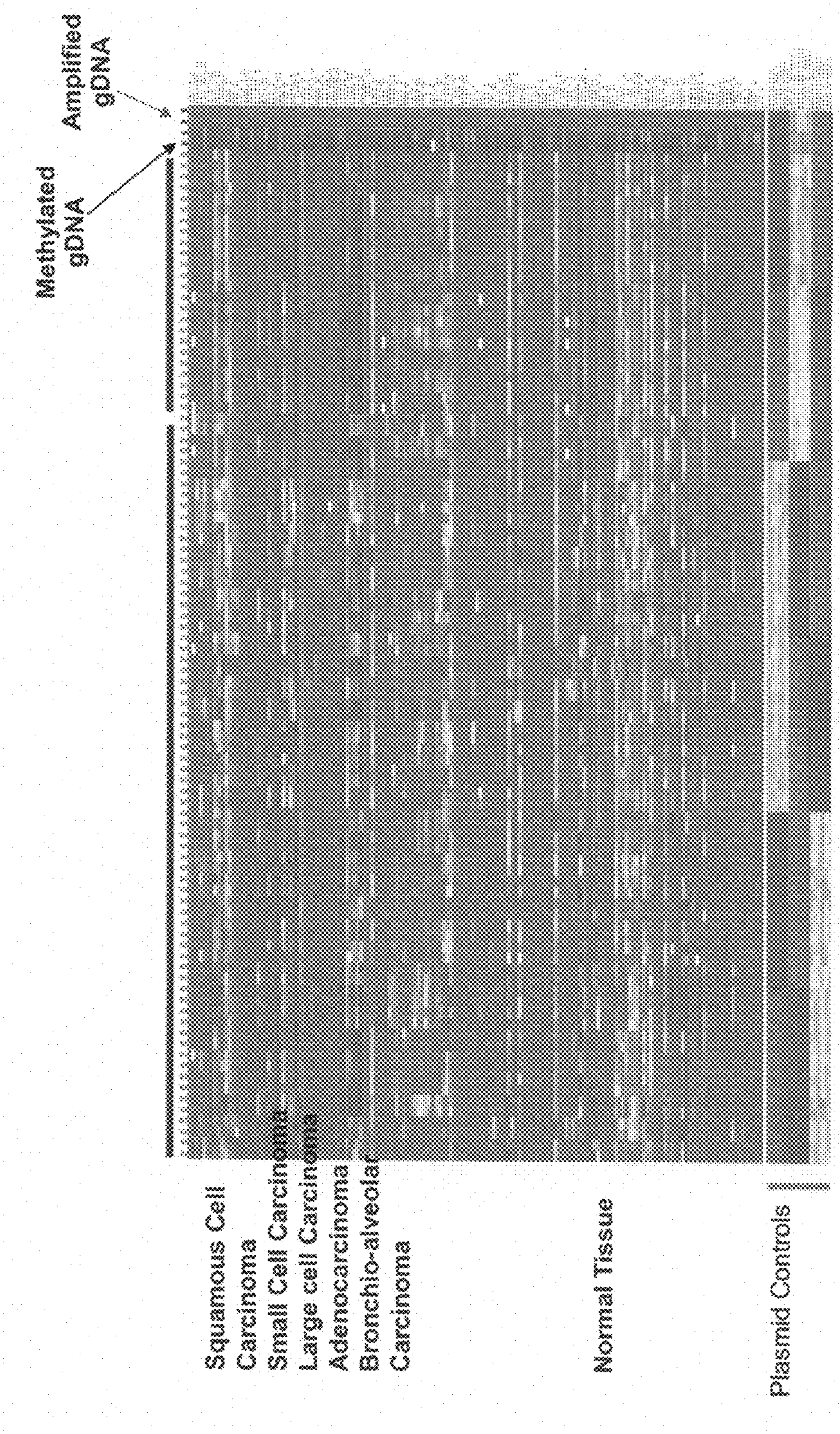
FIG. 17 shows methylation profiling in 46 lung cancer and matched normal tissues based on interrogation of 162 CpG sites. Unmethylated (green), semi-methylated (yellow), methylated (red).
Figure 18:
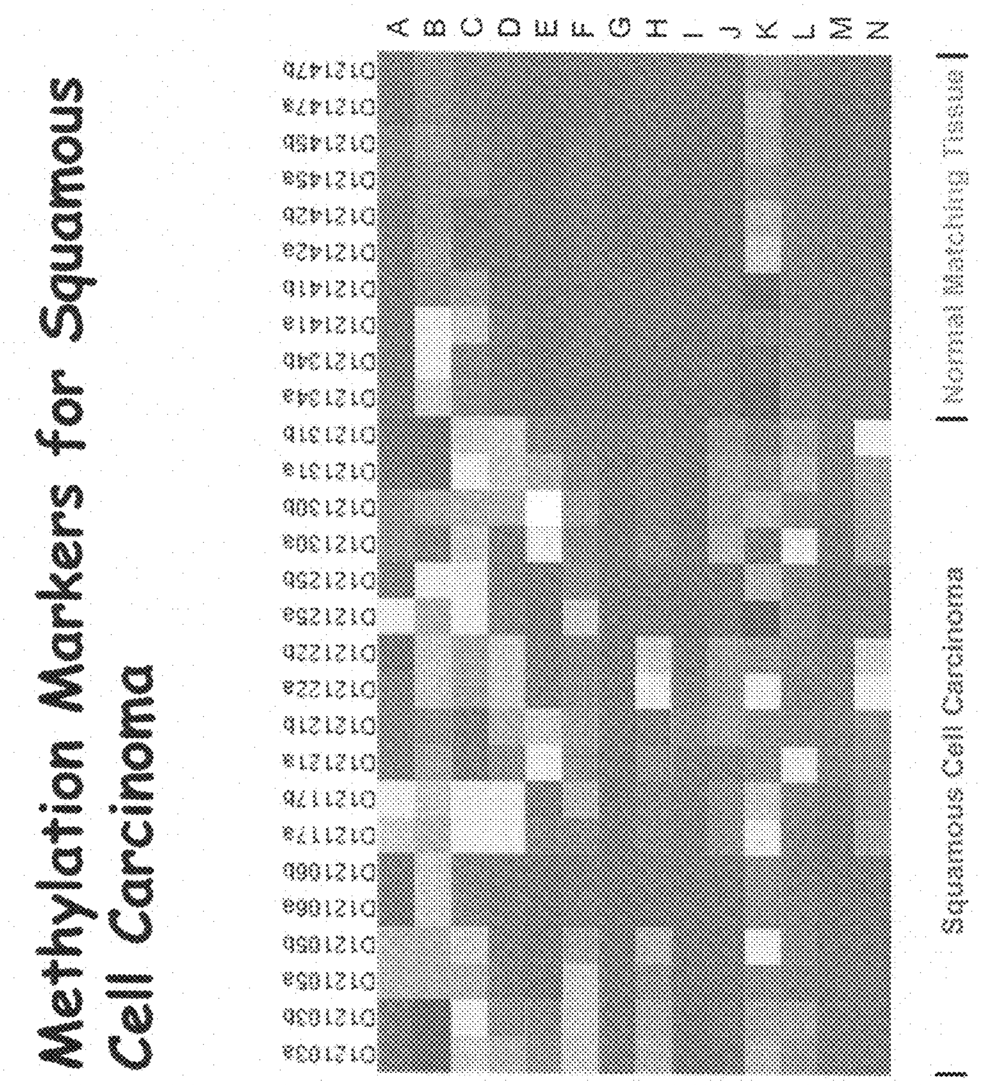
FIG. 18 shows distinct methylation patterns observed for 14 markers in sqamous cell carcinoma versus normal matching tissue.
Figure 19:
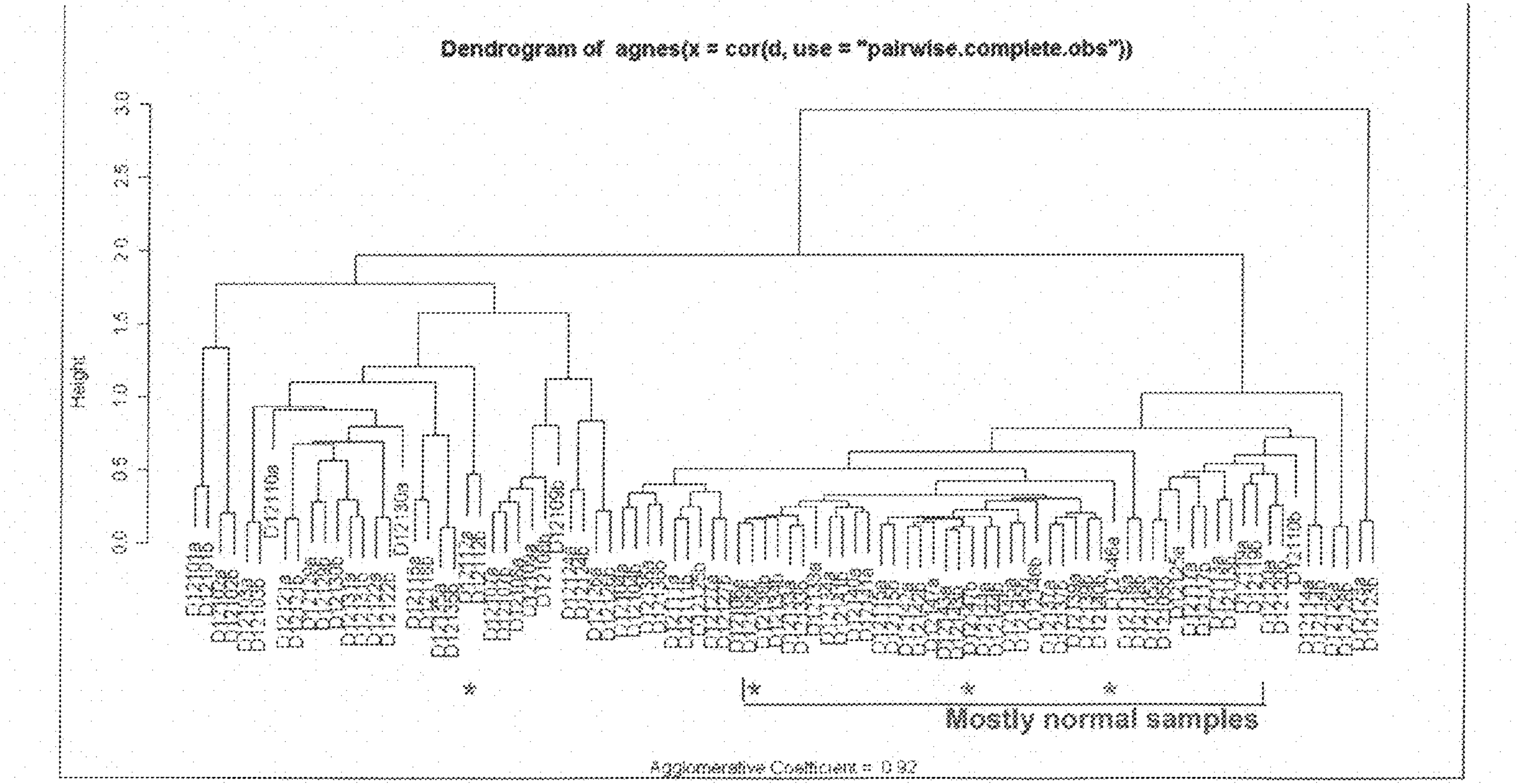
FIG. 19 shows cluster analysis of methylation profiles in 46 lung cancer samples which demonstrates good separation of cancer samples from normal matching pairs.
Figure 22:
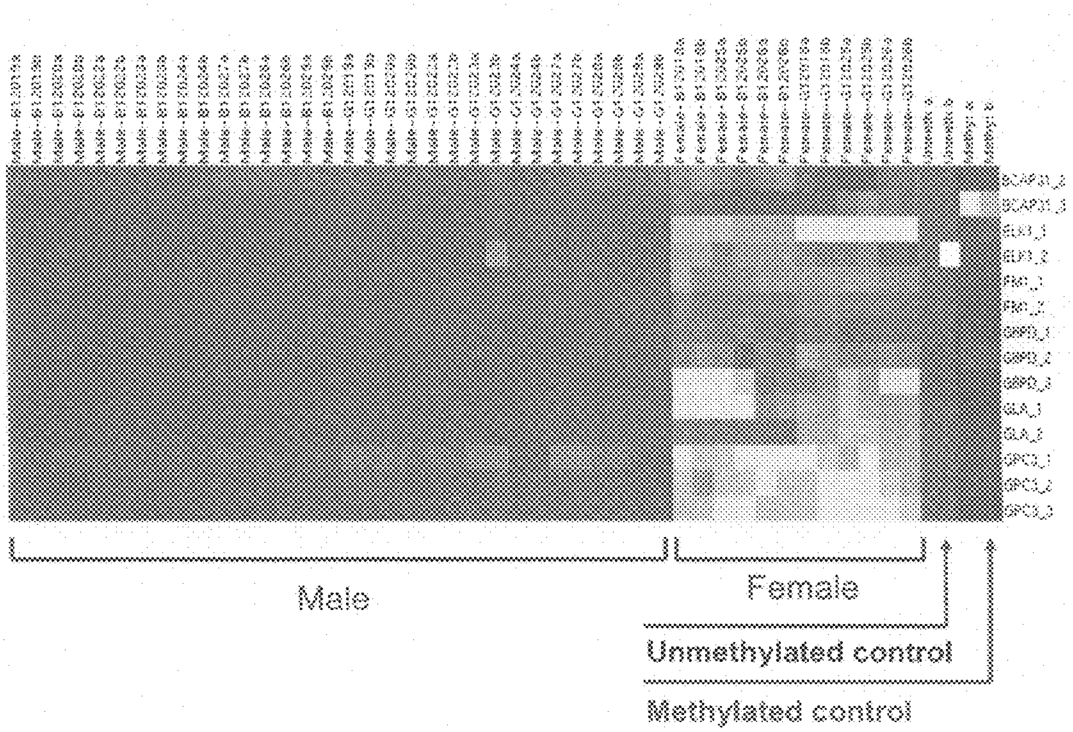
FIG. 22 shows methylation profiles of 6 housekeeping genes located on the X-chromosome. Data are shown for 14 CpG loci in 16 males and 6 females, which include adenocarcinomas and their matching normal tissue samples, and the two reference samples. Replicate measurements are shown in adjacent for each sample.

As described above, DNA methylation is involved in transcriptional inactivation of genes on one of the two X-chromosomes in female somatic cells (i.e. X-chromosome silencing), compensating the dosage of functional X-linked genes between male and female. The methylation status of six X-linked housekeeping genes—BCAP31, GPC3, FMR, ELK1, G6PD and GLA, was analyzed to test if the assay could detect the methylation difference between males and females. As shown in FIGS. 16 and 22, methylation levels of these genes correlated well with the gender of the sample source.

There are four major histologic types of lung carcinomas: squamous cell carcinoma, small cell carcinoma, large cell carcinoma, and adenocarcinoma. The methylation status of 369 CpG sites located in the 5'-regulatory regions of 141 genes in 14 squamous cell carcinoma, 24 adenocarcinoma and 33 normal tissue samples was measured. The genes were selected based on their biological relevance. These include tumor suppressor genes and oncogenes, genes that are indirectly involved in cancer development, for example, DNA repair genes; metastasis-inhibitor genes, genes regulated by various signaling pathways, and/or responsible for altered cell growth, differentiation and apoptosis; genes considered to be targets for oncogenic transformation; imprinting genes; previously reported differentially methylated genes (Esteller, *Oncogene* 21, 5427-40 (2002), Tsou et al., *Oncogene* 21, 5450-61 (2002); Adorjan et al., *Nucleic Acids Res* 30, e21 (2002)).

A data matrix of β values was used to identify CpG loci that show differential methylation in cancer. Using a Mann-Whitney test, 21 normal samples were first compared to 11 adenocarcinoma samples referred thereafter the “training set”. With a p-value cutoff of 1/369, 79 differentially methylated loci were identified. By choice of this p-value threshold, only one false positive marker was expected and this prediction was verified by randomly permuting columns in the data matrix and repeating Mann-Whitney test. Since the permutation process is independent of disease status, it provides an accurate estimate of actual false positive rate. On average, 0.63 differentially methylated markers were observed, indicating a lower than expected actual false positive rate, which is not surprising since not all CpG loci can be considered as independent variables. To select markers which have the largest difference between cancer and normal tissues (assuming this would cause the largest biological changes), an additional filter requiring $|\Delta\beta|>0.2$ was required. Ultimately, a list of 14 differentially methylated markers was obtained: ADCYAP1_2, CDH13_3, GDF10_2, GDF10_3, HOXA5_2, MAGEA1_3, RUNX3_1, SCGB3A1_3, SERPINB5_1, SFN_2, SFTPA1_2, TERT_1, TERT_2, and TNF_2 (FIG. 23A).

The same differential methylation analysis was subsequently performed for the same 21 normal samples and 14 squamous cell carcinoma samples. When the same p-value threshold and $|\Delta\beta|>0.2$ filtering was used, the following list of 21 differentially methylated markers was obtained: ADCYAP1_1, ADCYAP1_2, ADCYAP1_3, BCR_2, CALCA_1, GDF10_3, HOXA5_1, HOXA5_2, HOXA5_3, MAGEA1_1, MAGEA1_2, PGR_2, PRKCDBP_3, SCGB3A1_3, SERPINB5_1, SFN_2, SFTPC_3, TERT_I, TERT_2, TERT_3, TNF_2 (FIG. 23B).

Figure 24A:
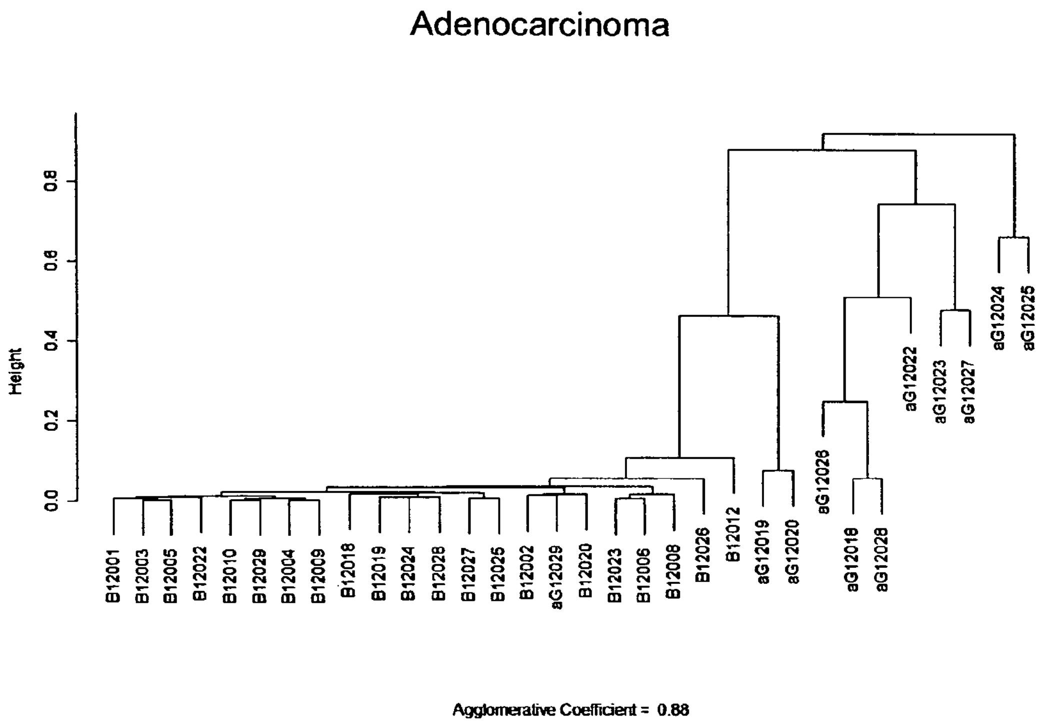
FIG. 24 shows a cluster analysis of lung cancer samples based on methylation profiles. Panel 24A shows adenocarcinoma (training set). Panel 24B shows squamous cell carcinoma (training set). Panel 24C shows adenocarcinoma (test set).
Figure 24B:
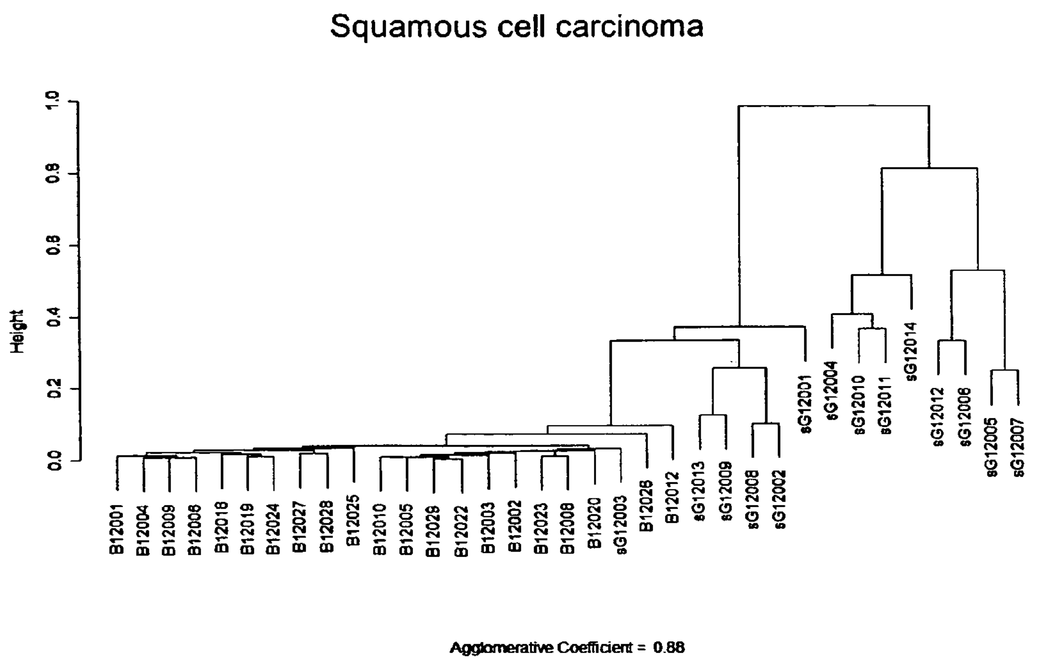

In addition, methylation profiles of the cancer and normal samples were clustered using the selected markers. Normal samples formed a tight cluster (i.e. small cluster distances) in both adenocarcinoma and squamous cell carcinoma groups (FIGS. 24A & 24B). Two early stage cancer samples, G12029 (FIG. 24A) and G12003 (FIG. 24B), were co-clustered with normal samples. Quite large cluster distances existed among cancer samples which may reflect different disease stages.

An independent set of test samples was used to assess the specificity and sensitivity of the 14 adenocarcinoma markers. This test set contained 11 normal and 14 adenocarcinoma samples. We classified these samples using a k-nearest neighbor algorithm. The misclassification rate in the test set was 0.04, with one cancer sample (D12190) misclassified as normal. The 14 markers also were evaluated by measuring their p-values from Mann-Whitney test with the test sample set. The p-values ranged between 0.00017 and 0.029. Finally, the classification accuracy derived from these 14 specific markers and randomly selected 1,000 sets of 14 CpG loci was measured. Only 2.2% of the 1,000 random sets produced same or lower misclassification rates as compared to the 14 markers, with an average misclassification rate being 28%. The above-described analyses indicate that the differential methylation pattern for the identified markers is preserved in the two completely unrelated sample sets and the identified markers can be used to distinguish adenocarcinoma from normal tissue with high specificity and sensitivity.

Figure 24C:
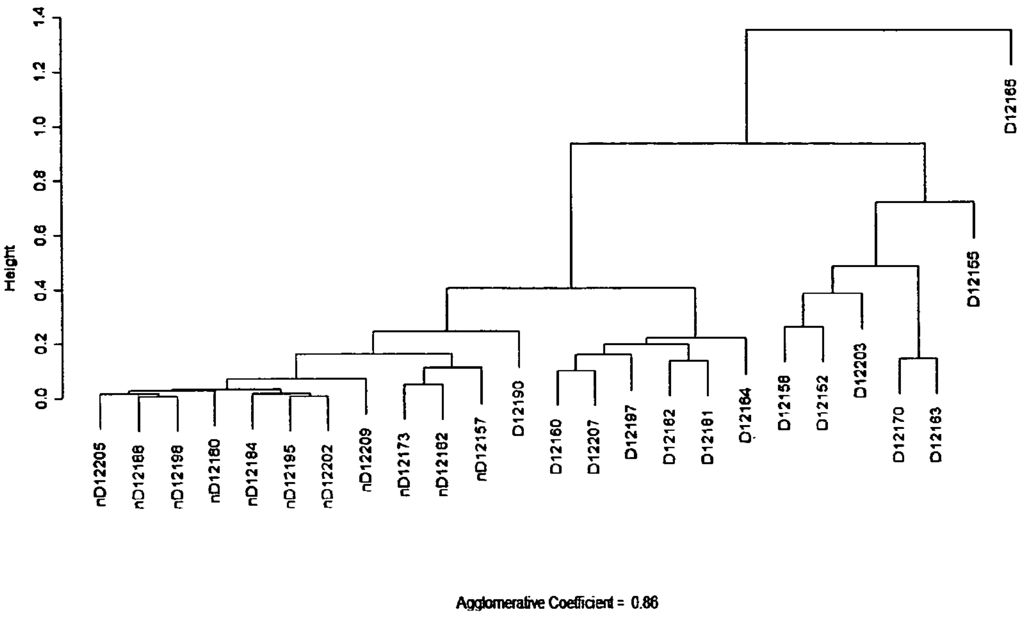
Figure 25:
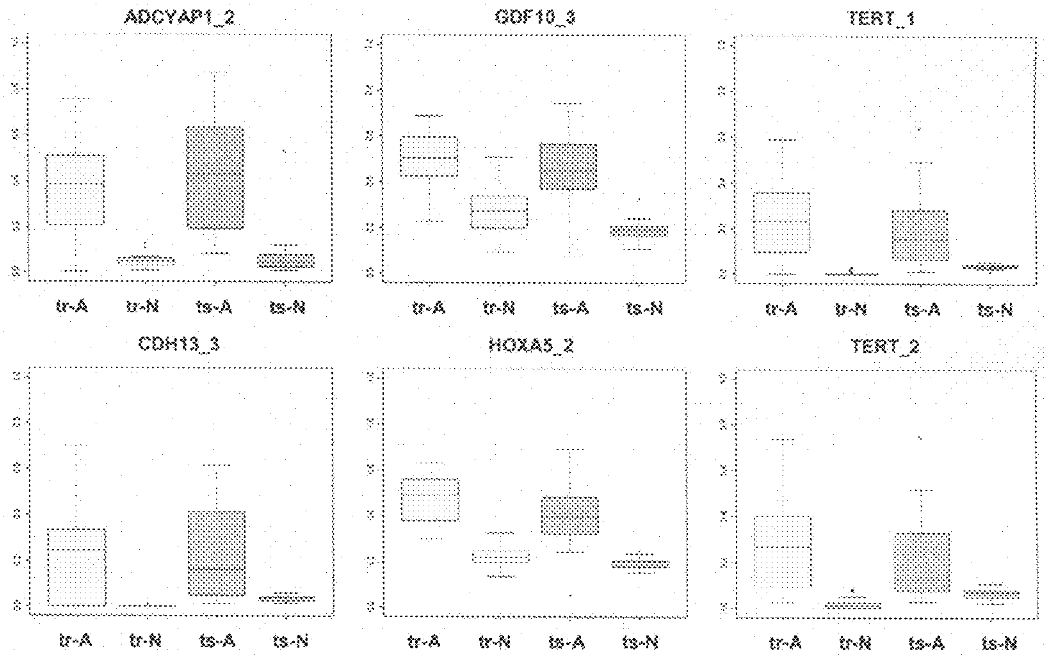
FIG. 25 shows box plots of the array data for selected cancer-specific methylation markers. β-values (y-axis) were calculated for the six adenocarcinoma cancer markers. For the training set (yellow plots), 11 adenocarcinoma and 21 normal tissues were used. For the validation set (grey plots), 13 adenocarcinoma and 12 normal tissues were used. The black bar represents the mean β-value. The box defines quartiles (25% and 75%, respectively). The error bars are upper and lower adjacent limits (median +/−1.5*IQR). Dots represent the outliers.

These results are further demonstrated by cluster analysis of the methylation patterns of the 14 identified markers in the test set samples. As shown in FIG. 24C, the cancer and normal samples are clearly separated. The array data for some of the markers which show increased methylation in cancer samples was plotted to illustrate their performance in both training set and test set of samples (FIG. 25).

Throughout this application various publications have been referenced. The disclosures of these publications in their entireties are hereby incorporated by reference in this application in order to more fully describe the state of the art to which this invention pertains.

The term "comprising" is intended herein to be open-ended, including not only the cited elements, but further encompassing any additional elements.

Unless defined otherwise, all technical and scientific terms used herein have the same meaning as commonly understood by one of ordinary skill in the art to which the invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29736559_ESR2_1R (SEQ ID 1) | NT_026437 | GGATGCTCCTCAGCTCTGGGGACGCGGTGC AGAAGTGTGAGGGCGCC | GCCCTCACACTTCTACACCG | GTCCCCAAAACTAAAAAACATC | AACACCCTCACACTTCTACACCA |
| GI29736559_ESR2_2R (SEQ ID 2) | NT_026437 | CTTCCGACTTTGTCACACACCTGCGCCGCC AGACTGGGGTCGGGCCCC | CCGACTTTATCACACACCTACG | CGCCAAACTAAAATCGAACC | CTTCCAACTTTATCACACACCTACA |
| GI29736559_ESR1_3R (SEQ ID 3) | NT_026437 | CCCGGCTTCCAGGCAGTAATGGGCGGGTCC CTGCGCGGGAGCGTGGCGGGCG | CGACTTCCAAACAATAATAAAG | ATCCCTACGCGAAAACGTAAC | CCCAACTTCCAAACAATAATAAACA |
| GI29791372_TGFBR2_1R (SEQ ID 4) | NT_022517 | AATCTGAAGAAAGCTGAGGGGAGGCGGCAG ATGTTCTGATCTACTAGGGA | CCCTAATAAATCAAAACATCCG | CTCCCCTCAACTTTCTTCAAAT | TCCCTAATAAATCAAAACATCTACCA |
| GI29791372_TGFBR2_2R (SEQ ID 5) | NT_022517 | AACTCCTGAGTGGTGTGGGAGGGCGGTGAG GGGCAGCTGAAAGTC | ACTTTCAACTACCCCTCACCG | CCTCCCACACCACTCAAAAATT | AACTTTCAACTACCCCTCACCA |
| GI29791372_TGFBR2_3R (SEQ ID 6) | NT_022517 | TGGTCTAGGAAACGATGATTGGCAGCTACG AGAGAGCTAGGGGCTGGACGT | GTCCAACCCCTAACTCTCTCG | AACTACCAATCATATTTCCTAAACCA | ACATCCAACCCCTAACTCTCTCA |
| GI29791384_TP73_1R (SEQ ID 7) | NT_004321 | CCGAGGAGCCCAGCGCTACTGGCGGCGGCC AGGAGAGACCCGGGTGTCA | ACCCGAATCTCTCCTAACCG | CGCCACTAACGCTAAACTCCT | TAACACCCAAATCTCTCCTAACCA |
| GI29791384_TP73_2R (SEQ ID 8) | NT_004321 | GACAGCAGGGAGTCCGGGGGAAACGCAGGC GTCGGGCACAGAGTCGG | ACTCTATACCCGACGCCTACG | TTCCCCCGAACTCCCTACTAT | CCAACCTATACCCAACACCTACA |
| GI29791384_TP73_3R (SEQ ID 9) | NT_004321 | GGCCCTGGCGCCGGACCTGCTTCGGCCCTG CGTGGGCGGCCTCGCCGG | CTAACGCCGAACCTACTTCG | CCCTACGTAAACGACCTCGC | AACCCTAACACCAAACCTACTTCA |
| GI29791621_PTGS2_1R (SEQ ID 10) | NT_004487 | TCGGAAGCGCTCGGGCAAAGACTGCGAAGA AGAAAAGACATCTGGCGG | CGCCAAATATCTTTTCTTCTTCG | AATCTTTACCCGAACGCTTCC | CCACCAAATATCTTTTCTTCTTCA |
| GI29791621_PTGS2_3R (SEQ ID 11) | NT_004487 | AGTCTGTCCCGACGTGACTTCCTCGTACCC TCTAAAGACGTACAGACCAGA | TATCCCGACGTAACTTCCTCG | CCCTCTAAAAACGTACAAACCAA | AATCTATCCCAACATAACTTCCTCA |
| GI29793179_DAPK1_1R (SEQ ID 12) | NT_023935 | GCGCCGGCCTGGCAGGGCAGCTCGGAGGTG GGTGGGCCGCGCCGCCAGC | CCGACCTAACAAAACAACTCG | AAATAAATAAACCGCGCCG | ACACCAACCTAACAAAACAACTCA |
| GI29793179_DAPK1_3R (SEQ ID 13) | NT_023935 | AAACCTTCTTGCCTTCAAGCCTCGGCTCCA ACACCAGTCCGGCAGA | AACCTTCTTACCTTCAAACCTCG | CTCCAACACCAATCCGACA | AAACCTTCTTACCTTCAAACCTCA |
| GI29794150_CASP8_1R (SEQ ID 14) | NT_005403 | GGAAGTGAGAAACAACTGTGTGATAAACGG TGGAGAATGGGAGCACTCTC | AAATACTCCCATTCTCCACCG | TTATCACACACTTATTTCTCACTTCC | AAAAATACTCCCATTCTCCACCA |
| GI29794150_CASP8_2R (SEQ ID 15) | NT_005403 | GCGGGAGGAGACGAGGAGGGCGTTCCCTGG GGAGTGGCAGTG | ACTACCACTCCCCAAAAAACG | CCCCTCGTCTCCTCCC | CACTACCACTCCCCAAAAAACA |
| GI029794150_STAT1_1R (SEQ ID 16) | NT_005403 | AAGCCGGCGGAAATACCCCAGCGCGTGGGC GGAGCAGCGGCCCGCAGA | CGACGAAAATACCCCAACG | GTAAACGAAACAACGACCCG | AAACCAACAAAAATACCCCAACA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29794150_STAT1_2R (SEQ ID 17) | NT_005403 | GGCGGTGGCGCCCACGGAACAGCCGCGTCT AATTGGCTGAGCGCGGAGC | GCGCTCAACCAATTAAACG | GACTATTCCGTAAACGCCACC | ACTCCACACTCAACCAATTAAACA |
| GI29794150_STAT1_3R (SEQ ID 18) | NT_005403 | CCAGTTCCCAGCCTGGCAACACGGGACTGG GCTGCAGCTCACCCAGCCG | AATTCCCAACGTAACAACACG | AACTAAACTACAACTCACCCAACC | CCAATTCCCAACATAACAACACA |
| GI29794559_CDKN2A_1R (SEQ ID 19) | NT_008413 | GACTCACCCCTCCTTTCTGCCGCTCCTTCC TTTCCTTGCCCTGCTTT | ACTCACCCCTCCTTTCTACCG | TCCTTCCTTTCCTTACCCTACTTT | AACTCAGCCCTCCTTTCTACCA |
| GI29794559_CDKN2A_2R (SEQ ID 20) | NT_008413 | GCCCGCGTCCGAGTTCCTGGACGAGAGCCG AGCCTCGCTTAGACCGC | GCGTCCGAATTCCTAAACG | AAACCGAACCTCGCTTAAACC | ACCCACATCCAAATTCCTAAACA |
| GI29794559_CDKN2A_3R (SEQ ID 21) | NT_008413 | TCCAGCCCGCGAGGTTTAGGACGGATCCAG GCAGACCGCAGGCTCC | AACCCGCGAAAMAAAACG | ATCCAAACAAACCGCAAACT | TCCAACCCACAAAATTTAAAACA |
| GI29794559_CDKN2B_1R (SEQ ID 22) | NT_008413 | AGCAGTGCAGCCAGCATTCCTGGCGGCTCC CTGGCCCAGTCTCTGGCGCA | CAATACAACCAACATTCCTAACG | CTCCCTAACCCAATCTCTAACG | AACAATACAACCAACATTCCTAACA |
| GI29794559_CDKN2B_2R (SEQ ID 23) | NT_008413 | GGCTGAAGGMCAGAAATCCTCTGCTCCGCC TACTGGGGATTAGGAGCTG | CAACTCCTAATCCCCAATAAACG | AACAAAAAATTTCTATTCCTTCAACC | CAACTCCTAATCCCCAATAAACA |
| GI29794559_CDKN2B_3R (SEQ ID 24) | NT_008413 | AGCATCTTTGGGCAGGCTTCCCCGCCCTCG TGACGCGTCGGCCCGGGC | CATCTTTAAACAAACTTCCCCG | CCTCGTAACGCGTCGAC | AACATCAAAAACAAACTTCCCCA |
| GI29796774_MYC_1R (SEQ ID 25) | NT_008046 | AGAGCAGGCAACCTCCCTCTCGCCCTAGCC CAGCTCTGGAACAGGCAG | AAACAAACAACCTCCCTCTCG | CCTAACCCAACTCTAAAACAAACAA | AAAACAAACAACCTCCCTCTCA |
| GI29796774_MYC_2R (SEQ ID 26) | NT_008046 | ACCMGATTTCTCCCAAACCCGGCAGCCCGA GACTGTTGCAAACCGG | CTTTAATITCTCCCAAACCCG | CAACCCGAAACTATTACAAACCG | ACCAAAATTTCTCCCAAACCCA |
| GI29796774_MYC_3R (SEQ ID 27) | NT_008046 | CAAGGGTCTCTGCTGACTCCCCCGGCTCGG TCCACAAGCTCTCCACTT | AAAAATCTCTACTAACTCCCCCG | CTCGATCCACAAACTCTCCACT | CAAAAATCTCTACTAACTCCCCCA |
| GI29797939_APC_1R (SEQ ID 28) | NT_034772 | CAGCAACACCTCTCACGCATGCGCATTGTA GTCTTCCCACCTCCCAC | AACAACACCTCTCACGCATACG | ATTATAATCTTCCCACCTCCCAC | CAACAACACCTCTCACACATACA |
| GI29797939_APC_2R (SEQ ID 29) | NT_034772 | GACAGAACAGCGAAGCAGTGCCCGGCAAGC GGAGCGCAGCACCCATTG | CAAAACAACGAAACAATACCCG | CAAACGAAACGCAACACC | AACAAAACAACAAAACAATACCCA |
| GI29797939_APC_3R (SEQ ID 30) | NT_034772 | CGCCGGAAGCCTAGCCGCTGCTCGGGGGGG ACCTGCGGGCTCAGGCCCG | CGAAAACCTAACCGCTACTCG | AAAAAACCTACGAACTCAAACCC | CACCAAAAACCTAACCACTACTCA |
| GI29798364_HIC1_1R (SEQ ID 31) | NT_010718 | TGCCCAGGCCGCAGGGCTGATGCCCCCGCT CAGCTGAGGGAAGGGGAAG | CCCCTTCCCTCAACTAAACG | AAACATCAACCCTACGACCTAAA | CTTCCCCTTCCCTCAACTAAACA |
| GI29798364_HIC1_2R (SEQ ID 32) | NT_010718 | CTCCTGCTCCTTCTCCTGGTCCGGGCGGGC CGGCCTGGGCTCCCACT | CTCCTACTCCTTCTCCTAATCCG | ACGAACCGACCTAAACTCCC | CTCCTACTCCTTCTCCTAATCCA |
| GI29798364_HIC1_3R (SEQ ID 33) | NT_010718 | AACTGGGGCAACTTCTCCCGAGGCGGGAGG CGCTGGTTCCTCGGCTCCC | TAAAACAACTTCTCCCGAAACG | AAAACGCTAATTCCTCGACTCC | AACTAAAACAACTTCTCCCAAAACA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29798364_TP53_1R (SEQ ID 34) | NT_010718 | GTTAGTATCTACGGCACCAGGTCGGCGAGA ATCCTGACTCTGCACCCTCCTC | TATCTACGACACCAAATCGACG | AAATCCTAACTCTACACCCTCCTC | ATTAATATCTACAACACCAAATCAACA |
| GI29798364_TP53_2R (SEQ ID 35) | NT_010718 | CTCCATTTCCMGCTTCCTCCGGCAGGCGGA TTACTTGCCC1TACTIGTCA | CCATTTCCMACTTCCTCCG | CAAACGAATTACTTACCCTTACTTATCA | CTCCATTTCCTTTACTTCCTCCA |
| GI29798364_TP53_3R (SEQ ID 36) | NT_010718 | CCCCGCCGCCTGCAGAGGGCGCAGCAGGTC TTGCACCTCTTCTGCATCTC | CGCCGCCTACAAAAAACG | AACAAATCTTACACCTCTTCTACATCTC | CCCCACCACCTACAAAAAACA |
| GI29798595_BRCA1_1R (SEQ ID 37) | NT_010755 | TTTCGTATTCTGAGAGGCTGCTGCTTAGCG GTAGCCCCTTGGTTTCCGTGG | CACGAAAACCAAAAAACTACCG | TAAACAACAACCTCTCAAAATACG | CCACAAAAACCAAAAAACTACCA |
| GI29798595_BRCA1_2R (SEQ ID 38) | NT_010755 | TGGGTGGCCAATCCAGAGCCCCGAGAGACG CTIGGCTCTTTCTGTCCCTCC | AATAACCAATCCAAAACCCCG | AAAACGCTTAACTCTTTCTATCCC | TAAATAACCAATCCAAAACCCCA |
| GI29798595_BRCA1_3R (SEQ ID 39) | NT_010755 | CTCAGGTAGAATTCTTCCTCTTCCGTCTCT TTCCTTTTACGTCATCCGGGG | CAAATAAAATTCTTCCTCTTCCG | CTCMCCUTTACGTCATCCG | CTCAAATAAAATTCTTCCTCTTCCA |
| GI29800185_PTEN_1R (SEQ ID 40) | NT_030059 | AGACTCGAGTCAGTGACACTGCTCAACGCA CCCATCTCAGCTTTCATCATCA | CTCGAATCAATAACACTACTCAACG | ACCCATCTCAACTTTCATCATCA | AAACTCAAATCAATAACACTACTCAACA |
| GI29800185_PTEN_2R (SEQ ID 41) | NT_030059 | AGGGTATTCCCCTTGCAGGGACCGTCCCTG CATTTTTCCTCTACACTGAG | AAATATTCCCCTTACAAAAACCG | CCCTACATTTCCCTCTACACTAAA | AAAATATTCCCCTTACAAAAACCA |
| GI29800185_PTEN_3R (SEQ ID 42) | NT_030059 | AAGGGAGCCGGATGAGGTGATACACGCTGG CGACACAATAGCAGGTTGCTCT | CAACCTACTATTATATCGCCAACG | ATATCACCTCATCCGACTCCCTT | AAAACAACCTACTATTATATCACCAACA |
| GI29800407_REL1 R (SEQ ID 43) | NT_033985 | CGGCTCTGCGTAGGTGCGCGGACCCGGGCT CCTGGGTTCCATCCCCGC | TACGTAAATACGCGAACCCG | ACTCCTAAATTCCATCCCCG | CAACTCTACATAAATACACAAACCCA |
| GI29800407_RET_2R (SEQ ID 44) | NT_033985 | GTCGGCCAGACCTGCATCCCGCGTAGCATC CCTGCCCTCTCTGTGCAGCG | CAAACCTACATCCCGCG | AACATCCCTACCCTCTCTATACAA | ATCAACCAAACCTACATCCCACA |
| GI29800407_RET_3R (SEQ ID 45) | NT_033985 | CCGCGGAGAGCCTGGAGGCGGGGCGCCCTT CTCTGAGTCCGCGGGGTCGC | CGAAAAACCTAAAAACGAAACG | CCTTCTCTAAATCCGCGAAAT | CCACAAAAAACCTAAAAACAAAACA |
| GI29800594_TGF131_1R (SEQ ID 46) | NT_011109 | CCCGTGCGCTTCCTGGGTGGGGCCGGGGGC GGCTTCAAAACCCCCTGCC | CGTACGCTTCCTAAATAAAACCG | AAACGACTTCAAAACCCCCTAC | CCCATACACTTCCTAAATAAAACCA |
| GI29800594_TGFB1_2R (SEQ ID 47) | NT_011109 | CTCTTTCTCTGGTGACCCACACCGCCCGCA AAGCCACAGCGCATCTGG | TCTTTCTCTAATAACCCACACCG | CCGCAAAACCACAACGC | CTCTTTCTCTAATAACCCACACCA |
| GI29800594_TGFB1_3R (SEQ ID 48) | NT_011109 | CCCAGCCTGACTCTCCTTCCGTTCTGGGTC CCCCTCCTCTGGTCG | CCAACCTAACTCTCCTTCCG | TCTAAATCCCCCTCCTCTAATCG | CCCAACCTAACTCTCCTTCCA |
| GI29802188_SNRPN_1R (SEQ ID 49) | NT_026446 | TCTCTTGAATCTTGACAATCCCCGAACACT GCTCCCCGCTTTATTTGTTTAG | TCTTAAATCTTAACAATCCCCG | ACACTACTCCCCGCTTTATTTATT | TCTCTTAAATCTTAACAATCCCCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29802188_SNRPN_2R (SEQ ID 50) | NT_026446 | TCCCTGGGTGCCTCCTGCGCAAGCGCAGTT GTCCTCCTGCGCCGACCTCG | CCTAAATACCTCCTACGCAAACG | AATTATCCTCCTACGCCGACCT | TCCCTAAATACCTCCTACACAAACA |
| GI29802395_GLA_1R (SEQ ID 51) | NT_011651 | GAAAGGAAGAGGGTGATTGGTTAGCGGAAC GTTTTACGTGACTGATTATTG | ATCAATCACGTAATTTCGTTCCG | TAACCAATCACCCTCTTCCTTTC | CAATAATCAATCACATAAAACATTCCA |
| GI29802395_GLA_2R (SEQ ID 52) | NT_011651 | ACACACCAACCTCTAACGATACCGGGTAAT TTTCCTCCTTCTTCCCTC | ACACCAACCTCTAACGATACCG | ATAATTTTCCTCCITCTTCCCTC | ACACACCAACCTCTAACAATACCA |
| GI29802395_GLA_3R (SEQ ID 53) | NT_011651 | AACTCAGGGCCGTGGTTTTCAAACGTTTTT CGCCTTACGGTCACCCTTAG | CTCAAAACCGTAATTTTCAAACG | TTTTCGCCTTACGATCACC | AACTCAAAACCATAATTTTCAAACA |
| GI29802670_AR_1R (SEQ ID 54) | NT_011669 | TAGAGCTAGCCTCTCCTGCCCTCGCCCACG CTGCGCCAGCACTAGTTTCT | AAAACTAACCTCTCCTACCCTCG | CCACGCTACGCCAACACTTAT | TAAAACTAACCTCTCCTACCCTCA |
| GI29802670_AR_2R (SEQ ID 55) | NT_011669 | TCCTAGAGCAAATGGCACAATGCCACGAGG CCCGATCTATCCCTATGACGGA | CCTAAAACAAATAACACAATACCACG | AACCCGATCTATCCCTATAACGA | TCCTAAAACAAATAACACAATACCACA |
| GI29802670_AR_3R (SEQ ID 56) | NT_011669 | CCGGTGGGGGCGGGACCCGACTCGCAAACT GTTGCATTTGCTCTCCACCTCC | ATAAAAACGAAACCCGACTCG | AAACTATTACATTTACTCACCACCTCC | CCAATAAAAACAAAACCCAACTCA |
| GI29802882_MAGEA1_1R (SEQ ID 57) | NT_011726 | TCCCGCCAGGAAACATCCGGGTGCCCGGAT GTGACGCCACTGACTTGCG | CAAATCAATAACGTCACATCCG | ACACCCGAATATTTCCTAACGTTT | CACAAATCAATAACATCACATCCA |
| GI29802882_MAGEA1_2R (SEQ ID 58) | NT_011726 | CTCAACCCTGATGCCCATCCGCCCAGCCAT TCCACCCTCA | CTCAACCCTAATACCCATCCG | CCAACCATTCCACCCTCA | CTCAACCCTAATACCCATCCA |
| GI29802882_MAGEA1_3R (SEQ ID 59) | NT_011726 | CCACTCCAATGCTCACTCCCGTGACCCAAC CCCCTCTTCATTGT | CCACTCCAATACTCACTCCCG | AACCCAACCCCCTCTTCATTAT | CCACTCCAATACTCACTCCCA |
| GI29804485_CTAG2_1R (SEQ ID 60) | NT_025965 | GACGGACAGGGCAGGCAGGGTCCGGGACGA TGGCCGCACAGTCCCGGC | CGAACAAAACAAACAAAATCCG | AACGATAACCGCACAATCC | AACAAACAAAACAAACAAAATCCA |
| GI29804485_CTAG2_2R (SEQ ID 61) | NT_025965 | GAGACCTTGGCTGGCGCGAGGCCACGCCCA CCAGACATGCAGTTCCAGCT | CTTAACTAACGCGAAACCACG | CCACCAAACATACAATTCCAACT | AAAACCTTAACTAACACAAAACCACA |
| GI29804485_CTAG2_3R (SEQ ID 62) | NT_025965 | GGGCGACTAGGACAGGGACAGAACCCGTTG AACCCAGGAGTGAGATCCGG | GAATCTCACTCCTAAATTCAACG | ATTCTATCCCTATCCTAATCGCC | CCAAATCTCACTCCTAAATTCAACA |
| GI29804185_G6PD_1R (SEQ ID 63) | NT_025965 | TCCCGCTCCGGAGAGAAGTCTGAGTCCGCC AGGCTCTGCAGGCCCGCGGA | GCGAACCTACAAAACCTAACG | ACTCAAACTTCTCTCCGAAACG | TCCACAAACCTACAAAACCTAACA |
| GI29804485_G6PD_2R (SEQ ID 64) | NT_025965 | CGGAAGCTCGGTAATGATAAGCACGCCGGC CACTTTGCAGGGCGTCACCGCC | ACTCGATAATAATAAACACGCCG | CCACTTTACAAAACGTCACCG | CAAAAACTCAATAATAATAAACACACCA |
| GI29804485_G6PD_3R (SEQ ID 65) | NT_025965 | CCCAATAGGGCCGGCTTGACCCGCGAACAG GCGAGGGTTCCCGGGGG | CCAATAAAACCGACTTAACCCG | GAACAAACGAAAATTCCCGA | CCCAATAAAACCAACTTAACCCA |
| GI29804485_SLC6A8_1R (SEQ ID 66) | NT_025965 | GGGAAGCTGTAGCCCCCAGTGGGCAGCGGT GGAGAGAGCTCAAGGAAGG | CTTCCTTAAACTCTCTCCACCG | TACCCACTAAAACTACAACTTCCC | CCTTCCTTAAACTCTCTCCACCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29804485_SLC6A8_2R (SEQ ID 67) | NT_025965 | GGTAGCAACCATCCTGCCTCCCGCTGGAGC GGCGTCTCCTCCCCGG | ATAACAACCATCCTACCTCCCG | TAAAACGACGTCTCCTCCCC | AATAACAACCATCCTACCTCCCA |
| GI29804485_SLC6A8_3R (SEQ ID 68) | NT_025965 | CCGGCCGGCCGTGGGGGTGGGGCGATAGTG ACATCACCCCGGAGTCGG | GACCGACCGTAAAAATAAAACG | TAATAACATCACCCCGAAATCG | CCAACCAACCATAAAAATAAAACA |
| GI29805823_GSTP1_2R (SEQ ID 69) | NT_033903 | CCTCTCCCCTGCCCTGTGAAGCGGGTGTGC AAGCTCCGGGATCGCAGCGG | CCTCTCCCCTACCCTATAAAACG | ATATACAAACTCCGAAATCGCAA | CCTCTCCCCTACCCTATAAAACA |
| GI29805823_GSTP1_3R (SEQ ID 70) | NT_033903 | CGGCCAGCTGCGCGGCGACTCCGGGGACTC CAGGGCGCCCCTCTGCG | AACTACGCGACGACTCCG | AAACTCCAAAACGCCCCTCTAC | CAACCAACTACACAACAACTCCA |
| GI29807292_BCR_1 R (SEQ ID 71) | NT 011520 | GCTGTGAGGTGTGAGGAACTTACCTGCGTC TCCATGGAAGGTGCCCTCCG | GAAAAACACCTTCCATAAAAACG | AAATAAATTCCTCACACCTCACAAC | CAAAAAACACCTTCCATAAAAACA |
| GI29807292_BCR_2R (SEQ ID 72) | NT_011520 | CTCTGACACGACGACTGGGCAGTGCCGGTG ACGCTTATGGCACTGCGGC | GCAATACCATAAACGTCACCG | CACTACCCAATCGTCGTATCAAA | ACCACAATACCATAAACATCACCA |
| GI29807292_BCR_3R (SEQ ID 73) | NT_011520 | GGGCTGCGAGTTGCACAGTCCAATTCGCTG TTGTTAGGGCCTCAGTTTCCCAAA | ACGAATTACACAATCCAATTCG | TATTATTAAAACCTCAATTTCCCAAA | AAACTACAAATTACACAATCCAATTCA |
| GI29807292_TIMP3_1R (SEQ ID 74) | NT_011520 | AAGGAGCAGTGGAAAGGGGTGACGAGTTCC TGGCTGGCCACCAATCATC | AATTAATAACCAACCAAAAACTCG | CACCCCTTTCCACTACTCCTT | AATAATTAATAACCAACCAAAAACTCA |
| GI29807292_TIMP3_2R (SEQ ID 75) | NT_011520 | AACTTGTGGCATTTCTAACAGGATGAAGCG GAAGAGAAAGGGAAAGAGA | TCTCTTCCCTTCTCTTCCG | TTCATCCTATTAAAAATACCACAAATT | TCTCTTCCCTTCTCTTCCA |
| GI29807454_CALCA_1R (SEQ ID 76) | NT_009237 | GGGGCGAGGGTTCAAAACCAGGCCGGACTG AGAGGTGAAATTCACCATG | AATAAATTTCACCTCTCAATCCG | CCTAATTTTAAACCCTCGCCC | CATAATAAATTTCACCTCTCAATCCA |
| GI29807454_CALCA_2R (SEQ ID 77) | NT_009237 | CAGGTTCTGGAAGCATGAGGGTGACGCAAC CCAGGGGCAAAGGACCCCT | AAAATCCTTTACCCCTAAATTACG | CACCCTCATACTTCCAAAACCTA | AAAAATCCTTTACCCCTAAATTACA |
| GI29807454_KAI1_1R (SEQ ID 78) | NT_009237 | CAGGGCAGGGCAGGATTAGGAAGGCGCTGA GCCCAGGCTGGTGCGG | GCACCAACCTAAACTCAACG | CTTCCTAATCCTACCCTACCCTA | CCACACCAACCTAAACTCAACA |
| GI29807454_KAI1_2R (SEQ ID 79) | NT_009237 | GATAGAGGAGAGACTCCGTAGCGGGGCGGG GCCTCAGCTCCAGCTGGGC | CCCAACTAAAACTAAAACCCCG | CCCGCTACGAAATCTCTCCT | ACCCAACTAAAACTAAAACCCCA |
| GI29807454_KAI1_3R (SEQ ID 80) | NT_009237 | GCCGCCTCCTGATAGAGGCCCCGACTTAGG ACACAAACCGCTCCCAC | GCCTCCTAATAAAAACCCCG | CTTAAAACACAAACCGCTCCC | ACCACCTCCTAATAAAAACCCCA |
| GI29807454_MYOD1_1R (SEQ ID 81) | NT_009237 | TTGCCTCTCTCCAAATCTCTCACGACCTGA TTTCTACAGCCGCTCTACCC | TACCTCTCTCCAAATCTCTCACG | CCTAATTTCTACAACCGCTCTACC | TTACCTCTCTCCAAATCTCTCACA |
| GI29807454_MYOD1_2R (SEQ ID 82) | NT_009237 | CTTTCTGCGTGTCTCTCAGCCTCTTTCGGT CCCTCTTTCACGGTCTCACTCC | TACGTATCTCTCAACCTCTTTCG | TCCCTCTTTCACGATCTCACTC | CTTTCTACATATCTCTCAACCTCTTTCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29807454_MYOD1_3R (SEQ ID 83) | NT_009237 | GGAATATCAGAGCCTCTACGACCCGTTTGT CTCGGGCTCGCCCACTTCAA | AATATCAAAACCTCTACGACCCG | TTATCTCGAACTCGCCCACTT | AAAATATCAAAACCTCTACAACCCA |
| GI29808625_CDH1_2R (SEQ ID 84) | NT_010498 | CGAACCCAGTGGAATCAGAACCGTGCAGGT CCCATAACCCACCTAGA | GAACCCAATAAAATCAAAACCG | ACAAATCCCATAACCCACCTAAA | CAAACCCAATAAAATCAAAACCA |
| GI29808625_CDH1_3R (SEQ ID 85) | NT_010498 | ACCCTCAGCCAATCAGCGGTACGGGGGGCG GTGCCTCCGGGGCTCACC | CCTCAACCAATCAACGATACG | AAAACGATACCTCCGAAACTCAC | ACCCTCAACCAATCAACAATACA |
| GI29823164_TYMS_1R (SEQ ID 86) | NT_010859 | CTGTGCTGCTGGCTTAGAGAAGGCGCGGTC GACCAGACGGTTCCCAAAGG | TTAAAAACCGTCTAATCGACCG | GCCTTCTCTAAACCAACAACACA | CCTTTAAAAACCATCTAATCAACCA |
| GI29823164_TYMS_2R (SEQ ID 87) | NT_010859 | GGCTCCGTTCTGTGCCACACCCGTGGCTCC TGCGTTTCCCCCTGGCG | TCCGTTCTATACCACACCCG | AACTCCTACGTTTCCCCCTAAC | AACTCCATTCTATACCACACCCA |
| GI29823171_BCL2_1R (SEQ ID 88) | NT_025028 | CGTGTGACGTTACGCACAGGAAACCGGTCG GGCTGTGCAGAGAATGAAGTAAG | TACTTCATTCTCTACACAACCCG | CCGATTTCCTATACGTAACGTCA | CTTACTTCATTCTCTACACAACCCA |
| GI29823171_BCL2_2R (SEQ ID 89) | NT_025028 | CGGGAGGCGGCCGTAGCCAGCGCCGCCGCG CAGGACCAGGAGGAGG | CCTCCTAATCCTACGCGACG | CGCTAACTACGACCGCCTC | CCTCCTCCTAATCCTACACAACA |
| GI29823171_BCL2_3R (SEQ ID 90) | NT_025028 | CCGTCAGCGCTCGGAGCGGGCTGCGCGGCG GGAGCTCCGGGAGGCGGCC | AACGCTCGAAACGAACTACG | GACGAAAACTCCGAAAAACGAC | CCATCAACACTCAAAACAAACTACA |
| GI29734309_SYK_1R (SEQ ID 91) | NT_008476 | GCCCAGCTCCGGGCTCATGGGCGCGGTCAG CAGGGCGGGCCAGGGCGG | CCAACTCCGAACTCATAAACG | GATCAACAAAACGAACCAAAACG | ACCCAACTCCAAACTCATAAACA |
| GI29734309_SYK_2R (SEQ ID 92) | NT_008476 | GGGCTCCTCTACACCTGCCGCCGCCTGGGC CGATTCCGCGGGCCTCG | ACTCCTCTACACCTACCGCCG | CTAAACCGATTCCGCGAAC | AAACTCCTCTACACCTACCACCA |
| GI29734309_SYK_3R (SEQ ID 93) | NT_008476 | GGACCGATGCGGTCCATGTCCCGGGCAGCC CCACCTTCTCTGCCTGC | ACCGATACGATCCATATCCCG | ACAACCCCACCTTCTCTACCTAC | AAACCAATACAATCCATATCCCA |
| GI29740881_HTR1B_1R (SEQ ID 94) | NT_007299 | GGGAATGCAAGATCTCGGGACCTCTCGCTG GCCTGCAAGCTTTGGTCTC | AAACCAAAACTTACAAACCAACG | AAAATCCCGAAATCTTACATTCC | AAAACCAAAACTTACAAACCAACA |
| GI29740881_HTR1B_2R (SEQ ID 95) | NT_007299 | GGCGGAGGAATAATTGAGGAACTCACGGAA CTATCAACTGGGGACAAACC | TTTATCCCCAATTAATAATTCCG | AAATTCCTCAATTATTCCTCCGC | AATTTATCCCCAATTAATAATTCCA |
| GI29740881_HTR1B_3R (SEQ ID 96) | NT_007299 | CCCTTTTATGGCTCCGTCTCCGCGGGGCAG CTCGTCCGAGTGGCCAGA | TTTATAACTCCGTCTCCGCG | AACAACTCGTCCGAATAACCAA | CCCTTTTATAACTCCATCTCCACA |
| GI29741420_MGMT_1R (SEQ ID 97) | NT_008818 | GGCTTGTACCGGCCGAAGGGCCATCCGGGT CAGGCGCACAGGGCAGCGG | CTACCCTATACGCCTAACCCG | ATAACCCTTCGACCGATACAAAC | CCACTACCCTATACACCTAACCCA |
| GI29741420_MGMT_2R (SEQ ID 98) | NT_008818 | GGCCGGCGTGCCGGCGTCCAGCGAGGATGC GCAGACTGCCTCAGGCCCG | ACGTACCGACGTCCAACG | AAATACGCAAACTACCTCAAACC | AACCAACATACCAACATCCAACA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29741420_MGMT_3R (SEQ ID 99) | NT_008818 | GACCACTCGGGCACGTGGCAGGTCGCTTGC ACGCCCGCGGACTATCCCT | CACTCGAACACGTAACAAATCG | TTACACGCCCGCGAACTAT | AACCACTCAAACACATAACAAATCA |
| GI29791697_CDC25A_1R (SEQ ID 100) | NT_005825 | GAAGTTGCTTACTGATTGGTGGATTCCGTT TGGCGCCAACTAGGAAAGGG | CTTTCCTAATTAACGCCAAACG | AATCCACCAATCAATAAACAACTTC | CCCTTTCCTAATTAACACCAAACA |
| GI29791697_CDC25A_2R (SEQ ID 101) | NT_005825 | GAGGCCGAGCCAAGGCTGGATCCGGCCAGA CCTCCACAGGTCTTCCTT | AACCGAACCAAAACTAAATCCG | CCAAACCTCCACAAATCTTCCTT | AAAACCAAACCAAAACTAAATCCA |
| GI29791697_CDC25A_3R (SEQ ID 102) | NT_005825 | CTCCAGAGTTGGGCCCTGGTGGTCGAGTCC AGTCCTGGGGGTCATTG | AATAACCCCCAAAACTAAACTCG | CCACCAAAACCCAACTCTAAAA | CAATAACCCCCAAAACTAAACTCA |
| GI29791697_PTHR1_1R (SEQ ID 103) | NT_005825 | GGGCCCAGCCCTGGGCATCTGAACACCGGC ACACTTGGATCTGCCTCTGTT | CAAAAACAAATCCAAATATACCG | TATTCAAATACCCAAAACTAAACCC | AACAAAAACAAATCCAAATATACCA |
| GI29791697_PTHR1_2R (SEQ ID 104) | NT_005825 | CAGCCCTGGGCATCTGAACACCGGCACACT TGGATCTGCCTCTGTTGCCTCC | CAACCCTAAACATCTAAACACCG | CACACTTAAATCTACCTCTATTACCTCC | CAACCCTAAACATCTAAACACCA |
| GI29791697_PTHR1_3R (SEQ ID 105) | NT_005825 | GGGGCTGTAGGGGTCAGGACACGGGCTGGA GTGGAATGA | TCATTCCACTCCAACCCG | ATCCTAACCCCTACAACCCC | TCATTCCACTCCAACCCA |
| GI29792366_SOD3_1R (SEQ ID 106) | NT_006316 | TCTGGGAAGTCTCCCTCTTATCTCGCAGAA TGCCTGTCCCTGGATAAAGATCATT | CTAAAAAATCTCCCTCTTATCTCG | AAAATACCTATCCCTAAATAAAAATCATT | TCTAAAAAATCTCCCTCTTATCTCA |
| GI29792366_SOD3_2R (SEQ ID 107) | NT_006316 | TTCTCAGCGGGCCAGAAGGAAGGACGGTAG GGTGGAAGGGCTG | AACCCTTCCACCCTACCG | CCTTCCTTCTAACCCGCTAAA | CAACCCTTCCACCCTACCA |
| GI29792366_SOD3_3R (SEQ ID 108) | NT_006316 | CACAAGTCCTAGAATACCAGAACGGAGACG TGCTTTCTTGGACCTTAAACGAAA | CACAAATCCTAAAATACCAAAACG | AAACGTACMCTTAAACCTTAAACG | CACAAATCCTAAAATACCAAAACA |
| GI29792503_VHL_1R (SEQ ID 109) | NT_005927 | CAAGGCTGCAGTGAGCCAAGCTCGCGCCAC TGCACTCCAGCCCGGGCGAC | AACTACAATAAACCAAACTCGCG | CACTACACTCCAACCCGAAC | CAAAACTACAATAAACCAAACTCACA |
| GI29792503_VHL_3R (SEQ ID 110) | NT_005927 | CCCGTGTGAGATGCGCCACCCTCGAACCTT GTTACGACGTCGGCACATTGCG | GTATAAAATACGCCACCCTCG | ACCTTATTACGACGTCGACACAT | CCCATATAAAATACACCACCCTCA |
| GI29793120_CD1A_1R (SEQ ID 111) | NT_004668 | GGGGAATTAAGACCCAATGGGCAATCCGTG ACTATTAGGGGATGGGA | CCCATCCCCTAATAATCACG | ATTACCCATTAAATCTTAATTCCCC | TCCCATCCCCTAATAATCACA |
| GI29793120_CD1A_2R (SEQ ID 112) | NT_004668 | CATAGCAGTAGCAGACATCTCTTGTACCGT GCCTTACACCTCAGCCCATTT | AACAATAACAAACATCTCTTATACCG | ACCTTACACCTCAACCCATTT | CATAACAATAACAAACATCTCTTATACCA |
| GI29793120_S100A2_1R (SEQ ID 113) | NT_004668 | AGACTGTGGCCCAGCCCAACTGCGGCTGTG TGTAGAGCAACCCCATTTCTCA | ACTATAACCCAACCCAACTACG | CTATATATAAAACAACCCCATTTCTCA | AAACTATAACCCAACCCAACTACA |
| GI29793120_S100A2_2R (SEQ ID 114) | NT_004668 | GAGCACTGGACCATGAAGTCTCAGCGTGTG CTCACAGCCTCTCACACAGGA | AACACTAAACCATAAAATCTCAACG | ATACTCACAACCTCTCACACAAAA | AAACACTAAACCATAAAATCTCAACA |
| GI29793234_ABCC5_1R (SEQ ID 115) | NT_005962 | GGGCAGTTGGTGTTAAAGTGAGAAAGGCGG TATCTGCGCAGACTGCAGGGTC | CCTACAATCTACGCAAATACCG | CTTTCTCACTTTAACACCAACTACCC | AACCCTACAATCTACACAAATACCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29793234_ABCC5_2R (SEQ ID 116) | NT_005962 | CGCAGGGTGGACTGCTCTGCCTACGAACA GCACTGTGTGCGAACACAGGG | CCTATATTCGCACACAATACTATTCG | AAACAAAACAATCCCACCCTAC | CCCTATATTCACACACAATACTATTCA |
| GI29793234_ABCC5_3R (SEQ ID 117) | NT_005962 | CTGGCCGGCCTGACGACTCTCAACGGGTTA GACGCGGGCTACGATGACCTTCACG | ACCGACCTAACGACTCTCAACG | ATTAAACGCGAACTACGATAACC | CTAACCAACCTAACAACTCTCAACA |
| GI29793234_HRASLS_2R (SEQ ID 118) | NT_005962 | TGGAGGTCTCTGCTGGCTATCTGGCGTGTG TGTGTGTGTGGTGTG | ACACCACACACACACACACG | CAAATAACCAACAAAAACCTCCA | CACACCACACACACACACACA |
| GI29793234_HRASLS_3R (SEQ ID 119) | NT_005962 | CAAAACCGATTATCTTTATAACCGCGGCGC CTAGCACAGCGCCTGGTGCCCT | AACCGATTATCTTTATAACCGCG | CGCCTAACACAACGCCTAATAC | CAAAACCAATTATCTTTATAACCACA |
| GI29793705_CD2_1R (SEQ ID 120) | NT_004754 | GGAGCACATCAGAAGGGCTGGCTTGTGCGC GCTCTTGCTCTCTGTGTATGTG | CACAAAAAACAAAAACGCG | ACAAACCAACCCTTCTAATATACTCC | CACATACACAAAAAACAAAAACACA |
| GI29793872_RASSF1_1R (SEQ ID 121) | NT_006014 | TCCTCACCCCAAGTGAAGGCTCGAGACTTC CTGCCCCACCCAGTGGG | CCTCACCCCAAATAAAAACTCG | AACTTCCTACCCCACCCAATAAA | TCCTCACCCCAAATAAAAACTCA |
| GI29793872_RASSF1_2R (SEQ ID 122) | NT_006014 | CCTGCACCCAGGTTTCCATTGCGCGGCTCT CCTCAGCTCCTTCCCGC | CTACACCCAAATTTCCATTACG | GACTCTCCTCAACTCCTTCCC | CCTACACCCAAATTTCCATTACA |
| GI29793872_RASSF1_3R (SEQ ID 123) | NT_006014 | AGATCACGGTCCAGCCTCTGCCGGAGCCCC AGTCTCCGCAGTGGAG | AATCACGATCCAACCTCTACCG | AACCCCAATCTCCGCAATAAA | AAATCACAATCCAACCTCTACCA |
| GI29794089_PRDM2_1R (SEQ ID 124) | NT_004873 | CTGGAACATCGCGGGCACAGGGCAGCGTTG GTCACTGCTCCTGGGTACT | ATACCCAAAAACAATAACCAACG | TACCCTATACCCGCGATATTCC | AATACCCAAAAACAATAACCAACA |
| GI29794089_PRDM2_2R (SEQ ID 125) | NT_004873 | GGGGGTCCCGGAGCCCCCCAGCCCCGCAGG CCACTGCCTCGCCGCCCGA | GAACCACGAAACAATAACCTACG | AACTAAAAAACTCCGAAACCCC | TCAAACAACAAAACAATAACCTACA |
| GI29794089_PRDM2_3R (SEQ ID 126) | NT_004873 | TCTTCATCAGAACATCTATGAGTCGTCGTC TCTGCAGTCCATTTGTTTGCCCGC | TCATCAAAACATCTATAAATCGTCG | CTCTACAATCCATTTATTTACCCG | TCTTCATCAAAACATCTATAAATCATCA |
| GI29794150_NCL_1R (SEQ ID 127) | NT_005403 | ACTCCAAGGCTGCCCAAGCCTACGGACCCA GCCACATTGGCGAACCG | TCCAAAACTACCCAAACCTACG | ACCCAACCACATTAACGAACC | ACTCCAAAACTACCCAAACCTACA |
| GI29794150_NCL_2R (SEQ ID 128) | NT_005403 | ACTCCGCGGTCCCTGAACTTCCGGTGCTGG CGGACTCCTCGCTCCAGG | GCCATCCCTAAACTTCCG | TACTAACGAACTCCTCGCTCCAA | ACTCCACAATCCCTAAACTTCCA |
| GI29794150_NCL_3R (SEQ ID 129) | NT_005403 | GGGGTGCCTCCGGCCCCATGCTCGCGGGCA AGCAGGGATAAGCTGTGCC | CACAACTTATCCCTACTTACCCG | GAACATAAAACCGAAAACACCC | AACACAACTTATCCCTACTTACCCA |
| GI29784150_TMEFF2_1R (SEQ ID 130) | NT_005403 | GGCCATCCGGCAAAGACCCGAGTAAGGAAC GCAGGGTCACTGCCTGGGCCAAC | TTAACCCAAACAATAACCCTACG | TCCTTACTCCAATCTTTACCCAA | ATTAACCCAAACAATAACCCTACA |
| GI29794150_TMEFF2_2R (SEQ ID 131) | NT_005403 | TTTCTCTCAGACCACTTGTCCCGACCAATC TGACCTTCCAAACACAT | TTCTCTCAAACCACTTATCCCG | CCAATCTAACCTTCCAAACACAT | TTTCTCTCAAACCACTTATCCCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29794150_TMEFF2_3R (SEQ ID 132) | NT_005403 | CGCAGAGCCAGAGACTCCTGCCCAGTTAGA CCTTCTCTCGTCGCCCC | GCAAAACCAAAAACTCCTACCG | ATTAAACCTTCTCTCGTCGCC | CACAAAACCAAAAACTCCTACCA |
| GI29795229_DBCCR1_1R (SEQ ID 133) | NT_008470 | GCGCGGTCCCTTTGGATGCTCGTGCGCATA GACACAACACCCTACACGCC | CGATCCCTTTAAATACTCGTACG | ATAAACACAACACCCTACACGC | ACACAATCCCTTTAAATACTCATACA |
| GI29795229_DBCCR1_2R (SEQ ID 134) | NT_008470 | CCCCAGAAACACTCAGGTACTCGCGACACA CACAGTACAGTCACGCTTAA | CCCAAAAACACTCAAATACTCG | GACACACACAATACAATCACGCT | CCCCAAAAACACTCAAATACTCA |
| GI29795229_DBCCR1_3R (SEQ ID 135) | NT_008470 | GCAGACACAAACGGACCCACACGGGCAACT CCCGAGACAAAACCC | ACACAAACCAACCCACACG | ACAACTCCCGAAACAAAACC | ACAAACACAAACAAACCCACACA |
| GI29795229_TMEFF1_1R (SEQ ID 136) | NT 008470 | GGACACAAAGGGAAGGCGAGGAGGCGAGCA AGAGGCTGGGCCTGCCT | AACAAACCCAACCTCTTACTCG | CTCCTCGCCTTCCCTTTATATC | AAACAAACCCAACCTCTTACTCA |
| GI29795229_TMEFF1_2R (SEQ ID 137) | NT_008470 | CGGGCGGGCCGGGGTCTTTGTGACGCGGTG GCAACGGCCACGGACACAAAG | GAACCGAAAGGTTTATAACGCG | TAACAACGACCACGAACACAA | CAAACAAACCAAAATCTTTATAACACA |
| GI29795229_TMEFF1_3R (SEQ ID 138) | NT_008470 | GACAAGTCACCTTTACCTCTTCCGTGACTC AGTTTCTTCCACCTAAAAAC | CAAATCACCTTTACCTCTTCCG | AACTCAATTTCTTCCACCTAAAAAC | AACAAATCACCTTTACCTCTTCCA |
| GI29796755_HOXA5_1R (SEQ ID 139) | NT_007819 | TGCAGCCCCCGGTCGGAAGCTGGGCGATGA GCCCTGCCTCCAGCGGGT | CCGCTAAAAACAAAACTCATCG | CCAACTTCCGACCGAAAACTAC | ACCCACTAAAAACAAAACTCATCA |
| GI29796755_HOXA6_2R (SEQ ID 140) | NT_007819 | GGGCGATGAGCCCTGCCTCCAGCGGGTGGC GCTCGAGTCCGGCTGAACGGCG | CGATAAACCCTACCTCCAACG | ATAACGCTCGAATCCGACTAAAC | AAACAATAAACCCTACCTCCAACA |
| GI29796755_HOXA5_3R (SEQ ID 141) | NT_007819 | ATCCTCTGCATCCTCGCCGGGCGCGCGATC GGCAGCTGACGGCCTAACAA | CTACATCCTCGCCGAACG | GCGATCGACAACTAACGACCTAA | ATCCTCTACATCCTCACCAAACA |
| GI29796755_IGFBP1_2R (SEQ ID 142) | NT_007819 | GGCGCGGCCTGTGCCCTTTATAAGGTGCGC GCTGTGTCCAGCGAGCATCGGCC | ATACTCGCTAAACACAACGCG | ACCTTATAAAAAACACAAACCGC | AACCAATACTCACTAAACACAACACA |
| GI29796755_IGFBP1_3R (SEQ ID 143) | NT_007819 | CGCGGCCTGTGCCCTTTATAAGGTGCGCGC TGTGTCCAGCGAGCATCGGCCACC | GACCTATACCCTTTATAAAATACGCG | TATATCCAACGAACATCGACCA | CACAACCTATACCCTTTATAAAATACACA |
| GI29796755_IL6_1R (SEQ ID 144) | NT_007819 | TCTGCTTCTTAGCGCTAGCCTCAATGACGA CCTAAGCTGCACTTTTCCCCCT | TCTTAACGCTAACCTCAATAACG | CCTAAACTACACTTTTCCCCCT | TCTACTTCTTAACACTAACCTCAATAACA |
| GI29796755_IL6_2R (SEQ ID 145) | NT_007819 | CCTGGAGACGCCTTGAAGTAACTGCACGAA ATTTGAGGATGGCCAGGCAG | TACCTAACCATCCTCAAATTTCG | ACAATTACTTCAAAACGTCTCCAA | CTACCTAACCATCCTCAAATTTCA |
| GI29796755_TWIST1_1R (SEQ ID 146) | NT_007819 | GTTTTTGAATGGTTTGGGAGGACGAATTGT TAGACCCCGAGGAAGG | CTTCCTCGAAATCTAACAATTCG | CCTCCCAAACCATTCAAAAAC | CCTTCCTCAAAATCTAACAATTCA |
| GI29796755_TWIST1_2R (SEQ ID 147) | NT_007819 | CCACTCCGGATGGGGCTGCCACCGCGGCCA GGACAGTCTCCTCCGAC | ACTCCGAATAAAACTACCACCG | GACCAAAACAATCTCCTCCGAC | CCACTCCAAATAAAACTACCACCA |
| GI29796755_TWIST1_3R (SEQ ID 148) | NT_007819 | GGCCTTTGGAACTCCAAGGGGTTCGTCTAC CTGACCATTGGGTGGG | CCCACCCAATAATCAAATAAACG | ACCCCTTAAAATTCCAAAAACC | CCCACCCAATAATCAAATAAACA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29796774_TRC8_1R (SEQ ID 149) | NT_008046 | GAAGCTAGAGTAAGCTGAGGAGGTGGGCGG AAACCATGGCAACCATGGGTG | ACCCATAATTACCATAATTTCCG | CCACCTCCTCAACTTACTCTAACTTC | CACCCATAATTACCATAATTTCCA |
| GI29796774_TRC8_2R (SEQ ID 150) | NT_008046 | ACCACACCCAGCCTAGTGCCACGCACCGCA AGCGCTCCATAAACGCA | CACACCCAACCTAATACCACG | ACCGCAAACGCTCCATAA | ACCACACCCAACCTAATACCACA |
| GI29796774_TRC8_3R (SEQ ID 151) | NT_008046 | CGCAGGCAGTGGGCGCGGACTCTGCGGTTC GCTTGACTGACGGCGCAGCCTCC | AAACAATAAACGCGAACTCTACG | TTCGCTTAACTAACGACGCAAC | CACAAACAATAAACACAAACTCTACA |
| GI29804415_C4B_1R (SEQ ID 152) | NT_007592 | TTGTGAGGGCCTTTAAATATCCTGTACTCG TGGGCCATGTTGGGCCCT | AAACCCAACATAACCCACG | ATACAAAATATTTAAAAACCCTCACAA | AAAACCCAACATAACCCACA |
| GI29804415_C4B_2R (SEQ ID 153) | NT_007592 | TCAGGCACTGGAATGAGAGGAGTTAACGGG GAAGGACAGGGTTATTTC | AACCCTATCCTTCCCCG | TAACTCCTCTCATTCCAATACCTAA | AAAATAACCCTATCCTTCCCCA |
| GI29804415_C4B_3R (SEQ ID 154) | NT_007592 | CCCATGGACACCCAGGTGTCCGGGGTGCCC CCACAACTCTGGGCCT | CCATAAACACCCAAATATCCG | AATACCCCCACAACTCTAAACCT | CCCATAAACACCCAAATATCCA |
| GI29804415_CDKN1A_1R (SEQ ID 155) | NT_007592 | TGGCTCTGATTGGCTTTCTGGCCGTCAGGA ACATGTCCCAACATGTTGAGC | TCAACATATTAAAACATATTCC TAACG | CCAAAAAACCAATCAAAACCA | ACTCAACATATTAAAACATATTCCTAACA |
| GI29804415_CSNK2B_1R (SEQ ID 156) | NT_007592 | CCCACATTACTTGAGGGCTCGGGCGTGCGC AAAGCTCCGGGTTCAGTTTC | CCACATTACTTAAAAACTCGAACG | ACGCAAAACTCCGAATTCAAT | CCCACATTACTTAAAAACTCAAACA |
| GI29804415_CSNK2B_2R (SEQ ID 157) | NT_007592 | ACAATCAAATAGCCACACGGCACGAAGACG CATGCGTGGCGACAACAACAAC | AATCAAATAACCACACGACACG | AAACGCATACGTAACGACAACA | ACAATCAAATAACCACACAACACA |
| GI29804415_CSNK2B_3R (SEQ ID 158) | NT_007592 | CAGCCTGGCCCTTTAAGTCTTCCGCGATCC CATTTCGGAGTTTCCTCT | AACCTAACCCTTTAAATCTTCCG | GATCCCATTTCGAAATTTCCTCT | CAACCTAACCCTTTAAATCTTCCA |
| GI29804415_EDN1_1R (SEQ ID 159) | NT_007592 | TCTTTTTCTTAGCCCTGCCCCCGAATTGTC AGACGGCGGGCGTCTGCCTCT | CTTTTTCTTAACCCTACCCCCG | ATTATCAAACGACGAACGTCTACC | TCTTTTTCTTAACCCTACCCCCA |
| GI29804415_EDN1_2R (SEQ ID 160) | NT_007592 | GGCTGGCAGCTTGCAAAGGGGAAGCGGACT CCAGCACTGCACGGGCAGG | TACCCGTACAATACTAAAATCCG | TTCCCCTTTACAAACTACCAACC | CCTACCCATACAATACTAAAATCCA |
| GI29804415_EDN1_3R (SEQ ID 161) | NT_007592 | GGCCTGGCCTTATCTCCGGCTGCACGTTGC CTGTTGGTGACTAATAACACAA | ATTATTAATCACCAACAAACAACG | ACAACCGAAAATAAAACCAAACC | TTATATTATTAATCACCAACAAACAACA |
| GI29804415_HLA-F_1R (SEQ ID 162) | NT_007592 | AAGTTCAATCAAGGGACTGGGATTTCGGAA TGAATAATGAAGGGAGATG | TCTCCCTTCATTATTCATTCCG | AATCCCAATCCCTTAATTAAACTT | CATCTCCCTTCATTATTCATTCCA |
| GI29804415_HLA-F_2R (SEQ ID 163) | NT_007592 | TCCTTCTTCCTGGATACTCATAACGCGGCC CCATTTCTCACTCCCATTGG | TCTTCCTAAATACTCATAACGCG | CCCCATTTCTCACTCCCATTAA | TCCTTCTTCCTAAATACTCATAACACA |
| GI29804415_LY6G6E_1R (SEQ ID 164) | NT_007592 | GGGGCAGGCTGGGGGCCCCCGCTGCCTGCT GGGTCAGGCTG | AACCTAACCCAACAAACAACG | AAACCCCCAACCTACCCC | CAACCTAACCCAACAAACAACA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29804415_LY6G6E_2R (SEQ ID 165) | NT_007592 | AACTCTACAAATCCCGGGATCTCGGGGTGCAGATCACCTCTCCCAGA | TCTACAAATCCCGAAATCTCG | AATACAAATCACCTCTCCCAAA | AACTCTACAAATCCCAAAATCTCA |
| GI29804415_LY6G6E_3R (SEQ ID 166) | NT_007592 | TCTGAAGCTGGGTGGGGTCCGCCCTTACACAGCTGGGCTTTGTGT | CACAAAACCCAACTATATAAAAACG | ACCCCACCCAACTTCAAA | ACACAAAACCCAACTATATAAAAACA |
| GI29804415_NEU1_1R (SEQ ID 167) | NT_007592 | GCTGAGGCAGGAGAATCGCTTGAACCCGGGAGGCAGAGGTTGCAGTGAGC | TCACTACAACCTCTACCTCCCG | ATTCAAACGATTCTCCTACCTCA | ACTCACTACAACCTCTACCTCCCA |
| GI29804415_NEU1_2R (SEQ ID 168) | NT_007592 | GAGGGCCAATCGGAAGGGCAAGCTTCGAGATGCTGCGTGATCACGTGG | ACGTAATCACGCAACATCTCG | AACTTACCCTTCCGATTAACCCT | CCACATAATCACACAACATCTCA |
| GI29804415_NEU1_3R (SEQ ID 169) | NT_007592 | GGGCGGATCACCTGAGTCAGGAGTTCGAGACCAGCCTGGCCAACATGGTGAA | TCACCATATTAACCAAACTAATCTCG | ACTCCTAACTCAAATAATCCGCC | TTCACCATATTAACCAAACTAATCTCA |
| GI29804415_RDBP_1R (SEQ ID 170) | NT_007592 | GGTGAAGGAGGTTTGGACTCAATGCGGGTCAAAGGTTAGGGTCAAAAG | TTTTAACCCTAACCTTTAACCCG | ATTAAATCCAAACCTCCTTCACC | CTTTTAACCCTAACCTTTAACCCA |
| GI29804415_RDBP_2R (SEQ ID 171) | NT_007592 | GGGATCTGGAGGGGGTAGCACTACGGGGAAAGGTCAAAAGTCAGGG | CCTAACTTTTAACCTTTCCCCG | AATACTACCCCCTCCAAATCCC | CCCTAACTTTTAACCTTTCCCCA |
| GI29804415_RDBP_3R (SEQ ID 172) | NT_007592 | TGGCAGCCCGGAAGTGCGGCAAGTAGTCGCTGCGAAGTAAGCCCCGCCCCGG | AAACGAAACTTACTTCGCAACG | CTACTTACCGCACTTCCCAACTA | CCAAAACAAAACTTACTTCACAACA |
| GI29804415_TNF_1R (SEQ ID 173) | NT_007592 | ATAGGTTTTGAGGGGCATGGGGACGGGGTTCAGCCTCCAGGGTCCT | AAACCCTAAAAACTAAACCCCG | CCCCATACCCCTCAAAACCTAT | AAAACCCTAAAAACTAAACCCCA |
| GI29804415_TNF_2R (SEQ ID 174) | NT_007592 | CCCGCCCCCGCGATGGAGAAGAAACCGAGACAGAAGGTGCAGGGCCCACTAC | AATAAACCCTACACCTTCTATCTCG | TTTCTTCTCCATCGCGAAA | ATAATAAACCCTACACCTTCTATCTCA |
| GI29804415_TNF_3R (SEQ ID 175) | NT_007592 | CAGAAGGTGCAGGGCCCACTACCGCTTCCTCCAGATGAGCTCATGGGTTTC | AAAAAATACAAAACCCACTACCG | TTCCTCCAAATAAACTCATAAATTTC | CAAAAAATACAAAACCCACTACCA |
| GI29804415_VEGF_1R (SEQ ID 176) | NT_007592 | GTCTCTGGACAGAGTTTCCGGGGGCGGATGGGTAATTTTCAGGCTGTG | ACAACCTAAAAATTACCCATCCG | CCCCGAAAACTCTATCCAAAA | CACAACCTAAAAATTACCCATCCA |
| GI29804415_VEGF_2R (SEQ ID 177) | NT_007592 | TCCCCTTCATTGCGGCGGGCTGCGGGCCAGGCTTCACTGAGCGTCCGCA | CCCTTCATTACGACCAACTACG | ACCAAACTTCACTAAACGTCCG | TCCCCTTCATTACAACAAACTACA |
| GI29804415_VEGF_3R (SEQ ID 178) | NT_007592 | GAACGGCTCTCAGGCCCTGTCCGCACGTAACCTCACTTTCCTGCTCCCT | AACGACTCTCAAACCCTATCCG | ACGTAACCTCACTTTCCTACTCC | AAACAACTCTCAAACCCTATCCA |
| GI29807454_WT1_1R (SEQ ID 179) | NT_009237 | CATCTCTACTCCCACCGCATTCGACCCTGCCCGGACTCACTGCTTACC | CTACTCCCACCGCATTCG | CCCTACCCGAACTCACTACTTAC | CATCTCTACTCCCACCACATTCA |
| GI29824571_MOS_1R (SEQ ID 180) | NT_008183 | TCAGTCATGTTTCCAAAGTCCCGCGGTTTCCCCTAGTCTCTTCATTCA | CAATCATATTTCCAAAATCCCG | GATTTCCCCTAATCTCTTCATTCA | TCAATCATATTTCCAAAATCCCA |
| GI29789877_CSF1_2R (SEQ ID 181) | NT_019273 | GTTTGCTGAAGGCTTGGAAGTGCAGCGCAGAAGACAGAGGGTGACTAGGAA | TCCTAATCACCCTCTATCTTCTACG | TACACTTCCAAACCTTCAACAAAC | TTCCTAATCACCCTCTATCTTCTACA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29789877_CSF1_3R (SEQ ID 182) | NT_019273 | TGTGTGTGTGTATGTGTGTGTCTGGCGCCT GGCCAGGGTGATTTCCCAT | AAAAAATCACCCTAACCAAACG | CAAACACACACATACACACACACA | ATAAAAAATCACCCTAACCAAACA |
| GI29789881_MTHFR_1R (SEQ ID 183) | NT_021937 | GAGCATCTCTGGTTGGAATCATAATGCTTC GGCCTGAAGTGACCAGGCCACTCACT | AAATAACCTAATCACTTCAAACCG | AACATTATAATTCCAACCAAAAATACTC | AATAAATAACCTAATCACTTCAAACCA |
| GI29791372_MLH1_1R (SEQ ID 184) | NT_022517 | CGGGAGGCCACAAGAGCAGGGCCAACGTTA GAAAGGCCGCAAGGGGAGA | CCCCTTACGACCTTTCTAACG | TAACCCTACTCTTATAACCTCCCG | TCTCCCCTTACAACCTTTCTAACA |
| GI29791372_MLH1_2R (SEQ ID 185) | NT_022517 | TGGCGTAAGCTACAGCTGAAGGAAGAACGT GAGCACGAGGCACTGAGGTGA | CACCTCAATACCTCGTACTCACG | TCTTCCTTCAACTATAACTTACGCC | TCACCTCAATACCTCATACTCACA |
| GI29791372_MLH1_3R (SEQ ID 186) | NT_022517 | CCGCCACATACCGCTCGTAGTATTCGTGCT CAGCCTCGTAGTGGCGCCTGACG | CACATACCGCTCGTAATATTCG | ACTCAACCTCGTAATAACGCCTA | CCACCACATACCACTCATAATATTCA |
| GI29791392_EGR4_1R (SEQ ID 187) | NT_022184 | CCACAGGAAATGCACAGGTGAGAAACTGAC GTTAAGGGGGACTGAGTGTCAA | TAACACTCAATCCCCCTTAACG | CAATTTCTCACCTATACATTTCCTATAA | TTAACACTCAATCCCCCTTACA |
| GI29791392_EGR4_2R (SEQ ID 188) | NT_022184 | AGGGCAGATTCAAACCCAACACGGTCCTCC CCTGCTGCCCCTCGGC | AAACAAATTCAAACCCAACACG | TCCTCCCCTACTACCCCTCG | AAAACAAATTCAAACCCAACACA |
| GI29791392_EGR4_3R (SEQ ID 189) | NT_022184 | CGGTCGGCCCGGTGAGGCGCAGCGCCCCAG ACTGGCGCATCCGCGGC | ACCCGATAAAACGCAACG | CCCAAACTAACGCATCCG | CAATCAACCCAATAAAACACAACA |
| GI29791392_POMC_1R (SEQ ID 190) | NT_022184 | GGCGAGCGGCCAGGTGCGCCTTCGGCAGGA CAGTGCTAATTCCAGCCCC | AACGACCAAATACGCCTTCG | CAAAACAATACTAATTCCAACCCC | AACAAACAACCAAATACACCTTCA |
| GI29791392_POMC_2R (SEQ ID 191) | NT_022184 | CACACGGGGGTGCTAAGCCTCCCGCCCGTT CTAAGCGGAGACCCAACG | CACGAAAATACTAAACCTCCCG | CCGTTCTAAACGAAAACCCAAC | CACACAAAAATACTAAACCTCCCA |
| GI29791392_POMC_3R (SEQ ID 192) | NT_022184 | CGCACGCAGGTAACTTCACCCTCGCCTCAA CGACCTCAGAGGCTGCCC | ACGCAAATAACTTCACCCTCG | CTCAACGACCTCAAAAACTACCC | CACACACAAATAACTTCACCCTCA |
| GI29791392_SFTPB_1R (SEQ ID 193) | NT_022184 | GAGGTCGCTGCCACTCCTACAGAGCCCCCA CGCCCCGCCCAGCTATAAGGGGCCATG | CCCCTTATAACTAAACGAAACG | AAAAACTCTATAAAAATAACAACGACCT | CATAACCCCTTATAACTAAACAAAACA |
| GI29791392_SFTPB_2R (SEQ ID 194) | NT_022184 | ACTCCTACAGAGCCCCCACGCCCCGCCCAG CTATAAGGGGCCA | TCCTACAAAACCCCCACG | CCCGCCCAACTATAAAAAA | ACTCCTACAAAACCCCCACA |
| GI29791392_TGFA_1R (SEQ ID 195) | NT_022184 | ACGGTAGCCGCCTTCCTATTTCCGCCCGGC GGGCAGCGCTGCGGGGCGA | ATAACCGCCTTCCTATTTCCG | CCGACGAACAACGCTACG | ACAATAACCACCTTCCTATTTCCA |
| GI29791392_TGFA_2R (SEQ ID 196) | NT_022184 | CGCCGCCTAGAGCCTGGAAGCCGCCACTGC GGCCCAGGACAATCCGG | CCGCCTAAAACCTAAAAACCG | CACTACGACCCAAAACAATCC | CACCACCTAAAACCTAAAAACCA |
| GI29791392_TGFA_3R (SEQ ID 197) | NT_022184 | CCAAGTCTTGGCAAGCGGCCGGCGAAACTC ACAGGTCCCTTTCCTGGC | AAATCTTAACAAACGACCGACG | AACTCACAAATCCCTTTCCTAAC | CCAAATCTTAACAAACAACCAACA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29794065_N33_1R (SEQ ID 198) | NT_015280 | CTCCTCTCCTCAGCGCTGGTCCGGGAAAGG CAAGCTCCGGGCGGGAGCG | CTCTCCTCAACGCTAATCCG | AAAAAACAAACTCCGAACGAAA | CTCCTCTCCTCAACACTAATCCA |
| GI29794065_N33_2R (SEQ ID 199) | NT_015280 | GGGAATAGAGATTGCTGGGGACCGCAGGGG CCAGGTTGTCATTCCC | AAAATAACAACCTAACCCCTACG | TCCCCAACAATCTCTATTCCC | AAAAATAACAACCTAACCCCTACA |
| GI29794065_N33_3R (SEQ ID 200) | NT_015280 | CCCGAAGCCTGGCTCCCTCGCCACGCCCAC TTCCTGCCCC | CCGAAACCTAACTCCCTCG | CACGCCCACTTCCTACCC | CCCAAAACCTAACTCCCTCA |
| GI29798364_UBB_1R (SEQ ID 201) | NT_010718 | CACCAATCAGCGCCGACCTCGCCTTCGCAG GCCTAACCAATCAGT | AATCAACGCCGACCTCG | CTTCGCAAACCTAACCAATCAAT | CACCAATCAACACCAACCTCA |
| GI29798364_UBB_2R (SEQ ID 202) | NT_010718 | CGCGCTCAGTTACTTAGCAACCTCGGCGCT AAGCCACCCCAGGTGGAGC | CGCTCAATTACTTAACAACCTCG | CGCTAAACCACCCCAAATAAAAC | CACACTCAATTACTTAACAACCTCA |
| GI29798364_UBB_3R (SEQ ID 203) | NT_010718 | GGAGAATCGCTTGAACCCGGGAGGCGGAGG TTGCGATGAGCCGAGAT | GACTCATCGCAACCTCCG | CTCCCGAATTCAAACGATTCT | ATCTCAACTCATCACAACCTCCA |
| GI29798595_ERBB2_1R (SEQ ID 204) | NT_010755 | GGCAGCCTAGGGAATTTATCCCGGACTCCG GGGGAGGGGGCAGAGTCAC | CTCTACCCCCTCCCCCG | AATCCGAAATAAATTCCCTAAACT | ATAACTCTACCCCCTCCCCCA |
| GI29798595_ERBB2_2R (SEQ ID 205) | NT_010755 | GATTCTCCGAGGAAAAGTGTGAGAACGGCT GCAGGCAACCCAGGCGTCCCG | AACGCCTAAATTACCTACAACCG | TCTCACACTTTTCCTCGAAAAAT | CAAAACACCTAAATTACCTACAACCA |
| GI29798595_ERBB2_3R (SEQ ID 206) | NT_010755 | AGGAGGGACGCACCCAGGCCTGCGCGAAGA GAGGGAGAAAGTGAAGCT | ACTTCACTTTCTCCCTCTCTTCG | GCAAACCTAAATACGTCCCTCCT | AACTTCACTTTCTCCCTCTCTTCA |
| GI29799031_ATP5G1_1R (SEQ ID 207) | NT_010783 | GTGGCCCAAGCGCCCGAATGAAGGCTCGGG GCCAAAGTCATGTGTCTGACT | TCAAACACATAACTTTAACCCCG | ACCTTCATTCGAACGCTTAAAC | AATCAAACACATAACTTTAACCCCA |
| GI29799031_ATP5G1_2R (SEQ ID 208) | NT_010783 | CTGTGGAGGGAGAGGAAGCAGCTGCGGAAA GCCAATAAGAGTGGGGAA | TCCCCACTCTTATTAACTTTCCG | AACTACTTCCTCTCCCTCCACAA | TTCCCCACTCTTATTAACTTTCCA |
| GI29799031_ATP5G1_3R (SEQ ID 209) | NT_010783 | TCCCGCCAACTCTATGGTCGAGCGTTTCAG GGATCGGCCAATCGTAATCC | CGCCAACTCTATAATCGAACG | TTCAAAAATCGACCAATCGTAAT | TCCCACCAACTCTATAATCAAACA |
| GI29799031_NME1_1R (SEQ ID 210) | NT_010783 | CTCGGGAAGCCAATTTGCTCGCGAACGAAG GAAGTGAGTCAGAGAACCCG | GAATTCTCTAACTCACTTCCTTCG | TCGCGAACAAATTAACTTCCC | CAAATTCTCTAACTCACTTCCTTCA |
| GI29799031_NME1_2R (SEQ ID 211) | NT_010783 | GGGTGGAGAGAAGAAAGCAAGCAGCTAACC GGAAAGGTCTGAAAAAGCTAGCG | GCTAACTTTTTCAAACCTTTCCG | TTAACTACTTACTTTCTTCTCTCCACC | CACTAACTTTTTCAAACCTTTCCA |
| GI29799031_NME1_3R (SEQ ID 212) | NT_010783 | CGCAACGTGTGAGCGCCACCTCTCGGGAAG CCAATTTGCTCGCGAACGAAG | AACGTATAAACGCCACCTCTCG | AAAACCAATTTACTCGCGAACG | CACAACATATAAACACCACCTCTCA |
| GI29799354_NF1_1R (SEQ ID 213) | NT_010799 | CTCCCGGGTCAGCTCTGGCACTCGCCAGCT GAGCCCAGCGCCAGTCTAG | CCCGAATCAACTCTAACACTCG | CAACTAAACCCAACGCCAATCTA | CTCCCAAATCAACTCTAACACTCA |
| GI29799354_NF1_2R (SEQ ID 214) | NT_010799 | GGGCGCCCTAACTTCCAACTCCGGGAGCAA TCCAAACCCGGAGGCC | GCCCTAACTTCCAACTCCG | AAACAATCCAAACCCGAAAAC | AAACACCCTAACTTCCAACTCCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29799354_NF1_3R (SEQ ID 215) | NT_010799 | TTTTCATTAATGAAACCGGCCGGCGCGGGC GCATGCGCGGCAGGCCGCC | TCATTAATAAAACCGACCGACG | GAACGCATACGCGACAAAC | TTTTCATTAATAAAACCAACCAACA |
| GI29800594_APOC2_1R (SEQ ID 216) | NT_011109 | TTCAGGAGGGTGAGGGCAGGAGCGTGGGTG GAGTCAGCAGGTCCCC | AAACCTACTAACTCCACCCACG | TCCTACCCTCACCCTCCTAAA | AAAAACCTACTAACTCCACCCACA |
| GI29800594_APOC2_2R (SEQ ID 217) | NT_011109 | CAACCCAGCCTCTGTCGGAGGCGAATTCTC AGAGTGAGGGTTCCCTGTCA | AACCCAACCTCTATCGAAAACG | ATTCTCAAAATAAAAATTCCCTATCA | CAACCCAACCTCTATCAAAAACA |
| GI29800594_APOC2_3R (SEQ ID 218) | NT_011109 | TTCCCTGTGACGTGACCTTGGGGGACGTCA TTGCCCTTTCTGTCCCCACC | TCCCTATAACGTAACCTTAAAAAACG | CATTACCCTTTCTATCCCCACC | TTCCCTATAACATAACCTTAAAAAACA |
| GI29800594_KLK10_3R (SEQ ID 219) | NT_011109 | GGTTTCACTATGTTGGCCAGGCTGGTCTCG AACTCCTGACCTCGTGATCCGCC | GAATCACGAAATCAAAAATTCG | AACCAACCTAACCAACATAATAAAACC | AACAAATCACAAAATCAAAAATTCA |
| GI29800594_TSLL2_2R (SEQ ID 220) | NT_011109 | CGGTGGCTCAGCTCACAGCCTCTCGCTAGA CTCCAGACACCCACCTGCC | ATAACTCAACTCACAACCTCTCG | TAAACTCCAAACACCCACCTACC | CAATAACTCAACTCACAACCTCTCA |
| GI29800594_TSLL2_3R (SEQ ID 221) | NT_011109 | ATCCTTGACCTGCCTCGACCTCCGGACCCT CCGGACCTCCAGCTGC | CTTAACCTACCTCGACCTCCG | ACCCTCCGAACCTCCAACTAC | ATCCTTAACCTACCTCAACCTCCA |
| GI29801019_STK11_1R (SEQ ID 222) | NT_011255 | AGCCAGCCTGGGGACTGGAGGGTGGCGGCT GCATCTGCTCATTTCCTCCCA | ACCAACCTAAAAACTAAAAAATAACG | CTACATCTACTCATTTCCTCCCA | AACCAACCTAAAAACTAAAAAATAACA |
| GI29801019_STK11_2R (SEQ ID 223) | NT_011255 | GGAGTCTTGCTGTGTCTCCCAGGCCGGAGT GCAATGGCATGACCTCTGCCTCCC | AAATCTTACTATATCTCCCAAACCG | AATACAATAACATAACCTCTACCTCCC | AAAATCTTACTATATCTCCCAAACCA |
| GI29801019_STK11_3R (SEQ ID 224) | NT_011255 | TGGAGTCTTGCTGTGTCTCCCAGGCCGGAG TGCAATGGCATGACCTCTG | CAAAAATCATACCATTACACTCCG | CCTAAAAAACACAACAAAACTCCA | CAAAAATCATACCATTACACTCCA |
| GI29801560_CDKN2D_1R (SEQ ID 225) | NT_011295 | GCCATTGCCGGCGGTCCACCGGTTGCCACA CTCTGACCAATCAGGA | ATTACCGACGATCCACCG | TTACCACACTCTAACCAATCAAAA | ACCATTACCAACAATCCACCA |
| GI29801560_CDKN2D_2R (SEQ ID 226) | NT_011295 | AGTTAAACCAGCCTTCTTTCCCGCCTGCCG GGTTCATTTGAAAACCGAAA | ATTAAACCAACCTTCTTTCCCG | CTACCGAATTCATTTAAAAACCG | AATTAAACCAACCTTCTTTCCCA |
| GI29801560_CDKN2D_3R (SEQ ID 227) | NT_011295 | CTCATCCACTCCGTCTCTCCGTTTCCCTTT CTTCACGGTGCTTGACA | CATCCACTCCGTCTCTCCG | TTCCCTTTCTTCACGATACTTAACA | CTCATCCACTCCATCTCTCCA |
| GI29801560_ICAM1_1R (SEQ ID 228) | NT_011295 | AGCTTGGAAATTCCGGAGCTGAAGCGGCCA GCGAGGGAGGATGACCC | ATCCTCCCTCGCTAACCG | TTCAACTCCGAAATTTCCAAACT | AAATCATCCTCCCTCACTAACCA |
| GI29801560_ICAM1_2R (SEQ ID 229) | NT_011295 | TCCCCGGACGTGGTGAGACCGCGCTTCGTC ACTCCCACGGTTAGCGG | CGAACGTAATAAAACCGCG | TTCGTCACTCCCACGATTAAC | TCCCCAAACATAATAAAACCACA |
| GI29801560_ICAM1_3R (SEQ ID 230) | NT_011295 | CCTGGCTCTGCTCTGGCCGCTTCTCGAGAA ATGCCCGTGTCAGCTAGGTG | CCTAACTAACACGAACATTTCTCG | AAAACGACCAAAACAAAACCAA | CACCTAACTAACACAAACATTTCTCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29801767_THBS1_1R (SEQ ID 231) | NT_010194 | CCAGTCTCTAGTATCCACCTCTCGCCATCA ACCAGGCATTCCGGGAG | CCAATCTCTAATATCCACCTCTCG | CATCAACCAAACATTCCGAAA | CCAATCTCTAATATCCACCTCTCA |
| GI29801767_THBS1_2R (SEQ ID 232) | NT_010194 | GGGCCAGCTCAGGACAGGCGCTCGGGGGAC GCGTGTCCTCACCCCAC | CAACTCAAAACAAACGCTCG | AAAACGCGTATCCTCACCC | AAACCAACTCAAAACAAACACTCA |
| GI29801767_THBS1_3R (SEQ ID 233) | NT_010194 | GTGGAGGAGAGTCAGCGAGGGCCCGAGGGG CAGGTACTTTAACGAATG | TTCGTTAAAATACCTACCCCTCG | ACCCTCGCTAACTCTCCTCC | CATTCATTAAAATACCTACCCCTCA |
| GI29801784_ELK1_1R (SEQ ID 234) | NT_011568 | GCCTTTTCAGTTGCTCACAGTCCGTCAGTC CTTGAGCCAATCGGCGTGGA | CCTTTTCAATTACTCACAATCCG | CAATCCTTAAACCAATCGACGTA | ACCTTTTCAATTACTCACAATCCA |
| GI29801784_ELK1_2R (SEQ ID 235) | NT_011568 | AGCGCTTTGGCCAATCAGCGAGCGGCGGGA CATTGGGCTCCTCCTCCTC | GCTTTAACCAATCAACGAACG | CGAAACATTAAACTCCTCCTCCT | AACACTTTAACCAATCAACAAACA |
| GI29801784_ELK1_3R (SEQ ID 236) | NT_011568 | CCATTTCTATACAAGCCCTGCTTCCGCTGA GCAGCATGGCGTGCGACACCGCC | CATTTCTATACAAACCCTACTTCCG | TAAACAACATAACGTACGACACCG | CCATTTCTATACAAACCCTACTTCCA |
| GI29802832_FMR1_1R (SEQ ID 237) | NT_011681 | CGGGGGTTCGGCCTCAGTCAGGCGCTCAGC TCCGTTTCGGTTTCACTTC | AAAATTCGACCTCAATCAAACG | TCAACTCCGTTTCGATTTCACT | CAAAAATTCAACCTCAATCAAACA |
| GI29802832_FMR1_2R (SEQ ID 238) | NT_011681 | CAGAAATGGGCGTTCTGGCCCTCGCGAGGC AGTGCGACCTGTCACCGCCCT | AATAAACGTTCTAACCCTCGCG | AACAATACGACCTATCACCGC | CAAAAATAAACATTCTAACCCTCACA |
| GI29802832_FMR1_3R (SEQ ID 239) | NT_011681 | ACCTCCCGCTCAGTCAGACTGCGCTACTTT GAACCGGACCAAACCAAA | TCCCGCTCAATCAAACTACG | TACTTTAAACCGAACCAAACCAA | ACCTCCCACTCAATCAAACTACA |
| GI29802923_APAF1_1R (SEQ ID 240) | NT_019546 | TCCACTGCGATATTGCTCCAAATCCGAGGA AATTCAAACTCCCGGGCGCG | CACTACGATATTACTCCAAATCCG | AAAAATTCAAACTCCCGAACG | TCCACTACAATATTACTCCAAATCCA |
| GI29802923_APAF1_2R (SEQ ID 241) | NT_019546 | AGCAGGGGCTCCCTTGGGCCCCGACTTCTT CCGGCTCTTCACCTCAG | ACAAAAACTCCCTTAAACCCCG | CTTCTTCCGACTCTTCACCTCAA | AACAAAAACTCCCTTAAACCCCA |
| GI29802923_APAF1_3R (SEQ ID 242) | NT_019546 | CCCGAGTCCGGCATTGGTGGGAACGCGGCG CGTCCCTGAGGCTTAGCCACG | CGAATCCGACATTAATAAAAACG | GACGCGTCCCTAAAACTTAACC | CCCAAATCCAACATTAATAAAAACA |
| GI29803889_GPC3_1R (SEQ ID 243) | NT_011786 | GCTGAAAGAAGGCCTGTGGCGAAGCGGAGG GGGACCTAAGTCAGG | CCTAACTTAAATCCCCCTCCG | TTCGCCACAAACCTTCTTTC | CCTAACTTAAATCCCCCTCCA |
| GI29803889_GPC3_2R (SEQ ID 244) | NT_011786 | CCAGAGCGCCCTGTGTAGAGCGGCTGCGAG CGGGCAGCTGGGCTCGGCTGCCGGG | ACGCCCTATATAAAACGACTACG | ACGAACAACTAAACTCGACTACCG | CCAAAACACCCTATATAAAACAACTAA |
| GI29803889_GPC3_3R (SEQ ID 245) | NT_011786 | CCAGAGCCAGTCAGAGCGGACGGCTGCTGG GAAGCCAATCAGCGCGCTCG | CAAAACCAATCAAAACGAACG | CTACTAAAAAACCAATCAACGCG | CCAAAACCAATCAAAACAAACA |
| GI29805200_CCND2_1R (SEQ ID 246) | NT_009759 | AAATACAAGGGCAGGAGGATTAGGATCCGT TTTGAAGAAGCCAAAGTTGGAG | CCAACTTTAACTTCTTCAAAACG | ATCCTAATCCTCCTACCCTTATATTT | CTCCAACTTTAACTTCTTCAAAACA |
| GI29805200_CCND2_3R (SEQ ID 247) | NT_009759 | GGGAGGAGAGCTAACTGCCCAGCCAGCTTG CGTCACCGCTTCAGAGCGGAGAAGAG | TCTCCGCTCTAAAACGATAACG | AAACTAACTAAACAATTAACTCTCCTC | CTCTTCTCCACTCTAAAACAATAACA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29806267_SOD1_1R (SEQ ID 248) | NT_011512 | AGAAGGTTGTTTTCTCCACATTTCGGGGTT CTGGACGTTTCCCGGCTGCGGG | AAAAATTATTTTCTCCACATTTCG | AATTCTAAACGTTTCCCGACTAC | AAAAAATTATTTTCTCCACATTTCA |
| GI29806267_SOD1_2R (SEQ ID 249) | NT_011512 | TTTACATCATTTTGCCAATTTCGCGTACTG CAACCGGCGGGCCACGCC | ACATCATTTTACCAATTTCGCG | ACTACAACCGACGAACCACG | TTTACATCATTTTACCAATTTCACA |
| GI29806267_SOD1_3R (SEQ ID 250) | NT_011512 | CAGTCATTCCCGGCCACTCGCGACCCGAGG CTGCCGCAGGGGGC | AATCATTCCCGACCACTCG | GACCCGAAACTACCGCAAA | CAATCATTCCCAACCACTCA |
| GI29806588_GP1BB_1R (SEQ ID 251) | NT_011519 | CCCCAGCACCGCTGTGGTGTGCCGGGATCC TGAGCCTAGGCCTCCCGA | CCAACACCGCTATAATATACCG | AATCCTAAACCTAAACCTCCCGA | CCCCAACACCACTATAATATACCA |
| GI29806588_GP1BB_2R (SEQ ID 252) | NT_011519 | GAGACCCCATTTTCTGTCGAGGCGGGCCGA GTCTTCCCTTATCCCC | AACCCCATTTTCTATCGAAACG | ACCGAATCTTCCCTTATCCC | AAAACCCCATTTTCTATCAAAACA |
| GI29806588_GP1BB_3R (SEQ ID 253) | NT_011519 | AAGGAGGCCAGAGGCTGCAAGGAGCGGGGT CGTGACCGCTTACACCCC | AATATAAACGATCACGACCCCG | TCCTTACAACCTCTAACCTCCTT | AAAATATAAACAATCACAACCCCA |
| GI29807454_WT1_2R (SEQ ID 254) | NT_009237 | TTTCTGCGCTTTCCTGAAGTTCCCGCCCTC TTGGAGCCTACCTGCCCCTC | TACGCTTTCCTAAAATTCCCG | CCTCTTAAAACCTACCTACCCCTC | TTTCTACACTTTCCTAAAATTCCCA |
| GI29807454_W71_3R (SEQ ID 255) | NT_009237 | CGCCCGGCTTATAACTGGTGCAACTCCCGG CCACCCAACTGAGGGACGTTC | AACGTCCCTCAATTAAATAACCG | AAATTACACCAATTATAAACCGAACG | AAACATCCCTCAATTAAATAACCA |
| GI29808062_SOCS1_1R (SEQ ID 256) | NT_010393 | CGAACAGGCGGGCAGAGGGCCCCGCGGGAG GGTCCAGAAGAGAGG | CCTCTCTTCTAAACCCTCCCG | GAAACCCTCTACCCGCCTATT | CCTCTCTTCTAAACCCTCCCA |
| GI29808062_SOCS1_2R (SEQ ID 257) | NT_010393 | GGGTCCGAGAAGTGGCCGGAAGGCGCAGGG TCGGGGCCAGAGCCCCTC | CCGAAAAATAACCGAAAAACG | AAAATCGAAACCAAAACCCC | AAATCCAAAAAATAACCAAAAACA |
| GI29808062_SOCS1_3R (SEQ ID 258) | NT_010393 | CGGGCGCCGAACAGAGCGAGCTGCGGCCGT GGCAGCTGCACGGCTCCTGGCC | GCCGAACAAAACGAACTACG | CCGTAACAACTACACGACTCCTAA | CAAACACCAAACAAAACAAACTACA |
| GI29808625_CDH3_2R (SEQ ID 259) | NT_010498 | GAGAATCGCTTCAGCCCGGGAGGTCGAGGC TGTAGTGAGCCGAGATCG | GATCTCGACTCACTACAACCTCG | CCTCCCGAACTAAAACGATTCT | CAATCTCAACTCACTACAACCTCA |
| GI29808625_CDH3_3R (SEQ ID 260) | NT_010498 | CGAGATCGCGCTACTGCACTCCTGGGCGAC AGAGCGAGACCCTGTCTCCAAA | CGCGCTACTACACTCCTAAACG | CAAAACGAAACCCTATCTCCAA | CAAAATCACACTACTACACTCCTAAAA |
| GI29808952_TUBB4_1R (SEQ ID 261) | NT_010542 | AAAGACAGGGAGCTGGGATGGTGCGGGTTG GTCTCTAAACCGGCGT | CCGATTTAAAAACCAACCCG | ACCATCCCAACTCCCTATCTTT | ACACCAATTTAAAAACCAACCCA |
| GI29808952_TUBB4_2R (SEQ ID 262) | NT_010542 | CGCGCGGTGCGGAGCCTGCGGGCCGGGCGG GGCTCTGCGGCGGCGCCTCC | CGATACGAAACCTACGAACCG | ACGAAACTCTACGACGACGC | CACACAATACAAAACCTACAAACCA |
| GI29808952_TUBB4_3R (SEQ ID 263) | NT_010542 | CCCGCGGTGACATCAGCCGATGCGAAGGGC GGGGCCGCGGCTATAAGAGCG | GCGATAACATCAACCGATACG | AAAACGAAACCGCGACTATAAA | CCCACAATAACATCAACCAATACA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29823164_ADCYAP1_1R (SEQ ID 264) | NT_010859 | ATGCCTCTCGGGTGGTGACTCCAGCGCAGG AACTTGAAGAAGCGCAAG | AACGCTTCTTCAAATTCCTACG | TAAAATCACCACCCGAAAAACAT | CAAAACACTTCTTCAAATTCCTACA |
| GI29823164_ADCYAP1_2R (SEQ ID 265) | NT_010859 | GGTAAGGGAGGGAAAATCTTACCAAAGCGA CCGGCTCACTCGACTGCTGATTC | CAACAATCGAATAAACCGATCG | TTTAATAAAATTTTCCCTCCCTTACC | AAATCAACAATCAAATAAACCAATCA |
| GI29823164_ADCYAP1_3R (SEQ ID 266) | NT_010859 | TCCTGCTGCTCCCGCTGGTTCCTGCGGCTT CTGCTCAGACACCAACGCCA | TACTACTCCCGCTAATTCCTACG | CTTCTACTCAAACACCAACGCC | TCCTACTACTCCCACTAATTCCTACA |
| GI29823164_MC2R_1 R (SEQ ID 267) | NT_010859 | CCTGAAGAATCAATCAAGTTTTCCGTGAAG TCAAGTCCAAGTAACATCCC | AAAAAATCAATCAAATTTTCCG | AAAATCAAATCCAAATAACATCCC | CCTAAAAAATCAATCAAATTTTCCA |
| GI29823167_ATP5A1_1R (SEQ ID 268) | NT_010966 | TCTCCTCCTGCGGCTCCATAGCTGCGGCTC CCGCCACTTTACTAGGAACTCC | CCTCCTACGACTCCATAACTACG | CTCCCGCCACTTTACTAAAAACT | TCTCCTCCTACAACTCCATAACTACA |
| GI29823167_ATP5A1_2R (SEQ ID 269) | NT_010966 | GGCTCTGGCATTGCAAGCCTCGCTTCGTTG CCACTTCCCAGCTCTTCCC | CTAACATTACAAACCTCGCTTG | TACCACTTCCCAACTCTTCCC | AACTCTAACATTACAAACCTCACTTCA |
| GI29823167_ATP5A1_3R (SEQ ID 270) | NT_010966 | CTCCCAGTGTTGGGATGCAGGGCGCGGAAG CAGTTCAGATGTGGAAGCCG | CTTCCACATCTAAACTACTTCCG | GCCCTACATCCCAACACTAAAA | CAACTTCCACATCTAAACTACTTCCA |
| GI17458490_PLAGL2_1R (SEQ ID 271) | NT_028392 | CGGGTCCCAGGAGCCCGCAGGCATCCCCGG GAGCGGCAGAAGCAGCAGCAGGAA | TACTACTACTTCTACCGCTCCCG | AAATACCTACGAACTCCTAAAACCC | TTCCTACTACTACTTCTACCACTCCCA |
| GI17458490_PLAGL2_2R (SEQ ID 272) | NT_028392 | ACGCTCAGCGGCCGTGCCCACGCGGCGGCG CCCATGTCGGCCCG | TCAACGACCGTACCCACG | GACGACGCCCATATCGAC | ACACTCAACAACCATACCCACA |
| GI17458490_PLAGL2_3R (SEQ ID 273) | NT_028392 | GGCTTAGACCTCAAGCAAGTCACGTAACCT CTCCCAGCCTCAGTTTT | ACTTAAACCTCAAACAAATCACG | AACCTCTCCCAACCTCAATTTT | AACTTAAACCTCAAACAAATCACA |
| GI29732427_ABL1_1R (SEQ ID 274) | NT_035014 | AAAGCAGAGAAGCGAGAGCGGCCACTAGTT CGGCAGGAAATTTGTTGGAAGAT | TTCCAACAAATTTCCTACCG | ACTAATAACCGCTCTCGCTTCT | ATCTTCCAACAAATTTCCTACCA |
| GI29732427_ABL1_2R (SEQ ID 275) | NT_035014 | CAATGCATTCCTTTTCGTCAGAGTCGAGGG CAAACTCGCTGAAATCTGGGTGACCC | ACATTCCTTTTCGTCAAAATCG | AAACAAACTCGCTAAAATCTAAATAAC | CAATACATTCCTTTTCATCAAAATCA |
| GI29732427_ABL1_3R (SEQ ID 276) | NT_035014 | GGATTGGTTCCACAGGCCTTTTAAAAAGCG GACTTAAAAGTTGCTGGCAATG | CATTACCAACAACTTTTAAATCCG | TTTTTAAAAAACCTATAAAACCAATCC | CATTACCAACAACTTTTAAATCCA |
| GI29736559_CRIP1_1R (SEQ ID 277) | NT_026437 | GGGACAGACTCCGCCTGGCACCGGGACCAT CCTCCGCCTCAACTTTG | ACAAACTCCGCCTAACACCG | AACCATCCTCCGCCTCA | AAAACAAACTCCACCTAACACCA |
| GI29736559_CRIP1_2R (SEQ ID 278) | NT_026437 | GTGCCAGACGCCTGTGCCTTGGCCGTCCTA CAGCCCTGCTGCCCCTGCC | CCAAACGCCTATACCTTAACCG | CCTACAACCCTACTACCCCTACC | ATACCAAACACCTATACCTTAACCA |
| GI29736559_CRIP1_3R (SEQ ID 279) | NT_026437 | CTGGAGTGTGGCCTCTGTGCCAGACGCCTG TGCCTTGGCCGTCCTACAG | TAAAACGACCAAAACACAAACG | CTAACACAAAAACCACACTCCAA | CTATAAAACAACCAAAACACAAACA |
| GI29736559_DAD1_1R (SEQ ID 280) | NT_026437 | CCTAGAGGAAGTTTAGTCCTTGGGACGCTT GGCCTGCCAGTCTCTGAAA | TCAAAAACTAACAAACCAAACG | CCCAAAAACTAAACTTCCTCTAAA | TTTCAAAAACTAACAAACCAAACA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29736559_DAD1_2R (SEQ ID 281) | NT_026437 | GATGGTGGTGGTGGTAGTGCACGTTGGGTT GAGGGGAC | ATCCCCTCAACCCAACG | ACACTACCACCACCACCATC | ATCCCCTCAACCCAACA |
| GI29736559_FOS_1R (SEQ ID 282) | NT_026437 | TCTGAGACAGGAACTGCGAAATGCTCACGA GATTAGGACACGCGCCAAGGCGG | CCTTAACGCGTATCCTAATCTCG | AAACATTTCGCAATTCCTATCTC | CCACCTTAACACATATCCTAATCTCA |
| GI29736559_FOS_2R (SEQ ID 283) | NT_026437 | CAAGGGTCCGCATTGAACCAGGTGCGAATG TTCTCTCTCATTTCTGCGCCGTTCC | AATCCGCATTAAACCAAATACG | ATATTCTCTCTCATTCTACGCCG | CAAAAATCCACATTAAACCAAATACA |
| GI29736559_FOS_3R (SEQ ID 284) | NT_026437 | CGGGAGCCGAGGCTTAAGTCCTCGGGGTCC TGTACTCGATGCCGTTTCTCC | GAAAACCGAAACTTAAATCCTCG | AATCCTATACTCGATACCGTTTCTC | CAAAAACCAAAACTTAAATCCTCA |
| GI29736559_HSPA2_1R (SEQ ID 285) | NT_026437 | AGACATAGGGTTTGGTGTGGCTGTGCGGGG TTCCCGGGCCTTGC | AAAACCCGAAAACCCCG | ACAACCACACCAAACCCTATATCT | ACAAAACCCAAAAACCCCA |
| GI29736559_HSPA2_2R (SEQ ID 286) | NT_026437 | GCTGGCCTGTCGGCCTCTGATGCACTCGAA CTTCCAGCCCTTGGAGCAGACA | CCTATCGACCTCTAATACACTCG | ACTTCCAACCCTTAAAACAAACA | ACTAACCTATCAACCTCTAATACACTA |
| GI29738185_ESR1_1R (SEQ ID 287) | NT_023451 | TCAGGGAAGCTGCTCTTTGGGATCGCTCCA AATCGAGTTGTGCCTGGA | CAAACACAACTCGATTTAAAACG | TCCCAAAAAACAACTTCCCTAA | TCCAAACACAACTCAATTTAAAACA |
| GI29738185_ESR1_2R (SEQ ID 288) | NT_023451 | GGCCCCTGGATCCGTCTTTCGCGTTTATTT TAAGCCCAGTCTTCCCT | CCTAAATCCGTCTTTCGCG | TTATTTTAAACCCAATCTTCCCT | AACCCCTAAATCCATCTTTCACA |
| GI29738185_ESR1_3R (SEQ ID 289) | NT_023451 | CCCCATTCTATCTGCCCTATCTCGGTTACA GTGTAGTCCTCCCCAGGGTC | CCCATTCTATCTACCCTATCTCG | TTACAATATAATCCTCCCCAAAATC | CCCCATTCTATCTACCCTATCTCA |
| GI29738645_RB1_1R (SEQ ID 290) | NT_024524 | CCTGGAAGGCGCCTGGACCCACGCCAGGTT TCCCAGTTTAATTCCTCA | TAAAAAACGCCTAAACCCACG | CAAATTTCCCAATTTAATTCCTCA | CCTAAAAAACACCTAAACCCACA |
| GI29738645_RB1_3R (SEQ ID 291) | NT_024524 | GCGGGCGGAAGTGACGTTTTCCCGCGGTTG GACGCGGCGCTCAGTTGCCGGG | AACGAAAATAACGTTTTCCCG | GATTAAACGCGACGCTCAATTAC | ACAAACAAAAATAACATTTTCCCA |
| GI29738863_GDF10_1R (SEQ ID 292) | NT_030772 | TCGCAGCCAGGGCAGGCTGCGGCGCCGACA CACAGGAGCCGGCTGCGGG | GCAACCAAAACAAACTACGACG | CGACACACAAAAACCGACTAC | TCACAACCAAAACAAACTACAACA |
| GI29738863_GDF10_2R (SEQ ID 293) | NT_030772 | TCATCTTGCAATCACATAGCCATCGCATGC CATTGCAGGGGCAACCCAGCA | TCATCTTACAATCACATAACCATCG | ATACCATTACAAAAACAACCCAACA | TCATCTTACAATCACATAACCATCA |
| GI29738863_GDF10_3R (SEQ ID 294) | NT_030772 | CATACGCTGACTCCGAGGCAACTGGGCGCA CACATATCCCCTCTCTGGTCCTC | GCTAACTCCGAAACAACTAAACG | ACACATATCCCCTCTCTAATCCTC | CATACACTAACTCCAAAACAACTAAAA |
| GI29739550_OAT_1R (SEQ ID 295) | NT_035040 | CAGGGTTCAAGGGCATGGGGCTCCCGCAGC TGTGGCTGGGGCAGAGC | CTCTACCCCAACCACAACTACG | AAACCCCATACCCTTAAACCCTA | ACTCTACCCCAACCACAACTACA |
| GI29739550_OAT_2R (SEQ ID 296) | NT_035040 | GCCCAACAGACTTTTCCTTTTCGGGCCTCA GTCTTCTCGTCAGCAAG | CCCAACAAACTTTTCCTTTTCG | ACCTCAATCTTCTCGTCAACAAA | ACCCAACAAACTTTTCCTTTTCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29739550_OAT_3R (SEQ ID 297) | NT_035040 | CACGCGATTGGTATCCTGCCCTCCGCCCCA GCCAATGAGCGGCGAGGGT | GCGATTAATATCCTACCCTCCG | CCCAACCAATAAACGACGAAA | CACACAATTAATATCCTACCCTCCA |
| GI29789893_CTNNB1_1R (SEQ ID 298) | NT_037565 | TCCCCGATGCAGACCACAGCGCCCTCACGG GCTGCCCTCAGGCC | CCCGATACAAACCACAACG | CCTCACGAACTACCCTCAAAC | TCCCCAATACAAACCACAACA |
| GI29791372_RARB_1R (SEQ ID 299) | NT_022517 | AAAGGGAGAGAAGTTGGTGCTCAACGTGAG CCAGGAGCAGCGTCCCGGCT | GAAACGCTACTCCTAACTCACG | TAAACACCAACTTCTCTCCCTTT | AACCAAAACACTACTCCTAACTCACA |
| GI29791372_RARB_2R (SEQ ID 300) | NT_022517 | CGTGAGCCAGGAGCAGCGTCCCGGCTCCTC CCCTGCTCATTTTAAAA | GTAAACCAAAAACAACGTCCCG | CTCCTCCCCTACTCATTTTAAAA | CATAAACCAAAAACAACATCCCA |
| GI29791372_RARB_3R (SEQ ID 301) | NT_022517 | GAGCGGGCGCAGGCGGAACACCGTTTTCCA AGCTAAGCCGCCGCAAA | AACGCAAACGAAACACCG | TTTCCAAACTAAACCGCCG | AAACAAACACAAACAAAACACCA |
| GI29791375_ARHI_1R (SEQ ID 302) | NT_032977 | GGCTGGGGCACACAAAACCAGGTGCTACCG TCAACGACTAGGCCCATAGGGTACTG | ACCCTATAAACCTAATCGTTAACG | TAACACCTAATTTTATATACCCCAACC | CAATACCCTATAAACCTAATCATTAAA |
| GI29791375_ARHI_2R (SEQ ID 303) | NT_032977 | AAGGGAGAAAGAAGCCAGACGGAGCTCGGA GATGTGGAGGGCAGACGCA | GTCTACCCTCCACATCTCCG | ACTCCGTCTAACTTCTTTCTCCC | TACATCTACCCTCCACATCTCCA |
| GI29791375_ARHI_3R (SEQ ID 304) | NT_032977 | CCCAAAACGCTCGGTAGGCGGTGGTGCGCA GCTTTCAATGCATCCGCCGCCA | AACGCTCGATAAACGATAATACG | AACTTTCAATACATCCGCCG | CCCAAAACACTCAATAAACAATAATAA |
| GI29791382_SFN_2R (SEQ ID 305) | NT_037485 | CTCCTGAACCTTTATGGGCTCTGTCGAGGC TGAAGCAGCCAGGGGCT | ACCCCTAACTACTTCAACCTCG | CAAAACCCATAAAAATTCAAAAA | AACCCCTAACTACTTCAACCTCA |
| GI29791382_SFN_3R (SEQ ID 306) | NT_037485 | GCAGGTCTTGGGCCCTGGTCCCGCCCCCTG CTCCTCCCCAC | CAAATCTTAAACCCTAATCCCG | CCCCTACTCCTCCCCAC | ACAAATCTTAAACCCTAATCCCA |
| GI29794267_SFTPC_1R (SEQ ID 307) | NT_023666 | GAGGGGCTGGAGGAGGAAACGGGGAGGCCC ACACAGAAGGG | CCCTTCTATATAAACCTCCCCG | TTCCTCCTCCAACCCCTC | CCCTTCTATATAAACCTCCCCA |
| GI29794267_SFTPC_2R (SEQ ID 308) | NT_023666 | GGGCAACTGTCCCCACCCGTCCCTGGCACG GCTCTGCCCAGT | AAACAACTATCCCCACCCG | CCCTAACACGACTCTACCCAA | AAACAACTATCCCCACCCA |
| GI29794267_SFTPC_3R (SEQ ID 309) | NT_023666 | TCCTTGCTGCCACACATTTAGCCGCCCTCC CCATGCCAGCTTGGGG | CCTTACTACCACACATTTAACCG | CCTCCCCATACCAACTTAAAA | TCCTTACTACCACACATTTAACCA |
| GI29794674_EGFR_1R (SEQ ID 310) | NT_033968 | GTTGGGTGCCCTCATTTCAGATGATTTCGA GGGTGCTTGACAAGATCTGAA | TCAAATCTTATCAAACACCCTCG | AATCATCTAAAATAAAAACACCCAAC | TTCAAATCTTATCAAACACCCTCA |
| GI29794674_EGFR_2R (SEQ ID 311) | NT_033968 | GGGGACCCTGGCACAGATTTGGCTCGACCT GGACATAGGCTGGGCCTG | AAACCCAACCTATATCCAAATCG | ACCAAATCTATACCAAAATCCCC | CAAACCCAACCTATATCCAAATCA |
| GI29794674_EGFR_3R (SEQ ID 312) | NT_033968 | GGCAGTGCTGGGAACGCCCCTCTCGGAAAT TAACTCCTCAGGGCACCCGC | AATACTAAAAACGCCCCTCTCG | AAATTAACTCCTCAAAACACCCG | AACAATACTAAAAACACCCCTCTCA |
| GI29796148_TERT_1R (SEQ ID 313) | NT_023089 | GACCTGGAGGCAGCCCTGGGTCTCCGGATC AGGCCAGCGGCCAAAGGG | CTTTAACCGCTAACCTAATCCG | AAACCCAAAACTACCTCCAAATC | CCCTTTAACCACTAACCTAATCCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29796148_TERT_2R (SEQ ID 314) | NT_023089 | CCGCCCGGAGCAGCTGCGCTGTCGGGGCCA GGCCGGGCTCCCAGTGGA | CCCGAAACAACTACGCTATCG | AACCAAACCGAACTCCCAATAA | CCACCCAAAACAACTACACTATCA |
| GI29796148_TERT_3R (SEQ ID 315) | NT_023089 | GGGTTACCCCACAGCCTAGGCCGATTCGAC CTCTCTCCGCTGGGGCC | AATTACCCCACAACCTAAACCG | TTCGACCTCTCTCCGCTAAA | AAATTACCCCACAACCTAAACCA |
| GI29797939_IL13_1R (SEQ ID 316) | NT_034772 | GGCCGCGCAGATCCCGCTTATCGGGCCCAT CTCCCGTTACATAAGGC | CGCAAATCCCGCTTATCG | ACCCATCTCCCGTTACATAAAAC | AACCACACAAATCCCACTTATCA |
| GI29797939_IL13_2R (SEQ ID 317) | NT_034772 | GAGCCGCTGGCCCGGGTGTCCAGCCGGCCC TTGCCCTGCCTGGCGCT | GCCAAACAAAACAAAAACCG | CTAAACACCCGAACCAACGACT | AACACCAAACAAAACAAAAACCA |
| GI29797939_IL13_3R (SEQ ID 318) | NT_034772 | CACGCAGCGCATTGCAGGCAGGTGCGAGCC ACATGCGCCAAGTGCCCGGA | GCAACGCATTACAAACAAATACG | ACCACATACGCCAAATACCC | CACACAACACATTACAAACAAATACA |
| GI29797939_LOX_1R (SEQ ID 319) | NT_034772 | ATCCTGGGGTTTATTTGCTGAGGGCGCTTC CCATAAAAGCGAGAGAGTGTG | CACTCTCTCGCTTTTATAAAAAACG | CCTCAACAAATAAACCCCAAAAT | CACACTCTCTCACTTTTATAAAAAACA |
| GI29797939_LOX_2R (SEQ ID 320) | NT_034772 | GTGAACAAATAGCTGAGGGGCGGCCGGGCC AGAACGGCTTGTGTAACTT | ATTACACAAACCGTTCTAACCCG | CCGCCCCTCAACTATTTATTC | AAATTACACAAACCATTCTAACCCA |
| GI29797939_LOX_3R (SEQ ID 321) | NT_034772 | AGGCGAGGAGCTGTCCGCCTTGCACGTTTC CAATCGCATTACGTGAACAAATAG | GAAAAACTATCCGCCTTACACG | TTCCAATCGCATTACGTAAACA | AAACAAAAAACTATCCACCTTACACA |
| GI29800185_SFTPD_1R (SEQ ID 322) | NT_030059 | TTGTGAATATCAGTGGCAGGTTTCCAGAAC GCAGGTGGGGATAAGAGTGAGT | TCACTCTTATCCCCACCTACG | TCTAAAAACCTACCACTAATATTCACA | ACTCACTCTTATCCCCACCTACA |
| GI29800185_SNCG_1R (SEQ ID 323) | NT_030059 | CGGTTTCATGGCAGCCCAGGGTCCAGCGGC ATCCAGGATGCTGGTGGG | CCACCAACATCCTAAATACCG | TAAACCCTAAACTACCATAAAACCG | CCCACCAACATCCTAAATACCA |
| GI29800185_SNCG_2R (SEQ ID 324) | NT_030059 | AGCTGCACAGCCCAGGCCGCGGGAGGTTGG CTGCTCTCACCTAACAGGCC | ACACAACCCAAACCGCG | AAAATTAACTACTCTCACCTAACAAAC | AACTACACAACCCAAACCACA |
| GI29800185_SNCG_3R (SEQ ID 325) | NT_030059 | ACCTCAGATCCTCCAACCGGTTTCATGGCA GCCCAGGGTCCA | ACCTCAAATCCTCCAACCG | TTTCATAACAACCCAAAATCCA | ACCTCAAATCCTCCAACCA |
| GI29801752_PLAGL1_1R (SEQ ID 326) | NT_025741 | AGTGCCTGGCTCACGGTCAGTGCTCACGTT TGGGCAGCTGCACTTGGGC | CCCAAATACAACTACCCAAACG | AAACACTAACCGTAAACCAAACAC | ACCCAAATACAACTACCCAAACA |
| GI29801752_PLAGL1_2R (SEQ ID 327) | NT_025741 | CCAGGCCGGCTCGGGTCTACCTGCGCCAGC GCTGTACCTGGGCGACCTTGGCTT | AACCGACTCGAATCTACCTACG | CAACGCTATACCTAAACGACCTT | CCAAACCAACTCAAATCTACCTACA |
| GI29801752_PLAGL1_3R (SEQ ID 328) | NT_025741 | GGGCTCTGGCGGCCCATCCTGGCGGAGACT TCGGCTAGCAGGCCCCGC | ACTCTAACGACCCATCCTAACG | AAACTTCGACTAACAAACCCCG | AAACTCTAACAACCCATCCTAACA |
| GI29803948_CD63_1R (SEQ ID 329) | NT_029419 | CTGGCTTTGTCTTCTGGGATAAGACGGGGA AATCCAGAGGATGTAAGC | CTTCATCCTCTAAATTTCCCCG | CTTATCCCAAAAAACAAAACCAA | ACTTACATCCTCTAAATTTCCCCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29803948_CD63_2R (SEQ ID 330) | NT_029419 | GGCAGCTTGATCCCCCTAGCCCGCTTCCAG CCCTCACCTGGCTTTGTC | ACAACTTAATCCCCCTAACCCG | TTCCAACCCTCACCTAACTTTATC | AACAACTTAATCCCCCTAACCCA |
| GI29803948_CD63_3R (SEQ ID 331) | NT_029419 | GGTGTGACGGCCGGTCCTACTCTCCGGCCT GTTCAGATCAGCTCCTTCTGGG | ATAACGACCGATCCTACTCTCCG | CCTATTCAAATCAACTCCTTCTAAA | AATATAACAACCAATCCTACTCTCCA |
| GI29803948_CDK4_1R (SEQ ID 332) | NT_029419 | TCCTGGGGACCCTTGACCCTCCGACACAAA CAAGCGCTCCAGGAGTC | CTAAAAACCCTTAACCCTCCG | CACAAACAAACGCTCCAAAA | TCCTAAAAACCCTTAACCCTCCA |
| GI29803948_CDK4_2R (SEQ ID 333) | NT_029419 | CCCTTAGCTTACGGAGACCCTGGGGCGAGG GAAATAGGAGAGAACAGCAGTC | ACTATTCTCTCCTATTTCCCTCG | CCCAAAATCTCCGTAAACTAAAA | AACTACTATTCTCTCCTATTTCCCTCA |
| GI29803948_CDK4_3R (SEQ ID 334) | NT_029419 | TGTTAATGGGTGAGAGGGATTTTGCGCTCT CCGGGGAGAAAGCCCCAC | TAAAACTTTCTCCCCGAAAAACG | AAAATCCCTCTCACCCATTAACA | ATAAAACTTTCTCCCCAAAAAACA |
| GI29804485_BCAP31_1R (SEQ ID 335) | NT_025965 | GGCCCTCCAGGGTCGCGGCCTCTTCGGGCA GCCCAAGTGGAGGAACTT | AATTCCTCCACTTAAACTACCCG | AAAAACCGCGACCCTAAAAA | AAATTCCTCCACTTAAACTACCCA |
| GI29804485_BCAP31_2R (SEQ ID 336) | NT_025965 | GGGCTCAGGGCCCTCCAGGGTCGCGGCCTC TTCGGGCAGCCCAAGTG | AACTCAAAACCCTCCAAAATCG | GACCTCTTCGAACAACCCAAATA | AAACTCAAAACCCTCCAAAATCA |
| GI29804485_CTAG1_1R (SEQ ID 337) | NT_025965 | CCAGCTGGGCGACCAGGACAGGGACGGAGG CTGCTGAGCCCAGTTAGAG | CTAACTAAACTCAACAACCTCCG | CCCTATCCTAATCGCCCAACTAA | CTCTAACTAAACTCAACAACCTCCA |
| GI29804485_CTAG1_2R (SEQ ID 338) | NT_025965 | GAGACCTTGGCTGGCGCGAGGCCACGCCCA CCAGACATGCAGTTCCAGCT | CTTAACTAACGCGAAACCACG | CCACCAAACATACAATTCCAACT | AAAACCTTAACTAACACAAAACCACA |
| GI29804485_CTAG1_3R (SEQ ID 339) | NT_025965 | GGGCGACTAGGACAGGGACAGAACCCGTTG AACCCAGGAGTGAGATCCGG | GAATCTCACTCCTAAATTCAACG | ATTCTATCCCTATCCTAATCGCC | CCAAATCTCACTCCTAAATTCAACA |
| GI29804485_STK23_1R (SEQ ID 340) | NT_025965 | GGGGGGCCTCTGCCCGGGGGCCGGGCTCTC TGGGGCCGCCGTCGCGCC | AAAACCTCTACCCGAAAACCG | ACTCTCTAAAACCGCCGTCG | AAAAAACCTCTACCCAAAAACCA |
| GI29804485_STK23_2R (SEQ ID 341) | NT_025965 | GGGGTACGGGCTGCTTCACCCCCGCGTGGA CCTCCCCCTCAGCTGGGG | AATACGAACTACTTCACCCCCG | GTAAACCTCCCCCTCAACTAAAA | AAAATACAAACTACTTCACCCCCA |
| GI29804485_STK23_3R (SEQ ID 342) | NT_025965 | CTGGGAGCCAGAGCGCCAGGCAGCGTCGCA GGAGCAGGTTCTGGGCTGG | CAACCCAAAACCTACTCCTACG | CGCTACCTAACGCTCTAACTCC | CCAACCCAAAACCTACTCCTACA |
| GI29804900_PRKCDBP_1R (SEQ ID 343) | NT_028310 | TGAAACAGGCACACCAGGGAATTGGAGCGG AGGAGGGTAACTCAAACTCAGAG | AAATTTAAATTACCCTCCTCCG | TCCAATTCCCTAATATACCTATTTCA | CTCTAAATTTAAATTACCCTCCTCCA |
| GI29804900_PRKCDBP_2R (SEQ ID 344) | NT_028310 | GGCCCCCTGGTTATCTCTTTGCCGTGCCAA CACAGTCTCTGCGCCCAC | CCCCTCTAATTATCTCTTTACCG | ACCAACACAATCTCTACGCCC | AACCCCTCTAATTATCTCTTTACCA |
| GI29804900_PRKCDBP_3R (SEQ ID 345) | NT_028310 | GCAGCCTGTCCAAGTCACAAAGCGGGGCCT CGGGCCTTGACAGTTCGCG | CAACCTATCCAAATCACAAAACG | AACCTCGAACCTTAACAATTCG | ACAACCTATCCAAATCACAAAACA |
| GI29805597_APOA1_1R (SEQ ID 346) | NT_033899 | AAGGGGATGAGTGCAGGGAACCCCGACCCC ACCCGGGAGACCTGCAAG | CAAATCTCCCGAATAAAATCG | AATTCCCTACACTCATCCCCTT | CTTACAAATCTCCCAAATAAAATCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29805597_APOA1_2R (SEQ ID 347) | NT_033899 | GCAGACACTCCCCTCCCGCCCCCACTGAACCCTTGACCC | CAAACACTCCCCTCCCG | CCCCACTAAACCCTTAACCC | ACAAACACTCCCCTCCCA |
| GI29805597_APOA1_3R (SEQ ID 348) | NT_033899 | CGAAACCTCAGTCTGGGAGCCACGGAGGGCTCTCCCCTCTCCCC | AAACCTCAATCTAAAAACCACG | AAAACTCTCCCCTCTCCCC | CAAAACCTCAATCTAAAAACCACA |
| GI29805597_PGR_1R (SEQ ID 349) | NT_033899 | GCCCCTCCCCAGATGATCGAGGGGTCCAGGCTCCTTACCTCTAGT | CCCCTCCCCAAATAATCG | AAAATCCAAACTCCTTACCTCTAAT | ACCCCTCCCCAAATAATCA |
| GI29805597_PGR_2R (SEQ ID 350) | NT_033899 | CATATTATATCCTGCCATTTGATGCCCGGTGAACATTCTATACCTGCTTCCCAGAA | CATATTATATCCTACCATTTAATACCCG | TAAACATTCTATACCTACTTCCCAAAA | CATATTATATCCTACCATTTAATACCA |
| GI29809602_CDH13_1R (SEQ ID 351) | NT_024797 | GAAAAGTGGAATCAGCTGGCATTGCCCAGCGTGATTTGTGAGGCTGAGCCCCAA | AAACTCAACCTCACAAATCACG | TAAACAATACCAACTAATTCCACTTTC | TTAAAACTCAACCTCACAAATCACA |
| GI29809602_CDH13_2R (SEQ ID 352) | NT_024797 | ACGAGGGAGCGTTAGGAAGGAATCCGTCTTGTAAAGCCATTGGTCCTGG | CCAAAACCAATAACTTTACAAAACG | ATTCCTTCCTAACGCTCCCTC | CCAAAACCAATAACTTTACAAAACA |
| GI29809602_CDH13_3R (SEQ ID 353) | NT_024797 | AAGCAAATGGGATGCCACCTCCGCGGGGCTCGCTCCTCGCGAGGTGCTCAC | AAATAAAATACCACCTCCGCG | AACTCGCTCCTCGCGAAATAC | AAACAAATAAAATACCACCTCCACA |
| GI29809804_ASC _1R (SEQ ID 354) | NT_024812 | GGTTCGGGGAACCGCGGAGGTTTCGGGGTTCTAGAAATCCGAGGTTCTAAGCC | AAAAACCGCGAAAATTTCG | AATTCTAAAAATCCGAAATTCTAAACC | AATTCAAAAAACCACAAAAATTTCA |
| GI29809804_ASC_2R (SEQ ID 355) | NT_024812 | GGAGGTTTCGGGGTTCTAGAAATCCGAGGTTCTAAGCCTAGGTGCTCCAA | AAAACACCTAAACTTAAAACCTCG | ATTTCTAAAACCCCGAAACCTC | TTAAAACACCTAAACTTAAAACCTCA |
| GI29809804_ASC_3R (SEQ ID 356) | NT_024812 | GTGAGAGCCAGCCCAGGTTTCCGGTCTGTACCCGCTGGTGCAAGCCCAGA | AAACCAACCCAAATTTCCG | TCTATACCCGCTAATACAAACCC | ATAAAAACCAACCCAAATTTCCA |
| GI29809804_PRSS8_1R (SEQ ID 357) | NT_024812 | CACCACATACACACTACACACCGGGACACACACACAAAAGGCCTATGCA | ACCACATACACACTACACACCG | AACACACACACAAAAAACCTATACA | CACCACATACACACTACACACCA |
| GI29809804_PRSS8_2R (SEQ ID 358) | NT_024812 | CACACACACAAACCACATGCACGTGCATGCACGCACACTCAGACACAC | ACACACACAAACCACATACACG | ACATACACGCACACTCAAACA | CACACACACAAACCACATACACA |
| GI29809804_PRSS8_3R (SEQ ID 359) | NT_024812 | TGAGCTCAGGGCTCAAGGGGGACGGGGCTGGTGCCTGTTTT | AAACAAACACCAACCCCG | CCCCCTTAAACCCTAAACTCA | AAAACAAACACCAACCCCA |
| GI29823171_SERPINB5_1R (SEQ ID 360) | NT_025028 | TTCACCTTCCGGTCCTGCGTGGGCCGAGAGGATTGCCGTACGCATGTCTG | ACATACGTACGACAATCCTCTCG | CCCACGCAAAACCGAAAA | CAAACATACATACAACAATCCTCTCA |
| GI29823171_SERPINB5_3R (SEQ ID 361) | NT_025028 | CAAACTCCTGGGCTCAAGCAATCCGCTCACGTCAACCTCCCCAAATGCT | AACTCCTAAACTCAAACAATCCG | TCACGTCAACCTCCCCAAATA | CAAACTCCTAAACTCAAACAATCCA |
| GI29789893_CTNNB1_2R (SEQ ID 362) | NT_037565 | AGCGGTACTCGAAGGCCGGGGCCGAGATGCCACCTTCCGCAGGCCGC | GATACTCGAAAACCGAAACCG | AATACCACCTTCCGCAAACC | AACAATACTCAAAAACCAAAACCA |

-continued

| TARGET CPG SITE | "GenBank®" ACCESSION # | TARGET SEQUENCE | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29789893_CTNNB1_3R (SEQ ID 363) | NT_037565 | GGGTGCTGTGAGACTGGGCTGCGACCCAGG TCCAGCAGGGAGTGTG | CACACTCCCTACTAAACCTAAATCG | AACCCAATCTCACAACACCC | CACACTCCCTACTAAACCTAAATCA |
| GI29794147_RUNX3_1R (SEQ ID 364) | NT_077383 | TGAGCCAAGGCCGCGAGCAGGCTTCTCGCA TCCTGTGAGCTGAGGTTGG | CCAACCTCAACTCACAAAATACG | AAAACCTACTCGCGACCTTAACT | CCAACCTCAACTCACAAAATACA |
| GI29794147_RUNX3_2R (SEQ ID 365) | NT_077383 | GTGACATCACGGCCCAGGTGACCGCGGCCC AGCCAATGAGCCAAGGCC | TAACATCACGACCCAAATAACCG | GACCCAACCAATAAACCAAAAC | ATAACATCACAACCCAAATAACCA |
| GI29794147_RUNX3_3R (SEQ ID 366) | NT_077383 | TGGTGGACAATGGCAGGGAGTCAGCCGCAG CCCAGGGGCGAGGTGGCAT | ACCTCGCCCCTAAACTACG | CTAACTCCCTACCATTATCCACCA | ATACCACCTCACCCCTAAACTACA |
| GI29794313_MYCL1_1R (SEQ ID 367) | NT_077386 | CCCAGCTCGGAGTGGGCAAGGAGCACGGTT TAGCTCAGCCGGCTGGCACCG | TACCAACCGACTAAACTAAACCG | ACTCCTTACCCACTCCGAACTAA | CAATACCMCCAACTAAACTAAACCA |
| GI29794313_MYCL1_2R (SEQ ID 368) | NT_077386 | CGACGGGTGACCAGACGGACGCCGGGACCA GCCCAAGTTCAGGGCTGA | AATAACCAAACGAACGCCG | AACCAACCCAAATTCAAAACTAA | CAACAAATAACCAAACAAACACCA |
| GI29799662_SCGB3A1_1R (SEQ ID 369) | NT_077451 | GGCAGGGACCAGGGAGCCAGGAACTGCGCC GCCCCCGCCCCTGCCCTGGC | CAAAACAAAAACGAAAACGACG | AATTCCTAACTCCCTAATCCCTACC | ACCAAAACAAAAACAAAAACAACA |
| GI29799662_SCGB3A1_2R (SEQ ID 370) | NT_077451 | GGCGAGGACCGGGTATAAGAAGCCTCGTGG CCTTGCCCGGGCAGCCGC | ACTACCCGAACAAAACCACG | AACTTCTTATACCCGATCCTCG | ACAACTACCCAAACAAAACCACA |
| GI29799662_SCGB3A1_3R (SEQ ID 371) | NT_077451 | CGCGTGGGGTCAGACCGCAAAGCGAAGGTG CGGGCCGGGGTGGGCCTCGCG | GTAAAATCAAACCGCAAAACG | AAATACGAACCGAAATAAACCTC | CACATAAAATCAAACCACAAAACA |
| GI29801002_SFTPA1_1R (SEQ ID 372) | NT_077575 | TGGGGCTCATGGCTGAGCCAGGTCGCAGGA CAGACAAGTTGGCCTGGA | CCAAACCAACTTATCTATCCTACG | CCTAACTCAACCATAAACCCCA | TCCAAACCAACTTATCTATCCTACA |
| GI29801002_SFTPA1_2R (SEQ ID 373) | NT_077575 | TTACAGACCTGGAGTTCCTCTTTCGCAGGT TCTGTGCTCCCCTCAAGGGTC | CAAACCTAAAATTCCTCTTTCG | AAATTCTATACTCCCCTCAAAAATC | TTACAAACCTAAAATTCCTCTTTCA |
| GI29801002_SFTPA1_3R (SEQ ID 374) | NT_077575 | AGACAGAAACTGCAGCTCTCCCGTGACCTT CCAGGTGCTGCCCTGACTC | AACAAAAACTACAACTCTCCCG | AACCTTCCAAATACTACCCTAACTC | AAACAAAAACTACAACTCTCCCA |
| GI29804083_UNG_1R (SEQ ID 375) | NT_078089 | CCGAGAGACAGGGTCTCGCTCTGTCGCCCA GGCCTGGAGTGCATTGGC | CCAATACACTCCAAACCTAAACG | CAAAACGAAACCCTATCTCTCG | ACCAATACACTCCAAACCTAAACA |
| GI29804083_UNG_2R (SEQ ID 376) | NT_078089 | CGCTAGGATTACAGGCGTGGGCCACCGCGC CTGACCAGTCTTCTCTTCTTGCAG | AAAATTACAAACGTAAACCACCG | GCCTAACCAATCTTCTCTTCTTACA | CACTAAAATTACAAACATAAACCACCA |
| GI29804083_UNG_3R (SEQ ID 377) | NT_078089 | GCTCAGACCCTCTGGCCTCAAGCGATCCTC CAGCCTGGGCCTCCC | TCAAACCCTCTAACCTCAAACG | TCCTCCAACCTAAACCTCCC | ACTCAAACCCTCTAACCTCAAACA |

TABLE 2

Methylation Markers for Squamous Cell Carcinoma
METHYLATION MARKERS FOR SQUAMOUS CELL CARCINOMA

| Panel_I | | Panel_II | | Panel_III | | Panel_IV | |
|---|---|---|---|---|---|---|---|
| Marker Name | p-value | Marker Name | p-value | Marker Name | p-value | Marker Name | p-value |
| HTR1B_2r | 2.559E−06 | MTHFR_1r | 0.00004 | HTR1B_2r | 0.00043 | HTR1B_2r | 0.00043 |
| GDF10_3r | 1.065E−05 | TSLL2_2r | 0.00053 | MTHFR_1r | 0.00080 | MTHFR_1r | 0.00080 |
| ARHI_2r | 2.616E−05 | HTR1B_2r | 0.00056 | MLH1_2r | 0.00099 | MLH1_2r | 0.00099 |
| SFN_1r | 4.169E−05 | ABCC5_2r | 0.00206 | GDF10_3r | 0.00183 | GDF10_3r | 0.00183 |
| CALCA1_1r | 4.187E−05 | GDF10_3r | 0.00244 | APC_1r | 0.00228 | APC_1r | 0.00228 |
| ADCYAP1_2r | 4.533E−05 | MLH1_2r | 0.00290 | TP53_3r | 0.00279 | TP53_3r | 0.00279 |
| TERT_1r | 1.094E−04 | VHL_1r | 0.00350 | ARHI_2r | 0.00339 | ARHI_2r | 0.00339 |
| RASSF1_3r | 1.384E−04 | UBB_2r | 0.00400 | BRCA1_3r | 0.00397 | BRCA1_3r | 0.00397 |
| MOS_1r | 1.497E−04 | CALCA_1r | 0.00474 | CALCA_1r | 0.00468 | CALCA_1r | 0.00468 |
| SFTPC_3r | 4.626E−04 | SNCG_3r | 0.00522 | ADCYAP1_2r | 0.00505 | ADCYAP1_2r | 0.00505 |
| TERT_3r | 4.681E−04 | S100A2_1r | 0.00532 | SFTPC_3r | 0.00555 | SFTPC_3r | 0.00555 |
| MYOD1_2r | 6.924E−04 | SFN_2r | 0.00639 | TSLL2_2r | 0.00676 | TSLL2_2r | 0.00676 |
| C4B_2r | 7.712E−04 | SFTPC_3r | 0.00817 | TERT_1r | 0.00713 | TERT_1r | 0.00713 |
| CALCA_2r | 7.857E−04 | ADCYAP1_2r | 0.00910 | MYC_2r | 0.00745 | MYC_2r | 0.00745 |
| | | SFN_3r | 0.00923 | RASSF1_3r | 0.00825 | RASSF1_3r | 0.00825 |
| | | | | MOS_1r | 0.00872 | MOS_1r | 0.00872 |
| | | | | SNCG_3r | 0.00876 | SNCG_3r | 0.00876 |
| | | | | TGFBR2_3r | 0.00957 | TGFBR2_3r | 0.00957 |
| | | | | | | APC_2r | 0.01187 |
| | | | | | | HOXA5_3r | 0.01204 |
| | | | | | | TYMS_2r | 0.01442 |
| | | | | | | CDKN2B_3r | 0.01455 |
| | | | | | | CALCA_2r | 0.01579 |
| | | | | | | MYOD1_2r | 0.01594 |
| | | | | | | TERT_3r | 0.01734 |
| | | | | | | PTEN_1r | 0.01896 |
| | | | | | | C4B_2r | 0.01927 |
| | | | | | | GSTP1_3r | 0.01964 |

TABLE 3

Methylation Markers for Adenocarcinoma
Methylation Markers for Adenocarcinoma

| Panel_I | | Panel_II | |
|---|---|---|---|
| Marker Name | p-value | Marker Name | p-value |
| SFN_2r | 0.00000000007 | SFN_2r | 0.000009 |
| TWIST1_3r | 0.00000093146 | CD1A_1r | 0.000511 |
| SERPINB5_1r | 0.00000098742 | TNF_2r | 0.000526 |
| GDF10_3r | 0.00000130650 | SERPINB5_1r | 0.000638 |
| PGR_1r | 0.00000188610 | PGR_1r | 0.001117 |
| SFTPD_1r | 0.00000420738 | TWIST1_3r | 0.001288 |
| ARHI_3r | 0.00000598158 | GDF10_3r | 0.001469 |
| CALCA_1r | 0.00000933174 | SFTPD_1r | 0.002031 |
| SFTPB_1r | 0.00004835043 | ADCYAP1_2r | 0.002176 |
| CALCA_2r | 0.00008410116 | ARHI_3r | 0.002211 |
| WT1_1r | 0.00013356747 | IL13_3r | 0.002844 |
| PRDM2_3r | 0.00014989843 | HOXA5_2r | 0.002966 |

TABLE 3-continued

Methylation Markers for Adenocarcinoma
Methylation Markers for Adenocarcinoma

| Panel_I | | Panel_II | |
|---|---|---|---|
| Marker Name | p-value | Marker Name | p-value |
| TERT_1r | 0.00019412964 | CALCA_1r | 0.003758 |
| S100A2_2r | 0.00031181656 | HOXA5_1r | 0.004410 |
| ADCYAP1_3r | 0.00033644602 | SFTPB_1r | 0.004675 |
| RUNX3_2r | 0.00045917044 | MC2R_1r | 0.005590 |
| MYOD1_2r | 0.00061315386 | HOXA5_3r | 0.005836 |
| TWIST1_2r | 0.00077702738 | WT1_1r | 0.005920 |
| | | SERPINB5_3r | 0.008011 |
| | | CDH13_3r | 0.008365 |
| | | CALCA_2r | 0.008434 |
| | | RUNX3_1r | 0.008640 |

TABLE 4

Samples for Methylation Analysis

| Sample | Diagnosis | Age | Sex | Norm Match | Staging | Grading | $R^2$ correlation |
|---|---|---|---|---|---|---|---|
| D12152 | Adenocarcinoma | 73 | F | | no data | | 0.958 |
| D12155 | Adenocarcinoma | 60 | M | | no data | | 0.964 |
| D12157 | Normal | 79 | M | | | | 0.811 |
| D12158 | Adenocarcinoma | 87 | M | | no data | | 0.963 |
| D12160 | Adenocarcinoma | 79 | M | | no data | | 0.986 |
| D12162 | Adenocarcinoma | 47 | M | | no data | | 0.970 |
| D12163 | Adenocarcinoma | 54 | M | | no data | | 0.990 |
| D12164 | Normal | 21 | M | | | | 0.980 |
| D12165 | Adenocarcinoma | 76 | F | | no data | | 0.964 |
| D12170 | Adenocarcinoma | 62 | M | | no data | | 0.984 |
| D12173 | Normal | 77 | M | | | | 0.988 |
| D12180 | Normal | 69 | M | | | | 0.876 |

TABLE 4-continued

| Samples for Methylation Analysis | | | | | | | |
|---|---|---|---|---|---|---|---|
| Sample | Diagnosis | Age | Sex | Norm Match | Staging | Grading | $R^2$ correlation |
| D12181 | Adenocarcinoma | 64 | M | | no data | | 0.962 |
| D12182 | Normal | 64 | M | | | | 0.981 |
| D12184 | Normal | 75 | F | | | | 0.984 |
| D12188 | Normal | 66 | M | | | | 0.940 |
| D12190 | Adenocarcinoma | 49 | M | | no data | | 0.961 |
| D12195 | Normal | 62 | F | | | | 0.982 |
| D12197 | Adenocarcinoma | 50 | F | | no data | | 0.982 |
| D12198 | Normal | 74 | F | | | | 0.976 |
| D12202 | Normal | 71 | M | | | | 0.988 |
| D12203 | Adenocarcinoma | 71 | M | D12202 | no data | | 0.940 |
| D12205 | Normal | 68 | M | | | | 0.961 |
| D12207 | Adenocarcinoma | 62 | M | | no data | | 0.978 |
| D12209 | Normal | 6 | M | | | | 0.990 |
| G12001 | Squamous cell carcinoma | 74 | M | B12001 | pT1 N0 Mx | 1 | 0.995 |
| G12002 | Squamous cell carcinoma | 63 | M | B12002 | pT4 N2 Mx | 3 | 0.988 |
| G12003 | Squamous cell carcinoma | 67 | M | B12003 | pT1 N3 Mx | 2 | 0.981 |
| G12004 | Squamous cell carcinoma | 69 | M | B12004 | pT2 N1 Mx | 3 | 0.983 |
| G12005 | Squamous cell carcinoma | 59 | M | B12005 | pT2 N0 M0 | 2 | 0.994 |
| G12006 | Squamous cell carcinoma | 49 | M | B12006 | pT2 N1 Mx | 2 | 0.989 |
| G12007 | Squamous cell carcinoma | 71 | M | | pT2 N1 Mx | 2 | 0.988 |
| G12008 | Squamous cell carcinoma | 57 | F | B12008 | pT2 N0 Mx | 3 | 0.964 |
| G12009 | Squamous cell carcinoma | 62 | M | B12009 | pT2 N1 Mx | 3 | 0.986 |
| G12010 | Squamous cell carcinoma | 67 | M | B12010 | pT2 N1 Mx | 2 | 0.921 |
| G12011 | Squamous cell carcinoma | 73 | M | | pT2 N0 Mx | 2 | 0.977 |
| G12012 | Squamous cell carcinoma | 71 | M | B12012 | pT2 N0 Mx | 2 | 0.994 |
| G12013 | Squamous cell carcinoma | 73 | M | | pT2 N0 Mx | 1 | 0.938 |
| G12014 | Squamous cell carcinoma | 64 | M | | pT2 N2 Mx | 3 | 0.933 |
| G12018 | Adenocarcinoma | 60 | F | B12018 | pT1 N0 Mx | 2 | 0.996 |
| G12019 | Adenocarcinoma | 78 | M | B12019 | pT2 N1 M0 | 3 | 0.985 |
| G12020 | Adenocarcinoma | 64 | M | B12020 | pT2 N0 Mx | 3 | 0.990 |
| G12022 | Adenocarcinoma | 76 | M | B12022 | pT2 N0 Mx | 3 | 0.989 |
| G12023 | Adenocarcinoma | 55 | M | B12023 | pT2 N0 Mx | 2 | 0.832 |
| G12024 | Adenocarcinoma | 54 | M | B12024 | pT2 N3 Mx | 3 | 0.971 |
| G12025 | Adenocarcinoma | 52 | F | B12025 | pT2 N2 Mx | 2 | 0.987 |
| G12026 | Adenocarcinoma | 57 | F | B12026 | pT2 N2 Mx | 3 | 0.992 |
| G12027 | Adenocarcinoma | 65 | M | B12027 | pT2 N0 Mx | 1 | 0.990 |
| G12028 | Adenocarcinoma | 75 | M | B12028 | pT3 N3 Mx | 3 | 0.980 |
| G12029 | Adenocarcinoma | 71 | M | B12029 | pT2 N0 M0 | 3 | 0.992 |
| B12001 | Normal | 74 | M | | | | 0.994 |
| B12002 | Normal | 63 | M | | | | 0.977 |
| B12003 | Normal | 67 | M | | | | 0.994 |
| B12004 | Normal | 69 | M | | | | 0.982 |
| B12005 | Normal | 59 | M | | | | 0.997 |
| B12006 | Normal | 49 | M | | | | 0.985 |
| B12008 | Normal | 57 | F | | | | 0.987 |
| B12009 | Normal | 62 | M | | | | 0.994 |
| B12010 | Normal | 67 | M | | | | 0.991 |
| B12012 | Normal | 71 | M | | | | 0.995 |
| B12018 | Normal | 60 | F | | | | 0.992 |
| B12019 | Normal | 78 | M | | | | 0.978 |
| B12020 | Normal | 64 | M | | | | 0.978 |

TABLE 4-continued

| Samples for Methylation Analysis | | | | | | | |
|---|---|---|---|---|---|---|---|
| Sample | Diagnosis | Age | Sex | Norm Match | Staging | Grading | $R^2$ correlation |
| B12022 | Normal | 76 | M | | | | 0.993 |
| B12023 | Normal | 55 | M | | | | 0.979 |
| B12024 | Normal | 54 | M | | | | 0.964 |
| B12025 | Normal | 52 | F | | | | 0.973 |
| B12026 | Normal | 57 | F | | | | 0.931 |
| B12027 | Normal | 65 | M | | | | 0.984 |
| B12028 | Normal | 75 | M | | | | 0.995 |
| B12029 | Normal | 71 | M | | | | 0.995 |

What is claimed is:

1. A method for identification of differentially methylated genomic CpG dinucleotide sequences associated with adenocarcinoma in an individual, said method comprising:

(a) obtaining a biological sample comprising genomic DNA from said individual;

(b) measuring the level of methylation in said biological sample at a CpG dinucleotide sequence in a genomic target designated as SEQ ID NO: 265 and SEQ ID NO: 293; and (c) comparing the level of methylation at said genomic CpG dinucleotide sequences in the biological sample to a reference level of methylation of said genomic CpG dinucleotide sequences, wherein said reference level comprises the level of methylation at said genomic CpG dinucleotide sequences in a normal sample; wherein an increase in the level of methylation of said genomic CpG dinucleotide sequences in the biological sample for genomic target designated as SEQ ID NO: 265 and SEQ ID NO: 293 compared to the reference level identifies differentially methylated genomic CpG dinucleotide sequences associated with adenocarcinoma.

2. The method of claim 1, wherein step (b) further comprises measuring the level of methylation in said biological sample at a CpG dinucleotide sequence in at least one of the genomic targets designated as SEQ ID NO: 140, 174, 305, 314, 360 or 371, wherein an increase in the level of methylation of said genomic CpG dinucleotide sequences in the biological sample for the genomic targets designated as SEQ ID NO: 140, 314 or 371, or a decrease in the level of methylation of said genomic CpG dinucleotide sequences in the biological sample for the genomic targets designated as SEQ ID NO: 174, 305 or 360, compared to the reference level identifies differentially methylated genomic CpG dinucleotide sequences associated with adenocarcinoma.

3. The method of claim 1, wherein the level of methylation of said differentially methylated genomic CpG dinucleotide sequences is used to diagnose adenocarcinoma in the individual.

4. A method for identification of differentially methylated genomic CpG dinucleotide sequences associated with squamous cell carcinoma in an individual, said method comprising:

(a) obtaining a biological sample comprising genomic DNA from said individual;

(b) measuring the level of methylation in said biological sample at a CpG dinucleotide sequence in a genomic target designated as SEQ ID NO: 265 and SEQ ID NO. 315; and (c) comparing the level of methylation at said genomic CpG dinucleotide sequences in the biological sample to a reference level of methylation of said genomic CpG dinucleotide sequences, wherein said reference level comprises the level of methylation at said genomic CpG dinucleotide sequences in a normal sample; wherein an increase in the level of methylation of said genomic CpG dinucleotide sequences in the biological sample for genomic target designated as SEQ ID NO: 265 and SEQ ID NO. 315 compared to the reference level identifies differentially methylated genomic CpG dinucleotide sequences associated with squamous cell carcinoma.

5. The method of claim 4, wherein step (b) further comprises measuring the level of methylation in said biological sample at a CpG dinucleotide sequence in at least one of the genomic targets designated as SEQ ID NO: 140, 174, 305, 314, 360 or 371, wherein an increase in the level of methylation of said genomic CpG dinucleotide sequences for the genomic targets designated as SEQ ID NO: 140, 314 or 371, or a decrease in the level of methylation of said genomic CpG dinucleotide sequences for the genomic targets designated as SEQ ID NO: 174, 305 or 360, compared to the reference level identifies differentially methylated genomic CpG dinucleotide sequences associated with squamous cell carcinoma.

6. The method of claim 4, wherein the level of methylation of said differentially methylated genomic CpG dinucleotide sequences is used to diagnose squamous cell carcinoma in the individual.

7. A method for identification of differentially methylated genomic CpG dinucleotide sequences associated with adenocarcinoma and squamous cell carcinoma in an individual, said method comprising:

(a) obtaining a biological sample comprising genomic DNA from said individual;

(b) measuring the level of methylation in said biological sample at a CpG dinucleotide sequence in a genomic target designated as SEQ ID NO: 265 and at least one of SEQ ID NO: 140, 174, 305, 314, 360 or 371; and (c) comparing the level of methylation at said genomic CpG dinucleotide sequences in the biological sample to a reference level of methylation of said genomic CpG dinucleotide sequences, wherein said reference level comprises the level of methylation at said genomic CpG dinucleotide sequences in a normal sample; wherein an increase in the level of methylation of said genomic CpG dinucleotide sequences in the biological sample for the genomic targets designated as SEQ ID NO: 140, 265, 314 or 371, or a decrease in the level of methylation of said genomic CpG dinucleotide sequences in the biological sample for the genomic targets designated as SEQ ID NO: 174, 305 or 360, compared to the reference level identifies differentially methylated genomic CpG dinucleotide sequences associated with adenocarcinoma and squamous cell carcinoma.

8. The method of claim 7, wherein step (b) further comprises measuring the level of methylation in said biological sample at a CpG dinucleotide sequence in at least two of the genomic target designated as SEQ ID NO: 140, 174, 305, 314, 360 or 371.

9. The method of claim 7, wherein the level of methylation of said differentially methylated genomic CpG dinucleotide sequences is used to diagnose adenocarcinoma or squamous cell carcinoma in the individual.

* * * * *

SEQUENCE LISTING

<160> NUMBER OF SEQ ID NOS: 1513

<210> SEQ ID NO 1
<211> LENGTH: 47
<212> TYPE: DNA
<213> ORGANISM: Homo sapiens

<400> SEQUENCE: 1
ggatgctcct cagctctggg gacgcggtgc agaagtgtga gggcgcc 47

<210> SEQ ID NO 2
<211> LENGTH: 48
<212> TYPE: DNA
<213> ORGANISM: Homo sapiens

<400> SEQUENCE: 2
cttccgactt tgtcacacac ctgcgccgcc agactggggt cgggcccc 48

<210> SEQ ID NO 3
<211> LENGTH: 52
<212> TYPE: DNA
<213> ORGANISM: Homo sapiens

<400> SEQUENCE: 3
cccggcttcc aggcagtaat gggcgggtcc ctgcgcggga gcgtggcggg cg 52

<210> SEQ ID NO 4
<211> LENGTH: 50
<212> TYPE: DNA
<213> ORGANISM: Homo sapiens

<400> SEQUENCE: 4
aatctgaaga aagctgaggg gaggcggcag atgttctgat ctactaggga 50

<210> SEQ ID NO 5
<211> LENGTH: 45
<212> TYPE: DNA
<213> ORGANISM: Homo sapiens

<400> SEQUENCE: 5
aactcctgag tggtgtggga gggcggtgag gggcagctga aagtc 45

<210> SEQ ID NO 6
<211> LENGTH: 50
<212> TYPE: DNA
<213> ORGANISM: Homo sapiens

<400> SEQUENCE: 6
tggtctagga aacatgattg gcagctacga gagagctagg ggctggacgt 50

<210> SEQ ID NO 7
<211> LENGTH: 49
<212> TYPE: DNA
<213> ORGANISM: Homo sapiens

<400> SEQUENCE: 7
ccgaggagcc cagcgctagt ggcggcggcc aggagagacc cgggtgtca 49

<210> SEQ ID NO 8
<211> LENGTH: 47
<212> TYPE: DNA
<213> ORGANISM: Homo sapiens

<400> SEQUENCE: 8
gacagcaggg agtccggggg aaacgcaggc gtcgggcaca gagtcgg 47

<210> SEQ ID NO 9
<211> LENGTH: 48
<212> TYPE: DNA
<213> ORGANISM: Homo sapiens

<400> SEQUENCE: 9
ggccctggcg ccggacctgc ttcggccctg cgtgggcggc ctcgccgg 48

<210> SEQ ID NO 10
<211> LENGTH: 48
<212> TYPE: DNA
<213> ORGANISM: Homo sapiens

<400> SEQUENCE: 10
tcggaagcgc tcgggcaaag actgcgaaga agaaaagaca tctggcgg 48

<210> SEQ ID NO 11
<211> LENGTH: 50
<212> TYPE: DNA
<213> ORGANISM: Homo sapiens

<400> SEQUENCE: 11
agtctgtccc gacgtgactt cctcgaccct ctaaagacgt acagaccaga 50

<210> SEQ ID NO 12
<211> LENGTH: 49
<212> TYPE: DNA
<213> ORGANISM: Homo sapiens

<400> SEQUENCE: 12
gcgccggcct ggcagggcag ctcggaggtg ggtgggccgc gccgccagc 49

<210> SEQ ID NO 13
<211> LENGTH: 46
<212> TYPE: DNA
<213> ORGANISM: Homo sapiens

<400> SEQUENCE: 13
aaaccttctt gccttcaagc ctcggctcca acaccagtcc ggcaga 46

<210> SEQ ID NO 14
<211> LENGTH: 50
<212> TYPE: DNA
<213> ORGANISM: Homo sapiens

<400> SEQUENCE: 14
ggaagtgaga aacaagtgtg tgataaacgg tggagaatgg gagcactctc 50

<210> SEQ ID NO 15
<211> LENGTH: 42
<212> TYPE: DNA
<213> ORGANISM: Homo sapiens

<400> SEQUENCE: 15
gcgggaggag acgaggaggg cgttccctgg ggagtggcag tg 42

<210> SEQ ID NO 16
<211> LENGTH: 48
<212> TYPE: DNA
<213> ORGANISM: Homo sapiens

<400> SEQUENCE: 16
aagccggcgg aaataccccca gcgcgtgggc ggagcagcgg cccgcaga 48

<210> SEQ ID NO 17
<211> LENGTH: 49
<212> TYPE: DNA
<213> ORGANISM: Homo sapiens

<400> SEQUENCE: 17
ggcggtggcg cccacggaac agccgcgtct aattggctga gcgcggagc 49

<210> SEQ ID NO 18
<211> LENGTH: 49
<212> TYPE: DNA
<213> ORGANISM: Homo sapiens

<400> SEQUENCE: 18
ccagttccca gcgtggcaac acgggactgg gctgcagctc acccagccg 49

<210> SEQ ID NO 19
<211> LENGTH: 47
<212> TYPE: DNA
<213> ORGANISM: Homo sapiens

<400> SEQUENCE: 19
gactcacccc tcctttctgc cgctccttcc tttccttgcc ctgcttt 47

<210> SEQ ID NO 20
<211> LENGTH: 47
<212> TYPE: DNA
<213> ORGANISM: Homo sapiens

<400> SEQUENCE: 20
gcccgcgtcc gagttcctgg acgagagccg agcctcgctt agaccgc 47

<210> SEQ ID NO 21
<211> LENGTH: 46
<212> TYPE: DNA
<213> ORGANISM: Homo sapiens

<400> SEQUENCE: 21
tccagcccgc gaggtttagg acggatccag gcagaccgca ggctcc 46

<210> SEQ ID NO 22
<211> LENGTH: 50
<212> TYPE: DNA
<213> ORGANISM: Homo sapiens

<400> SEQUENCE: 22
agcagtgcag ccagcattcc tggcggctcc ctggcccagt ctctggcgca 50

<210> SEQ ID NO 23
<211> LENGTH: 50
<212> TYPE: DNA
<213> ORGANISM: Homo sapiens

<400> SEQUENCE: 23
ggctgaagga acagaaatcc tctgctccgc ctactgggga ttaggagctg 50

<210> SEQ ID NO 24
<211> LENGTH: 48
<212> TYPE: DNA
<213> ORGANISM: Homo sapiens

<400> SEQUENCE: 24
agcatctttg ggcaggcttc cccgccctcg tgacgcgtcg gcccgggc 48

<210> SEQ ID NO 25
<211> LENGTH: 48
<212> TYPE: DNA
<213> ORGANISM: Homo sapiens

<400> SEQUENCE: 25
agagcaggca acctccctct cgccctagcc cagctctgga acaggcag 48

<210> SEQ ID NO 26
<211> LENGTH: 48
<212> TYPE: DNA
<213> ORGANISM: Homo sapiens

<400> SEQUENCE: 26
acctttgatt tctcccaaac ccggcagccc gagactgttg caaaccgg 48

<210> SEQ ID NO 27
<211> LENGTH: 48
<212> TYPE: DNA
<213> ORGANISM: Homo sapiens

<400> SEQUENCE: 27
caagggtctc tgctgactcc cccggctcgg tccacaagct ctccactt 48

<210> SEQ ID NO 28
<211> LENGTH: 47
<212> TYPE: DNA
<213> ORGANISM: Homo sapiens

<400> SEQUENCE: 28
cagcaacacc tctcacgcat gcgcattgta gtcttcccac ctcccac 47

<210> SEQ ID NO 29
<211> LENGTH: 48
<212> TYPE: DNA
<213> ORGANISM: Homo sapiens

<400> SEQUENCE: 29
gacagaacag cgaagcagtg cccggcaagc ggagcgcagc acccattg 48

<210> SEQ ID NO 30
<211> LENGTH: 49
<212> TYPE: DNA
<213> ORGANISM: Homo sapiens

<400> SEQUENCE: 30

-continued cgccggaagc ctagccgctg ctcggggggg acctgcgggc tcaggcccg 49

<210> SEQ ID NO 31
<211> LENGTH: 49
<212> TYPE: DNA
<213> ORGANISM: Homo sapiens

<400> SEQUENCE: 31
tgcccaggcc gcagggctga tgcccccgct cagctgaggg aaggggaag 49

<210> SEQ ID NO 32
<211> LENGTH: 47
<212> TYPE: DNA
<213> ORGANISM: Homo sapiens

<400> SEQUENCE: 32
ctcctgctcc ttctcctggt ccgggcgggc cggcctgggc tcccact 47

<210> SEQ ID NO 33
<211> LENGTH: 49
<212> TYPE: DNA
<213> ORGANISM: Homo sapiens

<400> SEQUENCE: 33
aactggggca acttctcccg aggcgggagg cgctggttcc tcggctccc 49

<210> SEQ ID NO 34
<211> LENGTH: 52
<212> TYPE: DNA
<213> ORGANISM: Homo sapiens

<400> SEQUENCE: 34
gttagtatct acggcaccag gtcggcgaga atcctgactc tgcaccctcc tc 52

<210> SEQ ID NO 35
<211> LENGTH: 52
<212> TYPE: DNA
<213> ORGANISM: Homo sapiens

<400> SEQUENCE: 35
ctccatttcc tttgcttcct ccggcaggcg gattacttgc ccttacttgt ca 52

<210> SEQ ID NO 36
<211> LENGTH: 50
<212> TYPE: DNA
<213> ORGANISM: Homo sapiens

<400> SEQUENCE: 36
ccccgccgcc tgcagagggc gcagcaggtc ttgcacctct tctgcatctc 50

<210> SEQ ID NO 37
<211> LENGTH: 51
<212> TYPE: DNA
<213> ORGANISM: Homo sapiens

<400> SEQUENCE: 37
tttcgtattc tgagaggctg ctgcttagcg gtagcccctt ggtttccgtg g 51

<210> SEQ ID NO 38
<211> LENGTH: 51
<212> TYPE: DNA
<213> ORGANISM: Homo sapiens

<400> SEQUENCE: 38

-continued tgggtggcca atccagagcc ccgagagacg cttggctctt tctgtccctc c 51

<210> SEQ ID NO 39
<211> LENGTH: 51
<212> TYPE: DNA
<213> ORGANISM: Homo sapiens

<400> SEQUENCE: 39
ctcaggtaga attcttcctc ttccgtctct ttccttttac gtcatccggg g 51

<210> SEQ ID NO 40
<211> LENGTH: 52
<212> TYPE: DNA
<213> ORGANISM: Homo sapiens

<400> SEQUENCE: 40
agactcgagt cagtgacact gctcaacgca cccatctcag ctttcatcat ca 52

<210> SEQ ID NO 41
<211> LENGTH: 49
<212> TYPE: DNA
<213> ORGANISM: Homo sapiens

<400> SEQUENCE: 41
agggtattcc ccttgcaggg accgtccctg catttccctc tacactgag 49

<210> SEQ ID NO 42
<211> LENGTH: 52
<212> TYPE: DNA
<213> ORGANISM: Homo sapiens

<400> SEQUENCE: 42
aagggagccg gatgaggtga tacacgctgg cgacacaata gcaggttgct ct 52

<210> SEQ ID NO 43
<211> LENGTH: 48
<212> TYPE: DNA
<213> ORGANISM: Homo sapiens

<400> SEQUENCE: 43
cggctctgcg taggtgcgcg gacccgggct cctgggttcc atccccgc 48

<210> SEQ ID NO 44
<211> LENGTH: 50
<212> TYPE: DNA
<213> ORGANISM: Homo sapiens

<400> SEQUENCE: 44
gtcggccaga cctgcatccc gcgtagcatc cctgccctct ctgtgcagcg 50

<210> SEQ ID NO 45
<211> LENGTH: 50
<212> TYPE: DNA
<213> ORGANISM: Homo sapiens

<400> SEQUENCE: 45
ccgcggagag cctggaggcg gggcgccctt ctctgagtcc gcggggtcgc 50

<210> SEQ ID NO 46
<211> LENGTH: 49
<212> TYPE: DNA
<213> ORGANISM: Homo sapiens

<400> SEQUENCE: 46
cccgtgcgct tcctgggtgg ggccgggggc ggcttcaaaa ccccctgcc 49

<210> SEQ ID NO 47
<211> LENGTH: 48
<212> TYPE: DNA
<213> ORGANISM: Homo sapiens

<400> SEQUENCE: 47
ctctttctct ggtgacccac accgcccgca aagccacagc gcatctgg 48

<210> SEQ ID NO 48
<211> LENGTH: 45
<212> TYPE: DNA
<213> ORGANISM: Homo sapiens

<400> SEQUENCE: 48
cccagcctga ctctccttcc gttctgggtc cccctcctct ggtcg 45

<210> SEQ ID NO 49
<211> LENGTH: 52
<212> TYPE: DNA
<213> ORGANISM: Homo sapiens

<400> SEQUENCE: 49
tctcttgaat cttgacaatc cccgaacact gctccccgct ttatttgttt ag 52

<210> SEQ ID NO 50
<211> LENGTH: 50
<212> TYPE: DNA
<213> ORGANISM: Homo sapiens

<400> SEQUENCE: 50
tccctgggtg cctcctgcgc aagcgcagtt gtcctcctgc gccgacctcg 50

<210> SEQ ID NO 51
<211> LENGTH: 51
<212> TYPE: DNA
<213> ORGANISM: Homo sapiens

<400> SEQUENCE: 51
gaaaggaaga gggtgattgg ttagcggaac gtcttacgtg actgattatt g 51

<210> SEQ ID NO 52
<211> LENGTH: 48
<212> TYPE: DNA
<213> ORGANISM: Homo sapiens

<400> SEQUENCE: 52
acacaccaac ctctaacgat accgggtaat tttcctcctt cttccctc 48

<210> SEQ ID NO 53
<211> LENGTH: 50
<212> TYPE: DNA
<213> ORGANISM: Homo sapiens

<400> SEQUENCE: 53
aactcagggc cgtggttttc aaacgttttt cgccttacgg tcacccttag 50

<210> SEQ ID NO 54
<211> LENGTH: 50
<212> TYPE: DNA
<213> ORGANISM: Homo sapiens

<400> SEQUENCE: 54
tagagctagc ctctcctgcc ctcgcccacg ctgcgccagc acttgtttct 50

<210> SEQ ID NO 55
<211> LENGTH: 52
<212> TYPE: DNA
<213> ORGANISM: Homo sapiens

<400> SEQUENCE: 55
tcctagagca aatggcacaa tgccacgagg cccgatctat ccctatgacg ga 52

<210> SEQ ID NO 56
<211> LENGTH: 52
<212> TYPE: DNA
<213> ORGANISM: Homo sapiens

<400> SEQUENCE: 56
ccggtggggg cgggacccga ctcgcaaact gttgcatttg ctctccacct cc 52

<210> SEQ ID NO 57
<211> LENGTH: 49
<212> TYPE: DNA
<213> ORGANISM: Homo sapiens

<400> SEQUENCE: 57
tcccgccagg aaacatccgg gtgcccggat gtgacgccac tgacttgcg 49

<210> SEQ ID NO 58
<211> LENGTH: 40
<212> TYPE: DNA
<213> ORGANISM: Homo sapiens

<400> SEQUENCE: 58
ctcaaccctg atgcccatcc gcccagccat tccaccctca 40

<210> SEQ ID NO 59
<211> LENGTH: 44
<212> TYPE: DNA
<213> ORGANISM: Homo sapiens

<400> SEQUENCE: 59
ccactccaat gctcactccc gtgacccaac cccctcttca ttgt 44

<210> SEQ ID NO 60
<211> LENGTH: 48
<212> TYPE: DNA
<213> ORGANISM: Homo sapiens

<400> SEQUENCE: 60
gacggacagg gcaggcaggg tccgggacga tggccgcaca gtcccggc 48

<210> SEQ ID NO 61
<211> LENGTH: 50
<212> TYPE: DNA
<213> ORGANISM: Homo sapiens

<400> SEQUENCE: 61
gagaccttgg ctggcgcgag gccacgccca ccagacatgc agttccagct 50

<210> SEQ ID NO 62
<211> LENGTH: 50
<212> TYPE: DNA
<213> ORGANISM: Homo sapiens

<400> SEQUENCE: 62

-continued gggcgactag gacagggaca gaacccgttg aacccaggag tgagatccgg 50

<210> SEQ ID NO 63
<211> LENGTH: 50
<212> TYPE: DNA
<213> ORGANISM: Homo sapiens

<400> SEQUENCE: 63
tcccgctccg gagagaagtc tgagtccgcc aggctctgca ggcccgcgga 50

<210> SEQ ID NO 64
<211> LENGTH: 52
<212> TYPE: DNA
<213> ORGANISM: Homo sapiens

<400> SEQUENCE: 64
cggaagctcg gtaatgataa gcacgccggc cactttgcag ggcgtcaccg cc 52

<210> SEQ ID NO 65
<211> LENGTH: 47
<212> TYPE: DNA
<213> ORGANISM: Homo sapiens

<400> SEQUENCE: 65
cccaataggg ccggcttgac ccgcgaacag gcgagggttc ccgggg 47

<210> SEQ ID NO 66
<211> LENGTH: 49
<212> TYPE: DNA
<213> ORGANISM: Homo sapiens

<400> SEQUENCE: 66
gggaagctgt agcccccagt gggcagcggt ggagagagct caaggaagg 49

<210> SEQ ID NO 67
<211> LENGTH: 46
<212> TYPE: DNA
<213> ORGANISM: Homo sapiens

<400> SEQUENCE: 67
ggtagcaacc atcctgcctc ccgctggagc ggcgtctcct ccccgg 46

<210> SEQ ID NO 68
<211> LENGTH: 48
<212> TYPE: DNA
<213> ORGANISM: Homo sapiens

<400> SEQUENCE: 68
ccggccggcc gtgggggtgg ggcgatagtg acatcacccc ggagtcgg 48

<210> SEQ ID NO 69
<211> LENGTH: 50
<212> TYPE: DNA
<213> ORGANISM: Homo sapiens

<400> SEQUENCE: 69
cctctcccct gccctgtgaa gcgggtgtgc aagctccggg atcgcagcgg 50

<210> SEQ ID NO 70
<211> LENGTH: 47
<212> TYPE: DNA
<213> ORGANISM: Homo sapiens

<400> SEQUENCE: 70

-continued cggccagctg cgcggcgact ccggggactc cagggcgccc ctctgcg 47

<210> SEQ ID NO 71
<211> LENGTH: 50
<212> TYPE: DNA
<213> ORGANISM: Homo sapiens

<400> SEQUENCE: 71
gctgtgaggt gtgaggaact tacctgcgtc tccatggaag gtgccctccg 50

<210> SEQ ID NO 72
<211> LENGTH: 49
<212> TYPE: DNA
<213> ORGANISM: Homo sapiens

<400> SEQUENCE: 72
ctctgacacg acgactgggc agtgccggtg acgcttatgg cactgcggc 49

<210> SEQ ID NO 73
<211> LENGTH: 54
<212> TYPE: DNA
<213> ORGANISM: Homo sapiens

<400> SEQUENCE: 73
gggctgcgag ttgcacagtc caattcgctg ttgttagggc ctcagtttcc caaa 54

<210> SEQ ID NO 74
<211> LENGTH: 49
<212> TYPE: DNA
<213> ORGANISM: Homo sapiens

<400> SEQUENCE: 74
aaggagcagt ggaaaggggt gacgagttcc tggctggcca ccaatcatc 49

<210> SEQ ID NO 75
<211> LENGTH: 49
<212> TYPE: DNA
<213> ORGANISM: Homo sapiens

<400> SEQUENCE: 75
aacttgtggc atttctaaca ggatgaagcg gaagagaaag ggaaagaga 49

<210> SEQ ID NO 76
<211> LENGTH: 49
<212> TYPE: DNA
<213> ORGANISM: Homo sapiens

<400> SEQUENCE: 76
ggggcgaggg ttcaaaacca ggccggactg agaggtgaaa ttcaccatg 49

<210> SEQ ID NO 77
<211> LENGTH: 49
<212> TYPE: DNA
<213> ORGANISM: Homo sapiens

<400> SEQUENCE: 77
caggttctgg aagcatgagg gtgacgcaac ccaggggcaa aggacccct 49

<210> SEQ ID NO 78
<211> LENGTH: 46
<212> TYPE: DNA
<213> ORGANISM: Homo sapiens

<400> SEQUENCE: 78

-continued

```
cagggcaggg caggattagg aaggcgctga gcccaggctg gtgcgg                    46


<210> SEQ ID NO 79
<211> LENGTH: 49
<212> TYPE: DNA
<213> ORGANISM: Homo sapiens

<400> SEQUENCE: 79

gatagaggag agactccgta gcggggcggg gcctcagctc cagctgggc                 49


<210> SEQ ID NO 80
<211> LENGTH: 47
<212> TYPE: DNA
<213> ORGANISM: Homo sapiens

<400> SEQUENCE: 80

gccgcctcct gatagaggcc ccgacttagg acacaaaccg ctcccac                   47


<210> SEQ ID NO 81
<211> LENGTH: 50
<212> TYPE: DNA
<213> ORGANISM: Homo sapiens

<400> SEQUENCE: 81

ttgcctctct ccaaatctct cacgacctga tttctacagc cgctctaccc                50


<210> SEQ ID NO 82
<211> LENGTH: 52
<212> TYPE: DNA
<213> ORGANISM: Homo sapiens

<400> SEQUENCE: 82

ctttctgcgt gtctctcagc ctctttcggt ccctctttca cggtctcact cc             52


<210> SEQ ID NO 83
<211> LENGTH: 50
<212> TYPE: DNA
<213> ORGANISM: Homo sapiens

<400> SEQUENCE: 83

ggaatatcag agcctctacg acccgtttgt ctcgggctcg cccacttcaa                50


<210> SEQ ID NO 84
<211> LENGTH: 47
<212> TYPE: DNA
<213> ORGANISM: Homo sapiens

<400> SEQUENCE: 84

cgaacccagt ggaatcagaa ccgtgcaggt cccataaccc acctaga                   47


<210> SEQ ID NO 85
<211> LENGTH: 48
<212> TYPE: DNA
<213> ORGANISM: Homo sapiens

<400> SEQUENCE: 85

accctcagcc aatcagcggt acggggggcg gtgcctccgg ggctcacc                  48


<210> SEQ ID NO 86
<211> LENGTH: 50
<212> TYPE: DNA
<213> ORGANISM: Homo sapiens

<400> SEQUENCE: 86
```

ctgtgctgct ggcttagaga aggcgcggtc gaccagacgg ttcccaaagg 50

<210> SEQ ID NO 87
<211> LENGTH: 47
<212> TYPE: DNA
<213> ORGANISM: Homo sapiens

<400> SEQUENCE: 87
ggctccgttc tgtgccacac ccgtggctcc tgcgtttccc cctggcg 47

<210> SEQ ID NO 88
<211> LENGTH: 53
<212> TYPE: DNA
<213> ORGANISM: Homo sapiens

<400> SEQUENCE: 88
cgtgtgacgt tacgcacagg aaaccggtcg ggctgtgcag agaatgaagt aag 53

<210> SEQ ID NO 89
<211> LENGTH: 46
<212> TYPE: DNA
<213> ORGANISM: Homo sapiens

<400> SEQUENCE: 89
cgggaggcgg ccgtagccag cgccgccgcg caggaccagg aggagg 46

<210> SEQ ID NO 90
<211> LENGTH: 49
<212> TYPE: DNA
<213> ORGANISM: Homo sapiens

<400> SEQUENCE: 90
ccgtcagcgc tcggagcggg ctgcgcggcg ggagctccgg gaggcggcc 49

<210> SEQ ID NO 91
<211> LENGTH: 48
<212> TYPE: DNA
<213> ORGANISM: Homo sapiens

<400> SEQUENCE: 91
gcccagctcc gggctcatgg gcgcggtcag cagggcgggc cagggcgg 48

<210> SEQ ID NO 92
<211> LENGTH: 47
<212> TYPE: DNA
<213> ORGANISM: Homo sapiens

<400> SEQUENCE: 92
gggctcctct acacctgccg ccgcctgggc cgattccgcg ggcctcg 47

<210> SEQ ID NO 93
<211> LENGTH: 47
<212> TYPE: DNA
<213> ORGANISM: Homo sapiens

<400> SEQUENCE: 93
ggaccgatgc ggtccatgtc ccgggcagcc ccaccttctc tgcctgc 47

<210> SEQ ID NO 94
<211> LENGTH: 49
<212> TYPE: DNA
<213> ORGANISM: Homo sapiens

<400> SEQUENCE: 94
gggaatgcaa gatctcggga cctctcgctg gcctgcaagc tttggtctc 49

<210> SEQ ID NO 95
<211> LENGTH: 50
<212> TYPE: DNA
<213> ORGANISM: Homo sapiens

<400> SEQUENCE: 95
ggcggaggaa taattgagga actcacggaa ctatcaactg gggacaaacc 50

<210> SEQ ID NO 96
<211> LENGTH: 48
<212> TYPE: DNA
<213> ORGANISM: Homo sapiens

<400> SEQUENCE: 96 ccctttttatg gctccgtctc cgcggggcag ctcgtccgag tggccaga 48

<210> SEQ ID NO 97
<211> LENGTH: 49
<212> TYPE: DNA
<213> ORGANISM: Homo sapiens

<400> SEQUENCE: 97
ggcttgtacc ggccgaaggg ccatccgggt caggcgcaca gggcagcgg 49

<210> SEQ ID NO 98
<211> LENGTH: 49
<212> TYPE: DNA
<213> ORGANISM: Homo sapiens

<400> SEQUENCE: 98
ggccggcgtg ccggcgtcca gcgaggatgc gcagactgcc tcaggcccg 49

<210> SEQ ID NO 99
<211> LENGTH: 49
<212> TYPE: DNA
<213> ORGANISM: Homo sapiens

<400> SEQUENCE: 99
gaccactcgg gcacgtggca ggtcgcttgc acgcccgcgg actatccct 49

<210> SEQ ID NO 100
<211> LENGTH: 50
<212> TYPE: DNA
<213> ORGANISM: Homo sapiens

<400> SEQUENCE: 100
gaagttgctt actgattggt ggattccgtt tggcgccaac taggaaaggg 50

<210> SEQ ID NO 101
<211> LENGTH: 48
<212> TYPE: DNA
<213> ORGANISM: Homo sapiens

<400> SEQUENCE: 101
gaggccgagc caaggctgga tccggccaga cctccacagg tcttcctt 48

<210> SEQ ID NO 102
<211> LENGTH: 47
<212> TYPE: DNA
<213> ORGANISM: Homo sapiens

<400> SEQUENCE: 102

```
ctccagagtt gggccctggt ggtcgagtcc agtcctgggg gtcattg        47
```

<210> SEQ ID NO 103
<211> LENGTH: 51
<212> TYPE: DNA
<213> ORGANISM: Homo sapiens

<400> SEQUENCE: 103

```
gggcccagcc ctgggcatct gaacaccggc acacttggat ctgcctctgt t   51
```

<210> SEQ ID NO 104
<211> LENGTH: 52
<212> TYPE: DNA
<213> ORGANISM: Homo sapiens

<400> SEQUENCE: 104

```
cagccctggg catctgaaca ccggcacact tggatctgcc tctgttgcct cc  52
```

<210> SEQ ID NO 105
<211> LENGTH: 39
<212> TYPE: DNA
<213> ORGANISM: Homo sapiens

<400> SEQUENCE: 105

```
ggggctgtag gggtcaggac acgggctgga gtggaatga                 39
```

<210> SEQ ID NO 106
<211> LENGTH: 55
<212> TYPE: DNA
<213> ORGANISM: Homo sapiens

<400> SEQUENCE: 106

```
tctgggaagt ctccctctta tctcgcagaa tgcctgtccc tggataaaga tcatt   55
```

<210> SEQ ID NO 107
<211> LENGTH: 43
<212> TYPE: DNA
<213> ORGANISM: Homo sapiens

<400> SEQUENCE: 107

```
ttctcagcgg gccagaagga aggacggtag ggtggaaggg ctg            43
```

<210> SEQ ID NO 108
<211> LENGTH: 54
<212> TYPE: DNA
<213> ORGANISM: Homo sapiens

<400> SEQUENCE: 108

```
cacaagtcct agaataccag aacggagacg tgctttcttg gaccttaaac gaaa    54
```

<210> SEQ ID NO 109
<211> LENGTH: 50
<212> TYPE: DNA
<213> ORGANISM: Homo sapiens

<400> SEQUENCE: 109

```
caaggctgca gtgagccaag ctcgcgccac tgcactccag cccgggcgac     50
```

<210> SEQ ID NO 110
<211> LENGTH: 52
<212> TYPE: DNA
<213> ORGANISM: Homo sapiens

<400> SEQUENCE: 110
cccgtgtgag atgcgccacc ctcgaacctt gttacgacgt cggcacattg cg 52

<210> SEQ ID NO 111
<211> LENGTH: 47
<212> TYPE: DNA
<213> ORGANISM: Homo sapiens

<400> SEQUENCE: 111
ggggaattaa gacccaatgg gcaatccgtg actattaggg gatggga 47

<210> SEQ ID NO 112
<211> LENGTH: 51
<212> TYPE: DNA
<213> ORGANISM: Homo sapiens

<400> SEQUENCE: 112
catagcagta gcagacatct cttgtaccgt gccttacacc tcagcccatt t 51

<210> SEQ ID NO 113
<211> LENGTH: 52
<212> TYPE: DNA
<213> ORGANISM: Homo sapiens

<400> SEQUENCE: 113
agactgtggc ccagcccaac tgcggctgtg tgtagagcaa ccccatttct ca 52

<210> SEQ ID NO 114
<211> LENGTH: 51
<212> TYPE: DNA
<213> ORGANISM: Homo sapiens

<400> SEQUENCE: 114
gagcactgga ccatgaagtc tcagcgtgtg ctcacagcct ctcacacagg a 51

<210> SEQ ID NO 115
<211> LENGTH: 52
<212> TYPE: DNA
<213> ORGANISM: Homo sapiens

<400> SEQUENCE: 115
gggcagttgg tgttaaagtg agaaaggcgg tatctgcgca gactgcaggg tc 52

<210> SEQ ID NO 116
<211> LENGTH: 51
<212> TYPE: DNA
<213> ORGANISM: Homo sapiens

<400> SEQUENCE: 116
cgcagggtgg gactgctctg cctacgaaca gcactgtgtg cgaacacagg g 51

<210> SEQ ID NO 117
<211> LENGTH: 55
<212> TYPE: DNA
<213> ORGANISM: Homo sapiens

<400> SEQUENCE: 117
ctggccggcc tgacgactct caacgggtta gacgcgggct acgatgacct tcacg 55

<210> SEQ ID NO 118
<211> LENGTH: 45
<212> TYPE: DNA
<213> ORGANISM: Homo sapiens

<400> SEQUENCE: 118
tggaggtctc tgctggctat ctggcgtgtg tgtgtgtgtg gtgtg 45

<210> SEQ ID NO 119
<211> LENGTH: 52
<212> TYPE: DNA
<213> ORGANISM: Homo sapiens

<400> SEQUENCE: 119
caaaaccgat tatctttata accgcggcgc ctagcacagc gcctggtgcc ct 52

<210> SEQ ID NO 120
<211> LENGTH: 52
<212> TYPE: DNA
<213> ORGANISM: Homo sapiens

<400> SEQUENCE: 120
ggagcacatc agaagggctg gcttgtgcgc gctcttgctc tctgtgtatg tg 52

<210> SEQ ID NO 121
<211> LENGTH: 47
<212> TYPE: DNA
<213> ORGANISM: Homo sapiens

<400> SEQUENCE: 121
tcctcacccc aagtgaaggc tcgagacttc ctgccccacc cagtggg 47

<210> SEQ ID NO 122
<211> LENGTH: 47
<212> TYPE: DNA
<213> ORGANISM: Homo sapiens

<400> SEQUENCE: 122
cctgcaccca ggtttccatt gcgcggctct cctcagctcc ttcccgc 47

<210> SEQ ID NO 123
<211> LENGTH: 46
<212> TYPE: DNA
<213> ORGANISM: Homo sapiens

<400> SEQUENCE: 123
agatcacggt ccagcctctg ccggagcccc agtctccgca gtggag 46

<210> SEQ ID NO 124
<211> LENGTH: 49
<212> TYPE: DNA
<213> ORGANISM: Homo sapiens

<400> SEQUENCE: 124
ctggaacatc gcgggcacag ggcagcgttg gtcactgctc ctgggtact 49

<210> SEQ ID NO 125
<211> LENGTH: 49
<212> TYPE: DNA
<213> ORGANISM: Homo sapiens

<400> SEQUENCE: 125
gggggtcccg gagcccccca gccccgcagg ccactgcctc gccgcccga 49

<210> SEQ ID NO 126
<211> LENGTH: 54
<212> TYPE: DNA
<213> ORGANISM: Homo sapiens

<400> SEQUENCE: 126
tcttcatcag aacatctatg agtcgtcgtc tctgcagtcc atttgtttgc ccgc 54

<210> SEQ ID NO 127
<211> LENGTH: 47
<212> TYPE: DNA
<213> ORGANISM: Homo sapiens

<400> SEQUENCE: 127
actccaaggc tgcccaagcc tacggaccca gccacattgg cgaaccg 47

<210> SEQ ID NO 128
<211> LENGTH: 48
<212> TYPE: DNA
<213> ORGANISM: Homo sapiens

<400> SEQUENCE: 128
actccgcggt ccctgaactt ccggtgctgg cggactcctc gctccagg 48

<210> SEQ ID NO 129
<211> LENGTH: 49
<212> TYPE: DNA
<213> ORGANISM: Homo sapiens

<400> SEQUENCE: 129
ggggtgcctc cggccccatg ctcgcgggca agcagggata agctgtgcc 49

<210> SEQ ID NO 130
<211> LENGTH: 53
<212> TYPE: DNA
<213> ORGANISM: Homo sapiens

<400> SEQUENCE: 130
ggccatccgg caaagacccg agtaaggaac gcagggtcac tgcctgggcc aac 53

<210> SEQ ID NO 131
<211> LENGTH: 47
<212> TYPE: DNA
<213> ORGANISM: Homo sapiens

<400> SEQUENCE: 131
tttctctcag accacttgtc ccgaccaatc tgaccttcca aacacat 47

<210> SEQ ID NO 132
<211> LENGTH: 47
<212> TYPE: DNA
<213> ORGANISM: Homo sapiens

<400> SEQUENCE: 132
cgcagagcca gagactcctg ccgagttaga ccttctctcg tcgcccc 47

<210> SEQ ID NO 133
<211> LENGTH: 50
<212> TYPE: DNA
<213> ORGANISM: Homo sapiens

<400> SEQUENCE: 133
gcgcggtccc tttggatgct cgtgcgcata gacacaacac cctacacgcc 50

<210> SEQ ID NO 134
<211> LENGTH: 50
<212> TYPE: DNA
<213> ORGANISM: Homo sapiens

<400> SEQUENCE: 134
ccccagaaac actcaggtac tcgcgacaca cacagtacag tcacgcttaa 50

<210> SEQ ID NO 135
<211> LENGTH: 45
<212> TYPE: DNA
<213> ORGANISM: Homo sapiens

<400> SEQUENCE: 135
gcagacacaa acggacccac acgggcaact cccgagacaa aaccc 45

<210> SEQ ID NO 136
<211> LENGTH: 47
<212> TYPE: DNA
<213> ORGANISM: Homo sapiens

<400> SEQUENCE: 136
ggacacaaag ggaaggcgag gaggcgagca agaggctggg cctgcct 47

<210> SEQ ID NO 137
<211> LENGTH: 51
<212> TYPE: DNA
<213> ORGANISM: Homo sapiens

<400> SEQUENCE: 137
cgggcgggcc ggggtctttg tgacgcggtg gcaacggcca cggacacaaa g 51

<210> SEQ ID NO 138
<211> LENGTH: 50
<212> TYPE: DNA
<213> ORGANISM: Homo sapiens

<400> SEQUENCE: 138
gacaagtcac ctttacctct tccgtgactc agtttcttcc acctaaaaac 50

<210> SEQ ID NO 139
<211> LENGTH: 48
<212> TYPE: DNA
<213> ORGANISM: Homo sapiens

<400> SEQUENCE: 139
tgcagccccc ggtcggaagc tgggcgatga gccctgcctc cagcgggt 48

<210> SEQ ID NO 140
<211> LENGTH: 52
<212> TYPE: DNA
<213> ORGANISM: Homo sapiens

<400> SEQUENCE: 140
gggcgatgag ccctgcctcc agcgggtggc gctcgagtcc ggctgaacgg cg 52

<210> SEQ ID NO 141
<211> LENGTH: 50
<212> TYPE: DNA
<213> ORGANISM: Homo sapiens

<400> SEQUENCE: 141
atcctctgca tcctcgccgg gcgcgcgatc ggcagctgac ggcctaacaa 50

<210> SEQ ID NO 142
<211> LENGTH: 53
<212> TYPE: DNA
<213> ORGANISM: Homo sapiens

<400> SEQUENCE: 142
ggcgcggcct gtgcccttta taaggtgcgc gctgtgtcca gcgagcatcg gcc 53

<210> SEQ ID NO 143
<211> LENGTH: 54
<212> TYPE: DNA
<213> ORGANISM: Homo sapiens

<400> SEQUENCE: 143
cgcggcctgt gccctttata aggtgcgcgc tgtgtccagc gagcatcggc cacc 54

<210> SEQ ID NO 144
<211> LENGTH: 52
<212> TYPE: DNA
<213> ORGANISM: Homo sapiens

<400> SEQUENCE: 144
tctgcttctt agcgctagcc tcaatgacga cctaagctgc acttttcccc ct 52

<210> SEQ ID NO 145
<211> LENGTH: 50
<212> TYPE: DNA
<213> ORGANISM: Homo sapiens

<400> SEQUENCE: 145
cctggagacg ccttgaagta actgcacgaa atttgaggat ggccaggcag 50

<210> SEQ ID NO 146
<211> LENGTH: 46
<212> TYPE: DNA
<213> ORGANISM: Homo sapiens

<400> SEQUENCE: 146
gtttttgaat ggtttgggag gacgaattgt tagaccccga ggaagg 46

<210> SEQ ID NO 147
<211> LENGTH: 47
<212> TYPE: DNA
<213> ORGANISM: Homo sapiens

<400> SEQUENCE: 147
ccactccgga tggggctgcc accgcggcca ggacagtctc ctccgac 47

<210> SEQ ID NO 148
<211> LENGTH: 46
<212> TYPE: DNA
<213> ORGANISM: Homo sapiens

<400> SEQUENCE: 148
ggcctttgga actccaaggg gttcgtctac ctgaccattg ggtggg 46

<210> SEQ ID NO 149
<211> LENGTH: 51
<212> TYPE: DNA
<213> ORGANISM: Homo sapiens

<400> SEQUENCE: 149
gaagctagag taagctgagg aggtgggcgg aaaccatggc aaccatgggt g 51

<210> SEQ ID NO 150
<211> LENGTH: 47
<212> TYPE: DNA
<213> ORGANISM: Homo sapiens

<400> SEQUENCE: 150
accacaccca gcctagtgcc acgcaccgca agcgctccat aaacgca 47

<210> SEQ ID NO 151
<211> LENGTH: 53
<212> TYPE: DNA
<213> ORGANISM: Homo sapiens

<400> SEQUENCE: 151
cgcaggcagt gggcgcggac tctgcggttc gcttgactga cggcgcagcc tcc 53

<210> SEQ ID NO 152
<211> LENGTH: 48
<212> TYPE: DNA
<213> ORGANISM: Homo sapiens

<400> SEQUENCE: 152
ttgtgagggc ctttaaatat cctgtactcg tgggccatgt tgggccct 48

<210> SEQ ID NO 153
<211> LENGTH: 48
<212> TYPE: DNA
<213> ORGANISM: Homo sapiens

<400> SEQUENCE: 153
tcaggcactg gaatgagagg agttaacggg gaaggacagg gttatttc 48

<210> SEQ ID NO 154
<211> LENGTH: 46
<212> TYPE: DNA
<213> ORGANISM: Homo sapiens

<400> SEQUENCE: 154
cccatggaca cccaggtgtc cggggtgccc ccacaactct gggcct 46

<210> SEQ ID NO 155
<211> LENGTH: 51
<212> TYPE: DNA
<213> ORGANISM: Homo sapiens

<400> SEQUENCE: 155
tggctctgat tggctttctg gccgtcagga acatgtccca acatgttgag c 51

<210> SEQ ID NO 156
<211> LENGTH: 50
<212> TYPE: DNA
<213> ORGANISM: Homo sapiens

<400> SEQUENCE: 156
cccacattac ttgagggctc gggcgtgcgc aaagctccgg gttcagtttc 50

<210> SEQ ID NO 157
<211> LENGTH: 52
<212> TYPE: DNA
<213> ORGANISM: Homo sapiens

<400> SEQUENCE: 157
acaatcaaat agccacacgg cacgaagacg catgcgtggc gacaacaaca ac 52

<210> SEQ ID NO 158
<211> LENGTH: 48
<212> TYPE: DNA
<213> ORGANISM: Homo sapiens

<400> SEQUENCE: 158

-continued cagcctggcc ctttaagtct tccgcgatcc catttcggag tttcctct 48

<210> SEQ ID NO 159
<211> LENGTH: 51
<212> TYPE: DNA
<213> ORGANISM: Homo sapiens

<400> SEQUENCE: 159
tctttttctt agccctgccc ccgaattgtc agacggcggg cgtctgcctc t 51

<210> SEQ ID NO 160
<211> LENGTH: 49
<212> TYPE: DNA
<213> ORGANISM: Homo sapiens

<400> SEQUENCE: 160
ggctggcagc ttgcaaaggg gaagcggact ccagcactgc acgggcagg 49

<210> SEQ ID NO 161
<211> LENGTH: 52
<212> TYPE: DNA
<213> ORGANISM: Homo sapiens

<400> SEQUENCE: 161
ggcctggcct tatctccggc tgcacgttgc ctgttggtga ctaataacac aa 52

<210> SEQ ID NO 162
<211> LENGTH: 49
<212> TYPE: DNA
<213> ORGANISM: Homo sapiens

<400> SEQUENCE: 162
aagttcaatc aagggactgg gatttcggaa tgaataatga agggagatg 49

<210> SEQ ID NO 163
<211> LENGTH: 50
<212> TYPE: DNA
<213> ORGANISM: Homo sapiens

<400> SEQUENCE: 163
tccttcttcc tggatactca taacgcggcc ccatttctca ctcccattgg 50

<210> SEQ ID NO 164
<211> LENGTH: 41
<212> TYPE: DNA
<213> ORGANISM: Homo sapiens

<400> SEQUENCE: 164
ggggcaggct gggggccccc gctgcctgct gggtcaggct g 41

<210> SEQ ID NO 165
<211> LENGTH: 47
<212> TYPE: DNA
<213> ORGANISM: Homo sapiens

<400> SEQUENCE: 165
aactctacaa atcccgggat ctcggggtgc agatcacctc tcccaga 47

<210> SEQ ID NO 166
<211> LENGTH: 45
<212> TYPE: DNA
<213> ORGANISM: Homo sapiens

<400> SEQUENCE: 166

-continued tctgaagctg ggtggggtcc gcccttacac agctgggctt tgtgt 45

<210> SEQ ID NO 167
<211> LENGTH: 50
<212> TYPE: DNA
<213> ORGANISM: Homo sapiens

<400> SEQUENCE: 167
gctgaggcag gagaatcgct tgaacccggg aggcagaggt tgcagtgagc 50

<210> SEQ ID NO 168
<211> LENGTH: 48
<212> TYPE: DNA
<213> ORGANISM: Homo sapiens

<400> SEQUENCE: 168
gagggccaat cggaagggca agcttcgaga tgctgcgtga tcacgtgg 48

<210> SEQ ID NO 169
<211> LENGTH: 52
<212> TYPE: DNA
<213> ORGANISM: Homo sapiens

<400> SEQUENCE: 169
gggcggatca cctgagtcag gagttcgaga ccagcctggc caacatggtg aa 52

<210> SEQ ID NO 170
<211> LENGTH: 48
<212> TYPE: DNA
<213> ORGANISM: Homo sapiens

<400> SEQUENCE: 170
ggtgaaggag gtttggactc aatgcgggtc aaaggttagg gtcaaaag 48

<210> SEQ ID NO 171
<211> LENGTH: 46
<212> TYPE: DNA
<213> ORGANISM: Homo sapiens

<400> SEQUENCE: 171
gggatctgga gggggtagca ctacggggaa aggtcaaaag tcaggg 46

<210> SEQ ID NO 172
<211> LENGTH: 52
<212> TYPE: DNA
<213> ORGANISM: Homo sapiens

<400> SEQUENCE: 172
tggcagcccg gaagtgcggc aagtagtcgc tgcgaagtaa gccccgcccc gg 52

<210> SEQ ID NO 173
<211> LENGTH: 46
<212> TYPE: DNA
<213> ORGANISM: Homo sapiens

<400> SEQUENCE: 173
ataggttttg aggggcatgg ggacggggtt cagcctccag ggtcct 46

<210> SEQ ID NO 174
<211> LENGTH: 52
<212> TYPE: DNA
<213> ORGANISM: Homo sapiens

<400> SEQUENCE: 174
cccgcccccg cgatggagaa gaaaccgaga cagaaggtgc agggcccact ac 52

<210> SEQ ID NO 175
<211> LENGTH: 51
<212> TYPE: DNA
<213> ORGANISM: Homo sapiens

<400> SEQUENCE: 175
cagaaggtgc agggcccact accgcttcct ccagatgagc tcatgggttt c 51

<210> SEQ ID NO 176
<211> LENGTH: 48
<212> TYPE: DNA
<213> ORGANISM: Homo sapiens

<400> SEQUENCE: 176
gtctctggac agagtttccg ggggcggatg ggtaattttc aggctgtg 48

<210> SEQ ID NO 177
<211> LENGTH: 49
<212> TYPE: DNA
<213> ORGANISM: Homo sapiens

<400> SEQUENCE: 177
tccccttcat tgcggcgggc tgcgggccag gcttcactga gcgtccgca 49

<210> SEQ ID NO 178
<211> LENGTH: 49
<212> TYPE: DNA
<213> ORGANISM: Homo sapiens

<400> SEQUENCE: 178
gaacggctct caggccctgt ccgcacgtaa cctcactttc ctgctccct 49

<210> SEQ ID NO 179
<211> LENGTH: 48
<212> TYPE: DNA
<213> ORGANISM: Homo sapiens

<400> SEQUENCE: 179
catctctact cccaccgcat tcgaccctgc ccggactcac tgcttacc 48

<210> SEQ ID NO 180
<211> LENGTH: 48
<212> TYPE: DNA
<213> ORGANISM: Homo sapiens

<400> SEQUENCE: 180
tcagtcatgt ttccaaagtc ccgcggtttc ccctagtctc ttcattca 48

<210> SEQ ID NO 181
<211> LENGTH: 51
<212> TYPE: DNA
<213> ORGANISM: Homo sapiens

<400> SEQUENCE: 181
gtttgctgaa ggcttggaag tgcagcgcag aagacagagg gtgactagga a 51

<210> SEQ ID NO 182
<211> LENGTH: 49
<212> TYPE: DNA
<213> ORGANISM: Homo sapiens

<400> SEQUENCE: 182
tgtgtgtgtg tatgtgtgtg tctggcgcct ggccagggtg atttcccat 49

<210> SEQ ID NO 183
<211> LENGTH: 56
<212> TYPE: DNA
<213> ORGANISM: Homo sapiens

<400> SEQUENCE: 183
gagcatctct ggttggaatc ataatgcttc ggcctgaagt gaccaggcca ctcact 56

<210> SEQ ID NO 184
<211> LENGTH: 49
<212> TYPE: DNA
<213> ORGANISM: Homo sapiens

<400> SEQUENCE: 184
cgggaggcca caagagcagg gccaacgtta gaaaggccgc aaggggaga 49

<210> SEQ ID NO 185
<211> LENGTH: 51
<212> TYPE: DNA
<213> ORGANISM: Homo sapiens

<400> SEQUENCE: 185
tggcgtaagc tacagctgaa ggaagaacgt gagcacgagg cactgaggtg a 51

<210> SEQ ID NO 186
<211> LENGTH: 53
<212> TYPE: DNA
<213> ORGANISM: Homo sapiens

<400> SEQUENCE: 186
ccgccacata ccgctcgtag tattcgtgct cagcctcgta gtggcgcctg acg 53

<210> SEQ ID NO 187
<211> LENGTH: 52
<212> TYPE: DNA
<213> ORGANISM: Homo sapiens

<400> SEQUENCE: 187
ccacaggaaa tgcacaggtg agaaactgac gttaaggggg actgagtgtc aa 52

<210> SEQ ID NO 188
<211> LENGTH: 46
<212> TYPE: DNA
<213> ORGANISM: Homo sapiens

<400> SEQUENCE: 188
agggcagatt caaacccaac acggtcctcc cctgctgccc ctcggc 46

<210> SEQ ID NO 189
<211> LENGTH: 47
<212> TYPE: DNA
<213> ORGANISM: Homo sapiens

<400> SEQUENCE: 189
cggtcggccc ggtgaggcgc agcgccccag actggcgcat ccgcggc 47

<210> SEQ ID NO 190
<211> LENGTH: 49
<212> TYPE: DNA
<213> ORGANISM: Homo sapiens

<400> SEQUENCE: 190
ggcgagcggc caggtgcgcc ttcggcagga cagtgctaat tccagcccc 49

<210> SEQ ID NO 191
<211> LENGTH: 48
<212> TYPE: DNA
<213> ORGANISM: Homo sapiens

<400> SEQUENCE: 191
cacacggggg tgctaagcct cccgcccgtt ctaagcggag acccaacg 48

<210> SEQ ID NO 192
<211> LENGTH: 48
<212> TYPE: DNA
<213> ORGANISM: Homo sapiens

<400> SEQUENCE: 192
cgcacgcagg taacttcacc ctcgcctcaa cgacctcaga ggctgccc 48

<210> SEQ ID NO 193
<211> LENGTH: 57
<212> TYPE: DNA
<213> ORGANISM: Homo sapiens

<400> SEQUENCE: 193
gaggtcgctg ccactcctac agagccccca cgccccgccc agctataagg ggccatg 57

<210> SEQ ID NO 194
<211> LENGTH: 43
<212> TYPE: DNA
<213> ORGANISM: Homo sapiens

<400> SEQUENCE: 194
actcctacag agcccccacg ccccgcccag ctataagggg cca 43

<210> SEQ ID NO 195
<211> LENGTH: 49
<212> TYPE: DNA
<213> ORGANISM: Homo sapiens

<400> SEQUENCE: 195
acggtagccg ccttcctatt tccgcccggc gggcagcgct gcggggcga 49

<210> SEQ ID NO 196
<211> LENGTH: 47
<212> TYPE: DNA
<213> ORGANISM: Homo sapiens

<400> SEQUENCE: 196
cgccgcctag agcctggaag ccgccactgc ggcccaggac aatccgg 47

<210> SEQ ID NO 197
<211> LENGTH: 48
<212> TYPE: DNA
<213> ORGANISM: Homo sapiens

<400> SEQUENCE: 197
ccaagtcttg gcaagcggcc ggcgaaactc acaggtccct ttcctggc 48

<210> SEQ ID NO 198
<211> LENGTH: 49
<212> TYPE: DNA
<213> ORGANISM: Homo sapiens

<400> SEQUENCE: 198
ctcctctcct cagcgctggt ccgggaaagg caagctccgg gcgggagcg 49

<210> SEQ ID NO 199
<211> LENGTH: 46
<212> TYPE: DNA
<213> ORGANISM: Homo sapiens

<400> SEQUENCE: 199
gggaatagag attgctgggg accgcagggg ccaggttgtc attccc 46

<210> SEQ ID NO 200
<211> LENGTH: 40
<212> TYPE: DNA
<213> ORGANISM: Homo sapiens

<400> SEQUENCE: 200
cccgaagcct ggctccctcg ccacgcccac ttcctgcccc 40

<210> SEQ ID NO 201
<211> LENGTH: 45
<212> TYPE: DNA
<213> ORGANISM: Homo sapiens

<400> SEQUENCE: 201
caccaatcag cgccgacctc gccttcgcag gcctaaccaa tcagt 45

<210> SEQ ID NO 202
<211> LENGTH: 49
<212> TYPE: DNA
<213> ORGANISM: Homo sapiens

<400> SEQUENCE: 202
cgcgctcagt tacttagcaa cctcggcgct aagccacccc aggtggagc 49

<210> SEQ ID NO 203
<211> LENGTH: 47
<212> TYPE: DNA
<213> ORGANISM: Homo sapiens

<400> SEQUENCE: 203
ggagaatcgc ttgaacccgg gaggcggagg ttgcgatgag ccgagat 47

<210> SEQ ID NO 204
<211> LENGTH: 49
<212> TYPE: DNA
<213> ORGANISM: Homo sapiens

<400> SEQUENCE: 204
ggcagcctag ggaatttatc ccggactccg ggggaggggg cagagtcac 49

<210> SEQ ID NO 205
<211> LENGTH: 51
<212> TYPE: DNA
<213> ORGANISM: Homo sapiens

<400> SEQUENCE: 205
gattctccga ggaaaagtgt gagaacggct gcaggcaacc caggcgtccc g 51

<210> SEQ ID NO 206
<211> LENGTH: 48
<212> TYPE: DNA
<213> ORGANISM: Homo sapiens

<400> SEQUENCE: 206
aggagggacg cacccaggcc tgcgcgaaga gagggagaaa gtgaagct 48

<210> SEQ ID NO 207
<211> LENGTH: 51
<212> TYPE: DNA
<213> ORGANISM: Homo sapiens

<400> SEQUENCE: 207
gtggcccaag cgcccgaatg aaggctcggg gccaaagtca tgtgtctgac t 51

<210> SEQ ID NO 208
<211> LENGTH: 48
<212> TYPE: DNA
<213> ORGANISM: Homo sapiens

<400> SEQUENCE: 208
ctgtggaggg agaggaagca gctgcggaaa gccaataaga gtggggaa 48

<210> SEQ ID NO 209
<211> LENGTH: 50
<212> TYPE: DNA
<213> ORGANISM: Homo sapiens

<400> SEQUENCE: 209
tcccgccaac tctatggtcg agcgtttcag ggatcggcca atcgtaatcc 50

<210> SEQ ID NO 210
<211> LENGTH: 50
<212> TYPE: DNA
<213> ORGANISM: Homo sapiens

<400> SEQUENCE: 210
ctcgggaagc caatttgctc gcgaacgaag gaagtgagtc agagaacccg 50

<210> SEQ ID NO 211
<211> LENGTH: 53
<212> TYPE: DNA
<213> ORGANISM: Homo sapiens

<400> SEQUENCE: 211
gggtggagag aagaaagcaa gcagctaacc ggaaaggtct gaaaaagcta gcg 53

<210> SEQ ID NO 212
<211> LENGTH: 51
<212> TYPE: DNA
<213> ORGANISM: Homo sapiens

<400> SEQUENCE: 212
cgcaacgtgt gagcgccacc tctcgggaag ccaatttgct cgcgaacgaa g 51

<210> SEQ ID NO 213
<211> LENGTH: 49
<212> TYPE: DNA
<213> ORGANISM: Homo sapiens

<400> SEQUENCE: 213
ctcccgggtc agctctggca ctcgccagct gagcccagcg ccagtctag 49

<210> SEQ ID NO 214
<211> LENGTH: 46
<212> TYPE: DNA
<213> ORGANISM: Homo sapiens

<400> SEQUENCE: 214
gggcgcccta acttccaact ccgggagcaa tccaaacccg gaggcc 46

<210> SEQ ID NO 215
<211> LENGTH: 49
<212> TYPE: DNA
<213> ORGANISM: Homo sapiens

<400> SEQUENCE: 215
ttttcattaa tgaaaccggc cggcgcgggc gcatgcgcgg caggccgcc 49

<210> SEQ ID NO 216
<211> LENGTH: 46
<212> TYPE: DNA
<213> ORGANISM: Homo sapiens

<400> SEQUENCE: 216
ttcaggaggg tgagggcagg agcgtgggtg gagtcagcag gtcccc 46

<210> SEQ ID NO 217
<211> LENGTH: 50
<212> TYPE: DNA
<213> ORGANISM: Homo sapiens

<400> SEQUENCE: 217
caacccagcc tctgtcggag gcgaattctc agagtgaggg ttccctgtca 50

<210> SEQ ID NO 218
<211> LENGTH: 50
<212> TYPE: DNA
<213> ORGANISM: Homo sapiens

<400> SEQUENCE: 218
ttccctgtga cgtgaccttg ggggacgtca ttgccctttc tgtccccacc 50

<210> SEQ ID NO 219
<211> LENGTH: 53
<212> TYPE: DNA
<213> ORGANISM: Homo sapiens

<400> SEQUENCE: 219
ggtttcacta tgttggccag gctggtctcg aactcctgac ctcgtgatcc gcc 53

<210> SEQ ID NO 220
<211> LENGTH: 49
<212> TYPE: DNA
<213> ORGANISM: Homo sapiens

<400> SEQUENCE: 220
cggtggctca gctcacagcc tctcgctaga ctccagacac ccacctgcc 49

<210> SEQ ID NO 221
<211> LENGTH: 46
<212> TYPE: DNA
<213> ORGANISM: Homo sapiens

<400> SEQUENCE: 221
atccttgacc tgcctcgacc tccggaccct ccggacctcc agctgc 46

<210> SEQ ID NO 222
<211> LENGTH: 51
<212> TYPE: DNA
<213> ORGANISM: Homo sapiens

<400> SEQUENCE: 222
agccagcctg gggactggag ggtggcggct gcatctgctc atttcctccc a 51

<210> SEQ ID NO 223
<211> LENGTH: 54
<212> TYPE: DNA
<213> ORGANISM: Homo sapiens

<400> SEQUENCE: 223
ggagtcttgc tgtgtctccc aggccggagt gcaatggcat gacctctgcc tccc 54

<210> SEQ ID NO 224
<211> LENGTH: 49
<212> TYPE: DNA
<213> ORGANISM: Homo sapiens

<400> SEQUENCE: 224
tggagtcttg ctgtgtctcc caggccggag tgcaatggca tgacctctg 49

<210> SEQ ID NO 225
<211> LENGTH: 46
<212> TYPE: DNA
<213> ORGANISM: Homo sapiens

<400> SEQUENCE: 225
gccattgccg gcggtccacc ggttgccaca ctctgaccaa tcagga 46

<210> SEQ ID NO 226
<211> LENGTH: 50
<212> TYPE: DNA
<213> ORGANISM: Homo sapiens

<400> SEQUENCE: 226
agttaaacca gccttctttc ccgcctgccg ggttcatttg aaaaccgaaa 50

<210> SEQ ID NO 227
<211> LENGTH: 47
<212> TYPE: DNA
<213> ORGANISM: Homo sapiens

<400> SEQUENCE: 227
ctcatccact ccgtctctcc gtttcccttt cttcacggtg cttgaca 47

<210> SEQ ID NO 228
<211> LENGTH: 47
<212> TYPE: DNA
<213> ORGANISM: Homo sapiens

<400> SEQUENCE: 228
agcttggaaa ttccggagct gaagcggcca gcgagggagg atgaccc 47

<210> SEQ ID NO 229
<211> LENGTH: 47
<212> TYPE: DNA
<213> ORGANISM: Homo sapiens

<400> SEQUENCE: 229
tccccggacg tggtgagacc gcgcttcgtc actcccacgg ttagcgg 47

<210> SEQ ID NO 230
<211> LENGTH: 50
<212> TYPE: DNA
<213> ORGANISM: Homo sapiens

<400> SEQUENCE: 230
cctggctctg ctctggccgc ttctcgagaa atgcccgtgt cagctaggtg 50

<210> SEQ ID NO 231
<211> LENGTH: 47
<212> TYPE: DNA
<213> ORGANISM: Homo sapiens

<400> SEQUENCE: 231
ccagtctcta gtatccacct ctcgccatca accaggcatt ccgggag 47

<210> SEQ ID NO 232
<211> LENGTH: 47
<212> TYPE: DNA
<213> ORGANISM: Homo sapiens

<400> SEQUENCE: 232
gggccagctc aggacaggcg ctcgggggac gcgtgtcctc accccac 47

<210> SEQ ID NO 233
<211> LENGTH: 48
<212> TYPE: DNA
<213> ORGANISM: Homo sapiens

<400> SEQUENCE: 233
gtggaggaga gtcagcgagg gcccgagggg caggtacttt aacgaatg 48

<210> SEQ ID NO 234
<211> LENGTH: 50
<212> TYPE: DNA
<213> ORGANISM: Homo sapiens

<400> SEQUENCE: 234
gccttttcag ttgctcacag tccgtcagtc cttgagccaa tcggcgtgga 50

<210> SEQ ID NO 235
<211> LENGTH: 49
<212> TYPE: DNA
<213> ORGANISM: Homo sapiens

<400> SEQUENCE: 235
agcgctttgg ccaatcagcg agcggcggga cattgggctc ctcctcctc 49

<210> SEQ ID NO 236
<211> LENGTH: 53
<212> TYPE: DNA
<213> ORGANISM: Homo sapiens

<400> SEQUENCE: 236
ccatttctat acaagccctg cttccgctga gcagcatggc gtgcgacacc gcc 53

<210> SEQ ID NO 237
<211> LENGTH: 49
<212> TYPE: DNA
<213> ORGANISM: Homo sapiens

<400> SEQUENCE: 237
cgggggttcg gcctcagtca ggcgctcagc tccgtttcgg tttcacttc 49

<210> SEQ ID NO 238
<211> LENGTH: 51
<212> TYPE: DNA
<213> ORGANISM: Homo sapiens

<400> SEQUENCE: 238
cagaaatggg cgttctggcc ctcgcgaggc agtgcgacct gtcaccgccc t 51

<210> SEQ ID NO 239
<211> LENGTH: 48
<212> TYPE: DNA
<213> ORGANISM: Homo sapiens

<400> SEQUENCE: 239
acctcccgct cagtcagact gcgctacttt gaaccggacc aaaccaaa 48

<210> SEQ ID NO 240
<211> LENGTH: 50
<212> TYPE: DNA
<213> ORGANISM: Homo sapiens

<400> SEQUENCE: 240
tccactgcga tattgctcca aatccgagga aattcaaact cccgggcgcg 50

<210> SEQ ID NO 241
<211> LENGTH: 47
<212> TYPE: DNA
<213> ORGANISM: Homo sapiens

<400> SEQUENCE: 241
agcaggggct cccttgggcc ccgacttctt ccggctcttc acctcag 47

<210> SEQ ID NO 242
<211> LENGTH: 51
<212> TYPE: DNA
<213> ORGANISM: Homo sapiens

<400> SEQUENCE: 242
cccgagtccg gcattggtgg gaacgcggcg cgtccctgag gcttagccac g 51

<210> SEQ ID NO 243
<211> LENGTH: 45
<212> TYPE: DNA
<213> ORGANISM: Homo sapiens

<400> SEQUENCE: 243
gctgaaagaa ggcctgtggc gaagcggagg gggacctaag tcagg 45

<210> SEQ ID NO 244
<211> LENGTH: 55
<212> TYPE: DNA
<213> ORGANISM: Homo sapiens

<400> SEQUENCE: 244
ccagagcgcc ctgtgtagag cggctgcgag cgggcagctg ggctcggctg ccggg 55

<210> SEQ ID NO 245
<211> LENGTH: 50
<212> TYPE: DNA
<213> ORGANISM: Homo sapiens

<400> SEQUENCE: 245
ccagagccag tcagagcgga cggctgctgg gaagccaatc agcgcgctcg 50

<210> SEQ ID NO 246
<211> LENGTH: 52
<212> TYPE: DNA
<213> ORGANISM: Homo sapiens

<400> SEQUENCE: 246
aaatacaagg gcaggaggat taggatccgt tttgaagaag ccaaagttgg ag 52

<210> SEQ ID NO 247
<211> LENGTH: 56
<212> TYPE: DNA
<213> ORGANISM: Homo sapiens

<400> SEQUENCE: 247
gggaggagag ctaactgccc agccagcttg cgtcaccgct tcagagcgga gaagag 56

<210> SEQ ID NO 248
<211> LENGTH: 52
<212> TYPE: DNA
<213> ORGANISM: Homo sapiens

<400> SEQUENCE: 248
agaaggttgt tttctccaca tttcggggtt ctggacgttt cccggctgcg gg 52

<210> SEQ ID NO 249
<211> LENGTH: 48
<212> TYPE: DNA
<213> ORGANISM: Homo sapiens

<400> SEQUENCE: 249
tttacatcat tttgccaatt tcgcgtactg caaccggcgg gccacgcc 48

<210> SEQ ID NO 250
<211> LENGTH: 44
<212> TYPE: DNA
<213> ORGANISM: Homo sapiens

<400> SEQUENCE: 250
cagtcattcc cggccactcg cgacccgagg ctgccgcagg gggc 44

<210> SEQ ID NO 251
<211> LENGTH: 48
<212> TYPE: DNA
<213> ORGANISM: Homo sapiens

<400> SEQUENCE: 251
ccccagcacc gctgtggtgt gccgggatcc tgagcctagg cctcccga 48

<210> SEQ ID NO 252
<211> LENGTH: 46
<212> TYPE: DNA
<213> ORGANISM: Homo sapiens

<400> SEQUENCE: 252
gagaccccat tttctgtcga ggcgggccga gtcttccctt atcccc 46

<210> SEQ ID NO 253
<211> LENGTH: 48
<212> TYPE: DNA
<213> ORGANISM: Homo sapiens

<400> SEQUENCE: 253
aaggaggcca gaggctgcaa ggagcggggt cgtgaccgct tacacccc 48

<210> SEQ ID NO 254
<211> LENGTH: 50
<212> TYPE: DNA
<213> ORGANISM: Homo sapiens

<400> SEQUENCE: 254
tttctgcgct ttcctgaagt tcccgccctc ttggagccta cctgcccctc 50

<210> SEQ ID NO 255
<211> LENGTH: 51
<212> TYPE: DNA
<213> ORGANISM: Homo sapiens

<400> SEQUENCE: 255
cgcccggctt ataactggtg caactcccgg ccacccaact gagggacgtt c 51

<210> SEQ ID NO 256
<211> LENGTH: 45
<212> TYPE: DNA
<213> ORGANISM: Homo sapiens

<400> SEQUENCE: 256
cgaacaggcg ggcagagggc cccgcgggag ggtccagaag agagg 45

<210> SEQ ID NO 257
<211> LENGTH: 48
<212> TYPE: DNA
<213> ORGANISM: Homo sapiens

<400> SEQUENCE: 257
gggtccgaga agtggccgga aggcgcaggg tcggggccag agcccctc 48

<210> SEQ ID NO 258
<211> LENGTH: 52
<212> TYPE: DNA
<213> ORGANISM: Homo sapiens

<400> SEQUENCE: 258
cgggcgccga acagagcgag ctgcggccgt ggcagctgca cggctcctgg cc 52

<210> SEQ ID NO 259
<211> LENGTH: 48
<212> TYPE: DNA
<213> ORGANISM: Homo sapiens

<400> SEQUENCE: 259
gagaatcgct tcagcccggg aggtcgaggc tgtagtgagc cgagatcg 48

<210> SEQ ID NO 260
<211> LENGTH: 52
<212> TYPE: DNA
<213> ORGANISM: Homo sapiens

<400> SEQUENCE: 260
cgagatcgcg ctactgcact cctgggcgac agagcgagac cctgtctcca aa 52

<210> SEQ ID NO 261
<211> LENGTH: 46
<212> TYPE: DNA
<213> ORGANISM: Homo sapiens

<400> SEQUENCE: 261
aaagacaggg agctgggatg gtgcgggttg gtctctaaac cggcgt 46

<210> SEQ ID NO 262
<211> LENGTH: 50
<212> TYPE: DNA
<213> ORGANISM: Homo sapiens

<400> SEQUENCE: 262
cgcgcggtgc ggagcctgcg ggccgggcgg ggctctgcgg cggcgcctcc 50

<210> SEQ ID NO 263
<211> LENGTH: 51
<212> TYPE: DNA
<213> ORGANISM: Homo sapiens

<400> SEQUENCE: 263
cccgcggtga catcagccga tgcgaagggc ggggccgcgg ctataagagc g 51

<210> SEQ ID NO 264
<211> LENGTH: 49
<212> TYPE: DNA
<213> ORGANISM: Homo sapiens

<400> SEQUENCE: 264
atgcctctcg ggtggtgact ccagcgcagg aacttgaaga agcgctttg 49

<210> SEQ ID NO 265
<211> LENGTH: 53
<212> TYPE: DNA
<213> ORGANISM: Homo sapiens

<400> SEQUENCE: 265
ggtaagggag ggaaaatctt accaaagcga ccggctcact cgactgctga ttc 53

<210> SEQ ID NO 266
<211> LENGTH: 50
<212> TYPE: DNA
<213> ORGANISM: Homo sapiens

<400> SEQUENCE: 266
tcctgctgct cccgctggtt cctgcggctt ctgctcagac accaacgcca 50

<210> SEQ ID NO 267
<211> LENGTH: 50
<212> TYPE: DNA
<213> ORGANISM: Homo sapiens

<400> SEQUENCE: 267
cctgaagaat caatcaagtt ttccgtgaag tcaagtccaa gtaacatccc 50

<210> SEQ ID NO 268
<211> LENGTH: 52
<212> TYPE: DNA
<213> ORGANISM: Homo sapiens

<400> SEQUENCE: 268
tctcctcctg cggctccata gctgcggctc ccgccacttt actaggaact cc 52

<210> SEQ ID NO 269
<211> LENGTH: 49
<212> TYPE: DNA
<213> ORGANISM: Homo sapiens

<400> SEQUENCE: 269
ggctctggca ttgcaagcct cgcttcgttg ccacttccca gctcttccc 49

<210> SEQ ID NO 270
<211> LENGTH: 50
<212> TYPE: DNA
<213> ORGANISM: Homo sapiens

<400> SEQUENCE: 270

-continued ctcccagtgt tgggatgcag ggcgcggaag cagttcagat gtggaagccg 50

<210> SEQ ID NO 271
<211> LENGTH: 54
<212> TYPE: DNA
<213> ORGANISM: Homo sapiens

<400> SEQUENCE: 271
cgggtcccag gagcccgcag gcatccccgg gagcggcaga agcagcagca ggaa 54

<210> SEQ ID NO 272
<211> LENGTH: 44
<212> TYPE: DNA
<213> ORGANISM: Homo sapiens

<400> SEQUENCE: 272
acgctcagcg gccgtgccca cgcggcggcg cccatgtcgg cccg 44

<210> SEQ ID NO 273
<211> LENGTH: 47
<212> TYPE: DNA
<213> ORGANISM: Homo sapiens

<400> SEQUENCE: 273
ggcttagacc tcaagcaagt cacgtaacct ctcccagcct cagtttt 47

<210> SEQ ID NO 274
<211> LENGTH: 53
<212> TYPE: DNA
<213> ORGANISM: Homo sapiens

<400> SEQUENCE: 274
aaagcagaga agcgagagcg gccactagtt cggcaggaaa tttgttggaa gat 53

<210> SEQ ID NO 275
<211> LENGTH: 56
<212> TYPE: DNA
<213> ORGANISM: Homo sapiens

<400> SEQUENCE: 275
caatgcattc cttttcgtca gagtcgaggg caaactcgct gaaatctggg tgaccc 56

<210> SEQ ID NO 276
<211> LENGTH: 52
<212> TYPE: DNA
<213> ORGANISM: Homo sapiens

<400> SEQUENCE: 276
ggattggttc cacaggcctt ttaaaaagcg gacttaaaag ttgctggcaa tg 52

<210> SEQ ID NO 277
<211> LENGTH: 47
<212> TYPE: DNA
<213> ORGANISM: Homo sapiens

<400> SEQUENCE: 277
gggacagact ccgcctggca ccgggaccat cctccgcctc aactttg 47

<210> SEQ ID NO 278
<211> LENGTH: 49
<212> TYPE: DNA
<213> ORGANISM: Homo sapiens

<400> SEQUENCE: 278

-continued gtgccagacg cctgtgcctt ggccgtccta cagccctgct gcccctgcc 49

<210> SEQ ID NO 279
<211> LENGTH: 49
<212> TYPE: DNA
<213> ORGANISM: Homo sapiens

<400> SEQUENCE: 279
ctggagtgtg gcctctgtgc cagacgcctg tgccttggcc gtcctacag 49

<210> SEQ ID NO 280
<211> LENGTH: 49
<212> TYPE: DNA
<213> ORGANISM: Homo sapiens

<400> SEQUENCE: 280
cctagaggaa gtttagtcct tgggacgctt ggcctgccag tctctgaaa 49

<210> SEQ ID NO 281
<211> LENGTH: 38
<212> TYPE: DNA
<213> ORGANISM: Homo sapiens

<400> SEQUENCE: 281
gatggtggtg gtggtagtgc acgttgggtt gaggggac 38

<210> SEQ ID NO 282
<211> LENGTH: 53
<212> TYPE: DNA
<213> ORGANISM: Homo sapiens

<400> SEQUENCE: 282
tctgagacag gaactgcgaa atgctcacga gattaggaca cgcgccaagg cgg 53

<210> SEQ ID NO 283
<211> LENGTH: 54
<212> TYPE: DNA
<213> ORGANISM: Homo sapiens

<400> SEQUENCE: 283
caagggtccg cattgaacca ggtgcgaatg ttctctctca ttctgcgccg ttcc 54

<210> SEQ ID NO 284
<211> LENGTH: 51
<212> TYPE: DNA
<213> ORGANISM: Homo sapiens

<400> SEQUENCE: 284
cgggagccga ggcttaagtc ctcggggtcc tgtactcgat gccgtttctc c 51

<210> SEQ ID NO 285
<211> LENGTH: 44
<212> TYPE: DNA
<213> ORGANISM: Homo sapiens

<400> SEQUENCE: 285
agacataggg tttggtgtgg ctgtgcgggg ttcccgggcc ttgc 44

<210> SEQ ID NO 286
<211> LENGTH: 52
<212> TYPE: DNA
<213> ORGANISM: Homo sapiens

<400> SEQUENCE: 286
gctggcctgt cggcctctga tgcactcgaa cttccagccc ttggagcaga ca 52

<210> SEQ ID NO 287
<211> LENGTH: 48
<212> TYPE: DNA
<213> ORGANISM: Homo sapiens

<400> SEQUENCE: 287
tcagggaagc tgctctttgg gatcgctcca aatcgagttg tgcctgga 48

<210> SEQ ID NO 288
<211> LENGTH: 47
<212> TYPE: DNA
<213> ORGANISM: Homo sapiens

<400> SEQUENCE: 288
ggcccctgga tccgtctttc gcgtttattt taagcccagt cttccct 47

<210> SEQ ID NO 289
<211> LENGTH: 50
<212> TYPE: DNA
<213> ORGANISM: Homo sapiens

<400> SEQUENCE: 289
ccccattcta tctgccctat ctcggttaca gtgtagtcct ccccagggtc 50

<210> SEQ ID NO 290
<211> LENGTH: 48
<212> TYPE: DNA
<213> ORGANISM: Homo sapiens

<400> SEQUENCE: 290
cctggaaggc gcctggaccc acgccaggtt tcccagttta attcctca 48

<210> SEQ ID NO 291
<211> LENGTH: 52
<212> TYPE: DNA
<213> ORGANISM: Homo sapiens

<400> SEQUENCE: 291
gcgggcggaa gtgacgtttt cccgcggttg gacgcggcgc tcagttgccg gg 52

<210> SEQ ID NO 292
<211> LENGTH: 49
<212> TYPE: DNA
<213> ORGANISM: Homo sapiens

<400> SEQUENCE: 292
tcgcagccag ggcaggctgc ggcgccgaca cacaggagcc ggctgcggg 49

<210> SEQ ID NO 293
<211> LENGTH: 51
<212> TYPE: DNA
<213> ORGANISM: Homo sapiens

<400> SEQUENCE: 293
tcatcttgca atcacatagc catcgcatgc cattgcaggg gcaacccagc a 51

<210> SEQ ID NO 294
<211> LENGTH: 53
<212> TYPE: DNA
<213> ORGANISM: Homo sapiens

<400> SEQUENCE: 294
catacgctga ctccgaggca actgggcgca cacatatccc ctctctggtc ctc 53

<210> SEQ ID NO 295
<211> LENGTH: 47
<212> TYPE: DNA
<213> ORGANISM: Homo sapiens

<400> SEQUENCE: 295
cagggttcaa gggcatgggg ctcccgcagc tgtggctggg gcagagc 47

<210> SEQ ID NO 296
<211> LENGTH: 47
<212> TYPE: DNA
<213> ORGANISM: Homo sapiens

<400> SEQUENCE: 296
gcccaacaga cttttccttt tcgggcctca gtcttctcgt cagcaag 47

<210> SEQ ID NO 297
<211> LENGTH: 49
<212> TYPE: DNA
<213> ORGANISM: Homo sapiens

<400> SEQUENCE: 297
cacgcgattg gtatcctgcc ctccgcccca gccaatgagc ggcgagggt 49

<210> SEQ ID NO 298
<211> LENGTH: 44
<212> TYPE: DNA
<213> ORGANISM: Homo sapiens

<400> SEQUENCE: 298
tccccgatgc agaccacagc gccctcacgg gctgccctca ggcc 44

<210> SEQ ID NO 299
<211> LENGTH: 50
<212> TYPE: DNA
<213> ORGANISM: Homo sapiens

<400> SEQUENCE: 299
aaagggagag aagttggtgc tcaacgtgag ccaggagcag cgtcccggct 50

<210> SEQ ID NO 300
<211> LENGTH: 47
<212> TYPE: DNA
<213> ORGANISM: Homo sapiens

<400> SEQUENCE: 300
cgtgagccag gagcagcgtc ccggctcctc ccctgctcat tttaaaa 47

<210> SEQ ID NO 301
<211> LENGTH: 47
<212> TYPE: DNA
<213> ORGANISM: Homo sapiens

<400> SEQUENCE: 301
gagcgggcgc aggcggaaca ccgttttcca agctaagccg ccgcaaa 47

<210> SEQ ID NO 302
<211> LENGTH: 56
<212> TYPE: DNA
<213> ORGANISM: Homo sapiens

<400> SEQUENCE: 302
ggctggggca cacaaaacca ggtgctaccg tcaacgacta ggcccatagg gtactg 56

<210> SEQ ID NO 303
<211> LENGTH: 49
<212> TYPE: DNA
<213> ORGANISM: Homo sapiens

<400> SEQUENCE: 303
aagggagaaa gaagccagac ggagctcgga gatgtggagg gcagacgca 49

<210> SEQ ID NO 304
<211> LENGTH: 52
<212> TYPE: DNA
<213> ORGANISM: Homo sapiens

<400> SEQUENCE: 304
cccaaaacgc tcggtaggcg gtggtgcgca gctttcaatg catccgccgc ca 52

<210> SEQ ID NO 305
<211> LENGTH: 47
<212> TYPE: DNA
<213> ORGANISM: Homo sapiens

<400> SEQUENCE: 305
ctcctgaacc tttatgggct ctgtcgaggc tgaagcagcc aggggct 47

<210> SEQ ID NO 306
<211> LENGTH: 41
<212> TYPE: DNA
<213> ORGANISM: Homo sapiens

<400> SEQUENCE: 306
gcaggtcttg ggccctggtc ccgccccctg ctcctcccca c 41

<210> SEQ ID NO 307
<211> LENGTH: 41
<212> TYPE: DNA
<213> ORGANISM: Homo sapiens

<400> SEQUENCE: 307
gaggggctgg aggaggaaac ggggaggccc acacagaagg g 41

<210> SEQ ID NO 308
<211> LENGTH: 42
<212> TYPE: DNA
<213> ORGANISM: Homo sapiens

<400> SEQUENCE: 308
gggcaactgt ccccacccgt ccctggcacg gctctgccca gt 42

<210> SEQ ID NO 309
<211> LENGTH: 46
<212> TYPE: DNA
<213> ORGANISM: Homo sapiens

<400> SEQUENCE: 309
tccttgctgc cacacattta gccgccctcc ccatgccagc ttgggg 46

<210> SEQ ID NO 310
<211> LENGTH: 51
<212> TYPE: DNA
<213> ORGANISM: Homo sapiens

<400> SEQUENCE: 310

-continued gttgggtgcc ctcatttcag atgatttcga gggtgcttga caagatctga a 51

<210> SEQ ID NO 311
<211> LENGTH: 48
<212> TYPE: DNA
<213> ORGANISM: Homo sapiens

<400> SEQUENCE: 311
ggggaccctg gcacagattt ggctcgacct ggacataggc tgggcctg 48

<210> SEQ ID NO 312
<211> LENGTH: 50
<212> TYPE: DNA
<213> ORGANISM: Homo sapiens

<400> SEQUENCE: 312
ggcagtgctg ggaacgcccc tctcggaaat taactcctca gggcacccgc 50

<210> SEQ ID NO 313
<211> LENGTH: 48
<212> TYPE: DNA
<213> ORGANISM: Homo sapiens

<400> SEQUENCE: 313
gacctggagg cagccctggg tctccggatc aggccagcgg ccaaaggg 48

<210> SEQ ID NO 314
<211> LENGTH: 48
<212> TYPE: DNA
<213> ORGANISM: Homo sapiens

<400> SEQUENCE: 314
ccgcccggag cagctgcgct gtcggggcca ggccgggctc ccagtgga 48

<210> SEQ ID NO 315
<211> LENGTH: 47
<212> TYPE: DNA
<213> ORGANISM: Homo sapiens

<400> SEQUENCE: 315
gggttacccc acagcctagg ccgattcgac ctctctccgc tggggcc 47

<210> SEQ ID NO 316
<211> LENGTH: 47
<212> TYPE: DNA
<213> ORGANISM: Homo sapiens

<400> SEQUENCE: 316
ggccgcgcag atcccgctta tcgggcccat ctcccgttac ataaggc 47

<210> SEQ ID NO 317
<211> LENGTH: 47
<212> TYPE: DNA
<213> ORGANISM: Homo sapiens

<400> SEQUENCE: 317
gagccgctgg cccgggtgtc cagccggccc ttgccctgcc tggcgct 47

<210> SEQ ID NO 318
<211> LENGTH: 50
<212> TYPE: DNA
<213> ORGANISM: Homo sapiens

<400> SEQUENCE: 318

-continued cacgcagcgc attgcaggca ggtgcgagcc acatgcgcca agtgcccgga 50

<210> SEQ ID NO 319
<211> LENGTH: 51
<212> TYPE: DNA
<213> ORGANISM: Homo sapiens

<400> SEQUENCE: 319
atcctggggt ttatttgctg agggcgcttc ccataaaagc gagagagtgt g 51

<210> SEQ ID NO 320
<211> LENGTH: 49
<212> TYPE: DNA
<213> ORGANISM: Homo sapiens

<400> SEQUENCE: 320
gtgaacaaat agctgagggg cggccgggcc agaacggctt gtgtaactt 49

<210> SEQ ID NO 321
<211> LENGTH: 54
<212> TYPE: DNA
<213> ORGANISM: Homo sapiens

<400> SEQUENCE: 321
aggcgaggag ctgtccgcct tgcacgtttc caatcgcatt acgtgaacaa atag 54

<210> SEQ ID NO 322
<211> LENGTH: 52
<212> TYPE: DNA
<213> ORGANISM: Homo sapiens

<400> SEQUENCE: 322
ttgtgaatat cagtggcagg tttccagaac gcaggtgggg ataagagtga gt 52

<210> SEQ ID NO 323
<211> LENGTH: 48
<212> TYPE: DNA
<213> ORGANISM: Homo sapiens

<400> SEQUENCE: 323
cggtttcatg gcagcccagg gtccagcggc atccaggatg ctggtggg 48

<210> SEQ ID NO 324
<211> LENGTH: 50
<212> TYPE: DNA
<213> ORGANISM: Homo sapiens

<400> SEQUENCE: 324
agctgcacag cccaggccgc gggaggttgg ctgctctcac ctaacaggcc 50

<210> SEQ ID NO 325
<211> LENGTH: 42
<212> TYPE: DNA
<213> ORGANISM: Homo sapiens

<400> SEQUENCE: 325
acctcagatc ctccaaccgg tttcatggca gcccagggtc ca 42

<210> SEQ ID NO 326
<211> LENGTH: 49
<212> TYPE: DNA
<213> ORGANISM: Homo sapiens

<400> SEQUENCE: 326

-continued agtgcctggc tcacggtcag tgctcacgtt tgggcagctg cacttgggc 49

<210> SEQ ID NO 327
<211> LENGTH: 54
<212> TYPE: DNA
<213> ORGANISM: Homo sapiens

<400> SEQUENCE: 327
ccaggccggc tcgggtctac ctgcgccagc gctgtacctg ggcgaccttg gctt 54

<210> SEQ ID NO 328
<211> LENGTH: 48
<212> TYPE: DNA
<213> ORGANISM: Homo sapiens

<400> SEQUENCE: 328
gggctctggc ggcccatcct ggcggagact tcggctagca ggccccgc 48

<210> SEQ ID NO 329
<211> LENGTH: 48
<212> TYPE: DNA
<213> ORGANISM: Homo sapiens

<400> SEQUENCE: 329
ctggctttgt cttctgggat aagacgggga aatccagagg atgtaagc 48

<210> SEQ ID NO 330
<211> LENGTH: 48
<212> TYPE: DNA
<213> ORGANISM: Homo sapiens

<400> SEQUENCE: 330
ggcagcttga tccccctagc ccgcttccag ccctcacctg gctttgtc 48

<210> SEQ ID NO 331
<211> LENGTH: 52
<212> TYPE: DNA
<213> ORGANISM: Homo sapiens

<400> SEQUENCE: 331
ggtgtgacgg ccggtcctac tctccggcct gttcagatca gctccttctg gg 52

<210> SEQ ID NO 332
<211> LENGTH: 47
<212> TYPE: DNA
<213> ORGANISM: Homo sapiens

<400> SEQUENCE: 332
tcctggggac ccttgaccct ccgacacaaa caagcgctcc aggagtc 47

<210> SEQ ID NO 333
<211> LENGTH: 52
<212> TYPE: DNA
<213> ORGANISM: Homo sapiens

<400> SEQUENCE: 333
cccttagctt acggagaccc tggggcgagg gaaataggag agaacagcag tc 52

<210> SEQ ID NO 334
<211> LENGTH: 48
<212> TYPE: DNA
<213> ORGANISM: Homo sapiens

<400> SEQUENCE: 334
tgttaatggg tgagagggat tttgcgctct ccggggagaa agccccac 48

<210> SEQ ID NO 335
<211> LENGTH: 48
<212> TYPE: DNA
<213> ORGANISM: Homo sapiens

<400> SEQUENCE: 335
ggccctccag ggtcgcggcc tcttcgggca gcccaagtgg aggaactt 48

<210> SEQ ID NO 336
<211> LENGTH: 47
<212> TYPE: DNA
<213> ORGANISM: Homo sapiens

<400> SEQUENCE: 336
gggctcaggg ccctccaggg tcgcggcctc ttcgggcagc ccaagtg 47

<210> SEQ ID NO 337
<211> LENGTH: 49
<212> TYPE: DNA
<213> ORGANISM: Homo sapiens

<400> SEQUENCE: 337
ccagctgggc gaccaggaca gggacggagg ctgctgagcc cagttagag 49

<210> SEQ ID NO 338
<211> LENGTH: 50
<212> TYPE: DNA
<213> ORGANISM: Homo sapiens

<400> SEQUENCE: 338
gagaccttgg ctggcgcgag gccacgccca ccagacatgc agttccagct 50

<210> SEQ ID NO 339
<211> LENGTH: 50
<212> TYPE: DNA
<213> ORGANISM: Homo sapiens

<400> SEQUENCE: 339
gggcgactag gacagggaca gaacccgttg aacccaggag tgagatccgg 50

<210> SEQ ID NO 340
<211> LENGTH: 48
<212> TYPE: DNA
<213> ORGANISM: Homo sapiens

<400> SEQUENCE: 340
ggggggcctc tgcccggggg ccgggctctc tggggccgcc gtcgcgcc 48

<210> SEQ ID NO 341
<211> LENGTH: 48
<212> TYPE: DNA
<213> ORGANISM: Homo sapiens

<400> SEQUENCE: 341
ggggtacggg ctgcttcacc cccgcgtgga cctccccctc agctgggg 48

<210> SEQ ID NO 342
<211> LENGTH: 49
<212> TYPE: DNA
<213> ORGANISM: Homo sapiens

<400> SEQUENCE: 342

-continued ctgggagcca gagcgccagg cagcgtcgca ggagcaggtt ctgggctgg 49

<210> SEQ ID NO 343
<211> LENGTH: 53
<212> TYPE: DNA
<213> ORGANISM: Homo sapiens

<400> SEQUENCE: 343
tgaaacaggc acaccaggga attggagcgg aggagggtaa ctcaaactca gag 53

<210> SEQ ID NO 344
<211> LENGTH: 49
<212> TYPE: DNA
<213> ORGANISM: Homo sapiens

<400> SEQUENCE: 344
ggcccctctg gttatctctt tgccgtgcca acacagtctc tgcgcccac 49

<210> SEQ ID NO 345
<211> LENGTH: 49
<212> TYPE: DNA
<213> ORGANISM: Homo sapiens

<400> SEQUENCE: 345
gcagcctgtc caagtcacaa agcggggcct cgggccttga cagttcgcg 49

<210> SEQ ID NO 346
<211> LENGTH: 48
<212> TYPE: DNA
<213> ORGANISM: Homo sapiens

<400> SEQUENCE: 346
aaggggatga gtgcagggaa ccccgacccc acccgggaga cctgcaag 48

<210> SEQ ID NO 347
<211> LENGTH: 39
<212> TYPE: DNA
<213> ORGANISM: Homo sapiens

<400> SEQUENCE: 347
gcagacactc ccctcccgcc cccactgaac ccttgaccc 39

<210> SEQ ID NO 348
<211> LENGTH: 44
<212> TYPE: DNA
<213> ORGANISM: Homo sapiens

<400> SEQUENCE: 348
cgaaacctca gtctgggagc cacggagggc tctcccctct cccc 44

<210> SEQ ID NO 349
<211> LENGTH: 45
<212> TYPE: DNA
<213> ORGANISM: Homo sapiens

<400> SEQUENCE: 349
gcccctcccc agatgatcga ggggtccagg ctccttacct ctagt 45

<210> SEQ ID NO 350
<211> LENGTH: 56
<212> TYPE: DNA
<213> ORGANISM: Homo sapiens

<400> SEQUENCE: 350
catattatat cctgccattt gatgcccggt gaacattcta tacctgcttc ccagaa 56

<210> SEQ ID NO 351
<211> LENGTH: 54
<212> TYPE: DNA
<213> ORGANISM: Homo sapiens

<400> SEQUENCE: 351
gaaaagtgga atcagctggc attgcccagc gtgatttgtg aggctgagcc ccaa 54

<210> SEQ ID NO 352
<211> LENGTH: 49
<212> TYPE: DNA
<213> ORGANISM: Homo sapiens

<400> SEQUENCE: 352
acgagggagc gttaggaagg aatccgtctt gtaaagccat tggtcctgg 49

<210> SEQ ID NO 353
<211> LENGTH: 51
<212> TYPE: DNA
<213> ORGANISM: Homo sapiens

<400> SEQUENCE: 353
aagcaaatgg gatgccacct ccgcggggct cgctcctcgc gaggtgctca c 51

<210> SEQ ID NO 354
<211> LENGTH: 53
<212> TYPE: DNA
<213> ORGANISM: Homo sapiens

<400> SEQUENCE: 354
ggttcgggga accgcggagg tttcggggtt ctagaaatcc gaggttctaa gcc 53

<210> SEQ ID NO 355
<211> LENGTH: 50
<212> TYPE: DNA
<213> ORGANISM: Homo sapiens

<400> SEQUENCE: 355
ggaggtttcg gggttctaga aatccgaggt tctaagccta ggtgctccaa 50

<210> SEQ ID NO 356
<211> LENGTH: 50
<212> TYPE: DNA
<213> ORGANISM: Homo sapiens

<400> SEQUENCE: 356
gtgagagcca gcccaggttt ccggtctgta cccgctggtg caagcccaga 50

<210> SEQ ID NO 357
<211> LENGTH: 49
<212> TYPE: DNA
<213> ORGANISM: Homo sapiens

<400> SEQUENCE: 357
caccacatac acactacaca ccgggacaca cacacaaaag gcctatgca 49

<210> SEQ ID NO 358
<211> LENGTH: 48
<212> TYPE: DNA
<213> ORGANISM: Homo sapiens

<400> SEQUENCE: 358
cacacacaca aaccacatgc acgtgcatgc acgcacactc agacacac 48

<210> SEQ ID NO 359
<211> LENGTH: 41
<212> TYPE: DNA
<213> ORGANISM: Homo sapiens

<400> SEQUENCE: 359
tgagctcagg gctcaagggg gacggggctg gtgcctgttt t 41

<210> SEQ ID NO 360
<211> LENGTH: 50
<212> TYPE: DNA
<213> ORGANISM: Homo sapiens

<400> SEQUENCE: 360
ttcaccttcc ggtcctgcgt gggccgagag gattgccgta cgcatgtctg 50

<210> SEQ ID NO 361
<211> LENGTH: 49
<212> TYPE: DNA
<213> ORGANISM: Homo sapiens

<400> SEQUENCE: 361
caaactcctg ggctcaagca atccgctcac gtcaacctcc ccaaatgct 49

<210> SEQ ID NO 362
<211> LENGTH: 47
<212> TYPE: DNA
<213> ORGANISM: Homo sapiens

<400> SEQUENCE: 362
agcggtactc gaaggccggg gccgagatgc caccttccgc aggccgc 47

<210> SEQ ID NO 363
<211> LENGTH: 46
<212> TYPE: DNA
<213> ORGANISM: Homo sapiens

<400> SEQUENCE: 363
gggtgctgtg agactgggct gcgacccagg tccagcaggg agtgtg 46

<210> SEQ ID NO 364
<211> LENGTH: 49
<212> TYPE: DNA
<213> ORGANISM: Homo sapiens

<400> SEQUENCE: 364
tgagccaagg ccgcgagcag gcttctcgca tcctgtgagc tgaggttgg 49

<210> SEQ ID NO 365
<211> LENGTH: 48
<212> TYPE: DNA
<213> ORGANISM: Homo sapiens

<400> SEQUENCE: 365
gtgacatcac ggcccaggtg accgcggccc agccaatgag ccaaggcc 48

<210> SEQ ID NO 366
<211> LENGTH: 49
<212> TYPE: DNA
<213> ORGANISM: Homo sapiens

<400> SEQUENCE: 366

-continued tggtggacaa tggcagggag tcagccgcag cccaggggcg aggtggcat 49

<210> SEQ ID NO 367
<211> LENGTH: 51
<212> TYPE: DNA
<213> ORGANISM: Homo sapiens

<400> SEQUENCE: 367
cccagctcgg agtgggcaag gagcacggtt tagctcagcc ggctggcacc g 51

<210> SEQ ID NO 368
<211> LENGTH: 48
<212> TYPE: DNA
<213> ORGANISM: Homo sapiens

<400> SEQUENCE: 368
cgacgggtga ccagacggac gccgggacca gcccaagttc agggctga 48

<210> SEQ ID NO 369
<211> LENGTH: 50
<212> TYPE: DNA
<213> ORGANISM: Homo sapiens

<400> SEQUENCE: 369
ggcagggacc agggagccag gaactgcgcc gcccccgccc ctgccctggc 50

<210> SEQ ID NO 370
<211> LENGTH: 48
<212> TYPE: DNA
<213> ORGANISM: Homo sapiens

<400> SEQUENCE: 370
ggcgaggacc gggtataaga agcctcgtgg ccttgcccgg gcagccgc 48

<210> SEQ ID NO 371
<211> LENGTH: 51
<212> TYPE: DNA
<213> ORGANISM: Homo sapiens

<400> SEQUENCE: 371
cgcgtggggt cagaccgcaa agcgaaggtg cgggccgggg tgggcctcgc g 51

<210> SEQ ID NO 372
<211> LENGTH: 48
<212> TYPE: DNA
<213> ORGANISM: Homo sapiens

<400> SEQUENCE: 372
tggggctcat ggctgagcca ggtcgcagga cagacaagtt ggcctgga 48

<210> SEQ ID NO 373
<211> LENGTH: 51
<212> TYPE: DNA
<213> ORGANISM: Homo sapiens

<400> SEQUENCE: 373
ttacagacct ggagttcctc tttcgcaggt tctgtgctcc cctcaagggt c 51

<210> SEQ ID NO 374
<211> LENGTH: 49
<212> TYPE: DNA
<213> ORGANISM: Homo sapiens

<400> SEQUENCE: 374

-continued agacagaaac tgcagctctc ccgtgacctt ccaggtgctg ccctgactc 49

<210> SEQ ID NO 375
<211> LENGTH: 48
<212> TYPE: DNA
<213> ORGANISM: Homo sapiens

<400> SEQUENCE: 375
ccgagagaca gggtctcgct ctgtcgccca ggcctggagt gcattggc 48

<210> SEQ ID NO 376
<211> LENGTH: 54
<212> TYPE: DNA
<213> ORGANISM: Homo sapiens

<400> SEQUENCE: 376
cgctaggatt acaggcgtgg gccaccgcgc ctgaccagtc ttctcttctt gcag 54

<210> SEQ ID NO 377
<211> LENGTH: 45
<212> TYPE: DNA
<213> ORGANISM: Homo sapiens

<400> SEQUENCE: 377
gctcagaccc tctggcctca agcgatcctc cagcctgggc ctccc 45

<210> SEQ ID NO 378
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 378
gccctcacac ttctacaccg 20

<210> SEQ ID NO 379
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 379
ccgactttat cacacaccta cg 22

<210> SEQ ID NO 380
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 380
cgacttccaa acaataataa acg 23

<210> SEQ ID NO 381
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 381
ccctaataaa tcaaaacatc taccg 25

<210> SEQ ID NO 382
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 382
actttcaact acccctcacc g 21

<210> SEQ ID NO 383
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 383
gtccaacccc taactctctc g 21

<210> SEQ ID NO 384
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 384
acccgaatct ctcctaaccg 20

<210> SEQ ID NO 385
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 385
actctatacc cgacgcctac g 21

<210> SEQ ID NO 386
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 386
ctaacgccga acctacttcg 20

<210> SEQ ID NO 387
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 387
cgccaaatat cttttcttct tcg 23

<210> SEQ ID NO 388
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 388
tatcccgacg taacttcctc g 21

<210> SEQ ID NO 389
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 389
ccgacctaac aaaacaactc g 21

<210> SEQ ID NO 390
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 390
aaccttctta ccttcaaacc tcg 23

<210> SEQ ID NO 391
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 391
aaatactccc attctccacc g 21

<210> SEQ ID NO 392
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 392
actaccactc cccaaaaaac g 21

<210> SEQ ID NO 393
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 393
cgacgaaaat accccaacg 19

<210> SEQ ID NO 394
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 394
gcgctcaacc aattaaacg 19

<210> SEQ ID NO 395
<211> LENGTH: 21
<212> TYPE: DNA

<213> ORGANISM: Artificial Sequence
<220> FEATURE:
<223> OTHER INFORMATION: Probe sequence (ASO1)

<400> SEQUENCE: 395
aattcccaac gtaacaacac g 21

<210> SEQ ID NO 396
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 396
actcacccct cctttctacc g 21

<210> SEQ ID NO 397
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 397
gcgtccgaat tcctaaacg 19

<210> SEQ ID NO 398
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 398
aacccgcgaa atttaaaacg 20

<210> SEQ ID NO 399
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 399
caatacaacc aacattccta acg 23

<210> SEQ ID NO 400
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 400
caactcctaa tccccaataa acg 23

<210> SEQ ID NO 401
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 401
catctttaaa caaacttccc cg 22

-continued

<210> SEQ ID NO 402
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 402
aaacaaacaa cctccctctc g 21

<210> SEQ ID NO 403
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 403
ctttaatttc tcccaaaccc g 21

<210> SEQ ID NO 404
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 404
aaaaatctct actaactccc ccg 23

<210> SEQ ID NO 405
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 405
aacaacacct ctcacgcata cg 22

<210> SEQ ID NO 406
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 406
caaaacaacg aaacaatacc cg 22

<210> SEQ ID NO 407
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 407
cgaaaaccta accgctactc g 21

<210> SEQ ID NO 408
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 408
ccccttccct caactaaacg 20

<210> SEQ ID NO 409
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 409
ctcctactcc ttctcctaat ccg 23

<210> SEQ ID NO 410
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 410
taaaacaact tctcccgaaa cg 22

<210> SEQ ID NO 411
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 411
tatctacgac accaaatcga cg 22

<210> SEQ ID NO 412
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 412
ccatttcctt tacttcctcc g 21

<210> SEQ ID NO 413
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 413
cgccgcctac aaaaaacg 18

<210> SEQ ID NO 414
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 414
cacgaaaacc aaaaaactac cg 22

<210> SEQ ID NO 415
<211> LENGTH: 21
<212> TYPE: DNA

<213> ORGANISM: Artificial Sequence
<220> FEATURE:
<223> OTHER INFORMATION: Probe sequence (ASO1)

<400> SEQUENCE: 415
aataaccaat ccaaaacccc g 21

<210> SEQ ID NO 416
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 416
caaataaaat tcttcctctt ccg 23

<210> SEQ ID NO 417
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 417
ctcgaatcaa taacactact caacg 25

<210> SEQ ID NO 418
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 418
aaatattccc cttacaaaaa ccg 23

<210> SEQ ID NO 419
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 419
caacctacta ttatatcgcc aacg 24

<210> SEQ ID NO 420
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 420
tacgtaaata cgcgaacccg 20

<210> SEQ ID NO 421
<211> LENGTH: 17
<212> TYPE: DNA
<213> ORGANISM: Artificial Sequence
<220> FEATURE:
<223> OTHER INFORMATION: Probe sequence (ASO1)

<400> SEQUENCE: 421
caaacctaca tcccgcg 17

<210> SEQ ID NO 422
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 422
cgaaaaacct aaaaacgaaa cg 22

<210> SEQ ID NO 423
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 423
cgtacgcttc ctaaataaaa ccg 23

<210> SEQ ID NO 424
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 424
tctttctcta ataacccaca ccg 23

<210> SEQ ID NO 425
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 425
ccaacctaac tctccttccg 20

<210> SEQ ID NO 426
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 426
tcttaaatct taacaatccc cg 22

<210> SEQ ID NO 427
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 427
cctaaatacc tcctacgcaa acg 23

<210> SEQ ID NO 428
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 428
atcaatcacg taaaacgttc cg 22

<210> SEQ ID NO 429
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 429
acaccaacct ctaacgatac cg 22

<210> SEQ ID NO 430
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 430
ctcaaaaccg taattttcaa acg 23

<210> SEQ ID NO 431
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 431
aaaactaacc tctcctaccc tcg 23

<210> SEQ ID NO 432
<211> LENGTH: 26
<212> TYPE: DNA
<213> ORGANISM: Artificial Sequence
<220> FEATURE:
<223> OTHER INFORMATION: Probe sequence (ASO1)

<400> SEQUENCE: 432
cctaaaacaa ataacacaat accacg 26

<210> SEQ ID NO 433
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 433
ataaaaacga aacccgactc g 21

<210> SEQ ID NO 434
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 434
caaatcaata acgtcacatc cg 22

<210> SEQ ID NO 435
<211> LENGTH: 21
<212> TYPE: DNA

-continued

<213> ORGANISM: Artificial Sequence
<220> FEATURE:
<223> OTHER INFORMATION: Probe sequence (ASO1)

<400> SEQUENCE: 435
ctcaacccta atacccatcc g 21

<210> SEQ ID NO 436
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 436
ccactccaat actcactccc g 21

<210> SEQ ID NO 437
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 437
cgaacaaaac aaacaaaatc cg 22

<210> SEQ ID NO 438
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 438
cttaactaac gcgaaaccac g 21

<210> SEQ ID NO 439
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 439
gaatctcact cctaaattca acg 23

<210> SEQ ID NO 440
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 440
gcgaacctac aaaacctaac g 21

<210> SEQ ID NO 441
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 441
actcgataat aataaacacg ccg 23

<210> SEQ ID NO 442
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 442
ccaataaaac cgacttaacc cg 22

<210> SEQ ID NO 443
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 443
cttccttaaa ctctctccac cg 22

<210> SEQ ID NO 444
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 444
ataacaacca tcctacctcc cg 22

<210> SEQ ID NO 445
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 445
gaccgaccgt aaaaataaaa cg 22

<210> SEQ ID NO 446
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 446
cctctcccct accctataaa acg 23

<210> SEQ ID NO 447
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 447
aactacgcga cgactccg 18

<210> SEQ ID NO 448
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 448
gaaaaacacc ttccataaaa acg 23

<210> SEQ ID NO 449
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 449
gcaataccat aaacgtcacc g 21

<210> SEQ ID NO 450
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 450
acgaattaca caatccaatt cg 22

<210> SEQ ID NO 451
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 451
aattaataac caaccaaaaa ctcg 24

<210> SEQ ID NO 452
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 452
tctctttccc tttctcttcc g 21

<210> SEQ ID NO 453
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 453
aataaatttc acctctcaat ccg 23

<210> SEQ ID NO 454
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 454
aaaatccttt acccctaaat tacg 24

<210> SEQ ID NO 455
<211> LENGTH: 20
<212> TYPE: DNA

<213> ORGANISM: Artificial Sequence
<220> FEATURE:
<223> OTHER INFORMATION: Probe sequence (ASO1)

<400> SEQUENCE: 455
gcaccaacct aaactcaacg 20

<210> SEQ ID NO 456
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 456
cccaactaaa actaaaaccc cg 22

<210> SEQ ID NO 457
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 457
gcctcctaat aaaaaccccg 20

<210> SEQ ID NO 458
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 458
tacctctctc caaatctctc acg 23

<210> SEQ ID NO 459
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 459
tacgtatctc tcaacctctt tcg 23

<210> SEQ ID NO 460
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 460
aatatcaaaa cctctacgac ccg 23

<210> SEQ ID NO 461
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 461
gaacccaata aaatcaaaac cg 22

<210> SEQ ID NO 462
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 462
cctcaaccaa tcaacgatac g 21

<210> SEQ ID NO 463
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 463
ttaaaaaccg tctaatcgac cg 22

<210> SEQ ID NO 464
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 464
tccgttctat accacacccg 20

<210> SEQ ID NO 465
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 465
tacttcattc tctacacaac ccg 23

<210> SEQ ID NO 466
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 466
cctcctaatc ctacgcgacg 20

<210> SEQ ID NO 467
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 467
aacgctcgaa acgaactacg 20

<210> SEQ ID NO 468
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 468
ccaactccga actcataaac g 21

<210> SEQ ID NO 469
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 469
actcctctac acctaccgcc g 21

<210> SEQ ID NO 470
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 470
accgatacga tccatatccc g 21

<210> SEQ ID NO 471
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 471
aaaccaaaac ttacaaacca acg 23

<210> SEQ ID NO 472
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 472
tttatcccca attaataatt ccg 23

<210> SEQ ID NO 473
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 473
tttataactc cgtctccgcg 20

<210> SEQ ID NO 474
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 474
ctaccctata cgcctaaccc g 21

<210> SEQ ID NO 475
<211> LENGTH: 18
<212> TYPE: DNA

<213> ORGANISM: Artificial Sequence
<220> FEATURE:
<223> OTHER INFORMATION: Probe sequence (ASO1)

<400> SEQUENCE: 475
acgtaccgac gtccaacg 18

<210> SEQ ID NO 476
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 476
cactcgaaca cgtaacaaat cg 22

<210> SEQ ID NO 477
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 477
ctttcctaat taacgccaaa cg 22

<210> SEQ ID NO 478
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 478
aaccgaacca aaactaaatc cg 22

<210> SEQ ID NO 479
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 479
aataaccccc aaaactaaac tcg 23

<210> SEQ ID NO 480
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 480
caaaaacaaa tccaaatata ccg 23

<210> SEQ ID NO 481
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 481
caaccctaaa catctaaaca ccg 23

<210> SEQ ID NO 482
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 482
tcattccact ccaacccg 18

<210> SEQ ID NO 483
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 483
ctaaaaaatc tccctcttat ctcg 24

<210> SEQ ID NO 484
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 484
aacccttcca ccctaccg 18

<210> SEQ ID NO 485
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 485
cacaaatcct aaaataccaa aacg 24

<210> SEQ ID NO 486
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 486
aactacaata aaccaaactc gcg 23

<210> SEQ ID NO 487
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 487
gtataaaata cgccaccctc g 21

<210> SEQ ID NO 488
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 488
cccatcccct aataatcacg 20

<210> SEQ ID NO 489
<211> LENGTH: 26
<212> TYPE: DNA
<213> ORGANISM: Artificial Sequence
<220> FEATURE:
<223> OTHER INFORMATION: Probe sequence (ASO1)

<400> SEQUENCE: 489
aacaataaca aacatctctt ataccg 26

<210> SEQ ID NO 490
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 490
actataaccc aacccaacta cg 22

<210> SEQ ID NO 491
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 491
aacactaaac cataaaatct caacg 25

<210> SEQ ID NO 492
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 492
cctacaatct acgcaaatac cg 22

<210> SEQ ID NO 493
<211> LENGTH: 26
<212> TYPE: DNA
<213> ORGANISM: Artificial Sequence
<220> FEATURE:
<223> OTHER INFORMATION: Probe sequence (ASO1)

<400> SEQUENCE: 493
cctatattcg cacacaatac tattcg 26

<210> SEQ ID NO 494
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 494
accgacctaa cgactctcaa cg 22

<210> SEQ ID NO 495
<211> LENGTH: 20
<212> TYPE: DNA

<213> ORGANISM: Artificial Sequence
<220> FEATURE:
<223> OTHER INFORMATION: Probe sequence (ASO1)

<400> SEQUENCE: 495
acaccacaca cacacacacg 20

<210> SEQ ID NO 496
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 496
aaccgattat ctttataacc gcg 23

<210> SEQ ID NO 497
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 497
cacaaaaaac aaaaacgcg 19

<210> SEQ ID NO 498
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 498
cctcacccca aataaaaact cg 22

<210> SEQ ID NO 499
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 499
ctacacccaa atttccatta cg 22

<210> SEQ ID NO 500
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 500
aatcacgatc caacctctac cg 22

<210> SEQ ID NO 501
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 501
atacccaaaa acaataacca acg 23

<210> SEQ ID NO 502
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 502
gaacgacgaa acaataacct acg 23

<210> SEQ ID NO 503
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 503
tcatcaaaac atctataaat cgtcg 25

<210> SEQ ID NO 504
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 504
tccaaaacta cccaaaccta cg 22

<210> SEQ ID NO 505
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 505
gcgatcccta aacttccg 18

<210> SEQ ID NO 506
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 506
cacaacttat ccctacttac ccg 23

<210> SEQ ID NO 507
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 507
ttaacccaaa caataaccct acg 23

<210> SEQ ID NO 508
<211> LENGTH: 22
<212> TYPE: DNA
<213> ORGANISM: Artificial Sequence
<220> FEATURE:
<223> OTHER INFORMATION: Probe sequence (ASO1)

-continued

<400> SEQUENCE: 508
ttctctcaaa ccacttatcc cg 22

<210> SEQ ID NO 509
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 509
gcaaaaccaa aaactcctac cg 22

<210> SEQ ID NO 510
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 510
cgatcccttt aaatactcgt acg 23

<210> SEQ ID NO 511
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 511
cccaaaaaca ctcaaatact cg 22

<210> SEQ ID NO 512
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 512
acacaaacga acccacacg 19

<210> SEQ ID NO 513
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 513
aacaaaccca acctcttact cg 22

<210> SEQ ID NO 514
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 514
gaaccgaaat ctttataacg cg 22

<210> SEQ ID NO 515
<211> LENGTH: 22
<212> TYPE: DNA

<213> ORGANISM: Artificial Sequence
<220> FEATURE:
<223> OTHER INFORMATION: Probe sequence (ASO1)

<400> SEQUENCE: 515
caaatcacct ttacctcttc cg 22

<210> SEQ ID NO 516
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 516
ccgctaaaaa caaaactcat cg 22

<210> SEQ ID NO 517
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 517
cgataaaccc tacctccaac g 21

<210> SEQ ID NO 518
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 518
ctacatcctc gccgaacg 18

<210> SEQ ID NO 519
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 519
atactcgcta aacacaacgc g 21

<210> SEQ ID NO 520
<211> LENGTH: 26
<212> TYPE: DNA
<213> ORGANISM: Artificial Sequence
<220> FEATURE:
<223> OTHER INFORMATION: Probe sequence (ASO1)

<400> SEQUENCE: 520
gacctatacc ctttataaaa tacgcg 26

<210> SEQ ID NO 521
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 521
tcttaacgct aacctcaata acg 23

<210> SEQ ID NO 522
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 522
tacctaacca tcctcaaatt tcg 23

<210> SEQ ID NO 523
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 523
cttcctcgaa atctaacaat tcg 23

<210> SEQ ID NO 524
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 524
actccgaata aaactaccac cg 22

<210> SEQ ID NO 525
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 525
cccacccaat aatcaaataa acg 23

<210> SEQ ID NO 526
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 526
acccataatt accataattt ccg 23

<210> SEQ ID NO 527
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 527
cacacccaac ctaataccac g 21

<210> SEQ ID NO 528
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 528
aaacaataaa cgcgaactct acg 23

<210> SEQ ID NO 529
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 529
aaacccaaca taacccacg 19

<210> SEQ ID NO 530
<211> LENGTH: 17
<212> TYPE: DNA
<213> ORGANISM: Artificial Sequence
<220> FEATURE:
<223> OTHER INFORMATION: Probe sequence (ASO1)

<400> SEQUENCE: 530
aaccctatcc ttccccg 17

<210> SEQ ID NO 531
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 531
ccataaacac ccaaatatcc g 21

<210> SEQ ID NO 532
<211> LENGTH: 27
<212> TYPE: DNA
<213> ORGANISM: Artificial Sequence
<220> FEATURE:
<223> OTHER INFORMATION: Probe sequence (ASO1)

<400> SEQUENCE: 532
tcaacatatt aaaacatatt cctaacg 27

<210> SEQ ID NO 533
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 533
ccacattact taaaaactcg aacg 24

<210> SEQ ID NO 534
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 534
aatcaaataa ccacacgaca cg 22

<210> SEQ ID NO 535
<211> LENGTH: 23
<212> TYPE: DNA

<213> ORGANISM: Artificial Sequence
<220> FEATURE:
<223> OTHER INFORMATION: Probe sequence (AS01)

<400> SEQUENCE: 535
aacctaaccc tttaaatctt ccg 23

<210> SEQ ID NO 536
<211> LENGTH: 22
<212> TYPE: DNA
<213> ORGANISM: Artificial Sequence
<220> FEATURE:
<223> OTHER INFORMATION: Probe sequence (AS01)

<400> SEQUENCE: 536
ctttttctta accctacccc cg 22

<210> SEQ ID NO 537
<211> LENGTH: 23
<212> TYPE: DNA
<213> ORGANISM: Artificial Sequence
<220> FEATURE:
<223> OTHER INFORMATION: Probe sequence (AS01)

<400> SEQUENCE: 537
tacccgtaca atactaaaat ccg 23

<210> SEQ ID NO 538
<211> LENGTH: 24
<212> TYPE: DNA
<213> ORGANISM: Artificial Sequence
<220> FEATURE:
<223> OTHER INFORMATION: Probe sequence (AS01)

<400> SEQUENCE: 538
attattaatc accaacaaac aacg 24

<210> SEQ ID NO 539
<211> LENGTH: 22
<212> TYPE: DNA
<213> ORGANISM: Artificial Sequence
<220> FEATURE:
<223> OTHER INFORMATION: Probe sequence (AS01)

<400> SEQUENCE: 539
tctcccttca ttattcattc cg 22

<210> SEQ ID NO 540
<211> LENGTH: 23
<212> TYPE: DNA
<213> ORGANISM: Artificial Sequence
<220> FEATURE:
<223> OTHER INFORMATION: Probe sequence (AS01)

<400> SEQUENCE: 540
tcttcctaaa tactcataac gcg 23

<210> SEQ ID NO 541
<211> LENGTH: 21
<212> TYPE: DNA
<213> ORGANISM: Artificial Sequence
<220> FEATURE:
<223> OTHER INFORMATION: Probe sequence (AS01)

<400> SEQUENCE: 541
aacctaaccc aacaaacaac g 21

<210> SEQ ID NO 542
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 542
tctacaaatc ccgaaatctc g 21

<210> SEQ ID NO 543
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 543
cacaaaaccc aactatataa aaacg 25

<210> SEQ ID NO 544
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 544
tcactacaac ctctacctcc cg 22

<210> SEQ ID NO 545
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 545
acgtaatcac gcaacatctc g 21

<210> SEQ ID NO 546
<211> LENGTH: 26
<212> TYPE: DNA
<213> ORGANISM: Artificial Sequence
<220> FEATURE:
<223> OTHER INFORMATION: Probe sequence (ASO1)

<400> SEQUENCE: 546
tcaccatatt aaccaaacta atctcg 26

<210> SEQ ID NO 547
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 547
ttttaaccct aacctttaac ccg 23

<210> SEQ ID NO 548
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 548
cctaactttt aacctttccc cg 22

<210> SEQ ID NO 549
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 549
aaacgaaact tacttcgcaa cg 22

<210> SEQ ID NO 550
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 550
aaaccctaaa aactaaaccc cg 22

<210> SEQ ID NO 551
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 551
aataaaccct acaccttcta tctcg 25

<210> SEQ ID NO 552
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 552
aaaaaataca aaacccacta ccg 23

<210> SEQ ID NO 553
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 553
acaacctaaa aattacccat ccg 23

<210> SEQ ID NO 554
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 554
cccttcatta cgacgaacta cg 22

<210> SEQ ID NO 555
<211> LENGTH: 22
<212> TYPE: DNA

<213> ORGANISM: Artificial Sequence
<220> FEATURE:
<223> OTHER INFORMATION: Probe sequence (ASO1)

<400> SEQUENCE: 555
aacgactctc aaaccctatc cg 22

<210> SEQ ID NO 556
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 556
ctactcccac cgcattcg 18

<210> SEQ ID NO 557
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 557
caatcatatt tccaaaatcc cg 22

<210> SEQ ID NO 558
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 558
tcctaatcac cctctatctt ctacg 25

<210> SEQ ID NO 559
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 559
aaaaaatcac cctaaccaaa cg 22

<210> SEQ ID NO 560
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 560
aaataaccta atcacttcaa accg 24

<210> SEQ ID NO 561
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 561
ccccttacga cctttctaac g 21

<210> SEQ ID NO 562
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 562
cacctcaata cctcgtactc acg                                           23

<210> SEQ ID NO 563
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 563
cacataccgc tcgtaatatt cg                                            22

<210> SEQ ID NO 564
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 564
taacactcaa tcccccttaa cg                                            22

<210> SEQ ID NO 565
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 565
aaacaaattc aaacccaaca cg                                            22

<210> SEQ ID NO 566
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 566
acccgataaa acgcaacg                                                 18

<210> SEQ ID NO 567
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 567
aacgaccaaa tacgccttcg                                               20

<210> SEQ ID NO 568
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 568
cacgaaaata ctaaacctcc cg 22

<210> SEQ ID NO 569
<211> LENGTH: 21
<212> TYPE: DNA
<213> ORGANISM: Artificial Sequence
<220> FEATURE:
<223> OTHER INFORMATION: Probe sequence (AS01)

<400> SEQUENCE: 569
acgcaaataa cttcaccctc g 21

<210> SEQ ID NO 570
<211> LENGTH: 22
<212> TYPE: DNA
<213> ORGANISM: Artificial Sequence
<220> FEATURE:
<223> OTHER INFORMATION: Probe sequence (AS01)

<400> SEQUENCE: 570
ccccttataa ctaaacgaaa cg 22

<210> SEQ ID NO 571
<211> LENGTH: 18
<212> TYPE: DNA
<213> ORGANISM: Artificial Sequence
<220> FEATURE:
<223> OTHER INFORMATION: Probe sequence (AS01)

<400> SEQUENCE: 571
tcctacaaaa cccccacg 18

<210> SEQ ID NO 572
<211> LENGTH: 21
<212> TYPE: DNA
<213> ORGANISM: Artificial Sequence
<220> FEATURE:
<223> OTHER INFORMATION: Probe sequence (AS01)

<400> SEQUENCE: 572
ataaccgcct tcctatttcc g 21

<210> SEQ ID NO 573
<211> LENGTH: 21
<212> TYPE: DNA
<213> ORGANISM: Artificial Sequence
<220> FEATURE:
<223> OTHER INFORMATION: Probe sequence (AS01)

<400> SEQUENCE: 573
ccgcctaaaa cctaaaaacc g 21

<210> SEQ ID NO 574
<211> LENGTH: 22
<212> TYPE: DNA
<213> ORGANISM: Artificial Sequence
<220> FEATURE:
<223> OTHER INFORMATION: Probe sequence (AS01)

<400> SEQUENCE: 574
aaatcttaac aaacgaccga cg 22

<210> SEQ ID NO 575
<211> LENGTH: 20
<212> TYPE: DNA

<213> ORGANISM: Artificial Sequence
<220> FEATURE:
<223> OTHER INFORMATION: Probe sequence (ASO1)

<400> SEQUENCE: 575
ctctcctcaa cgctaatccg 20

<210> SEQ ID NO 576
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 576
aaaataacaa cctaaccccct acg 23

<210> SEQ ID NO 577
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 577
ccgaaaccta actccctcg 19

<210> SEQ ID NO 578
<211> LENGTH: 17
<212> TYPE: DNA
<213> ORGANISM: Artificial Sequence
<220> FEATURE:
<223> OTHER INFORMATION: Probe sequence (ASO1)

<400> SEQUENCE: 578
aatcaacgcc gacctcg 17

<210> SEQ ID NO 579
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 579
cgctcaatta cttaacaacc tcg 23

<210> SEQ ID NO 580
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 580
gactcatcgc aacctccg 18

<210> SEQ ID NO 581
<211> LENGTH: 17
<212> TYPE: DNA
<213> ORGANISM: Artificial Sequence
<220> FEATURE:
<223> OTHER INFORMATION: Probe sequence (ASO1)

<400> SEQUENCE: 581
ctctaccccc tcccccg 17

<210> SEQ ID NO 582
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 582
aacgcctaaa ttacctacaa ccg 23

<210> SEQ ID NO 583
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 583
acttcacttt ctccctctct tcg 23

<210> SEQ ID NO 584
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 584
tcaaacacat aactttaacc ccg 23

<210> SEQ ID NO 585
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 585
tccccactct tattaacttt ccg 23

<210> SEQ ID NO 586
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 586
cgccaactct ataatcgaac g 21

<210> SEQ ID NO 587
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 587
gaattctcta actcacttcc ttcg 24

<210> SEQ ID NO 588
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 588
gctaactttt tcaaaccttt ccg 23

<210> SEQ ID NO 589
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 589
aacgtataaa cgccacctct cg 22

<210> SEQ ID NO 590
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 590
cccgaatcaa ctctaacact cg 22

<210> SEQ ID NO 591
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 591
gccctaactt ccaactccg 19

<210> SEQ ID NO 592
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 592
tcattaataa aaccgaccga cg 22

<210> SEQ ID NO 593
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 593
aaacctacta actccaccca cg 22

<210> SEQ ID NO 594
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 594
aacccaacct ctatcgaaaa cg 22

<210> SEQ ID NO 595
<211> LENGTH: 26
<212> TYPE: DNA

<213> ORGANISM: Artificial Sequence
<220> FEATURE:
<223> OTHER INFORMATION: Probe sequence (ASO1)

<400> SEQUENCE: 595
tccctataac gtaaccttaa aaaacg 26

<210> SEQ ID NO 596
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 596
gaatcacgaa atcaaaaatt cg 22

<210> SEQ ID NO 597
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 597
ataactcaac tcacaacctc tcg 23

<210> SEQ ID NO 598
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 598
cttaacctac ctcgacctcc g 21

<210> SEQ ID NO 599
<211> LENGTH: 26
<212> TYPE: DNA
<213> ORGANISM: Artificial Sequence
<220> FEATURE:
<223> OTHER INFORMATION: Probe sequence (ASO1)

<400> SEQUENCE: 599
accaacctaa aaactaaaaa ataacg 26

<210> SEQ ID NO 600
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 600
aaatcttact atatctccca aaccg 25

<210> SEQ ID NO 601
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 601
caaaaatcat accattacac tccg 24

-continued

<210> SEQ ID NO 602
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 602
attaccgacg atccaccg 18

<210> SEQ ID NO 603
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 603
attaaaccaa ccttctttcc cg 22

<210> SEQ ID NO 604
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 604
catccactcc gtctctccg 19

<210> SEQ ID NO 605
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 605
atcctccctc gctaaccg 18

<210> SEQ ID NO 606
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 606
cgaacgtaat aaaaccgcg 19

<210> SEQ ID NO 607
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 607
cctaactaac acgaacattt ctcg 24

<210> SEQ ID NO 608
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 608
ccaatctcta atatccacct ctcg 24

<210> SEQ ID NO 609
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 609
caactcaaaa caaacgctcg 20

<210> SEQ ID NO 610
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 610
ttcgttaaaa tacctacccc tcg 23

<210> SEQ ID NO 611
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 611
ccttttcaat tactcacaat ccg 23

<210> SEQ ID NO 612
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 612
gctttaacca atcaacgaac g 21

<210> SEQ ID NO 613
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 613
catttctata caaaccctac ttccg 25

<210> SEQ ID NO 614
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 614
aaaattcgac ctcaatcaaa cg 22

<210> SEQ ID NO 615
<211> LENGTH: 22
<212> TYPE: DNA

<213> ORGANISM: Artificial Sequence
<220> FEATURE:
<223> OTHER INFORMATION: Probe sequence (ASO1)

<400> SEQUENCE: 615
aataaacgtt ctaaccctcg cg 22

<210> SEQ ID NO 616
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 616
tcccgctcaa tcaaactacg 20

<210> SEQ ID NO 617
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 617
cactacgata ttactccaaa tccg 24

<210> SEQ ID NO 618
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 618
acaaaaactc ccttaaaccc cg 22

<210> SEQ ID NO 619
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 619
cgaatccgac attaataaaa acg 23

<210> SEQ ID NO 620
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 620
cctaacttaa atccccctcc g 21

<210> SEQ ID NO 621
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 621
acgccctata taaaacgact acg 23

<210> SEQ ID NO 622
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 622
caaaaccaat caaaacgaac g 21

<210> SEQ ID NO 623
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 623
ccaactttaa cttcttcaaa acg 23

<210> SEQ ID NO 624
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 624
tctccgctct aaaacgataa cg 22

<210> SEQ ID NO 625
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 625
aaaaattatt ttctccacat ttcg 24

<210> SEQ ID NO 626
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 626
acatcatttt accaatttcg cg 22

<210> SEQ ID NO 627
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 627
aatcattccc gaccactcg 19

<210> SEQ ID NO 628
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 628
ccaacaccgc tataatatac cg 22

<210> SEQ ID NO 629
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 629
aaccccattt tctatcgaaa cg 22

<210> SEQ ID NO 630
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 630
aatataaacg atcacgaccc cg 22

<210> SEQ ID NO 631
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 631
tacgctttcc taaaattccc g 21

<210> SEQ ID NO 632
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 632
aacgtccctc aattaaataa ccg 23

<210> SEQ ID NO 633
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 633
cctctcttct aaaccctccc g 21

<210> SEQ ID NO 634
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 634
ccgaaaaata accgaaaaac g 21

<210> SEQ ID NO 635
<211> LENGTH: 20
<212> TYPE: DNA

<213> ORGANISM: Artificial Sequence
<220> FEATURE:
<223> OTHER INFORMATION: Probe sequence (ASO1)

<400> SEQUENCE: 635
gccgaacaaa acgaactacg 20

<210> SEQ ID NO 636
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 636
gatctcgact cactacaacc tcg 23

<210> SEQ ID NO 637
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 637
cgcgctacta cactcctaaa cg 22

<210> SEQ ID NO 638
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 638
ccgatttaaa aaccaacccg 20

<210> SEQ ID NO 639
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 639
cgatacgaaa cctacgaacc g 21

<210> SEQ ID NO 640
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 640
gcgataacat caaccgatac g 21

<210> SEQ ID NO 641
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 641
aacgcttctt caaattccta cg 22

<210> SEQ ID NO 642
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 642
caacaatcga ataaaccgat cg 22

<210> SEQ ID NO 643
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 643
tactactccc gctaattcct acg 23

<210> SEQ ID NO 644
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 644
aaaaaatcaa tcaaattttc cg 22

<210> SEQ ID NO 645
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 645
cctcctacga ctccataact acg 23

<210> SEQ ID NO 646
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 646
ctaacattac aaacctcgct tcg 23

<210> SEQ ID NO 647
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 647
cttccacatc taaactactt ccg 23

<210> SEQ ID NO 648
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 648
tactactact tctaccgctc ccg 23

<210> SEQ ID NO 649
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 649
tcaacgaccg tacccacg 18

<210> SEQ ID NO 650
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 650
acttaaacct caaacaaatc acg 23

<210> SEQ ID NO 651
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 651
ttccaacaaa tttcctaccg 20

<210> SEQ ID NO 652
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 652
acattccttt tcgtcaaaat cg 22

<210> SEQ ID NO 653
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 653
cattaccaac aacttttaaa tccg 24

<210> SEQ ID NO 654
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 654
acaaactccg cctaacaccg 20

<210> SEQ ID NO 655
<211> LENGTH: 22
<212> TYPE: DNA

-continued

<213> ORGANISM: Artificial Sequence
<220> FEATURE:
<223> OTHER INFORMATION: Probe sequence (ASO1)

<400> SEQUENCE: 655
ccaaacgcct ataccttaac cg 22

<210> SEQ ID NO 656
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 656
taaaacgacc aaaacacaaa cg 22

<210> SEQ ID NO 657
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 657
tcaaaaacta acaaaccaaa cg 22

<210> SEQ ID NO 658
<211> LENGTH: 17
<212> TYPE: DNA
<213> ORGANISM: Artificial Sequence
<220> FEATURE:
<223> OTHER INFORMATION: Probe sequence (ASO1)

<400> SEQUENCE: 658
atcccctcaa cccaacg 17

<210> SEQ ID NO 659
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 659
ccttaacgcg tatcctaatc tcg 23

<210> SEQ ID NO 660
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 660
aatccgcatt aaaccaaata cg 22

<210> SEQ ID NO 661
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 661
gaaaaccgaa acttaaatcc tcg 23

<210> SEQ ID NO 662
<211> LENGTH: 17
<212> TYPE: DNA
<213> ORGANISM: Artificial Sequence
<220> FEATURE:
<223> OTHER INFORMATION: Probe sequence (ASO1)

<400> SEQUENCE: 662
aaaacccgaa aaccccg 17

<210> SEQ ID NO 663
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 663
cctatcgacc tctaatacac tcg 23

<210> SEQ ID NO 664
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 664
caaacacaac tcgatttaaa acg 23

<210> SEQ ID NO 665
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 665
cctaaatccg tctttcgcg 19

<210> SEQ ID NO 666
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 666
cccattctat ctaccctatc tcg 23

<210> SEQ ID NO 667
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 667
taaaaaacgc ctaaacccac g 21

<210> SEQ ID NO 668
<211> LENGTH: 21
<212> TYPE: DNA
<213> ORGANISM: Artificial Sequence
<220> FEATURE:
<223> OTHER INFORMATION: Probe sequence (ASO1)

-continued

```
<400> SEQUENCE: 668

aacgaaaata acgttttccc g                                          21

<210> SEQ ID NO 669
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 669

gcaaccaaaa caaactacga cg                                         22

<210> SEQ ID NO 670
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 670

tcatcttaca atcacataac catcg                                      25

<210> SEQ ID NO 671
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 671

gctaactccg aaacaactaa acg                                        23

<210> SEQ ID NO 672
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 672

ctctacccca accacaacta cg                                         22

<210> SEQ ID NO 673
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 673

cccaacaaac ttttcctttt cg                                         22

<210> SEQ ID NO 674
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 674

gcgattaata tcctaccctc cg                                         22

<210> SEQ ID NO 675
<211> LENGTH: 19
<212> TYPE: DNA
```

<213> ORGANISM: Artificial Sequence
<220> FEATURE:
<223> OTHER INFORMATION: Probe sequence (ASO1)

<400> SEQUENCE: 675
cccgatacaa accacaacg 19

<210> SEQ ID NO 676
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 676
gaaacgctac tcctaactca cg 22

<210> SEQ ID NO 677
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 677
gtaaaccaaa aacaacgtcc cg 22

<210> SEQ ID NO 678
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 678
aacgcaaacg aaacaccg 18

<210> SEQ ID NO 679
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 679
accctataaa cctaatcgtt aacg 24

<210> SEQ ID NO 680
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 680
gtctaccctc cacatctccg 20

<210> SEQ ID NO 681
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 681
aacgctcgat aaacgataat acg 23

<210> SEQ ID NO 682
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 682
acccctaact acttcaacct cg 22

<210> SEQ ID NO 683
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 683
caaatcttaa accctaatcc cg 22

<210> SEQ ID NO 684
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 684
cccttctata taaacctccc cg 22

<210> SEQ ID NO 685
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 685
aaacaactat ccccacccg 19

<210> SEQ ID NO 686
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 686
ccttactacc acacatttaa ccg 23

<210> SEQ ID NO 687
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 687
tcaaatctta tcaaacaccc tcg 23

<210> SEQ ID NO 688
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 688
aaacccaacc tatatccaaa tcg 23

<210> SEQ ID NO 689
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 689
aatactaaaa acgcccctct cg 22

<210> SEQ ID NO 690
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 690
ctttaaccgc taacctaatc cg 22

<210> SEQ ID NO 691
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 691
cccgaaacaa ctacgctatc g 21

<210> SEQ ID NO 692
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 692
aattacccca caacctaaac cg 22

<210> SEQ ID NO 693
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 693
cgcaaatccc gcttatcg 18

<210> SEQ ID NO 694
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 694
gccaaacaaa acaaaaaccg 20

<210> SEQ ID NO 695
<211> LENGTH: 23
<212> TYPE: DNA

<213> ORGANISM: Artificial Sequence
<220> FEATURE:
<223> OTHER INFORMATION: Probe sequence (ASO1)

<400> SEQUENCE: 695
gcaacgcatt acaaacaaat acg 23

<210> SEQ ID NO 696
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 696
cactctctcg cttttataaa aaacg 25

<210> SEQ ID NO 697
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 697
attacacaaa ccgttctaac ccg 23

<210> SEQ ID NO 698
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 698
gaaaaactat ccgccttaca cg 22

<210> SEQ ID NO 699
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 699
tcactcttat ccccacctac g 21

<210> SEQ ID NO 700
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 700
ccaccaacat cctaaatacc g 21

<210> SEQ ID NO 701
<211> LENGTH: 17
<212> TYPE: DNA
<213> ORGANISM: Artificial Sequence
<220> FEATURE:
<223> OTHER INFORMATION: Probe sequence (ASO1)

<400> SEQUENCE: 701
acacaaccca aaccgcg 17

<210> SEQ ID NO 702
<211> LENGTH: 19
<212> TYPE: DNA
<213> ORGANISM: Artificial Sequence
<220> FEATURE:
<223> OTHER INFORMATION: Probe sequence (AS01)

<400> SEQUENCE: 702
acctcaaatc ctccaaccg 19

<210> SEQ ID NO 703
<211> LENGTH: 22
<212> TYPE: DNA
<213> ORGANISM: Artificial Sequence
<220> FEATURE:
<223> OTHER INFORMATION: Probe sequence (AS01)

<400> SEQUENCE: 703
cccaaataca actacccaaa cg 22

<210> SEQ ID NO 704
<211> LENGTH: 22
<212> TYPE: DNA
<213> ORGANISM: Artificial Sequence
<220> FEATURE:
<223> OTHER INFORMATION: Probe sequence (AS01)

<400> SEQUENCE: 704
aaccgactcg aatctaccta cg 22

<210> SEQ ID NO 705
<211> LENGTH: 22
<212> TYPE: DNA
<213> ORGANISM: Artificial Sequence
<220> FEATURE:
<223> OTHER INFORMATION: Probe sequence (AS01)

<400> SEQUENCE: 705
actctaacga cccatcctaa cg 22

<210> SEQ ID NO 706
<211> LENGTH: 23
<212> TYPE: DNA
<213> ORGANISM: Artificial Sequence
<220> FEATURE:
<223> OTHER INFORMATION: Probe sequence (AS01)

<400> SEQUENCE: 706
cttacatcct ctaaatttcc ccg 23

<210> SEQ ID NO 707
<211> LENGTH: 22
<212> TYPE: DNA
<213> ORGANISM: Artificial Sequence
<220> FEATURE:
<223> OTHER INFORMATION: Probe sequence (AS01)

<400> SEQUENCE: 707
acaacttaat ccccctaacc cg 22

<210> SEQ ID NO 708
<211> LENGTH: 23
<212> TYPE: DNA
<213> ORGANISM: Artificial Sequence
<220> FEATURE:
<223> OTHER INFORMATION: Probe sequence (AS01)

<400> SEQUENCE: 708
ataacgaccg atcctactct ccg 23

<210> SEQ ID NO 709
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 709
ctaaaaaccc ttaaccctcc g 21

<210> SEQ ID NO 710
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 710
actattctct cctatttccc tcg 23

<210> SEQ ID NO 711
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 711
taaaactttc tccccgaaaa acg 23

<210> SEQ ID NO 712
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 712
aattcctcca cttaaactac ccg 23

<210> SEQ ID NO 713
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 713
aactcaaaac cctccaaaat cg 22

<210> SEQ ID NO 714
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 714
ctaactaaac tcaacaacct ccg 23

<210> SEQ ID NO 715
<211> LENGTH: 21
<212> TYPE: DNA

<213> ORGANISM: Artificial Sequence
<220> FEATURE:
<223> OTHER INFORMATION: Probe sequence (ASO1)

<400> SEQUENCE: 715
cttaactaac gcgaaaccac g 21

<210> SEQ ID NO 716
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 716
gaatctcact cctaaattca acg 23

<210> SEQ ID NO 717
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 717
aaaacctcta cccgaaaacc g 21

<210> SEQ ID NO 718
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 718
aatacgaact acttcacccc cg 22

<210> SEQ ID NO 719
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 719
caacccaaaa cctactccta cg 22

<210> SEQ ID NO 720
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 720
aaatttaaat taccctcctc cg 22

<210> SEQ ID NO 721
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 721
cccctctaat tatctcttta ccg 23

<210> SEQ ID NO 722
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 722
caacctatcc aaatcacaaa acg 23

<210> SEQ ID NO 723
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 723
caaatctccc gaataaaatc g 21

<210> SEQ ID NO 724
<211> LENGTH: 17
<212> TYPE: DNA
<213> ORGANISM: Artificial Sequence
<220> FEATURE:
<223> OTHER INFORMATION: Probe sequence (ASO1)

<400> SEQUENCE: 724
caaacactcc cctcccg 17

<210> SEQ ID NO 725
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 725
aaacctcaat ctaaaaacca cg 22

<210> SEQ ID NO 726
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 726
cccctcccca aataatcg 18

<210> SEQ ID NO 727
<211> LENGTH: 28
<212> TYPE: DNA
<213> ORGANISM: Artificial Sequence
<220> FEATURE:
<223> OTHER INFORMATION: Probe sequence (ASO1)

<400> SEQUENCE: 727
catattatat cctaccattt aatacccg 28

<210> SEQ ID NO 728
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 728
aaactcaacc tcacaaatca cg 22

<210> SEQ ID NO 729
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 729
ccaaaaccaa taactttaca aaacg 25

<210> SEQ ID NO 730
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 730
aaataaaata ccacctccgc g 21

<210> SEQ ID NO 731
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 731
aaaaaccgcg aaaatttcg 19

<210> SEQ ID NO 732
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 732
aaaacaccta aacttaaaac ctcg 24

<210> SEQ ID NO 733
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 733
aaaccaaccc aaatttccg 19

<210> SEQ ID NO 734
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 734
accacataca cactacacac cg 22

<210> SEQ ID NO 735
<211> LENGTH: 22
<212> TYPE: DNA

<213> ORGANISM: Artificial Sequence
<220> FEATURE:
<223> OTHER INFORMATION: Probe sequence (ASO1)

<400> SEQUENCE: 735
acacacacaa accacataca cg 22

<210> SEQ ID NO 736
<211> LENGTH: 18
<212> TYPE: DNA
<213> ORGANISM: Artificial Sequence
<220> FEATURE:
<223> OTHER INFORMATION: Probe sequence (ASO1)

<400> SEQUENCE: 736
aaacaaacac caaccccg 18

<210> SEQ ID NO 737
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 737
acatacgtac gacaatcctc tcg 23

<210> SEQ ID NO 738
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 738
aactcctaaa ctcaaacaat ccg 23

<210> SEQ ID NO 739
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 739
gatactcgaa aaccgaaacc g 21

<210> SEQ ID NO 740
<211> LENGTH: 25
<212> TYPE: DNA
<213> ORGANISM: Artificial Sequence
<220> FEATURE:
<223> OTHER INFORMATION: Probe sequence (ASO1)

<400> SEQUENCE: 740
cacactccct actaaaccta aatcg 25

<210> SEQ ID NO 741
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 741
ccaacctcaa ctcacaaaat acg 23

<210> SEQ ID NO 742
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 742
taacatcacg acccaaataa ccg 23

<210> SEQ ID NO 743
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 743
acctcgcccc taaactacg 19

<210> SEQ ID NO 744
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 744
taccaaccga ctaaactaaa ccg 23

<210> SEQ ID NO 745
<211> LENGTH: 19
<212> TYPE: DNA
<213> ORGANISM: Artificial Sequence
<220> FEATURE:
<223> OTHER INFORMATION: Probe sequence (ASO1)

<400> SEQUENCE: 745
aataaccaaa cgaacgccg 19

<210> SEQ ID NO 746
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 746
caaaacaaaa acgaaaacga cg 22

<210> SEQ ID NO 747
<211> LENGTH: 20
<212> TYPE: DNA
<213> ORGANISM: Artificial Sequence
<220> FEATURE:
<223> OTHER INFORMATION: Probe sequence (ASO1)

<400> SEQUENCE: 747
actacccgaa caaaaccacg 20

<210> SEQ ID NO 748
<211> LENGTH: 21
<212> TYPE: DNA
<213> ORGANISM: Artificial Sequence
<220> FEATURE:
<223> OTHER INFORMATION: Probe sequence (ASO1)

<400> SEQUENCE: 748
gtaaaatcaa accgcaaaac g 21

<210> SEQ ID NO 749
<211> LENGTH: 24
<212> TYPE: DNA
<213> ORGANISM: Artificial Sequence
<220> FEATURE:
<223> OTHER INFORMATION: Probe sequence (ASO1)

<400> SEQUENCE: 749
ccaaaccaac ttatctatcc tacg 24

<210> SEQ ID NO 750
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 750
caaacctaaa attcctcttt cg 22

<210> SEQ ID NO 751
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 751
aacaaaaact acaactctcc cg 22

<210> SEQ ID NO 752
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 752
ccaatacact ccaaacctaa acg 23

<210> SEQ ID NO 753
<211> LENGTH: 23
<212> TYPE: DNA
<213> ORGANISM: Artificial Sequence
<220> FEATURE:
<223> OTHER INFORMATION: Probe sequence (ASO1)

<400> SEQUENCE: 753
aaaattacaa acgtaaacca ccg 23

<210> SEQ ID NO 754
<211> LENGTH: 22
<212> TYPE: DNA
<213> ORGANISM: Artificial Sequence
<220> FEATURE:
<223> OTHER INFORMATION: Probe sequence (ASO1)

<400> SEQUENCE: 754
tcaaaccctc taacctcaaa cg 22

<210> SEQ ID NO 755
<211> LENGTH: 23
<212> TYPE: DNA

<213> ORGANISM: Artificial Sequence
<220> FEATURE:
<223> OTHER INFORMATION: Probe sequence (LSO1)

<400> SEQUENCE: 755
gtccccaaaa ctaaaaaaca tcc 23

<210> SEQ ID NO 756
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 756
cgccaaacta aaatcgaacc 20

<210> SEQ ID NO 757
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 757
atccctacgc gaaaacgtaa c 21

<210> SEQ ID NO 758
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 758
ctcccctcaa ctttcttcaa att 23

<210> SEQ ID NO 759
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 759
cctcccacac cactcaaaaa tt 22

<210> SEQ ID NO 760
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 760
aactaccaat catatttcct aaacca 26

<210> SEQ ID NO 761
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 761
cgccactaac gctaaactcc t 21

-continued

<210> SEQ ID NO 762
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 762
ttcccccgaa ctccctacta t 21

<210> SEQ ID NO 763
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 763
ccctacgtaa acgacctcgc 20

<210> SEQ ID NO 764
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 764
aatctttacc cgaacgcttc c 21

<210> SEQ ID NO 765
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 765
ccctctaaaa acgtacaaac caa 23

<210> SEQ ID NO 766
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 766
aaataaataa accgcgccg 19

<210> SEQ ID NO 767
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 767
ctccaacacc aatccgaca 19

<210> SEQ ID NO 768
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 768
ttatcacaca cttatttctc acttcc 26

<210> SEQ ID NO 769
<211> LENGTH: 17
<212> TYPE: DNA
<213> ORGANISM: Artificial Sequence
<220> FEATURE:
<223> OTHER INFORMATION: Probe sequence (LSO1)

<400> SEQUENCE: 769
cctcctcgtc tcctccc 17

<210> SEQ ID NO 770
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 770
gtaaacgaaa caacgacccg 20

<210> SEQ ID NO 771
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 771
gactattccg taaacgccac c 21

<210> SEQ ID NO 772
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 772
aactaaacta caactcaccc aacc 24

<210> SEQ ID NO 773
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 773
tccttccttt ccttacccta cttt 24

<210> SEQ ID NO 774
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 774
aaaccgaacc tcgcttaaac c 21

<210> SEQ ID NO 775
<211> LENGTH: 20
<212> TYPE: DNA

<213> ORGANISM: Artificial Sequence
<220> FEATURE:
<223> OTHER INFORMATION: Probe sequence (LSO1)

<400> SEQUENCE: 775
atccaaacaa accgcaaact 20

<210> SEQ ID NO 776
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 776
ctccctaacc caatctctaa cg 22

<210> SEQ ID NO 777
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 777
aacaaaaaat ttctattcct tcaacc 26

<210> SEQ ID NO 778
<211> LENGTH: 17
<212> TYPE: DNA
<213> ORGANISM: Artificial Sequence
<220> FEATURE:
<223> OTHER INFORMATION: Probe sequence (LSO1)

<400> SEQUENCE: 778
cctcgtaacg cgtcgac 17

<210> SEQ ID NO 779
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 779
cctaacccaa ctctaaaaca aacaa 25

<210> SEQ ID NO 780
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 780
caacccgaaa ctattacaaa ccg 23

<210> SEQ ID NO 781
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 781
ctcgatccac aaactctcca ct 22

-continued

<210> SEQ ID NO 782
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 782
attataatct tcccacctcc cac                                              23

<210> SEQ ID NO 783
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 783
caaacgaaac gcaacacc                                                    18

<210> SEQ ID NO 784
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 784
aaaaaaccta cgaactcaaa ccc                                              23

<210> SEQ ID NO 785
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 785
aaacatcaac cctacgacct aaa                                              23

<210> SEQ ID NO 786
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 786
acgaaccgac ctaaactccc                                                  20

<210> SEQ ID NO 787
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 787
aaaacgctaa ttcctcgact cc                                               22

<210> SEQ ID NO 788
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 788
aaatcctaac tctacaccct cctc 24

<210> SEQ ID NO 789
<211> LENGTH: 28
<212> TYPE: DNA
<213> ORGANISM: Artificial Sequence
<220> FEATURE:
<223> OTHER INFORMATION: Probe sequence (LSO1)

<400> SEQUENCE: 789
caaacgaatt acttaccctt acttatca 28

<210> SEQ ID NO 790
<211> LENGTH: 28
<212> TYPE: DNA
<213> ORGANISM: Artificial Sequence
<220> FEATURE:
<223> OTHER INFORMATION: Probe sequence (LSO1)

<400> SEQUENCE: 790
aacaaatctt acacctcttc tacatctc 28

<210> SEQ ID NO 791
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 791
taaacaacaa cctctcaaaa tacg 24

<210> SEQ ID NO 792
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 792
aaaacgctta actctttcta tccc 24

<210> SEQ ID NO 793
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 793
ctctttcctt ttacgtcatc cg 22

<210> SEQ ID NO 794
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 794
acccatctca actttcatca tca 23

<210> SEQ ID NO 795
<211> LENGTH: 24
<212> TYPE: DNA

<213> ORGANISM: Artificial Sequence
<220> FEATURE:
<223> OTHER INFORMATION: Probe sequence (LSO1)

<400> SEQUENCE: 795
ccctacattt ccctctacac taaa 24

<210> SEQ ID NO 796
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 796
atatcacctc atccgactcc ctt 23

<210> SEQ ID NO 797
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 797
actcctaaat tccatccccg 20

<210> SEQ ID NO 798
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 798
aacatcccta ccctctctat acaa 24

<210> SEQ ID NO 799
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 799
ccttctctaa atccgcgaaa t 21

<210> SEQ ID NO 800
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 800
aaacgacttc aaaaccccct ac 22

<210> SEQ ID NO 801
<211> LENGTH: 17
<212> TYPE: DNA
<213> ORGANISM: Artificial Sequence
<220> FEATURE:
<223> OTHER INFORMATION: Probe sequence (LSO1)

<400> SEQUENCE: 801
ccgcaaaacc acaacgc 17

<210> SEQ ID NO 802
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 802
tctaaatccc cctcctctaa tcg 23

<210> SEQ ID NO 803
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 803
acactactcc ccgctttatt tatt 24

<210> SEQ ID NO 804
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 804
aattatcctc ctacgccgac ct 22

<210> SEQ ID NO 805
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 805
taaccaatca ccctcttcct ttc 23

<210> SEQ ID NO 806
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 806
ataattttcc tccttcttcc ctc 23

<210> SEQ ID NO 807
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 807
ttttcgcctt acgatcacc 19

<210> SEQ ID NO 808
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 808
ccacgctacg ccaacactta t 21

<210> SEQ ID NO 809
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 809
aacccgatct atccctataa cga 23

<210> SEQ ID NO 810
<211> LENGTH: 27
<212> TYPE: DNA
<213> ORGANISM: Artificial Sequence
<220> FEATURE:
<223> OTHER INFORMATION: Probe sequence (LSO1)

<400> SEQUENCE: 810
aaactattac atttactctc cacctcc 27

<210> SEQ ID NO 811
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 811
acacccgaat atttcctaac gaa 23

<210> SEQ ID NO 812
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 812
ccaaccattc caccctca 18

<210> SEQ ID NO 813
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 813
aacccaaccc cctcttcatt at 22

<210> SEQ ID NO 814
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 814
aacgataacc gcacaatcc 19

<210> SEQ ID NO 815
<211> LENGTH: 23
<212> TYPE: DNA

<213> ORGANISM: Artificial Sequence
<220> FEATURE:
<223> OTHER INFORMATION: Probe sequence (LSO1)

<400> SEQUENCE: 815
ccaccaaaca tacaattcca act 23

<210> SEQ ID NO 816
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 816
attctatccc tatcctaatc gcc 23

<210> SEQ ID NO 817
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 817
actcaaactt ctctccgaaa cg 22

<210> SEQ ID NO 818
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 818
ccactttaca aaacgtcacc g 21

<210> SEQ ID NO 819
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 819
gaacaaacga aaattcccga 20

<210> SEQ ID NO 820
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 820
tacccactaa aaactacaac ttccc 25

<210> SEQ ID NO 821
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 821
taaaacgacg tctcctcccc 20

-continued

<210> SEQ ID NO 822
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 822
taataacatc accccgaaat cg 22

<210> SEQ ID NO 823
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 823
atatacaaac tccgaaatcg caa 23

<210> SEQ ID NO 824
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 824
aaactccaaa acgcccctct ac 22

<210> SEQ ID NO 825
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 825
aaataaattc ctcacacctc acaac 25

<210> SEQ ID NO 826
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 826
cactacccaa tcgtcgtatc aaa 23

<210> SEQ ID NO 827
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 827
tattattaaa acctcaattt cccaaa 26

<210> SEQ ID NO 828
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 828 caccccttc cactactcct t 21

<210> SEQ ID NO 829
<211> LENGTH: 27
<212> TYPE: DNA
<213> ORGANISM: Artificial Sequence
<220> FEATURE:
<223> OTHER INFORMATION: Probe sequence (LSO1)

<400> SEQUENCE: 829
ttcatcctat taaaaatacc acaaatt 27

<210> SEQ ID NO 830
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 830
cctaatttta aaccctcgcc c 21

<210> SEQ ID NO 831
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 831
caccctcata cttccaaaac cta 23

<210> SEQ ID NO 832
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 832
cttcctaatc ctaccctacc cta 23

<210> SEQ ID NO 833
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 833
cccgctacga aatctctcct 20

<210> SEQ ID NO 834
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 834
cttaaaacac aaaccgctcc c 21

<210> SEQ ID NO 835
<211> LENGTH: 24
<212> TYPE: DNA

<213> ORGANISM: Artificial Sequence
<220> FEATURE:
<223> OTHER INFORMATION: Probe sequence (LSO1)

<400> SEQUENCE: 835
cctaatttct acaaccgctc tacc 24

<210> SEQ ID NO 836
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 836
tccctctttc acgatctcac tc 22

<210> SEQ ID NO 837
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 837
ttatctcgaa ctcgcccact t 21

<210> SEQ ID NO 838
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 838
acaaatccca taacccacct aaa 23

<210> SEQ ID NO 839
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 839
aaaacgatac ctccgaaact cac 23

<210> SEQ ID NO 840
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 840
gccttctcta aaccaacaac aca 23

<210> SEQ ID NO 841
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 841
aactcctacg tttcccccta ac 22

<210> SEQ ID NO 842
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 842
ccgatttcct atacgtaacg tca 23

<210> SEQ ID NO 843
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 843
cgctaactac gaccgcctc 19

<210> SEQ ID NO 844
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 844
gacgaaaact ccgaaaaacg ac 22

<210> SEQ ID NO 845
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 845
gatcaacaaa acgaaccaaa acg 23

<210> SEQ ID NO 846
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 846
ctaaaccgat tccgcgaac 19

<210> SEQ ID NO 847
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 847
acaaccccac cttctctacc tac 23

<210> SEQ ID NO 848
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 848
aaaatcccga aatcttacat tcc 23

<210> SEQ ID NO 849
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 849
aaattcctca attattcctc cgc 23

<210> SEQ ID NO 850
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 850
aacaactcgt ccgaataacc aa 22

<210> SEQ ID NO 851
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 851
ataacccttc gaccgataca aac 23

<210> SEQ ID NO 852
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 852
aaatacgcaa actacctcaa acc 23

<210> SEQ ID NO 853
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 853
ttacacgccc gcgaactat 19

<210> SEQ ID NO 854
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 854
aatccaccaa tcaataaaca acttc 25

<210> SEQ ID NO 855
<211> LENGTH: 23
<212> TYPE: DNA

```
<213> ORGANISM: Artificial Sequence
<220> FEATURE:
<223> OTHER INFORMATION: Probe sequence (LSO1)

<400> SEQUENCE: 855

ccaaacctcc acaaatcttc ctt                                          23

<210> SEQ ID NO 856
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 856

ccaccaaaac ccaactctaa aa                                           22

<210> SEQ ID NO 857
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 857

tattcaaata cccaaaacta aaccc                                        25

<210> SEQ ID NO 858
<211> LENGTH: 28
<212> TYPE: DNA
<213> ORGANISM: Artificial Sequence
<220> FEATURE:
<223> OTHER INFORMATION: Probe sequence (LSO1)

<400> SEQUENCE: 858

cacacttaaa tctacctcta ttacctcc                                     28

<210> SEQ ID NO 859
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 859

atcctaaccc ctacaacccc                                              20

<210> SEQ ID NO 860
<211> LENGTH: 29
<212> TYPE: DNA
<213> ORGANISM: Artificial Sequence
<220> FEATURE:
<223> OTHER INFORMATION: Probe sequence (LSO1)

<400> SEQUENCE: 860

aaaataccta tccctaaata aaaatcatt                                    29

<210> SEQ ID NO 861
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 861

ccttccttct aacccgctaa a                                            21
```

<210> SEQ ID NO 862
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 862
aaacgtactt tcttaaacct taaacg 26

<210> SEQ ID NO 863
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 863
cactacactc caacccgaac 20

<210> SEQ ID NO 864
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 864
accttattac gacgtcgaca cat 23

<210> SEQ ID NO 865
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 865
attacccatt aaatcttaat tcccc 25

<210> SEQ ID NO 866
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 866
accttacacc tcaacccatt t 21

<210> SEQ ID NO 867
<211> LENGTH: 27
<212> TYPE: DNA
<213> ORGANISM: Artificial Sequence
<220> FEATURE:
<223> OTHER INFORMATION: Probe sequence (LSO1)

<400> SEQUENCE: 867
ctatatataa aacaacccca tttctca 27

<210> SEQ ID NO 868
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 868
atactcacaa cctctcacac aaaa 24

<210> SEQ ID NO 869
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 869
ctttctcact ttaacaccaa ctaccc 26

<210> SEQ ID NO 870
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 870
aaacaaaaca atcccaccct ac 22

<210> SEQ ID NO 871
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 871
attaaacgcg aactacgata acc 23

<210> SEQ ID NO 872
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 872
caaataacca acaaaaacct cca 23

<210> SEQ ID NO 873
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 873
cgcctaacac aacgcctaat ac 22

<210> SEQ ID NO 874
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 874
acaaaccaac ccttctaata tactcc 26

<210> SEQ ID NO 875
<211> LENGTH: 23
<212> TYPE: DNA

<213> ORGANISM: Artificial Sequence
<220> FEATURE:
<223> OTHER INFORMATION: Probe sequence (LSO1)

<400> SEQUENCE: 875
aacttcctac cccacccaat aaa 23

<210> SEQ ID NO 876
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 876
gactctcctc aactccttcc c 21

<210> SEQ ID NO 877
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 877
aaccccaatc tccgcaataa a 21

<210> SEQ ID NO 878
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 878
taccctatac ccgcgatatt cc 22

<210> SEQ ID NO 879
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 879
aactaaaaaa ctccgaaacc cc 22

<210> SEQ ID NO 880
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 880
ctctacaatc catttattta cccg 24

<210> SEQ ID NO 881
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 881
acccaaccac attaacgaac c 21

<210> SEQ ID NO 882
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 882
tactaacgaa ctcctcgctc caa 23

<210> SEQ ID NO 883
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 883
gaacataaaa ccgaaaacac cc 22

<210> SEQ ID NO 884
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 884
tccttactcg aatctttacc gaa 23

<210> SEQ ID NO 885
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 885
ccaatctaac cttccaaaca cat 23

<210> SEQ ID NO 886
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 886
attaaacctt ctctcgtcgc c 21

<210> SEQ ID NO 887
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 887
ataaacacaa caccctacac gc 22

<210> SEQ ID NO 888
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 888
gacacacaca atacaatcac gct 23

<210> SEQ ID NO 889
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 889
acaactcccg aaacaaaacc 20

<210> SEQ ID NO 890
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 890
ctcctcgcct tccctttata tc 22

<210> SEQ ID NO 891
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 891
taacaacgac cacgaacaca a 21

<210> SEQ ID NO 892
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 892
aactcaattt cttccaccta aaaac 25

<210> SEQ ID NO 893
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 893
ccaacttccg accgaaaact ac 22

<210> SEQ ID NO 894
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 894
ataacgctcg aatccgacta aac 23

<210> SEQ ID NO 895
<211> LENGTH: 23
<212> TYPE: DNA

<213> ORGANISM: Artificial Sequence
<220> FEATURE:
<223> OTHER INFORMATION: Probe sequence (LSO1)

<400> SEQUENCE: 895
gcgatcgaca actaacgacc taa 23

<210> SEQ ID NO 896
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 896
accttataaa aaacacaaac cgc 23

<210> SEQ ID NO 897
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 897
tatatccaac gaacatcgac ca 22

<210> SEQ ID NO 898
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 898
cctaaactac acttttcccc ct 22

<210> SEQ ID NO 899
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 899
acaattactt caaaacgtct ccaa 24

<210> SEQ ID NO 900
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 900
cctcccaaac cattcaaaaa c 21

<210> SEQ ID NO 901
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 901
gaccaaaaca atctcctccg ac 22

<210> SEQ ID NO 902
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 902
accccttaaa attccaaaaa cc                                              22

<210> SEQ ID NO 903
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 903
ccacctcctc aacttactct aacttc                                          26

<210> SEQ ID NO 904
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 904
accgcaaacg ctccataa                                                   18

<210> SEQ ID NO 905
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 905
ttcgcttaac taacgacgca ac                                              22

<210> SEQ ID NO 906
<211> LENGTH: 27
<212> TYPE: DNA
<213> ORGANISM: Artificial Sequence
<220> FEATURE:
<223> OTHER INFORMATION: Probe sequence (LSO1)

<400> SEQUENCE: 906
atacaaaata tttaaaaacc ctcacaa                                         27

<210> SEQ ID NO 907
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 907
taactcctct cattccaata cctaa                                           25

<210> SEQ ID NO 908
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 908 aatacccca caactctaaa cct 23

<210> SEQ ID NO 909
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 909
ccaaaaaacc aatcaaaacc a 21

<210> SEQ ID NO 910
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 910
acgcaaaact ccgaattcaa t 21

<210> SEQ ID NO 911
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 911
aaacgcatac gtaacgacaa ca 22

<210> SEQ ID NO 912
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 912
gatcccattt cgaaatttcc tct 23

<210> SEQ ID NO 913
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 913
attatcaaac gacgaacgtc tacc 24

<210> SEQ ID NO 914
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 914 ttcccctta caaactacca acc 23

<210> SEQ ID NO 915
<211> LENGTH: 23
<212> TYPE: DNA

<213> ORGANISM: Artificial Sequence
<220> FEATURE:
<223> OTHER INFORMATION: Probe sequence (LSO1)

<400> SEQUENCE: 915
acaaccgaaa ataaaaccaa acc 23

<210> SEQ ID NO 916
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 916
aatcccaatc ccttaattaa actt 24

<210> SEQ ID NO 917
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 917
ccccatttct cactcccatt aa 22

<210> SEQ ID NO 918
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 918
aaacccccaa cctacccc 18

<210> SEQ ID NO 919
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 919
aatacaaatc acctctccca aa 22

<210> SEQ ID NO 920
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 920
accccaccca acttcaaa 18

<210> SEQ ID NO 921
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 921
attcaaacga ttctcctacc tca 23

<210> SEQ ID NO 922
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 922
aacttaccct tccgattaac cct 23

<210> SEQ ID NO 923
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 923
actcctaact caaataatcc gcc 23

<210> SEQ ID NO 924
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 924
attaaatcca aacctccttc acc 23

<210> SEQ ID NO 925
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 925
aatactaccc cctccaaatc cc 22

<210> SEQ ID NO 926
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 926
ctacttaccg cacttccgaa cta 23

<210> SEQ ID NO 927
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 927
ccccataccc ctcaaaacct at 22

<210> SEQ ID NO 928
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 928
tttcttctcc atcgcgaaa 19

<210> SEQ ID NO 929
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 929
ttcctccaaa taaactcata aatttc 26

<210> SEQ ID NO 930
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 930
ccccgaaaac tctatccaaa a 21

<210> SEQ ID NO 931
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 931
accaaacttc actaaacgtc cg 22

<210> SEQ ID NO 932
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 932
acgtaacctc actttcctac tcc 23

<210> SEQ ID NO 933
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 933
ccctacccga actcactact tac 23

<210> SEQ ID NO 934
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 934
gatttcccct aatctcttca ttca 24

<210> SEQ ID NO 935
<211> LENGTH: 24
<212> TYPE: DNA

<213> ORGANISM: Artificial Sequence
<220> FEATURE:
<223> OTHER INFORMATION: Probe sequence (LSO1)

<400> SEQUENCE: 935
tacacttcca aaccttcaac aaac 24

<210> SEQ ID NO 936
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 936
caaacacaca catacacaca caca 24

<210> SEQ ID NO 937
<211> LENGTH: 28
<212> TYPE: DNA
<213> ORGANISM: Artificial Sequence
<220> FEATURE:
<223> OTHER INFORMATION: Probe sequence (LSO1)

<400> SEQUENCE: 937
aacattataa ttccaaccaa aaatactc 28

<210> SEQ ID NO 938
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 938
taaccctact cttataacct cccg 24

<210> SEQ ID NO 939
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 939
tcttccttca actataactt acgcc 25

<210> SEQ ID NO 940
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 940
actcaacctc gtaataacgc cta 23

<210> SEQ ID NO 941
<211> LENGTH: 28
<212> TYPE: DNA
<213> ORGANISM: Artificial Sequence
<220> FEATURE:
<223> OTHER INFORMATION: Probe sequence (LSO1)

<400> SEQUENCE: 941
caatttctca cctatacatt tcctataa 28

<210> SEQ ID NO 942
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 942
tcctccccta ctacccctcg 20

<210> SEQ ID NO 943
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 943
cccaaactaa cgcatccg 18

<210> SEQ ID NO 944
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 944
caaaacaata ctaattccaa cccc 24

<210> SEQ ID NO 945
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 945
ccgttctaaa cgaaaaccca ac 22

<210> SEQ ID NO 946
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 946
ctcaacgacc tcaaaaacta ccc 23

<210> SEQ ID NO 947
<211> LENGTH: 28
<212> TYPE: DNA
<213> ORGANISM: Artificial Sequence
<220> FEATURE:
<223> OTHER INFORMATION: Probe sequence (LSO1)

<400> SEQUENCE: 947
aaaaactcta taaaaataac aacgacct 28

<210> SEQ ID NO 948
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 948
cccgcccaac tataaaaaa 19

<210> SEQ ID NO 949
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 949
ccgacgaaca acgctacg 18

<210> SEQ ID NO 950
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 950
cactacgacc caaaacaatc c 21

<210> SEQ ID NO 951
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 951
aactcacaaa tccctttcct aac 23

<210> SEQ ID NO 952
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 952
aaaaaacaaa ctccgaacga aa 22

<210> SEQ ID NO 953
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 953
tccccaacaa tctctattcc c 21

<210> SEQ ID NO 954
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 954
cacgcccact tcctaccc 18

<210> SEQ ID NO 955
<211> LENGTH: 23
<212> TYPE: DNA

<213> ORGANISM: Artificial Sequence
<220> FEATURE:
<223> OTHER INFORMATION: Probe sequence (LSO1)

<400> SEQUENCE: 955
cttcgcaaac ctaaccaatc aat 23

<210> SEQ ID NO 956
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 956
cgctaaacca ccccaaataa aac 23

<210> SEQ ID NO 957
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 957
ctcccgaatt caaacgattc t 21

<210> SEQ ID NO 958
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 958
aatccgaaat aaattcccta aact 24

<210> SEQ ID NO 959
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 959
tctcacactt ttcctcgaaa aat 23

<210> SEQ ID NO 960
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 960
gcaaacctaa atacgtccct cct 23

<210> SEQ ID NO 961
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 961
accttcattc gaacgcttaa ac 22

<210> SEQ ID NO 962
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 962
aactacttcc tctccctcca caa 23

<210> SEQ ID NO 963
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 963
ttcaaaaatc gaccaatcgt aat 23

<210> SEQ ID NO 964
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 964
tcgcgaacaa attaacttcc c 21

<210> SEQ ID NO 965
<211> LENGTH: 28
<212> TYPE: DNA
<213> ORGANISM: Artificial Sequence
<220> FEATURE:
<223> OTHER INFORMATION: Probe sequence (LSO1)

<400> SEQUENCE: 965
ttaactactt actttcttct ctccaccc 28

<210> SEQ ID NO 966
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 966
aaaaccaatt tactcgcgaa cg 22

<210> SEQ ID NO 967
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 967
caactaaacc caacgccaat cta 23

<210> SEQ ID NO 968
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 968
aaacaatcca aacccgaaaa c 21

<210> SEQ ID NO 969
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 969
gaacgcatac gcgacaaac 19

<210> SEQ ID NO 970
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 970
tcctaccctc accctcctaa a 21

<210> SEQ ID NO 971
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 971
attctcaaaa taaaaattcc ctatca 26

<210> SEQ ID NO 972
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 972
cattaccctt tctatcccca cc 22

<210> SEQ ID NO 973
<211> LENGTH: 27
<212> TYPE: DNA
<213> ORGANISM: Artificial Sequence
<220> FEATURE:
<223> OTHER INFORMATION: Probe sequence (LSO1)

<400> SEQUENCE: 973
aaccaaccta accaacataa taaaacc 27

<210> SEQ ID NO 974
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 974
taaactccaa acacccacct acc 23

<210> SEQ ID NO 975
<211> LENGTH: 21
<212> TYPE: DNA

<213> ORGANISM: Artificial Sequence
<220> FEATURE:
<223> OTHER INFORMATION: Probe sequence (LSO1)

<400> SEQUENCE: 975
accctccgaa cctccaacta c 21

<210> SEQ ID NO 976
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 976
ctacatctac tcatttcctc cca 23

<210> SEQ ID NO 977
<211> LENGTH: 27
<212> TYPE: DNA
<213> ORGANISM: Artificial Sequence
<220> FEATURE:
<223> OTHER INFORMATION: Probe sequence (LSO1)

<400> SEQUENCE: 977
aatacaataa cataacctct acctccc 27

<210> SEQ ID NO 978
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 978
cctaaaaaac acaacaaaac tcca 24

<210> SEQ ID NO 979
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 979
ttaccacact ctaaccaatc aaaa 24

<210> SEQ ID NO 980
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 980
ctaccgaatt catttaaaaa ccg 23

<210> SEQ ID NO 981
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 981
ttccctttct tcacgatact taaca 25

<210> SEQ ID NO 982
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 982
ttcaactccg aaatttccaa act 23

<210> SEQ ID NO 983
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 983
ttcgtcactc ccacgattaa c 21

<210> SEQ ID NO 984
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 984
aaaacgacca aaacaaaacc aa 22

<210> SEQ ID NO 985
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 985
catcaaccaa acattccgaa a 21

<210> SEQ ID NO 986
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 986
aaaacgcgta tcctcaccc 19

<210> SEQ ID NO 987
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 987
accctcgcta actctcctcc 20

<210> SEQ ID NO 988
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 988
caatccttaa accaatcgac gta 23

<210> SEQ ID NO 989
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 989
cgaaacatta aactcctcct cct 23

<210> SEQ ID NO 990
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 990
taaacaacat aacgtacgac accg 24

<210> SEQ ID NO 991
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 991
tcaactccgt ttcgatttca ct 22

<210> SEQ ID NO 992
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 992
aacaatacga cctatcaccg c 21

<210> SEQ ID NO 993
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 993
tactttaaac cgaaccaaac caa 23

<210> SEQ ID NO 994
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 994
aaaaattcaa actcccgaac g 21

<210> SEQ ID NO 995
<211> LENGTH: 23
<212> TYPE: DNA

<213> ORGANISM: Artificial Sequence
<220> FEATURE:
<223> OTHER INFORMATION: Probe sequence (LSO1)

<400> SEQUENCE: 995
cttcttccga ctcttcacct caa 23

<210> SEQ ID NO 996
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 996
gacgcgtccc taaaacttaa cc 22

<210> SEQ ID NO 997
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 997
ttcgccacaa accttctttc 20

<210> SEQ ID NO 998
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 998
acgaacaact aaactcgact accg 24

<210> SEQ ID NO 999
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 999
ctactaaaaa accaatcaac gcg 23

<210> SEQ ID NO 1000
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 1000
atcctaatcc tcctaccctt atattt 26

<210> SEQ ID NO 1001
<211> LENGTH: 29
<212> TYPE: DNA
<213> ORGANISM: Artificial Sequence
<220> FEATURE:
<223> OTHER INFORMATION: Probe sequence (LSO1)

<400> SEQUENCE: 1001
aaactaacta aacaattaac tctcctccc 29

<210> SEQ ID NO 1002
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1002
aattctaaac gtttcccgac tac 23

<210> SEQ ID NO 1003
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1003
actacaaccg acgaaccacg 20

<210> SEQ ID NO 1004
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 1004
gacccgaaac taccgcaaa 19

<210> SEQ ID NO 1005
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1005
aatcctaaac ctaaacctcc cga 23

<210> SEQ ID NO 1006
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1006
accgaatctt cccttatccc 20

<210> SEQ ID NO 1007
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1007
tccttacaac ctctaacctc ctt 23

<210> SEQ ID NO 1008
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 1008
cctcttaaaa cctacctacc cctc 24

<210> SEQ ID NO 1009
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 1009
aaattacacc aattataaac cgaacg 26

<210> SEQ ID NO 1010
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1010
gaaaccctct acccgcctat t 21

<210> SEQ ID NO 1011
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1011
aaaatcgaaa ccaaaacccc 20

<210> SEQ ID NO 1012
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 1012
ccgtaacaac tacacgactc ctaa 24

<210> SEQ ID NO 1013
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1013
cctcccgaac taaaacgatt ct 22

<210> SEQ ID NO 1014
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1014
caaaacgaaa ccctatctcc aa 22

<210> SEQ ID NO 1015
<211> LENGTH: 22
<212> TYPE: DNA

<213> ORGANISM: Artificial Sequence
<220> FEATURE:
<223> OTHER INFORMATION: Probe sequence (LSO1)

<400> SEQUENCE: 1015
accatcccaa ctccctatct tt 22

<210> SEQ ID NO 1016
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1016
acgaaactct acgacgacgc 20

<210> SEQ ID NO 1017
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1017
aaaacgaaac cgcgactata aa 22

<210> SEQ ID NO 1018
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1018
taaaatcacc acccgaaaaa cat 23

<210> SEQ ID NO 1019
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 1019
tttaataaaa ttttccctcc cttacc 26

<210> SEQ ID NO 1020
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1020
cttctactca aacaccaacg cc 22

<210> SEQ ID NO 1021
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 1021
aaaatcaaat ccaaataaca tccc 24

<210> SEQ ID NO 1022
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1022
ctcccgccac tttactaaaa act 23

<210> SEQ ID NO 1023
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1023
taccacttcc caactcttcc c 21

<210> SEQ ID NO 1024
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1024
gccctacatc ccaacactaa aa 22

<210> SEQ ID NO 1025
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1025
aaatacctac gaactcctaa aaccc 25

<210> SEQ ID NO 1026
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 1026
gacgacgccc atatcgac 18

<210> SEQ ID NO 1027
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1027
aacctctccc aacctcaatt tt 22

<210> SEQ ID NO 1028
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1028
actaataacc gctctcgctt ct 22

<210> SEQ ID NO 1029
<211> LENGTH: 27
<212> TYPE: DNA
<213> ORGANISM: Artificial Sequence
<220> FEATURE:
<223> OTHER INFORMATION: Probe sequence (LSO1)

<400> SEQUENCE: 1029
aaacaaactc gctaaaatct aaataac 27

<210> SEQ ID NO 1030
<211> LENGTH: 27
<212> TYPE: DNA
<213> ORGANISM: Artificial Sequence
<220> FEATURE:
<223> OTHER INFORMATION: Probe sequence (LSO1)

<400> SEQUENCE: 1030
tttttaaaaa acctataaaa ccaatcc 27

<210> SEQ ID NO 1031
<211> LENGTH: 17
<212> TYPE: DNA
<213> ORGANISM: Artificial Sequence
<220> FEATURE:
<223> OTHER INFORMATION: Probe sequence (LSO1)

<400> SEQUENCE: 1031
aaccatcctc cgcctca 17

<210> SEQ ID NO 1032
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1032
cctacaaccc tactacccct acc 23

<210> SEQ ID NO 1033
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1033
ctaacacaaa aaccacactc caa 23

<210> SEQ ID NO 1034
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 1034
cccaaaaact aaacttcctc taaa 24

<210> SEQ ID NO 1035
<211> LENGTH: 20
<212> TYPE: DNA

<213> ORGANISM: Artificial Sequence
<220> FEATURE:
<223> OTHER INFORMATION: Probe sequence (LSO1)

<400> SEQUENCE: 1035
acactaccac caccaccatc 20

<210> SEQ ID NO 1036
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1036
aaacatttcg caattcctat ctc 23

<210> SEQ ID NO 1037
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1037
atattctctc tcattctacg ccg 23

<210> SEQ ID NO 1038
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1038
aatcctatac tcgataccgt ttctc 25

<210> SEQ ID NO 1039
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 1039
acaaccacac caaaccctat atct 24

<210> SEQ ID NO 1040
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1040
acttccaacc cttaaaacaa aca 23

<210> SEQ ID NO 1041
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1041
tcccaaaaaa caacttccct aa 22

<210> SEQ ID NO 1042
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1042
ttattttaaa cccaatcttc cct 23

<210> SEQ ID NO 1043
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1043
ttacaatata atcctcccca aaatc 25

<210> SEQ ID NO 1044
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 1044
caaatttccc aatttaattc ctca 24

<210> SEQ ID NO 1045
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1045
gattaaacgc gacgctcaat tac 23

<210> SEQ ID NO 1046
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1046
cgacacacaa aaaccgacta c 21

<210> SEQ ID NO 1047
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1047
ataccattac aaaaacaacc caaca 25

<210> SEQ ID NO 1048
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 1048
acacatatcc cctctctaat cctc 24

<210> SEQ ID NO 1049
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1049
aaaccccata cccttaaacc cta 23

<210> SEQ ID NO 1050
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1050
acctcaatct tctcgtcaac aaa 23

<210> SEQ ID NO 1051
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1051
cccaaccaat aaacgacgaa a 21

<210> SEQ ID NO 1052
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1052
cctcacgaac taccctcaaa c 21

<210> SEQ ID NO 1053
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1053
taaacaccaa cttctctccc ttt 23

<210> SEQ ID NO 1054
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1054
ctcctcccct actcatttta aaa 23

<210> SEQ ID NO 1055
<211> LENGTH: 19
<212> TYPE: DNA

<213> ORGANISM: Artificial Sequence
<220> FEATURE:
<223> OTHER INFORMATION: Probe sequence (LSO1)

<400> SEQUENCE: 1055
tttccaaact aaaccgccg 19

<210> SEQ ID NO 1056
<211> LENGTH: 27
<212> TYPE: DNA
<213> ORGANISM: Artificial Sequence
<220> FEATURE:
<223> OTHER INFORMATION: Probe sequence (LSO1)

<400> SEQUENCE: 1056
taacacctaa ttttatatac cccaacc 27

<210> SEQ ID NO 1057
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1057
actccgtcta acttctttct ccc 23

<210> SEQ ID NO 1058
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1058
aactttcaat acatccgccg 20

<210> SEQ ID NO 1059
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1059
caaaacccat aaaaattcaa aaa 23

<210> SEQ ID NO 1060
<211> LENGTH: 17
<212> TYPE: DNA
<213> ORGANISM: Artificial Sequence
<220> FEATURE:
<223> OTHER INFORMATION: Probe sequence (LSO1)

<400> SEQUENCE: 1060
cccctactcc tccccac 17

<210> SEQ ID NO 1061
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 1061
ttcctcctcc aacccctc 18

-continued

<210> SEQ ID NO 1062
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1062
ccctaacacg actctaccca a 21

<210> SEQ ID NO 1063
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1063
cctccccata ccaacttaaa a 21

<210> SEQ ID NO 1064
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 1064
aatcatctaa aataaaaaca cccaac 26

<210> SEQ ID NO 1065
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1065
accaaatcta taccaaaatc ccc 23

<210> SEQ ID NO 1066
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1066
aaattaactc ctcaaaacac ccg 23

<210> SEQ ID NO 1067
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1067
aaacccaaaa ctacctccaa atc 23

<210> SEQ ID NO 1068
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1068
aaccaaaccg aactcccaat aa 22

<210> SEQ ID NO 1069
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1069
ttcgacctct ctccgctaaa 20

<210> SEQ ID NO 1070
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1070
acccatctcc cgttacataa aac 23

<210> SEQ ID NO 1071
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1071
ctaaacaccc gaaccaacga ct 22

<210> SEQ ID NO 1072
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1072
accacatacg ccaaataccc 20

<210> SEQ ID NO 1073
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1073
cctcaacaaa taaaccccaa aat 23

<210> SEQ ID NO 1074
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1074
ccgcccctca actatttatt c 21

<210> SEQ ID NO 1075
<211> LENGTH: 22
<212> TYPE: DNA

<213> ORGANISM: Artificial Sequence
<220> FEATURE:
<223> OTHER INFORMATION: Probe sequence (LSO1)

<400> SEQUENCE: 1075
ttccaatcgc attacgtaaa ca 22

<210> SEQ ID NO 1076
<211> LENGTH: 28
<212> TYPE: DNA
<213> ORGANISM: Artificial Sequence
<220> FEATURE:
<223> OTHER INFORMATION: Probe sequence (LSO1)

<400> SEQUENCE: 1076
tctaaaaacc taccactaat attcacaa 28

<210> SEQ ID NO 1077
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1077
taaaccctaa actaccataa aaccg 25

<210> SEQ ID NO 1078
<211> LENGTH: 28
<212> TYPE: DNA
<213> ORGANISM: Artificial Sequence
<220> FEATURE:
<223> OTHER INFORMATION: Probe sequence (LSO1)

<400> SEQUENCE: 1078
aaaattaact actctcacct aacaaacc 28

<210> SEQ ID NO 1079
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1079
tttcataaca acccaaaatc ca 22

<210> SEQ ID NO 1080
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 1080
aaacactaac cgtaaaccaa acac 24

<210> SEQ ID NO 1081
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1081
caacgctata cctaaacgac ctt 23

-continued

<210> SEQ ID NO 1082
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1082
aaacttcgac taacaaaccc cg 22

<210> SEQ ID NO 1083
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1083
cttatcccaa aaaacaaaac caa 23

<210> SEQ ID NO 1084
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 1084
ttccaaccct cacctaactt tatc 24

<210> SEQ ID NO 1085
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1085
cctattcaaa tcaactcctt ctaaa 25

<210> SEQ ID NO 1086
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1086
cacaaacaaa cgctccaaaa 20

<210> SEQ ID NO 1087
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1087
cccaaaatct ccgtaaacta aaa 23

<210> SEQ ID NO 1088
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1088
aaaatccctc tcacccatta aca 23

<210> SEQ ID NO 1089
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1089
aaaaaccgcg accctaaaaa 20

<210> SEQ ID NO 1090
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1090
gacctcttcg aacaacccaa ata 23

<210> SEQ ID NO 1091
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1091
ccctatccta atcgcccaac taa 23

<210> SEQ ID NO 1092
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1092
ccaccaaaca tacaattcca act 23

<210> SEQ ID NO 1093
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1093
attctatccc tatcctaatc gcc 23

<210> SEQ ID NO 1094
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1094
actctctaaa accgccgtcg 20

<210> SEQ ID NO 1095
<211> LENGTH: 23
<212> TYPE: DNA

<213> ORGANISM: Artificial Sequence
<220> FEATURE:
<223> OTHER INFORMATION: Probe sequence (LSO1)

<400> SEQUENCE: 1095
gtaaacctcc ccctcaacta aaa 23

<210> SEQ ID NO 1096
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1096
cgctacctaa cgctctaact cc 22

<210> SEQ ID NO 1097
<211> LENGTH: 26
<212> TYPE: DNA
<213> ORGANISM: Artificial Sequence
<220> FEATURE:
<223> OTHER INFORMATION: Probe sequence (LSO1)

<400> SEQUENCE: 1097
tccaattccc taatatacct atttca 26

<210> SEQ ID NO 1098
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1098
accaacacaa tctctacgcc c 21

<210> SEQ ID NO 1099
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1099
aacctcgaac cttaacaatt cg 22

<210> SEQ ID NO 1100
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1100
aattccctac actcatcccc tt 22

<210> SEQ ID NO 1101
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1101
ccccactaaa cccttaaccc 20

<210> SEQ ID NO 1102
<211> LENGTH: 19
<212> TYPE: DNA
<213> ORGANISM: Artificial Sequence
<220> FEATURE:
<223> OTHER INFORMATION: Probe sequence (LSO1)

<400> SEQUENCE: 1102
aaaactctcc cctctcccc 19

<210> SEQ ID NO 1103
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1103
aaaatccaaa ctccttacct ctaat 25

<210> SEQ ID NO 1104
<211> LENGTH: 27
<212> TYPE: DNA
<213> ORGANISM: Artificial Sequence
<220> FEATURE:
<223> OTHER INFORMATION: Probe sequence (LSO1)

<400> SEQUENCE: 1104
taaacattct atacctactt cccaaaa 27

<210> SEQ ID NO 1105
<211> LENGTH: 28
<212> TYPE: DNA
<213> ORGANISM: Artificial Sequence
<220> FEATURE:
<223> OTHER INFORMATION: Probe sequence (LSO1)

<400> SEQUENCE: 1105
taaacaatac caactaattc cacttttc 28

<210> SEQ ID NO 1106
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1106
attccttcct aacgctccct c 21

<210> SEQ ID NO 1107
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1107
aactcgctcc tcgcgaaata c 21

<210> SEQ ID NO 1108
<211> LENGTH: 27
<212> TYPE: DNA
<213> ORGANISM: Artificial Sequence
<220> FEATURE:
<223> OTHER INFORMATION: Probe sequence (LSO1)

```
<400> SEQUENCE: 1108

aattctaaaa atccgaaatt ctaaacc                                         27

<210> SEQ ID NO 1109
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1109

atttctaaaa ccccgaaacc tc                                              22

<210> SEQ ID NO 1110
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1110

tctatacccg ctaatacaaa ccc                                             23

<210> SEQ ID NO 1111
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1111

aacacacaca caaaaaacct ataca                                           25

<210> SEQ ID NO 1112
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1112

acatacacgc acactcaaac a                                               21

<210> SEQ ID NO 1113
<211> LENGTH: 21
<212> TYPE: DNA
<213> ORGANISM: Artificial Sequence
<220> FEATURE:
<223> OTHER INFORMATION: Probe sequence (LSO1)

<400> SEQUENCE: 1113

cccccttaaa ccctaaactc a                                               21

<210> SEQ ID NO 1114
<211> LENGTH: 18
<212> TYPE: DNA
<213> ORGANISM: Artificial Sequence
<220> FEATURE:
<223> OTHER INFORMATION: Probe sequence (LSO1)

<400> SEQUENCE: 1114

cccacgcaaa accgaaaa                                                   18

<210> SEQ ID NO 1115
<211> LENGTH: 21
<212> TYPE: DNA
```

<213> ORGANISM: Artificial Sequence
<220> FEATURE:
<223> OTHER INFORMATION: Probe sequence (LSO1)

<400> SEQUENCE: 1115
tcacgtcaac ctccccaaat a 21

<210> SEQ ID NO 1116
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1116
aataccacct tccgcaaacc 20

<210> SEQ ID NO 1117
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1117
aacccaatct cacaacaccc 20

<210> SEQ ID NO 1118
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1118
aaaacctact cgcgacctta act 23

<210> SEQ ID NO 1119
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1119
gacccaacca ataaaccaaa ac 22

<210> SEQ ID NO 1120
<211> LENGTH: 24
<212> TYPE: DNA
<213> ORGANISM: Artificial Sequence
<220> FEATURE:
<223> OTHER INFORMATION: Probe sequence (LSO1)

<400> SEQUENCE: 1120
ctaactccct accattatcc acca 24

<210> SEQ ID NO 1121
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1121
actccttacc cactccgaac taa 23

<210> SEQ ID NO 1122
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1122
aaccaaccca aattcaaaac taa 23

<210> SEQ ID NO 1123
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1123
aattcctaac tccctaatcc ctacc 25

<210> SEQ ID NO 1124
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1124
aacttcttat acccgatcct cg 22

<210> SEQ ID NO 1125
<211> LENGTH: 23
<212> TYPE: DNA
<213> ORGANISM: Artificial Sequence
<220> FEATURE:
<223> OTHER INFORMATION: Probe sequence (LSO1)

<400> SEQUENCE: 1125
aaatacgaac cgaaataaac ctc 23

<210> SEQ ID NO 1126
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1126
cctaactcaa ccataaaccc ca 22

<210> SEQ ID NO 1127
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1127
aaattctata ctcccctcaa aaatc 25

<210> SEQ ID NO 1128
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1128
aaccttccaa atactaccct aactc 25

<210> SEQ ID NO 1129
<211> LENGTH: 22
<212> TYPE: DNA
<213> ORGANISM: Artificial Sequence
<220> FEATURE:
<223> OTHER INFORMATION: Probe sequence (LSO1)

<400> SEQUENCE: 1129
caaaacgaaa ccctatctct cg 22

<210> SEQ ID NO 1130
<211> LENGTH: 25
<212> TYPE: DNA
<213> ORGANISM: Artificial Sequence
<220> FEATURE:
<223> OTHER INFORMATION: Probe sequence (LSO1)

<400> SEQUENCE: 1130
gcctaaccaa tcttctcttc ttaca 25

<210> SEQ ID NO 1131
<211> LENGTH: 20
<212> TYPE: DNA
<213> ORGANISM: Artificial Sequence
<220> FEATURE:
<223> OTHER INFORMATION: Probe sequence (LSO1)

<400> SEQUENCE: 1131
tcctccaacc taaacctccc 20

<210> SEQ ID NO 1132
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1132
aacaccctca cacttctaca cca 23

<210> SEQ ID NO 1133
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1133
cttccaactt tatcacacac ctaca 25

<210> SEQ ID NO 1134
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1134
cccaacttcc aaacaataat aaaca 25

<210> SEQ ID NO 1135
<211> LENGTH: 26
<212> TYPE: DNA

```
<213> ORGANISM: Artificial Sequence
<220> FEATURE:
<223> OTHER INFORMATION: Probe sequence (ASO2)

<400> SEQUENCE: 1135

tccctaataa atcaaaacat ctacca                                    26

<210> SEQ ID NO 1136
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1136

aactttcaac tacccctcac ca                                        22

<210> SEQ ID NO 1137
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1137

acatccaacc cctaactctc tca                                       23

<210> SEQ ID NO 1138
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1138

taacacccaa atctctccta acca                                      24

<210> SEQ ID NO 1139
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1139

ccaactctat acccaacacc taca                                      24

<210> SEQ ID NO 1140
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1140

aaccctaaca ccaaacctac ttca                                      24

<210> SEQ ID NO 1141
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1141

ccaccaaata tcttttcttc ttca                                      24
```

<210> SEQ ID NO 1142
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1142
aatctatccc aacataactt cctca 25

<210> SEQ ID NO 1143
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1143
acaccaacct aacaaaacaa ctca 24

<210> SEQ ID NO 1144
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1144
aaaccttctt accttcaaac ctca 24

<210> SEQ ID NO 1145
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1145
aaaaatactc ccattctcca cca 23

<210> SEQ ID NO 1146
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1146
cactaccact ccccaaaaaa ca 22

<210> SEQ ID NO 1147
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1147
aaaccaacaa aaatacccca aca 23

<210> SEQ ID NO 1148
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1148
actccacact caaccaatta aaca 24

<210> SEQ ID NO 1149
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1149
ccaattccca acataacaac aca 23

<210> SEQ ID NO 1150
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1150
aactcacccc tcctttctac ca 22

<210> SEQ ID NO 1151
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1151
acccacatcc aaattcctaa aca 23

<210> SEQ ID NO 1152
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1152
tccaacccac aaaatttaaa aca 23

<210> SEQ ID NO 1153
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1153
aacaatacaa ccaacattcc taaca 25

<210> SEQ ID NO 1154
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1154
caactcctaa tccccaataa aca 23

<210> SEQ ID NO 1155
<211> LENGTH: 24
<212> TYPE: DNA

<213> ORGANISM: Artificial Sequence
<220> FEATURE:
<223> OTHER INFORMATION: Probe sequence (ASO2)

<400> SEQUENCE: 1155
aacatcttta aacaaacttc ccca 24

<210> SEQ ID NO 1156
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1156
aaaacaaaca acctccctct ca 22

<210> SEQ ID NO 1157
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1157
acctttaatt tctcccaaac cca 23

<210> SEQ ID NO 1158
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1158
caaaaatctc tactaactcc ccca 24

<210> SEQ ID NO 1159
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1159
caacaacacc tctcacacat aca 23

<210> SEQ ID NO 1160
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1160
aacaaaacaa caaaacaata ccca 24

<210> SEQ ID NO 1161
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1161
caccaaaaac ctaaccacta ctca 24

```
<210> SEQ ID NO 1162
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1162

cttccccttc cctcaactaa aca                                            23

<210> SEQ ID NO 1163
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1163

ctcctactcc ttctcctaat cca                                            23

<210> SEQ ID NO 1164
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1164

aactaaaaca acttctccca aaaca                                          25

<210> SEQ ID NO 1165
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1165

attaatatct acaacaccaa atcaaca                                        27

<210> SEQ ID NO 1166
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1166

ctccatttcc tttacttcct cca                                            23

<210> SEQ ID NO 1167
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1167

ccccaccacc tacaaaaaac a                                              21

<210> SEQ ID NO 1168
<211> LENGTH: 23
<212> TYPE: DNA
<213> ORGANISM: Artificial Sequence
<220> FEATURE:
<223> OTHER INFORMATION: Probe sequence (ASO2)
```

<400> SEQUENCE: 1168
ccacaaaaac caaaaaacta cca 23

<210> SEQ ID NO 1169
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1169
taaataacca atccaaaacc cca 23

<210> SEQ ID NO 1170
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1170
ctcaaataaa attcttcctc ttcca 25

<210> SEQ ID NO 1171
<211> LENGTH: 28
<212> TYPE: DNA
<213> ORGANISM: Artificial Sequence
<220> FEATURE:
<223> OTHER INFORMATION: Probe sequence (ASO2)

<400> SEQUENCE: 1171
aaactcaaat caataacact actcaaca 28

<210> SEQ ID NO 1172
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1172
aaaatattcc ccttacaaaa acca 24

<210> SEQ ID NO 1173
<211> LENGTH: 28
<212> TYPE: DNA
<213> ORGANISM: Artificial Sequence
<220> FEATURE:
<223> OTHER INFORMATION: Probe sequence (ASO2)

<400> SEQUENCE: 1173
aaaacaacct actattatat caccaaca 28

<210> SEQ ID NO 1174
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1174
caactctaca taaatacaca aaccca 26

<210> SEQ ID NO 1175
<211> LENGTH: 23
<212> TYPE: DNA

<213> ORGANISM: Artificial Sequence
<220> FEATURE:
<223> OTHER INFORMATION: Probe sequence (ASO2)

<400> SEQUENCE: 1175
atcaaccaaa cctacatccc aca 23

<210> SEQ ID NO 1176
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1176
ccacaaaaaa cctaaaaaca aaaca 25

<210> SEQ ID NO 1177
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1177
cccatacact tcctaaataa aacca 25

<210> SEQ ID NO 1178
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1178
ctctttctct aataacccac acca 24

<210> SEQ ID NO 1179
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1179
cccaacctaa ctctccttcc a 21

<210> SEQ ID NO 1180
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1180
tctcttaaat cttaacaatc ccca 24

<210> SEQ ID NO 1181
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1181
tccctaaata cctcctacac aaaca 25

<210> SEQ ID NO 1182
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1182
caataatcaa tcacataaaa cattcca 27

<210> SEQ ID NO 1183
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1183
acacaccaac ctctaacaat acca 24

<210> SEQ ID NO 1184
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1184
aactcaaaac cataattttc aaaca 25

<210> SEQ ID NO 1185
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1185
taaaactaac ctctcctacc ctca 24

<210> SEQ ID NO 1186
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1186
tcctaaaaca aataacacaa taccaca 27

<210> SEQ ID NO 1187
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1187
ccaataaaaa caaaacccaa ctca 24

<210> SEQ ID NO 1188
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1188
cacaaatcaa taacatcaca tcca 24

<210> SEQ ID NO 1189
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1189
ctcaacccta atacccatcc a 21

<210> SEQ ID NO 1190
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1190
ccactccaat actcactccc a 21

<210> SEQ ID NO 1191
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1191
aacaaacaaa acaaacaaaa tcca 24

<210> SEQ ID NO 1192
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1192
aaaaccttaa ctaacacaaa accaca 26

<210> SEQ ID NO 1193
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1193
ccaaatctca ctcctaaatt caaca 25

<210> SEQ ID NO 1194
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1194
tccacaaacc tacaaaacct aaca 24

<210> SEQ ID NO 1195
<211> LENGTH: 28
<212> TYPE: DNA

<213> ORGANISM: Artificial Sequence
<220> FEATURE:
<223> OTHER INFORMATION: Probe sequence (ASO2)

<400> SEQUENCE: 1195
caaaaactca ataataataa acacacca 28

<210> SEQ ID NO 1196
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1196
cccaataaaa ccaacttaac cca 23

<210> SEQ ID NO 1197
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1197
ccttccttaa actctctcca cca 23

<210> SEQ ID NO 1198
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1198
aataacaacc atcctacctc cca 23

<210> SEQ ID NO 1199
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1199
ccaaccaacc ataaaaataa aaca 24

<210> SEQ ID NO 1200
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1200
cctctcccct accctataaa aca 23

<210> SEQ ID NO 1201
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1201
caaccaacta cacaacaact cca 23

<210> SEQ ID NO 1202
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1202
caaaaaacac cttccataaa aaca 24

<210> SEQ ID NO 1203
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1203
accacaatac cataaacatc acca 24

<210> SEQ ID NO 1204
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1204
aaactacaaa ttacacaatc caattca 27

<210> SEQ ID NO 1205
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1205
aataattaat aaccaaccaa aaactca 27

<210> SEQ ID NO 1206
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1206
tctctttccc tttctcttcc a 21

<210> SEQ ID NO 1207
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1207
cataataaat ttcacctctc aatcca 26

<210> SEQ ID NO 1208
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1208
aaaaatcctt tacccctaaa ttaca 25

<210> SEQ ID NO 1209
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1209
ccacaccaac ctaaactcaa ca 22

<210> SEQ ID NO 1210
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1210
acccaactaa aactaaaacc cca 23

<210> SEQ ID NO 1211
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1211
accacctcct aataaaaacc cca 23

<210> SEQ ID NO 1212
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1212
ttacctctct ccaaatctct caca 24

<210> SEQ ID NO 1213
<211> LENGTH: 28
<212> TYPE: DNA
<213> ORGANISM: Artificial Sequence
<220> FEATURE:
<223> OTHER INFORMATION: Probe sequence (ASO2)

<400> SEQUENCE: 1213
ctttctacat atctctcaac ctctttca 28

<210> SEQ ID NO 1214
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1214
aaaatatcaa aacctctaca accca 25

<210> SEQ ID NO 1215
<211> LENGTH: 23
<212> TYPE: DNA

<213> ORGANISM: Artificial Sequence
<220> FEATURE:
<223> OTHER INFORMATION: Probe sequence (ASO2)

<400> SEQUENCE: 1215
caaacccaat aaaatcaaaa cca 23

<210> SEQ ID NO 1216
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1216
accctcaacc aatcaacaat aca 23

<210> SEQ ID NO 1217
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1217
cctttaaaaa ccatctaatc aacca 25

<210> SEQ ID NO 1218
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1218
aactccattc tataccacac cca 23

<210> SEQ ID NO 1219
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1219
cttacttcat tctctacaca accca 25

<210> SEQ ID NO 1220
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1220
cctcctccta atcctacaca aca 23

<210> SEQ ID NO 1221
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1221
ccatcaacac tcaaaacaaa ctaca 25

<210> SEQ ID NO 1222
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1222
acccaactcc aaactcataa aca 23

<210> SEQ ID NO 1223
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1223
aaactcctct acacctacca cca 23

<210> SEQ ID NO 1224
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1224
aaaccaatac aatccatatc cca 23

<210> SEQ ID NO 1225
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1225
aaaaccaaaa cttacaaacc aaca 24

<210> SEQ ID NO 1226
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1226
aatttatccc caattaataa ttcca 25

<210> SEQ ID NO 1227
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1227
cccttttata actccatctc caca 24

<210> SEQ ID NO 1228
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1228
ccactaccct atacacctaa ccca 24

<210> SEQ ID NO 1229
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1229
aaccaacata ccaacatcca aca 23

<210> SEQ ID NO 1230
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1230
aaccactcaa acacataaca aatca 25

<210> SEQ ID NO 1231
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1231
ccctttccta attaacacca aaca 24

<210> SEQ ID NO 1232
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1232
aaaaccaaac caaaactaaa tcca 24

<210> SEQ ID NO 1233
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1233
caataacccc caaaactaaa ctca 24

<210> SEQ ID NO 1234
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1234
aacaaaaaca aatccaaata tacca 25

<210> SEQ ID NO 1235
<211> LENGTH: 23
<212> TYPE: DNA

<213> ORGANISM: Artificial Sequence
<220> FEATURE:
<223> OTHER INFORMATION: Probe sequence (ASO2)

<400> SEQUENCE: 1235
caaccctaaa catctaaaca cca 23

<210> SEQ ID NO 1236
<211> LENGTH: 18
<212> TYPE: DNA
<213> ORGANISM: Artificial Sequence
<220> FEATURE:
<223> OTHER INFORMATION: Probe sequence (ASO2)

<400> SEQUENCE: 1236
tcattccact ccaaccca 18

<210> SEQ ID NO 1237
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1237
tctaaaaaat ctccctctta tctca 25

<210> SEQ ID NO 1238
<211> LENGTH: 19
<212> TYPE: DNA
<213> ORGANISM: Artificial Sequence
<220> FEATURE:
<223> OTHER INFORMATION: Probe sequence (ASO2)

<400> SEQUENCE: 1238
caacccttcc accctacca 19

<210> SEQ ID NO 1239
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1239
cacaaatcct aaaataccaa aaca 24

<210> SEQ ID NO 1240
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1240
caaaactaca ataaaccaaa ctcaca 26

<210> SEQ ID NO 1241
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1241
cccatataaa atacaccacc ctca 24

-continued

<210> SEQ ID NO 1242
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1242
tcccatcccc taataatcac a 21

<210> SEQ ID NO 1243
<211> LENGTH: 29
<212> TYPE: DNA
<213> ORGANISM: Artificial Sequence
<220> FEATURE:
<223> OTHER INFORMATION: Probe sequence (ASO2)

<400> SEQUENCE: 1243
cataacaata acaaacatct cttatacca 29

<210> SEQ ID NO 1244
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1244
aaactataac ccaacccaac taca 24

<210> SEQ ID NO 1245
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1245
aaacactaaa ccataaaatc tcaaca 26

<210> SEQ ID NO 1246
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1246
aaccctacaa tctacacaaa tacca 25

<210> SEQ ID NO 1247
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1247
ccctatattc acacacaata ctattca 27

<210> SEQ ID NO 1248
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1248
ctaaccaacc taacaactct caaca 25

<210> SEQ ID NO 1249
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1249
cacaccacac acacacacac a 21

<210> SEQ ID NO 1250
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1250
caaaaccaat tatctttata accaca 26

<210> SEQ ID NO 1251
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1251
cacatacaca aaaaacaaaa acaca 25

<210> SEQ ID NO 1252
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1252
tcctcacccc aaataaaaac tca 23

<210> SEQ ID NO 1253
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1253
cctacaccca aatttccatt aca 23

<210> SEQ ID NO 1254
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1254
aaatcacaat ccaacctcta cca 23

<210> SEQ ID NO 1255
<211> LENGTH: 24
<212> TYPE: DNA

<213> ORGANISM: Artificial Sequence
<220> FEATURE:
<223> OTHER INFORMATION: Probe sequence (ASO2)

<400> SEQUENCE: 1255
aatacccaaa aacaataacc aaca 24

<210> SEQ ID NO 1256
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1256
tcaaacaaca aaacaataac ctaca 25

<210> SEQ ID NO 1257
<211> LENGTH: 28
<212> TYPE: DNA
<213> ORGANISM: Artificial Sequence
<220> FEATURE:
<223> OTHER INFORMATION: Probe sequence (ASO2)

<400> SEQUENCE: 1257
tcttcatcaa aacatctata aatcatca 28

<210> SEQ ID NO 1258
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1258
actccaaaac tacccaaacc taca 24

<210> SEQ ID NO 1259
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1259
actccacaat ccctaaactt cca 23

<210> SEQ ID NO 1260
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1260
aacacaactt atccctactt accca 25

<210> SEQ ID NO 1261
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1261
attaacccaa acaataaccc taca 24

<210> SEQ ID NO 1262
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1262
tttctctcaa accacttatc cca 23

<210> SEQ ID NO 1263
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1263
cacaaaacca aaaactccta cca 23

<210> SEQ ID NO 1264
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1264
acacaatccc tttaaatact cataca 26

<210> SEQ ID NO 1265
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1265
ccccaaaaac actcaaatac tca 23

<210> SEQ ID NO 1266
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1266
acaaacacaa acaaacccac aca 23

<210> SEQ ID NO 1267
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1267
aaacaaaccc aacctcttac tca 23

<210> SEQ ID NO 1268
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1268
caaacaaacc aaaatcttta taacaca 27

<210> SEQ ID NO 1269
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1269
aacaaatcac ctttacctct tcca 24

<210> SEQ ID NO 1270
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1270
acccactaaa aacaaaactc atca 24

<210> SEQ ID NO 1271
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1271
aaacaataaa ccctacctcc aaca 24

<210> SEQ ID NO 1272
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1272
atcctctaca tcctcaccaa aca 23

<210> SEQ ID NO 1273
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1273
aaccaatact cactaaacac aacaca 26

<210> SEQ ID NO 1274
<211> LENGTH: 29
<212> TYPE: DNA
<213> ORGANISM: Artificial Sequence
<220> FEATURE:
<223> OTHER INFORMATION: Probe sequence (ASO2)

<400> SEQUENCE: 1274
cacaacctat accctttata aaatacaca 29

<210> SEQ ID NO 1275
<211> LENGTH: 29
<212> TYPE: DNA

<213> ORGANISM: Artificial Sequence
<220> FEATURE:
<223> OTHER INFORMATION: Probe sequence (ASO2)

<400> SEQUENCE: 1275
tctacttctt aacactaacc tcaataaca 29

<210> SEQ ID NO 1276
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1276
ctacctaacc atcctcaaat ttca 24

<210> SEQ ID NO 1277
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1277
ccttcctcaa aatctaacaa ttca 24

<210> SEQ ID NO 1278
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1278
ccactccaaa taaaactacc acca 24

<210> SEQ ID NO 1279
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1279
cccacccaat aatcaaataa aca 23

<210> SEQ ID NO 1280
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1280
cacccataat taccataatt tcca 24

<210> SEQ ID NO 1281
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1281
accacaccca acctaatacc aca 23

<210> SEQ ID NO 1282
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1282
cacaaacaat aaacacaaac tctaca 26

<210> SEQ ID NO 1283
<211> LENGTH: 20
<212> TYPE: DNA
<213> ORGANISM: Artificial Sequence
<220> FEATURE:
<223> OTHER INFORMATION: Probe sequence (ASO2)

<400> SEQUENCE: 1283
aaaacccaac ataacccaca 20

<210> SEQ ID NO 1284
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1284
aaaataaccc tatccttccc ca 22

<210> SEQ ID NO 1285
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1285
cccataaaca cccaaatatc ca 22

<210> SEQ ID NO 1286
<211> LENGTH: 29
<212> TYPE: DNA
<213> ORGANISM: Artificial Sequence
<220> FEATURE:
<223> OTHER INFORMATION: Probe sequence (ASO2)

<400> SEQUENCE: 1286
actcaacata ttaaaacata ttcctaaca 29

<210> SEQ ID NO 1287
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1287
cccacattac ttaaaaactc aaaca 25

<210> SEQ ID NO 1288
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1288
acaatcaaat aaccacacaa caca 24

<210> SEQ ID NO 1289
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1289
caacctaacc ctttaaatct tcca 24

<210> SEQ ID NO 1290
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1290
tctttttctt aaccctaccc cca 23

<210> SEQ ID NO 1291
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1291
cctacccata caatactaaa atcca 25

<210> SEQ ID NO 1292
<211> LENGTH: 28
<212> TYPE: DNA
<213> ORGANISM: Artificial Sequence
<220> FEATURE:
<223> OTHER INFORMATION: Probe sequence (ASO2)

<400> SEQUENCE: 1292
ttatattatt aatcaccaac aaacaaca 28

<210> SEQ ID NO 1293
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1293
catctccctt cattattcat tcca 24

<210> SEQ ID NO 1294
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1294
tccttcttcc taaatactca taacaca 27

<210> SEQ ID NO 1295
<211> LENGTH: 22
<212> TYPE: DNA

<213> ORGANISM: Artificial Sequence
<220> FEATURE:
<223> OTHER INFORMATION: Probe sequence (ASO2)

<400> SEQUENCE: 1295
caacctaacc caacaaacaa ca 22

<210> SEQ ID NO 1296
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1296
aactctacaa atcccaaaat ctca 24

<210> SEQ ID NO 1297
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1297
acacaaaacc caactatata aaaaca 26

<210> SEQ ID NO 1298
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1298
actcactaca acctctacct ccca 24

<210> SEQ ID NO 1299
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1299
ccacataatc acacaacatc tca 23

<210> SEQ ID NO 1300
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1300
ttcaccatat taaccaaact aatctca 27

<210> SEQ ID NO 1301
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1301
cttttaaccc taacctttaa ccca 24

<210> SEQ ID NO 1302
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1302
ccctaacttt taacctttcc cca 23

<210> SEQ ID NO 1303
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1303
ccaaaacaaa acttacttca caaca 25

<210> SEQ ID NO 1304
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1304
aaaaccctaa aaactaaacc cca 23

<210> SEQ ID NO 1305
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1305
ataataaacc ctacaccttc tatctca 27

<210> SEQ ID NO 1306
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1306
caaaaaatac aaaacccact acca 24

<210> SEQ ID NO 1307
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1307
cacaacctaa aaattaccca tcca 24

<210> SEQ ID NO 1308
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1308
tccccttcat tacaacaaac taca 24

<210> SEQ ID NO 1309
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1309
aaacaactct caaaccctat cca 23

<210> SEQ ID NO 1310
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1310
catctctact cccaccacat tca 23

<210> SEQ ID NO 1311
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1311
tcaatcatat ttccaaaatc cca 23

<210> SEQ ID NO 1312
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1312
ttcctaatca ccctctatct tctaca 26

<210> SEQ ID NO 1313
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1313
ataaaaaatc accctaacca aaca 24

<210> SEQ ID NO 1314
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1314
aataaataac ctaatcactt caaacca 27

<210> SEQ ID NO 1315
<211> LENGTH: 24
<212> TYPE: DNA

-continued

<213> ORGANISM: Artificial Sequence
<220> FEATURE:
<223> OTHER INFORMATION: Probe sequence (ASO2)

<400> SEQUENCE: 1315
tctcccctta caacctttct aaca 24

<210> SEQ ID NO 1316
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1316
tcacctcaat acctcatact caca 24

<210> SEQ ID NO 1317
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1317
ccaccacata ccactcataa tattca 26

<210> SEQ ID NO 1318
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1318
ttaacactca atccccctta aca 23

<210> SEQ ID NO 1319
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1319
aaaacaaatt caaacccaac aca 23

<210> SEQ ID NO 1320
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1320
caatcaaccc aataaaacac aaca 24

<210> SEQ ID NO 1321
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1321
aacaaacaac caaatacacc ttca 24

<210> SEQ ID NO 1322
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1322
cacacaaaaa tactaaacct ccca 24

<210> SEQ ID NO 1323
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1323
cacacacaaa taacttcacc ctca 24

<210> SEQ ID NO 1324
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1324
cataacccct tataactaaa caaaaca 27

<210> SEQ ID NO 1325
<211> LENGTH: 20
<212> TYPE: DNA
<213> ORGANISM: Artificial Sequence
<220> FEATURE:
<223> OTHER INFORMATION: Probe sequence (ASO2)

<400> SEQUENCE: 1325
actcctacaa aacccccaca 20

<210> SEQ ID NO 1326
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1326
acaataacca ccttcctatt tcca 24

<210> SEQ ID NO 1327
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1327
caccacctaa aacctaaaaa cca 23

<210> SEQ ID NO 1328
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1328
ccaaatctta acaaacaacc aaca 24

<210> SEQ ID NO 1329
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1329
ctcctctcct caacactaat cca 23

<210> SEQ ID NO 1330
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1330
aaaaataaca acctaacccc taca 24

<210> SEQ ID NO 1331
<211> LENGTH: 20
<212> TYPE: DNA
<213> ORGANISM: Artificial Sequence
<220> FEATURE:
<223> OTHER INFORMATION: Probe sequence (ASO2)

<400> SEQUENCE: 1331
cccaaaacct aactccctca 20

<210> SEQ ID NO 1332
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1332
caccaatcaa caccaacctc a 21

<210> SEQ ID NO 1333
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1333
cacactcaat tacttaacaa cctca 25

<210> SEQ ID NO 1334
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1334
atctcaactc atcacaacct cca 23

<210> SEQ ID NO 1335
<211> LENGTH: 21
<212> TYPE: DNA

<213> ORGANISM: Artificial Sequence
<220> FEATURE:
<223> OTHER INFORMATION: Probe sequence (ASO2)

<400> SEQUENCE: 1335
ataactctac cccctccccc a 21

<210> SEQ ID NO 1336
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1336
caaaacacct aaattaccta caacca 26

<210> SEQ ID NO 1337
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1337
aacttcactt tctccctctc ttca 24

<210> SEQ ID NO 1338
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1338
aatcaaacac ataactttaa cccca 25

<210> SEQ ID NO 1339
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1339
ttccccactc ttattaactt tcca 24

<210> SEQ ID NO 1340
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1340
tcccaccaac tctataatca aaca 24

<210> SEQ ID NO 1341
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1341
caaattctct aactcacttc cttca 25

<210> SEQ ID NO 1342
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1342
cactaacttt ttcaaacctt tcca 24

<210> SEQ ID NO 1343
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1343
cacaacatat aaacaccacc tctca 25

<210> SEQ ID NO 1344
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1344
ctcccaaatc aactctaaca ctca 24

<210> SEQ ID NO 1345
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1345
aaacacccta acttccaact cca 23

<210> SEQ ID NO 1346
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1346
ttttcattaa taaaaccaac caaca 25

<210> SEQ ID NO 1347
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1347
aaaaacctac taactccacc caca 24

<210> SEQ ID NO 1348
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1348
caacccaacc tctatcaaaa aca 23

<210> SEQ ID NO 1349
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1349
ttccctataa cataacctta aaaaaca 27

<210> SEQ ID NO 1350
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1350
aacaaatcac aaaatcaaaa attca 25

<210> SEQ ID NO 1351
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1351
caataactca actcacaacc tctca 25

<210> SEQ ID NO 1352
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1352
atccttaacc tacctcaacc tcca 24

<210> SEQ ID NO 1353
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1353
aaccaaccta aaaactaaaa aataaca 27

<210> SEQ ID NO 1354
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1354
aaaatcttac tatatctccc aaacca 26

<210> SEQ ID NO 1355
<211> LENGTH: 24
<212> TYPE: DNA

<213> ORGANISM: Artificial Sequence
<220> FEATURE:
<223> OTHER INFORMATION: Probe sequence (ASO2)

<400> SEQUENCE: 1355
caaaaatcat accattacac tcca 24

<210> SEQ ID NO 1356
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1356
accattacca acaatccacc a 21

<210> SEQ ID NO 1357
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1357
aattaaacca accttctttc cca 23

<210> SEQ ID NO 1358
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1358
ctcatccact ccatctctcc a 21

<210> SEQ ID NO 1359
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1359
aaatcatcct ccctcactaa cca 23

<210> SEQ ID NO 1360
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1360
tccccaaaca taataaaacc aca 23

<210> SEQ ID NO 1361
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1361
cacctaacta acacaaacat ttctca 26

<210> SEQ ID NO 1362
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1362
ccaatctcta atatccacct ctca 24

<210> SEQ ID NO 1363
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1363
aaaccaactc aaaacaaaca ctca 24

<210> SEQ ID NO 1364
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1364
cattcattaa aatacctacc cctca 25

<210> SEQ ID NO 1365
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1365
accttttcaa ttactcacaa tcca 24

<210> SEQ ID NO 1366
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1366
aacactttaa ccaatcaaca aaca 24

<210> SEQ ID NO 1367
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1367
ccatttctat acaaacccta cttcca 26

<210> SEQ ID NO 1368
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1368
caaaaattca acctcaatca aaca 24

<210> SEQ ID NO 1369
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1369
caaaaataaa cattctaacc ctcaca 26

<210> SEQ ID NO 1370
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1370
acctcccact caatcaaact aca 23

<210> SEQ ID NO 1371
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1371
tccactacaa tattactcca aatcca 26

<210> SEQ ID NO 1372
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1372
aacaaaaact cccttaaacc cca 23

<210> SEQ ID NO 1373
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1373
cccaaatcca acattaataa aaaca 25

<210> SEQ ID NO 1374
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1374
cctaacttaa atccccctcc a 21

<210> SEQ ID NO 1375
<211> LENGTH: 28
<212> TYPE: DNA

<213> ORGANISM: Artificial Sequence
<220> FEATURE:
<223> OTHER INFORMATION: Probe sequence (ASO2)

<400> SEQUENCE: 1375
ccaaaacacc ctatataaaa caactaca 28

<210> SEQ ID NO 1376
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1376
ccaaaaccaa tcaaaacaaa ca 22

<210> SEQ ID NO 1377
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1377
ctccaacttt aacttcttca aaaca 25

<210> SEQ ID NO 1378
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1378
ctcttctcca ctctaaaaca ataaca 26

<210> SEQ ID NO 1379
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1379
aaaaaattat tttctccaca tttca 25

<210> SEQ ID NO 1380
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1380
tttacatcat tttaccaatt tcaca 25

<210> SEQ ID NO 1381
<211> LENGTH: 20
<212> TYPE: DNA
<213> ORGANISM: Artificial Sequence
<220> FEATURE:
<223> OTHER INFORMATION: Probe sequence (ASO2)

<400> SEQUENCE: 1381
caatcattcc caaccactca 20

<210> SEQ ID NO 1382
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1382
ccccaacacc actataatat acca 24

<210> SEQ ID NO 1383
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1383
aaaaccccat tttctatcaa aaca 24

<210> SEQ ID NO 1384
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1384
aaaatataaa caatcacaac ccca 24

<210> SEQ ID NO 1385
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1385
tttctacact ttcctaaaat tccca 25

<210> SEQ ID NO 1386
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1386
aaacatccct caattaaata acca 24

<210> SEQ ID NO 1387
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1387
cctctcttct aaaccctccc a 21

<210> SEQ ID NO 1388
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1388
aaatccaaaa aataaccaaa aaaca 25

<210> SEQ ID NO 1389
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1389
caaacaccaa acaaaacaaa ctaca 25

<210> SEQ ID NO 1390
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1390
caatctcaac tcactacaac ctca 24

<210> SEQ ID NO 1391
<211> LENGTH: 28
<212> TYPE: DNA
<213> ORGANISM: Artificial Sequence
<220> FEATURE:
<223> OTHER INFORMATION: Probe sequence (ASO2)

<400> SEQUENCE: 1391
caaaatcaca ctactacact cctaaaca 28

<210> SEQ ID NO 1392
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1392
acaccaattt aaaaaccaac cca 23

<210> SEQ ID NO 1393
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1393
cacacaatac aaaacctaca aacca 25

<210> SEQ ID NO 1394
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1394
cccacaataa catcaaccaa taca 24

<210> SEQ ID NO 1395
<211> LENGTH: 25
<212> TYPE: DNA

<213> ORGANISM: Artificial Sequence
<220> FEATURE:
<223> OTHER INFORMATION: Probe sequence (ASO2)

<400> SEQUENCE: 1395
caaaacactt cttcaaattc ctaca        25

<210> SEQ ID NO 1396
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1396
aaatcaacaa tcaaataaac caatca        26

<210> SEQ ID NO 1397
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1397
tcctactact cccactaatt cctaca        26

<210> SEQ ID NO 1398
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1398
cctaaaaaat caatcaaatt ttcca        25

<210> SEQ ID NO 1399
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1399
tctcctccta caactccata actaca        26

<210> SEQ ID NO 1400
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1400
aactctaaca ttacaaacct cacttca        27

<210> SEQ ID NO 1401
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1401
caacttccac atctaaacta cttcca        26

<210> SEQ ID NO 1402
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1402
ttcctactac tacttctacc actccca 27

<210> SEQ ID NO 1403
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1403
acactcaaca accataccca ca 22

<210> SEQ ID NO 1404
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1404
aacttaaacc tcaaacaaat caca 24

<210> SEQ ID NO 1405
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1405
atcttccaac aaatttccta cca 23

<210> SEQ ID NO 1406
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1406
caatacattc cttttcatca aaatca 26

<210> SEQ ID NO 1407
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1407
cattaccaac aacttttaaa tcca 24

<210> SEQ ID NO 1408
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1408
aaaacaaact ccacctaaca cca 23

<210> SEQ ID NO 1409
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1409
ataccaaaca cctatacctt aacca 25

<210> SEQ ID NO 1410
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1410
ctataaaaca accaaaacac aaaca 25

<210> SEQ ID NO 1411
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1411
tttcaaaaac taacaaacca aaca 24

<210> SEQ ID NO 1412
<211> LENGTH: 17
<212> TYPE: DNA
<213> ORGANISM: Artificial Sequence
<220> FEATURE:
<223> OTHER INFORMATION: Probe sequence (ASO2)

<400> SEQUENCE: 1412
atcccctcaa cccaaca 17

<210> SEQ ID NO 1413
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1413
ccaccttaac acatatccta atctca 26

<210> SEQ ID NO 1414
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1414
caaaaatcca cattaaacca aataca 26

<210> SEQ ID NO 1415
<211> LENGTH: 24
<212> TYPE: DNA

<213> ORGANISM: Artificial Sequence
<220> FEATURE:
<223> OTHER INFORMATION: Probe sequence (ASO2)

<400> SEQUENCE: 1415
caaaaaccaa aacttaaatc ctca 24

<210> SEQ ID NO 1416
<211> LENGTH: 19
<212> TYPE: DNA
<213> ORGANISM: Artificial Sequence
<220> FEATURE:
<223> OTHER INFORMATION: Probe sequence (ASO2)

<400> SEQUENCE: 1416
acaaaaccca aaaacccca 19

<210> SEQ ID NO 1417
<211> LENGTH: 28
<212> TYPE: DNA
<213> ORGANISM: Artificial Sequence
<220> FEATURE:
<223> OTHER INFORMATION: Probe sequence (ASO2)

<400> SEQUENCE: 1417
actaacctat caacctctaa tacactca 28

<210> SEQ ID NO 1418
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1418
tccaaacaca actcaattta aaaca 25

<210> SEQ ID NO 1419
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1419
aacccctaaa tccatctttc aca 23

<210> SEQ ID NO 1420
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1420
ccccattcta tctaccctat ctca 24

<210> SEQ ID NO 1421
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1421
cctaaaaaac acctaaaccc aca 23

<210> SEQ ID NO 1422
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1422
acaaacaaaa ataacatttt ccca 24

<210> SEQ ID NO 1423
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1423
tcacaaccaa aacaaactac aaca 24

<210> SEQ ID NO 1424
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1424
tcatcttaca atcacataac catca 25

<210> SEQ ID NO 1425
<211> LENGTH: 28
<212> TYPE: DNA
<213> ORGANISM: Artificial Sequence
<220> FEATURE:
<223> OTHER INFORMATION: Probe sequence (ASO2)

<400> SEQUENCE: 1425
catacactaa ctccaaaaca actaaaca 28

<210> SEQ ID NO 1426
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1426
actctacccc aaccacaact aca 23

<210> SEQ ID NO 1427
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1427
acccaacaaa cttttccttt tca 23

<210> SEQ ID NO 1428
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1428
cacacaatta atatcctacc ctcca 25

<210> SEQ ID NO 1429
<211> LENGTH: 21
<212> TYPE: DNA
<213> ORGANISM: Artificial Sequence
<220> FEATURE:
<223> OTHER INFORMATION: Probe sequence (ASO2)

<400> SEQUENCE: 1429
tccccaatac aaaccacaac a 21

<210> SEQ ID NO 1430
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1430
aaccaaaaca ctactcctaa ctcaca 26

<210> SEQ ID NO 1431
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1431
cataaaccaa aaacaacatc cca 23

<210> SEQ ID NO 1432
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1432
aaacaaacac aaacaaaaca cca 23

<210> SEQ ID NO 1433
<211> LENGTH: 28
<212> TYPE: DNA
<213> ORGANISM: Artificial Sequence
<220> FEATURE:
<223> OTHER INFORMATION: Probe sequence (ASO2)

<400> SEQUENCE: 1433
caatacccta taaacctaat cattaaca 28

<210> SEQ ID NO 1434
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1434
tacatctacc ctccacatct cca 23

<210> SEQ ID NO 1435
<211> LENGTH: 28
<212> TYPE: DNA

<213> ORGANISM: Artificial Sequence
<220> FEATURE:
<223> OTHER INFORMATION: Probe sequence (ASO2)

<400> SEQUENCE: 1435
cccaaaacac tcaataaaca ataataca 28

<210> SEQ ID NO 1436
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1436
aacccctaac tacttcaacc tca 23

<210> SEQ ID NO 1437
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1437
acaaatctta aaccctaatc cca 23

<210> SEQ ID NO 1438
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1438
cccttctata taaacctccc ca 22

<210> SEQ ID NO 1439
<211> LENGTH: 19
<212> TYPE: DNA
<213> ORGANISM: Artificial Sequence
<220> FEATURE:
<223> OTHER INFORMATION: Probe sequence (ASO2)

<400> SEQUENCE: 1439
aaacaactat ccccaccca 19

<210> SEQ ID NO 1440
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1440
tccttactac cacacattta acca 24

<210> SEQ ID NO 1441
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1441
ttcaaatctt atcaaacacc ctca 24

<210> SEQ ID NO 1442
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1442
caaacccaac ctatatccaa atca 24

<210> SEQ ID NO 1443
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1443
aacaatacta aaaacacccc tctca 25

<210> SEQ ID NO 1444
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1444
ccctttaacc actaacctaa tcca 24

<210> SEQ ID NO 1445
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1445
ccacccaaaa caactacact atca 24

<210> SEQ ID NO 1446
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1446
aaattacccc acaacctaaa cca 23

<210> SEQ ID NO 1447
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1447
aaccacacaa atcccactta tca 23

<210> SEQ ID NO 1448
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1448
aacaccaaac aaaacaaaaa cca 23

<210> SEQ ID NO 1449
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1449
cacacaacac attacaaaca aataca 26

<210> SEQ ID NO 1450
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1450
cacactctct cacttttata aaaaaca 27

<210> SEQ ID NO 1451
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1451
aaattacaca aaccattcta accca 25

<210> SEQ ID NO 1452
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1452
aaacaaaaaa ctatccacct tacaca 26

<210> SEQ ID NO 1453
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1453
actcactctt atccccacct aca 23

<210> SEQ ID NO 1454
<211> LENGTH: 22
<212> TYPE: DNA
<213> ORGANISM: Artificial Sequence
<220> FEATURE:
<223> OTHER INFORMATION: Probe sequence (ASO2)

<400> SEQUENCE: 1454
cccaccaaca tcctaaatac ca 22

<210> SEQ ID NO 1455
<211> LENGTH: 21
<212> TYPE: DNA

<213> ORGANISM: Artificial Sequence
<220> FEATURE:
<223> OTHER INFORMATION: Probe sequence (ASO2)

<400> SEQUENCE: 1455
aactacacaa cccaaaccac a 21

<210> SEQ ID NO 1456
<211> LENGTH: 19
<212> TYPE: DNA
<213> ORGANISM: Artificial Sequence
<220> FEATURE:
<223> OTHER INFORMATION: Probe sequence (ASO2)

<400> SEQUENCE: 1456
acctcaaatc ctccaacca 19

<210> SEQ ID NO 1457
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1457
acccaaatac aactacccaa aca 23

<210> SEQ ID NO 1458
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1458
ccaaaccaac tcaaatctac ctaca 25

<210> SEQ ID NO 1459
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1459
aaactctaac aacccatcct aaca 24

<210> SEQ ID NO 1460
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1460
acttacatcc tctaaatttc ccca 24

<210> SEQ ID NO 1461
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1461
aacaacttaa tccccctaac cca 23

-continued

<210> SEQ ID NO 1462
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1462
aatataacaa ccaatcctac tctcca 26

<210> SEQ ID NO 1463
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1463
tcctaaaaac ccttaaccct cca 23

<210> SEQ ID NO 1464
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1464
aactactatt ctctcctatt tccctca 27

<210> SEQ ID NO 1465
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1465
ataaaacttt ctccccaaaa aaca 24

<210> SEQ ID NO 1466
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1466
aaattcctcc acttaaacta ccca 24

<210> SEQ ID NO 1467
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1467
aaactcaaaa ccctccaaaa tca 23

<210> SEQ ID NO 1468
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1468
ctctaactaa actcaacaac ctcca 25

<210> SEQ ID NO 1469
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1469
aaaaccttaa ctaacacaaa accaca 26

<210> SEQ ID NO 1470
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1470
ccaaatctca ctcctaaatt caaca 25

<210> SEQ ID NO 1471
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1471
aaaaaacctc tacccaaaaa cca 23

<210> SEQ ID NO 1472
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1472
aaaatacaaa ctacttcacc ccca 24

<210> SEQ ID NO 1473
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1473
ccaacccaaa acctactcct aca 23

<210> SEQ ID NO 1474
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1474
ctctaaattt aaattaccct cctcca 26

<210> SEQ ID NO 1475
<211> LENGTH: 25
<212> TYPE: DNA

<213> ORGANISM: Artificial Sequence
<220> FEATURE:
<223> OTHER INFORMATION: Probe sequence (ASO2)

<400> SEQUENCE: 1475
aacccctcta attatctctt tacca 25

<210> SEQ ID NO 1476
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1476
acaacctatc caaatcacaa aaca 24

<210> SEQ ID NO 1477
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1477
cttacaaatc tcccaaataa aatca 25

<210> SEQ ID NO 1478
<211> LENGTH: 18
<212> TYPE: DNA
<213> ORGANISM: Artificial Sequence
<220> FEATURE:
<223> OTHER INFORMATION: Probe sequence (ASO2)

<400> SEQUENCE: 1478
acaaacactc ccctccca 18

<210> SEQ ID NO 1479
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1479
caaaacctca atctaaaaac caca 24

<210> SEQ ID NO 1480
<211> LENGTH: 19
<212> TYPE: DNA
<213> ORGANISM: Artificial Sequence
<220> FEATURE:
<223> OTHER INFORMATION: Probe sequence (ASO2)

<400> SEQUENCE: 1480
acccctcccc aaataatca 19

<210> SEQ ID NO 1481
<211> LENGTH: 28
<212> TYPE: DNA
<213> ORGANISM: Artificial Sequence
<220> FEATURE:
<223> OTHER INFORMATION: Probe sequence (ASO2)

<400> SEQUENCE: 1481
catattatat cctaccattt aataccca 28

<210> SEQ ID NO 1482
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1482
ttaaaactca acctcacaaa tcaca 25

<210> SEQ ID NO 1483
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1483
ccaaaaccaa taactttaca aaaca 25

<210> SEQ ID NO 1484
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1484
aaacaaataa aataccacct ccaca 25

<210> SEQ ID NO 1485
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1485
aattcaaaaa accacaaaaa tttca 25

<210> SEQ ID NO 1486
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1486
ttaaaacacc taaacttaaa acctca 26

<210> SEQ ID NO 1487
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1487
ataaaaacca acccaaattt cca 23

<210> SEQ ID NO 1488
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1488
caccacatac acactacaca cca 23

<210> SEQ ID NO 1489
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1489
cacacacaca aaccacatac aca 23

<210> SEQ ID NO 1490
<211> LENGTH: 19
<212> TYPE: DNA
<213> ORGANISM: Artificial Sequence
<220> FEATURE:
<223> OTHER INFORMATION: Probe sequence (ASO2)

<400> SEQUENCE: 1490
aaaacaaaca ccaacccca 19

<210> SEQ ID NO 1491
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1491
caaacataca tacaacaatc ctctca 26

<210> SEQ ID NO 1492
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1492
caaactccta aactcaaaca atcca 25

<210> SEQ ID NO 1493
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1493
aacaatactc aaaaaccaaa acca 24

<210> SEQ ID NO 1494
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1494
cacactccct actaaaccta aatca 25

<210> SEQ ID NO 1495
<211> LENGTH: 23
<212> TYPE: DNA

<213> ORGANISM: Artificial Sequence
<220> FEATURE:
<223> OTHER INFORMATION: Probe sequence (ASO2)

<400> SEQUENCE: 1495
ccaacctcaa ctcacaaaat aca 23

<210> SEQ ID NO 1496
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1496
ataacatcac aacccaaata acca 24

<210> SEQ ID NO 1497
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1497
ataccacctc acccctaaac taca 24

<210> SEQ ID NO 1498
<211> LENGTH: 26
<212> TYPE: DNA
<213> ORGANISM: Artificial Sequence
<220> FEATURE:
<223> OTHER INFORMATION: Probe sequence (ASO2)

<400> SEQUENCE: 1498
caataccaac caactaaact aaacca 26

<210> SEQ ID NO 1499
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1499
caacaaataa ccaaacaaac acca 24

<210> SEQ ID NO 1500
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1500
accaaaacaa aaacaaaaac aaca 24

<210> SEQ ID NO 1501
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1501
acaactaccc aaacaaaacc aca 23

<210> SEQ ID NO 1502
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1502
cacataaaat caaaccacaa aaca 24

<210> SEQ ID NO 1503
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1503
tccaaaccaa cttatctatc ctaca 25

<210> SEQ ID NO 1504
<211> LENGTH: 25
<212> TYPE: DNA
<213> ORGANISM: Artificial Sequence
<220> FEATURE:
<223> OTHER INFORMATION: Probe sequence (ASO2)

<400> SEQUENCE: 1504
ttacaaacct aaaattcctc tttca 25

<210> SEQ ID NO 1505
<211> LENGTH: 23
<212> TYPE: DNA
<213> ORGANISM: Artificial Sequence
<220> FEATURE:
<223> OTHER INFORMATION: Probe sequence (ASO2)

<400> SEQUENCE: 1505
aaacaaaaac tacaactctc cca 23

<210> SEQ ID NO 1506
<211> LENGTH: 24
<212> TYPE: DNA
<213> ORGANISM: Artificial Sequence
<220> FEATURE:
<223> OTHER INFORMATION: Probe sequence (ASO2)

<400> SEQUENCE: 1506
accaatacac tccaaaccta aaca 24

<210> SEQ ID NO 1507
<211> LENGTH: 27
<212> TYPE: DNA
<213> ORGANISM: Artificial Sequence
<220> FEATURE:
<223> OTHER INFORMATION: Probe sequence (ASO2)

<400> SEQUENCE: 1507
cactaaaatt acaaacataa accacca 27

<210> SEQ ID NO 1508
<211> LENGTH: 24
<212> TYPE: DNA
<213> ORGANISM: Artificial Sequence
<220> FEATURE:
<223> OTHER INFORMATION: Probe sequence (ASO2)

-continued

<400> SEQUENCE: 1508
actcaaaccc tctaacctca aaca 24

<210> SEQ ID NO 1509
<211> LENGTH: 41
<212> TYPE: DNA
<213> ORGANISM: Homo sapiens

<400> SEQUENCE: 1509
cccctggagc ggcccctggg cgaggtgtac ctggacagca g 41

<210> SEQ ID NO 1510
<211> LENGTH: 41
<212> TYPE: RNA
<213> ORGANISM: Homo sapiens
<220> FEATURE:
<221> NAME/KEY: misc_feature
<222> LOCATION: (1)...(41)
<223> OTHER INFORMATION: n=t

<400> SEQUENCE: 1510
uuuunggagu gguuuunggg cgaggngnau unggauagua g 41

<210> SEQ ID NO 1511
<211> LENGTH: 19
<212> TYPE: DNA
<213> ORGANISM: Artificial Sequence
<220> FEATURE:
<223> OTHER INFORMATION: Primer (LSO)

<400> SEQUENCE: 1511
aaaaacctcr ccaaaaacc 19

<210> SEQ ID NO 1512
<211> LENGTH: 21
<212> TYPE: DNA
<213> ORGANISM: Artificial Sequence
<220> FEATURE:
<223> OTHER INFORMATION: Probe (ASO1)

<400> SEQUENCE: 1512
gctccacata aacctatcat c 21

<210> SEQ ID NO 1513
<211> LENGTH: 21
<212> TYPE: DNA
<213> ORGANISM: Artificial Sequence
<220> FEATURE:
<223> OTHER INFORMATION: Probe (ASO2)

<400> SEQUENCE: 1513
actccacata aacctatcat c 21